US009302999B2

(12) United States Patent
Campbell et al.

(10) Patent No.: US 9,302,999 B2
(45) Date of Patent: Apr. 5, 2016

(54) SUBSTITUTED TRIAZOLES AS HERBICIDES

(71) Applicant: E. I. DU PONT DE NEMOURS AND COMPANY, Wilmington, DE (US)

(72) Inventors: Matthew James Campbell, Rising Sun, MD (US); Thomas Martin Stevenson, Newark, DE (US)

(73) Assignee: E. I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/437,360

(22) PCT Filed: Oct. 18, 2013

(86) PCT No.: PCT/US2013/065663

§ 371 (c)(1),
(2) Date: Apr. 21, 2015

(87) PCT Pub. No.: WO2014/066164

PCT Pub. Date: May 1, 2014

(65) Prior Publication Data

US 2015/0284343 A1 Oct. 8, 2015

Related U.S. Application Data

(60) Provisional application No. 61/719,166, filed on Oct. 26, 2012.

(51) Int. Cl.

| | |
|---|---|
| ***C07D 249/04*** | (2006.01) |
| ***C07D 249/06*** | (2006.01) |
| ***A01N 43/647*** | (2006.01) |
| ***C07D 401/06*** | (2006.01) |
| ***C07D 403/06*** | (2006.01) |

(52) U.S. Cl.

CPC ............ *C07D 249/06* (2013.01); *A01N 43/647* (2013.01); *C07D 401/06* (2013.01); *C07D 403/06* (2013.01)

(58) Field of Classification Search

CPC .................................................... C07D 249/04

See application file for complete search history.

(56) References Cited

U.S. PATENT DOCUMENTS

2009/0156553 A1 6/2009 Hupe et al.
2010/0069644 A1 3/2010 Shi

FOREIGN PATENT DOCUMENTS

DE 1226591 A1 10/1960
EP 412849 A2 10/1990
WO 2007077201 A1 7/2007

OTHER PUBLICATIONS

Boddy, et al., "The Synthesis and Insecticidal Activity of a Series of 2-Aryl-1,2,3-triazoles", Pestic. Sci., 1996, 48, 189-196.
Henseke et al., "Reactivity of Methyl Groups in the Osotriazole Ring System", Journal für Praktische Chemie, series 4, vol. 33, 1966.

*Primary Examiner* — Michael Barker
*Assistant Examiner* — Karen Cheng
(74) *Attorney, Agent, or Firm* — Reed A. Coats

(57) ABSTRACT

Disclosed are compounds of Formula 1, including all stereoisomers, N-oxides, and salts thereof,

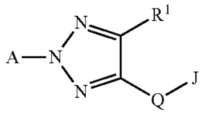

1 wherein A, $R^1$, Q and J are as defined in the disclosure. Also disclosed are compositions containing the compounds of Formula 1 and methods for controlling undesired vegetation comprising contacting the undesired vegetation or its environment with an effective amount of a compound or a composition of the invention.

12 Claims, No Drawings

SUBSTITUTED TRIAZOLES AS HERBICIDES

FIELD OF THE INVENTION

This invention relates to certain triazoles, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safe or have different sites of action.

SUMMARY OF THE INVENTION

This invention is directed to compounds of Formula 1 (including all stereoisomers), including N-oxides and salts thereof, agricultural compositions containing them and their use as herbicides:

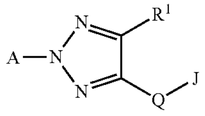

1 wherein $R^1$ is halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_n(R^{12})$, $C_2$-$C_4$ alkylthioalkyl, $C_2$-$C_4$ alkylsulfonylalkyl, $C_1$-$C_4$ alkylamino $C_2$-$C_4$ dialkylamino, $C_3$-$C_6$ cycloalkyl or hydroxy;

A is a radical selected from the group consisting of

A-1

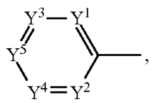

,

A-2

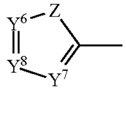

and

A-3

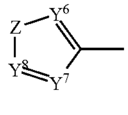

each $Y^1$, $Y^2$, $Y^3$, $Y^4$ and $Y^5$ is independently N or $CR^2$, provided no more than 3 of $Y^1$, $Y^2$, $Y^3$, $Y^4$ and $Y^5$ are N;

each $Y^6$, $Y^7$ and $Y^8$ is independently N or $CR^3$, provided no more than 2 of $Y^6$, $Y^7$ and $Y^8$ are N;

Z is O or S;

Q is $C(R^4)(R^5)$, O, S or $NR^6$;

J is phenyl substituted with 1 $R^7$ and optionally substituted with up to 2 $R^8$; or J is a 6-membered aromatic heterocyclic ring substituted with 1 $R^7$ and optionally substituted with up to 2 $R^8$ on carbon ring members; or J is a 5-membered aromatic heterocyclic ring substituted with 1 $R^9$ on carbon ring members and $R^{11}$ on nitrogen ring members; and optionally substituted with 1 $R^{10}$ on carbon ring members;

each $R^2$ is independently H, halogen, cyano, nitro, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy or $S(O)_nR^{12}$;

each $R^3$ is independently H, halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

$R^4$ is H, F, Cl, Br, cyano, $C_1$-$C_4$ alkyl, $C_1$-$C_4$ haloalkyl or $CO_2R^{13}$;

$R^5$ is H, F, $C_1$-$C_4$ alkyl, OH or $OR^{13}$; or $R^4$ and $R^5$ are taken together with the carbon to which they are attached to form C(═O), C(═$NOR^{13}$) or C(═N—$N(R^{14})(R^{15})$);

$R^6$ is H, $C_1$-$C_4$ alkyl or $C_1$-$C_4$ haloalkyl;

$R^7$ is halogen, cyano, $SF_5$, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

each $R^8$ is independently halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^{12}$; or $R^7$ and $R^8$ are taken together with two adjacent carbon atoms to form a 5-membered ring containing ring members selected from carbon atoms and up to two O atoms and up to two S atoms, and optionally substituted on carbon atom ring members with up to five halogen atoms;

$R^9$ is halogen, cyano, $SF_5$, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

$R^{10}$ is halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

$R^{11}$ is $C_1$-$C_4$ alkyl or $C_1$-$C_4$ haloalkyl;

each $R^{12}$ is independently $C_1$-$C_4$ alkyl or $C_1$-$C_4$ haloalkyl;

each $R^{13}$ is independently H or $C_1$-$C_4$ alkyl;

$R^{14}$ is $C_1$-$C_4$ alkyl or $C_1$-$C_4$ haloalkyl;

$R^{15}$ is $C_1$-$C_4$ alkyl or $C_1$-$C_4$ haloalkyl; and each n is independently 0, 1 or 2;

provided i) when $R^1$ is $CH_3$; A is A-1; $Y^1$, $Y^2$, $Y^3$ and $Y^4$ are each CH; and $Y^5$ is $CCF_3$ then J is other than 3-chloro-1H-1,2,4-thiadiazol-5-yl, 4-fluoro-2-pyridinyl, 4-chlorophenyl or 2,4-dichlorophenyl; and ii) when $R^1$ is $CH_3$; A is A-1; $Y^1$, $Y^2$, $Y^3$ and $Y^4$ are each CH; and $Y^5$ is CF then J is other than 4-fluoro-3-methylphenyl.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed. As referred to herein, the term "broadleaf" used either alone or in words such as "broadleaf weed" means dicot or dicotyledon, a term used to describe a group of angiosperms characterized by embryos having two cotyledons. As used herein, the term "alkylating reagent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "cycloalkyl" includes, for example, cyclopropyl, cyclobutyl, cyclopentyl and cyclohexyl. "Alkenyl" includes straight-chain or branched alkenes such as ethenyl, 1-propenyl, 2-propenyl, and the different butenyl isomers. "Alkenyl" also includes polyenes such as 1,2-propadienyl 1,3-butadienyl. "Alkynyl" includes straight-chain or branched alkynes such as ethynyl, 1-propynyl, 2-propynyl and the different butynyl and pentynyl isomers. "Alkynyl" can also include moieties comprised of multiple triple bonds such as 1,3-butadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$ and $CH_3CH_2OCH_2CH_2$. "Alkenyloxy" includes straight-chain or branched alkenyloxy moieties. Examples of "alkenyloxy" include $H_2C{=}CHCH_2O$, $(CH_3)CH{=}CHCH_2O$ and $CH_2{=}CHCH_2CH_2O$. "Alkynyloxy" includes straight-chain or branched alkynyloxy moieties. Examples of "alkynyloxy" include $HC{\equiv}CCH_2O$ and $CH_3C{\equiv}CCH_2O$. "Alkylcarbonyloxy" includes straight-chain or branched alkylcarbonyloxy moieties. Examples of "alkylcarbonyloxy" include $CH_3C({=}O)O$, $(CH_3)_2CH_2C({=}O)O$ and $CH_3CH_2CH_2CH_2C({=}O)O$. "Alkylthio" includes branched or straight-chain alkylthio moieties such as methylthio, ethylthio and the different propylthio, butylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$ and $CH_3CH_2SCH_2CH_2$. Examples of "alkylsulfonyl" include $CH_3S(O)_2$—, $CH_3CH_2S(O)_2$— and $CH_3CH_2CH_2S(O)_2$—, and the different butylsulfonyl isomers. The term "alkylsulfonylalkyl" denotes alkylsulfonyl substitution on alkyl. Examples of "alkylsulfonylalkyl" include $CH_3SO_2CH_2$, $CH_3SO_2CH_2CH_2$, $CH_3CH_2SO_2CH_2$ and $CH_3CH_2SO_2CH_2CH_2$. "Alkylthioalkoxy" denotes alkylthio substitution on alkoxy. "Hydroxyalkyl" denotes an alkyl group substituted with one hydroxy group. Examples of hydroxy alkyl include $HOCH_2CH_2CH_2$—, $CH_3CH_2CH(OH)CH_2$—, and $CH_3CH_2CHOH$—. "Alkylamino", "dialkylamino" and the like, are defined analogously to the above examples.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The term "haloalkoxy" and the like, is defined analogously to the term "haloalkyl". Examples of "haloalkoxy" include $CF_3O$—, $CCl_3CH_2O$—, $HCF_2CH_2CH_2O$— and $CF_3CH_2O$—.

The total number of carbon atoms in a substituent group is indicated by the "$C_i$-$C_j$" prefix where i and j are numbers from 1 to 4. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a group contains a substituent which can be hydrogen, for example $R^2$, $R^3$, $R^4$, $R^5$ and $R^6$, then when this substituent is taken as hydrogen, it is recognized that this is equivalent to said group being unsubstituted. When a variable group is shown to be optionally attached to a position, for example $R^8$, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" as a component of Formula 1 (e.g., substituent J) is heterocyclic. The term "ring member" refers to an atom or other moiety forming the backbone of a ring. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen. "Aromatic" indicates that each of the ring atoms is essentially in the same plane and has a p-orbital perpendicular to the ring plane, and that (4n+2) $\pi$ electrons, where n is a positive integer, are associated with the ring to comply with Hückel's rule.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When J is a 5- or 6-membered nitrogen-containing heterocyclic ring, it may be attached to the remainder of Formula 1 though any available carbon or nitrogen ring atom, unless otherwise described. As noted above, J can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is $R^7$ and $R^8$ as defined in the Summary of the Invention for substitution on J and r is an integer from 0 to 3 (i.e. substituted with one $R^7$ and up to two $R^8$).

As noted above, J can be phenyl or a 5- or 6-membered aromatic heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for J (i.e. $R^7$, $R^8$, $R^9$, $R^{10}$ and $R^{11}$) and r is an integer from 0 to 3, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

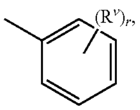
U-1

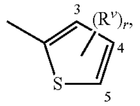
U-2

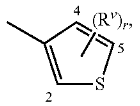
U-3

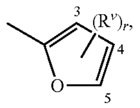
U-4

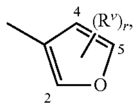
U-5

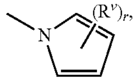
U-6

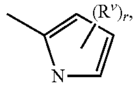
U-7

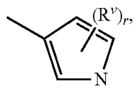
U-8

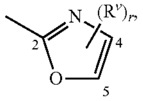
U-9

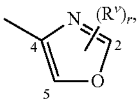
U-10

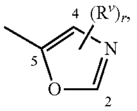
U-11

-continued
U-12
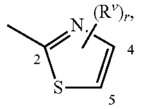
U-13
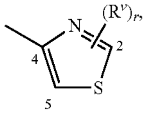
U-14
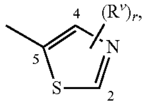
U-15
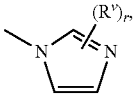
U-16
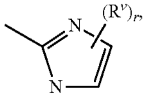
U-17
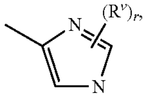
U-18
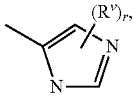
U-19
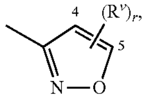
U-20
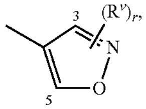
U-21
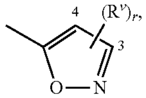
U-22
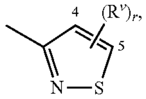
U-23
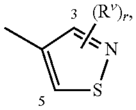
U-24
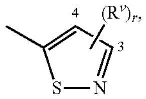
-continued
U-25
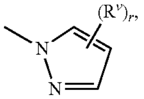
U-26
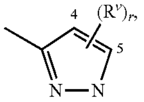
U-27
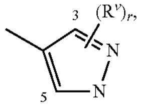
U-28
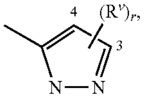
U-29
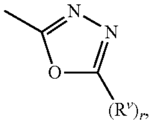
U-30
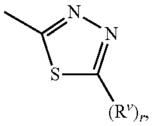
U-31
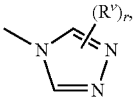
U-32
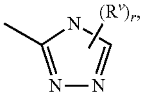
U-33
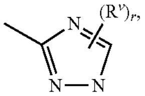
U-34
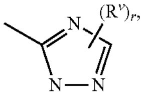
U-35
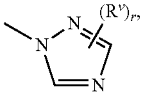
U-36
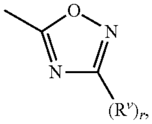
U-37
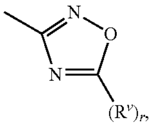

-continued
U-38
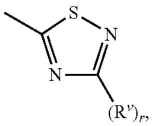
U-39
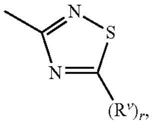
U-40
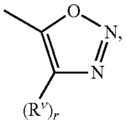
U-41
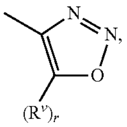
U-42
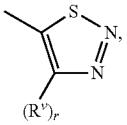
U-43
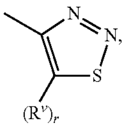
U-44
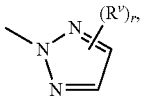
U-45
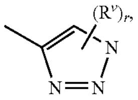
U-46
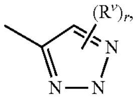
U-47
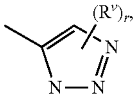
U-48
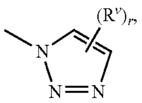
U-49
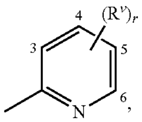
-continued
U-50
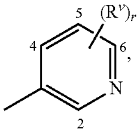
U-51
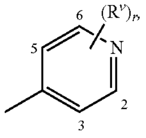
U-52
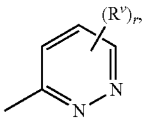
U-53
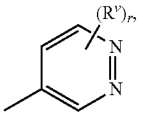
U-54
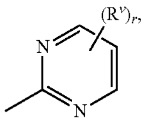
U-55
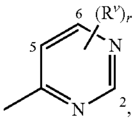
U-56
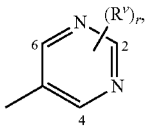
U-57
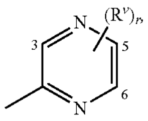
U-58
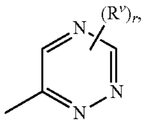
U-59
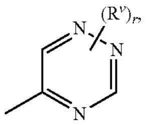
U-60
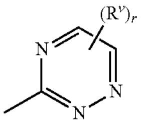
and -continued

U-61

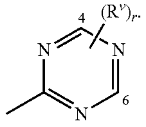

Note that when J is a 5- or 6-membered saturated or unsaturated non-aromatic heterocyclic ring optionally substituted with one or more substituents selected from the group of substituents as defined in the Summary of the Invention for J, one or two carbon ring members of the heterocycle can optionally be in the oxidized form of a carbonyl moiety.

Examples of a 5-membered carbocyclic ring containing ring members selected from up to two O atoms and up to two S atoms, and optionally substituted on carbon atom ring members with up to five halogen atoms includes the rings G-1 through G-5 as illustrated in Exhibit 2 (i.e. when $R^7$ and $R^8$ are taken together with two adjacent carbon atoms). Note that when the attachment point on the $R^v$ group is illustrated as floating, the $R^v$ group can be attached to the remainder of Formula 1 through any available carbon G group by replacement of a hydrogen atom. The optional substituents corresponding to $R^v$ can be attached to any available carbon or nitrogen by replacing a hydrogen atom. For these G rings, r is typically an integer from 0 to 5, limited by the number of available positions on each G group.

Exhibit 2

G-1

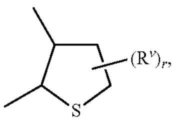

G-2

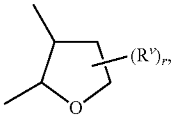

G-3

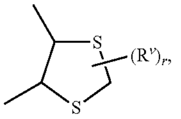

G-4

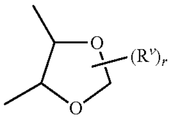

and

G-5

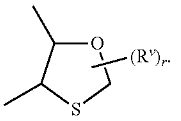

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof) the following:

Embodiment 1

A compound of Formula 1 (including all stereoisomers), N-oxides, and salts thereof, agricultural compositions containing them and their use as herbicides as described in the Summary of the Invention.

Embodiment 1A

A compound of Formula 1 wherein $R^1$ is H, halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_1$-$C_4$ hydroxyalkyl, $SO_n(R^{12})$, $C_2$-$C_4$ alkylthioalkyl, $C_2$-$C_4$ alkylsulfonylalkyl, $C_1$-$C_4$ alkylamino or $C_2$-$C_4$ dialkylamino.

Embodiment 1B

A compound of Embodiment 1A wherein $R^1$ is other than H,

Embodiment 1C

A compound of Embodiment 1 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_n(R^{12})$, $C_2$-$C_4$ alkylthioalkyl or $C_2$-$C_4$ alkylsulfonylalkyl.

Embodiment 2

A compound of Embodiment 1 or 1C wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_1$-$C_4$ hydroxyalkyl, $SO_n(R^{12})$, $C_2$-$C_4$ alkylthioalkyl or $C_2$-$C_4$ alkylsulfonylalkyl.

Embodiment 3

A compound of Embodiment 2 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl or $C_2$-$C_4$ alkenyl.

Embodiment 4

A compound of Embodiment 3 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl or $C_1$-$C_4$ haloalkyl.

Embodiment 5

A compound of Embodiment 4 wherein $R^1$ is $C_1$-$C_4$ alkoxy, $C_1$-$C_4$ haloalkoxy or $C_1$-$C_4$ alkyl.

Embodiment 6

A compound of Embodiment 5 wherein $R^1$ is $C_1$-$C_4$ alkoxy or $C_1$-$C_4$ alkyl.

Embodiment 7

A compound of Embodiment 6 wherein $R^1$ is $C_1$-$C_4$ alkyl.

Embodiment 7A

A compound of Embodiment 7 wherein $R^1$ is $C_1$-$C_3$ alkyl.

Embodiment 7B

A compound of Embodiment 7 wherein $R^1$ is $C_1$-$C_2$ alkyl.

Embodiment 8

A compound of Embodiment 7 wherein $R^1$ is $CH_3$.

Embodiment 8A

A compound of Embodiment 5 wherein $R^1$ is $CH_3CH_2O$—, $CH_3O$—, $CF_3CH_2O$— or $CH_3$.

Embodiment 8B

A compound of Embodiment 5 wherein $R^1$ is $CH_3CH_2O$—, $CH_3O$— or $CH_3$.

Embodiment 8C

A compound of Embodiment 5 wherein $R^1$ is $CH_3CH_2O$— or $CH_3O$—,

Embodiment 8D

A compound of Embodiment 5 wherein $R^1$ is $CH_3CH_2O$—.

Embodiment 9

A compound of any one of Embodiments 1 through 8D wherein A is a radical selected from the group consisting of A-1 and A-2.

Embodiment 10

A compound of Embodiment 9 wherein A is A-1.

Embodiment 11

A compound of Embodiment 10 wherein each $Y^1$, $Y^3$, $Y^4$ and $Y^5$ is independently N or $CR^2$; and $Y^2$ is $CR^2$.

Embodiment 12

A compound of Embodiment 11 wherein each $Y^1$ and $Y^5$ is independently N or $CR^2$; and each $Y^2$, $Y^3$ and $Y^4$ is $CR^2$.

Embodiment 13

A compound of Embodiment 12 wherein $Y^1$ is N or $CR^2$; and each $Y^2$, $Y^3$, $Y^4$ and $Y^5$ is independently $CR^2$.

Embodiment 14

A compound of Embodiment 13 wherein $Y^1$ is N; and each $Y^2$, $Y^3$, $Y^4$ and $Y^5$ is independently $CR^2$.

Embodiment 15

A compound of Embodiment 14 wherein $Y^1$ is N; each $Y^2$, $Y^3$ and $Y^4$ is CH; and $Y^5$ is CF.

Embodiment 16

A compound of Embodiment 13 wherein each $Y^1$, $Y^2$, $Y^3$ and $Y^4$ and is CH; and $Y^5$ is $CCF_3$ or CF.

Embodiment 17

A compound of Embodiment 9 wherein A is A-2.

Embodiment 18

A compound of Embodiment 17 wherein each $Y^6$ and $Y^7$ is independently N or $CR^3$; and $Y^8$ is $CR^3$.

Embodiment 19

A compound of Embodiment 18 wherein each $Y^6$ and $Y^7$ is N; and $Y^8$ is $CR^3$.

Embodiment 20

A compound of Embodiment 19 wherein each $Y^6$ and $Y^7$ is N; and $Y^8$ is CH.

Embodiment 21

A compound of any one of Embodiments 1 through 9 or 17 through 20 wherein Z is S.

Embodiment 22

A compound of any one of Embodiments 1 through 21 wherein Q is $C(R^4)(R^5)$, O or S.

Embodiment 23

A compound of Embodiment 22 wherein Q is $C(R^4)(R^5)$ or O.

Embodiment 24

A compound of Embodiment 23 wherein Q is $C(R^4)(R^5)$.

Embodiment 25

A compound of Embodiment 23 wherein Q is O.

Embodiment 26

A compound of any one of Embodiments 1 through 25 wherein J is selected from

J-1

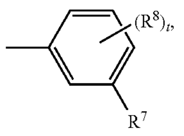

J-2

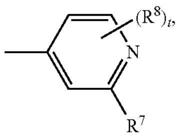

J-3

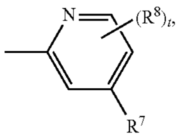

J-4

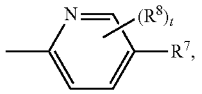

J-5

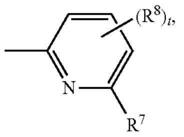

J-6

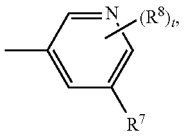

J-7

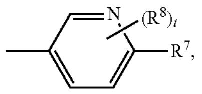

J-8

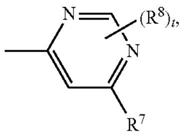

J-9

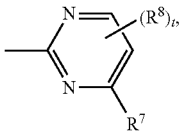

J-10

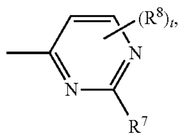

-continued
J-11
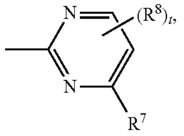
J-12
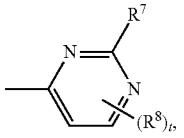
J-13
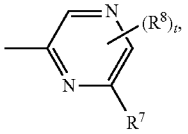
J-14
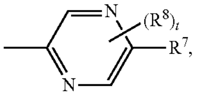
J-15
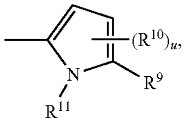
J-16
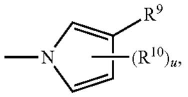
J-17
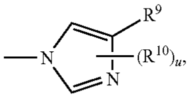
J-18
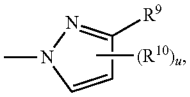
J-19
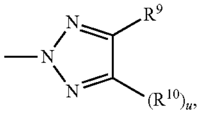
J-20
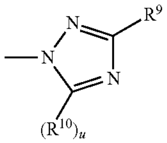
J-21
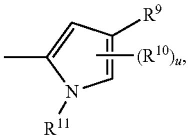
J-22
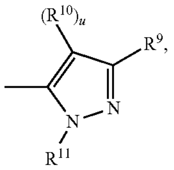
-continued
J-23
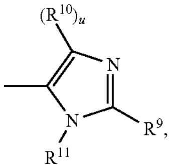
J-24
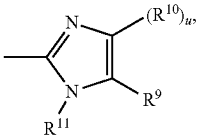
J-25
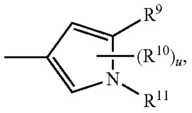
J-26
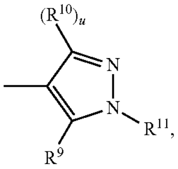
J-27
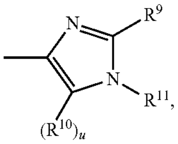
J-28
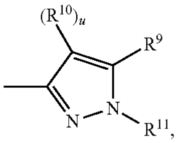
J-29
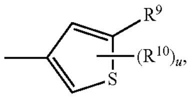
J-30
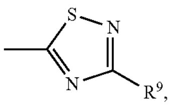
J-31
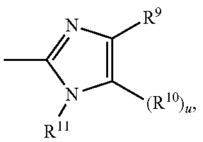
J-32
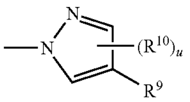
and
J-33
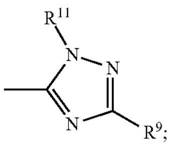

t is 0, 1 or 2; and u is 0 or 1.

Embodiment 27

A compound of Embodiment 26 wherein J is selected from J-1 through J-14 (i.e. J is a 6-membered aromatic heterocyclic ring selected from J-1 through J-14).

Embodiment 28

A compound of Embodiment 26 wherein J is selected from J-15 through J-33 (i.e. J is a 5-membered aromatic heterocyclic ring selected from J-15 through J-33).

Embodiment 29

A compound of Embodiment 26 wherein J is selected from J-1, J-2, J-3, J-4, J-5, J-6, J-7, J-9, J-12, J-17, J-18, J-20, J-22, J-26, J-29 and J-30 (i.e. all J groups prepared in Index Table A).

Embodiment 30

A compound of Embodiment 27 or 29 wherein J is selected from J-1, J-2, J-3, J-4, J-5, J-6, J-7, J-9 and J-12 (i.e. all 6-membered J groups prepared in Index Table A).

Embodiment 30A

A compound of Embodiment 27 or 29 wherein J is selected from J-2, J-3, J-4, J-5, J-6 and J-7 (i.e. all pyridine J groups).

Embodiment 30B

A compound of Embodiment 27 or 29 wherein J is selected from J-8, J-9, J-10, J-11, J-12, J-13 and J-14 (i.e. all pyrimidine J groups).

Embodiment 31

A compound of Embodiment 28 or 29 wherein J is selected from J-18, J-20, J-22, J-26, J-29 and J-30 (i.e. all 5-membered J groups prepared in Index Table A).

Embodiment 31A

A compound of Embodiment 28 wherein J is selected from J-15, J-21, J-22, J-23, J-24, J-25, J-26, J-27, J-28, J-31 and J-33 (i.e. all nitrogen containing 5-membered J groups linked through carbon).

Embodiment 31B

A compound of Embodiment 28 wherein J is selected from J-16, J-17, J-18, J-19, J-20 and J-32 (i.e. all nitrogen containing 5-membered J groups linked through nitrogen).

Embodiment 32

A compound of Embodiment 26 wherein J is selected from J-1, J-2, J-10, J-17, J-18 and J-20.

Embodiment 33

A compound of Embodiment 32 wherein J is selected from J-1, J-2, J-17 and J-18.

Embodiment 34

A compound of Embodiment 33 wherein J is J-1.

Embodiment 35

A compound of Embodiment 33 wherein J is J-2.

Embodiment 35A

A compound of any one of Embodiments 26, 27, 29, 30, 30A, 30B, 32 or 33 wherein t is 0 or 1.

Embodiment 35B

A compound of Embodiment 35A wherein t is 0.

Embodiment 35C

A compound of any one of Embodiments 26, 28, 29, 31, 31A, 31B, 32 or 33 wherein u is 0.

Embodiment 36

A compound of any one of Embodiments 1 through 26, 27, 29, 30 or 32 through 34 wherein J is other than J-1.

Embodiment 37

A compound of any one of Embodiments 1 through 36 wherein each $R^2$ is independently H, halogen, $C_1$-$C_4$ alkoxy, $C_1$-$C_4$ alkyl or $C_1$-$C_4$ haloalkyl.

Embodiment 38

A compound of Embodiment 37 wherein each $R^2$ is independently H, halogen, $C_1$-$C_4$ alkyl or $C_1$-$C_4$ haloalkyl.

Embodiment 39

A compound of Embodiment 38 wherein each $R^2$ is independently H, F, Cl, $CH_3$ or $CF_3$.

Embodiment 40

A compound of Embodiment 39 wherein each $R^2$ is independently H, F, Cl or $CF_3$.

Embodiment 41

A compound of Embodiment 40 wherein each $R^2$ is independently H or $CF_3$.

Embodiment 42

A compound of Embodiment 40 wherein each $R^2$ is independently H or F.

Embodiment 43

A compound of any one of Embodiments 1 through 42 wherein each $R^3$ is independently H, halogen or $C_1$-$C_4$ haloalkyl.

Embodiment 44

A compound of Embodiment 43 wherein each $R^3$ is independently H, F, Cl or $CF_3$.

Embodiment 45

A compound of Embodiment 44 wherein each $R^3$ is independently H or $CF_3$.

Embodiment 45A

A compound of any one of Embodiments 1 through 45 wherein $R^4$ is taken alone.

Embodiment 46

A compound of any one of Embodiments 1 through 45A wherein $R^4$ is H, F, Cl, Br or $C_1$-$C_4$ alkyl.

Embodiment 47

A compound of Embodiment 46 wherein $R^4$ is H, F or $CH_3$.

Embodiment 48

A compound of Embodiment 47 wherein $R^4$ is H.

Embodiment 48A

A compound of any one of Embodiments 1 through 48 wherein $R^5$ is taken alone.

Embodiment 49

A compound of any one of Embodiments 1 through 48A wherein $R^5$ is H, F or OH.

Embodiment 50

A compound of Embodiment 49 wherein $R^5$ is H or F.

Embodiment 51

A compound of Embodiment 50 wherein $R^5$ is H.

Embodiment 52

A compound of Embodiment 50 wherein $R^5$ is F.

Embodiment 53

A compound of any one of Embodiments 1 through 45 wherein $R^4$ and $R^5$ are taken together with the carbon to which they are attached to form C(═O).

Embodiment 54

A compound of any one of Embodiments 1 through 53 wherein $R^6$ is H or $C_1$-$C_4$ alkyl.

Embodiment 55

A compound of Embodiment 54 wherein $R^6$ is $CH_3$.

Embodiment 56

A compound of Embodiment 54 wherein $R^6$ is H.

Embodiment 56A

A compound of any one of Embodiments 1 through 56 wherein $R^7$ is taken alone.

Embodiment 57

A compound of any one of Embodiments 1 through 56A wherein $R^7$ is halogen, $C_1$-$C_4$ alkyl, $C_1$-$C_4$ haloalkyl, $C_1$-$C_4$ alkoxy or $C_1$-$C_4$ haloalkoxy.

Embodiment 58

A compound of Embodiment 57 wherein $R^7$ is halogen, $C_1$-$C_4$ alkyl or $C_1$-$C_4$ haloalkyl.

Embodiment 59

A compound of Embodiment 58 wherein $R^7$ is F, $CH_3$ or $CF_3$.

Embodiment 60

A compound of Embodiment 59 wherein $R^7$ is F or $CF_3$.

Embodiment 61

A compound of Embodiment 60 wherein $R^7$ is F.

Embodiment 62

A compound of Embodiment 60 wherein $R^7$ is $CF_3$.

Embodiment 62A

A compound of any one of Embodiments 1 through 62 wherein each $R^8$ is taken alone.

Embodiment 63

A compound of any one of Embodiments 1 through 62A wherein each $R^8$ is independently halogen or $C_1$-$C_4$ haloalkyl.

Embodiment 64

A compound of Embodiment 63 wherein each $R^8$ is independently F, Cl or $CF_3$.

Embodiment 65

A compound of Embodiment 63 wherein each $R^8$ is F.

Embodiment 66

A compound of any one of Embodiments 1 through 56 wherein $R^7$ and $R^8$ are taken together with two adjacent carbon atoms to form a 5-membered ring containing ring members selected from carbon atoms and up to two O atoms, and optionally substituted on carbon atom ring members with up to five halogen atoms.

Embodiment 67

A compound of Embodiment 66 wherein $R^7$ and $R^8$ are taken together with two adjacent carbon atoms to form a 5-membered ring containing ring members selected from carbon atoms and up to two O atoms, and optionally substituted on carbon atom ring members with up to two halogen atoms.

Embodiment 68

A compound of Embodiment 67 wherein $R^7$ and $R^8$ are taken together with two adjacent carbon atoms to form a 5-membered ring containing ring members selected from carbon atoms and up to two O atoms, and substituted on carbon atom ring members with up to two F atoms.

Embodiment 69

A compound of Embodiment 68 wherein $R^7$ and $R^8$ are taken together with two adjacent carbon atoms to form a 2,2-difluorodioxolane ring (i.e. J is J-1B)

J-1B

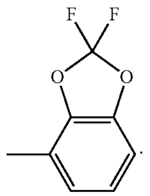

Embodiment 70

A compound of any one of Embodiments 1 through 69 wherein $R^9$ is halogen, $C_1$-$C_4$ alkyl, $C_1$-$C_4$ haloalkyl, $C_1$-$C_4$ alkoxy or $C_1$-$C_4$ haloalkoxy.

Embodiment 71

A compound of Embodiment 70 wherein $R^9$ is halogen, $C_1$-$C_4$ alkyl $C_1$-$C_4$ haloalkyl or $C_1$-$C_4$ alkoxy.

Embodiment 72

A compound of Embodiments 71 wherein $R^9$ is halogen, $C_1$-$C_4$ alkyl or $C_1$-$C_4$ haloalkyl.

Embodiment 73

A compound of Embodiment 72 wherein $R^9$ is F, $CH_3$ or $CF_3$.

Embodiment 74

A compound of Embodiment 73 wherein $R^9$ is F or $CF_3$.

Embodiment 75

A compound of Embodiment 74 wherein $R^9$ is F.

Embodiment 76

A compound of Embodiment 74 wherein $R^9$ is $CF_3$.

Embodiment 77

A compound of any one of Embodiments 1 through 76 wherein $R^{10}$ is halogen, $C_1$-$C_4$ alkyl, $C_1$-$C_4$ haloalkyl, $C_1$-$C_4$ alkoxy or $C_1$-$C_4$ haloalkoxy.

Embodiment 78

A compound of Embodiment 77 wherein $R^{10}$ is halogen, $C_1$-$C_4$ alkyl or $C_1$-$C_4$ haloalkyl.

Embodiment 79

A compound of Embodiment 78 wherein $R^{10}$ is F, $CH_3$ or $CF_3$.

Embodiment 80

A compound of Embodiment 79 wherein $R^{10}$ is F or $CF_3$.

Embodiment 81

A compound of Embodiment 80 wherein $R^{10}$ is F.

Embodiment 82

A compound of Embodiment 80 wherein $R^{10}$ is $CF_3$.

Embodiment 83

A compound of any one of Embodiments 1 through 82 wherein $R^{11}$ is $C_1$-$C_4$ alkyl or $C_1$-$C_4$ haloalkyl.

Embodiment 84

A compound of Embodiment 83 wherein $R^{11}$ is $C_1$-$C_4$ alkyl.

Embodiment 85

A compound of Embodiment 84 wherein $R^{11}$ is $CH_3$.

Embodiment 86

A compound of any one of Embodiments 1 through 85 wherein each $R^{12}$ is independently $C_1$-$C_4$ alkyl.

Embodiment 87

A compound of Embodiment 86 wherein each $R^{12}$ is $CH_3$.

Embodiment 88

A compound of any one of Embodiments 1 through 87 wherein each $R^{13}$ is independently $CH_3$ or $CH_2CH_3$.

Embodiment 89

A compound of Embodiment 88 wherein each $R^{13}$ is $CH_3$.

Embodiment 90

A compound of any one of Embodiments 1 through 89 wherein $R^{14}$ is $C_1$-$C_4$ alkyl.

Embodiment 91

A compound of Embodiment 90 wherein $R^{14}$ is $CH_3$.

Embodiment 92

A compound of any one of Embodiments 1 through 91 wherein $R^{15}$ is $C_1$-$C_4$ alkyl.

Embodiment 93

A compound of Embodiment 92 wherein $R^{15}$ is $CH_3$.

Embodiment 94

A compound of any one of Embodiments 1 through 93 wherein n is 0 or 2.

Embodiment 95

A compound of Embodiment 94 wherein n is 0.

Embodiment 96

A compound of Embodiment 94 wherein n is 2.

Embodiments of this invention, including Embodiments 1-96 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-96 above as well as any other embodiments described herein, and any combination thereof, pertain to the compositions and methods of the present invention.

Embodiment A

A compound of the Summary of the Invention wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_n(R^{12})$, $C_2$-$C_4$ alkylthioalkyl or $C_2$-$C_4$ alkylsulfonylalkyl;

A is a radical selected from the group consisting of A-1 and A-2;

each $Y^1$, $Y^3$, $Y^4$ and $Y^5$ is independently N or $CR^2$; and $Y^2$ is $CR^2$;

each $Y^6$ and $Y^7$ is independently N or $CR^3$; and $Y^8$ is $CR^3$;

Z is S;

Q is $C(R^4)(R^5)$, O or S;

J is selected from J-1 through J-33;

t is 0, 1 or 2;

u is 0;

each $R^2$ is independently H, halogen, $C_1$-$C_4$ alkoxy, $C_1$-$C_4$ alkyl or $C_1$-$C_4$ haloalkyl;

each $R^3$ is independently H, halogen or $C_1$-$C_4$ haloalkyl $R^4$ is H, F, Cl, Br or $C_1$-$C_4$ alkyl;

$R^5$ is H, F or OH; or $R^4$ and $R^5$ are taken together with the carbon to which they are attached to form C(=O);

$R^7$ is halogen, $C_1$-$C_4$ alkyl, $C_1$-$C_4$ haloalkyl, $C_1$-$C_4$ alkoxy or $C_1$-$C_4$ haloalkoxy;

$R^8$ is independently halogen or $C_1$-$C_4$ haloalkyl; or $R^7$ and $R^8$ are taken together with two adjacent carbon atoms to form a 2,2-difluorodioxolane ring;

$R^9$ is halogen, $C_1$-$C_4$ alkyl, $C_1$-$C_4$ haloalkyl, $C_1$-$C_4$ alkoxy or $C_1$-$C_4$ haloalkoxy;

$R^{10}$ is halogen, $C_1$-$C_4$ alkyl, $C_1$-$C_4$ haloalkyl, $C_1$-$C_4$ alkoxy or $C_1$-$C_4$ haloalkoxy;

$R^{11}$ is $C_1$-$C_4$ alkyl or $C_1$-$C_4$ haloalkyl each $R^{12}$ is independently $C_1$-$C_4$ alkyl;

each $R^{13}$ is independently $CH_3$ or $CH_2CH_3$;

$R^{14}$ is $C_1$-$C_4$ alkyl;

$R^{15}$ is $C_1$-$C_4$ alkyl; and n is O or 2.

Embodiment B

A compound of Embodiment A wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl or $C_2$-$C_4$ alkenyl;

each $Y^1$ and $Y^5$ is independently N or $CR^2$; and each $Y^2$, $Y^3$ and $Y^4$ is $CR^2$;

each $Y^6$ and $Y^7$ is N; and $Y^8$ is $CR^3$;

Q is $C(R^4)(R^5)$ or O;

J is selected from J-1, J-2, J-3, J-4, J-5, J-6, J-7, J-9, J-12, J-17, J-18, J-20, J-22, J-26, J-29 and J-30;

t is 0 or 1;

u is 0;

each $R^2$ is independently H, halogen, $C_1$-$C_4$ alkyl or $C_1$-$C_4$ haloalkyl;

each $R^3$ is independently H, F, Cl or $CF_3$;

$R^4$ is H, F or $CH_3$;

$R^5$ is H or F;

$R^7$ is F, $CH_3$ or $CF_3$;

$R^8$ is independently F, Cl or $CF_3$;

$R^9$ is halogen, $C_1$-$C_4$ alkyl or $C_1$-$C_4$ haloalkyl;

$R^{10}$ is halogen, $C_1$-$C_4$ alkyl or $C_1$-$C_4$ haloalkyl;

$R^{11}$ is $C_1$-$C_4$ alkyl;

each $R^{12}$ is $CH_3$; and each $R^{13}$ is $CH_3$.

Embodiment C

A compound of Embodiment A wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl or $C_1$-$C_4$ haloalkyl;

A is A-1;

$Y^1$ is N or $CR^2$; and each $Y^2$, $Y^3$, $Y^4$ and $Y^5$ is independently $CR^2$;

Q is $C(R^4)(R^5)$;

J is selected from J-1, J-2, J-10, J-17, J-18 and J-20;

t is 0;

each $R^2$ is independently H, F, Cl, $CH_3$ or $CF_3$;

$R^4$ is H;

$R^5$ is H; and $R^7$ is F or $CF_3$.

Embodiment D

A compound of Embodiment B wherein $R^1$ is $C_1$-$C_4$ alkoxy, $C_1$-$C_4$ haloalkoxy or $C_1$-$C_4$ alkyl;

A is A-1;

$Y^1$ is N or $CR^2$; and each $Y^2$, $Y^3$, $Y^4$ and $Y^5$ is independently $CR^2$;

Q is O;

J is selected from J-1, J-2, J-17 and J-18;

each $R^2$ is independently H, F, Cl or $CF_3$; and $R^7$ is $CF_3$.

Embodiment E

A compound of Embodiment D wherein $R^1$ is $CH_3$;

each $Y^1$, $Y^2$, $Y^3$, $Y^4$ and $Y^5$ is independently $CR^2$;

J is J-2;

t is 0; and each $R^2$ is independently H or F.

Specific embodiments include compounds of Formula 1 selected from the group consisting of:

4-[[2-(4-fluorophenyl)-5-methyl-2H-1,2,3-triazol-4-yl]oxy]-2-(trifluoromethyl)pyridine (Compound 129) and 4-[[5-Methoxy-2-[4-(trifluoromethyl)phenyl]-2H-1,2,3-triazol-4-yl]methyl]-2-(trifluoromethyl)pyridine (Compound 15).

Specific embodiments also include compounds of Formula 1 selected from the group consisting of:

4-[[2-(4-fluorophenyl)-5-methyl-2H-1,2,3-triazol-4-yl]methyl]-2-(trifluoromethyl)pyridine (Compound 16);

4-[[2-(4-fluorophenyl)-5-methyl-2H-1,2,3-triazol-4-yl]oxy]-2-(trifluoromethyl)pyridine (Compound 129);

4-[[5-ethoxy-2-(4-fluorophenyl)-2H-1,2,3-triazol-4-yl]methyl]-2-(trifluoromethyl)pyridine (Compound 196);

4-[[5-methoxy-2-[4-(trifluoromethyl)phenyl]-2H-1,2,3-triazol-4-yl]methyl]-2-(trifluoromethyl)pyridine (Compound 15);

4-[[5-methyl-2-[4-(trifluoromethyl)phenyl]-2H-1,2,3-triazol-4-yl]methyl]-2-(trifluoromethyl)pyridine (Compound 47);

4-[[5-ethoxy-2-[4-(trifluoromethyl)phenyl]-2H-1,2,3-triazol-4-yl]methyl]-2-(trifluoromethyl)pyridine (Compound 164); and 4-[[5-(2,2,2-trifluoroethoxy)-2-[4-(trifluoromethyl)phenyl]-2H-1,2,3-triazol-4-yl]methyl]-2-(trifluoromethyl)pyridine (Compound 14).

Specific embodiments also include compounds of Formula 1 selected from the group consisting of:

Compound 16, Compound 129, Compound 196, Compound 15 and Compound 47.

Specific embodiments also include compounds of Formula 1 selected from the group consisting of:

Compound 16, Compound 129 and Compound 196.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in cereal crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds as described in the embodiments above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, difenzoquat, bromobutide, flurenol, cinmethylin, cumyluron, dazomet, dymron, methyldymron, etobenzanid, fosamine, fosamine-ammonium, metam, oxaziclomefone, oleic acid, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, atrazine, cyanazine, desmetryne, dimethametryn, prometon, prometryne, propazine, simazine, simetryn, terbumeton, terbuthylazine, terbutryne, trietazine, hexazinone, metamitron, metribuzin, amicarbazone, bromacil, lenacil, terbacil, chloridazon, desmedipham, phenmedipham, chlorobromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, propanil, pentanochlor, bromofenoxim, bromoxynil, ioxynil, bentazon, pyridate and pyridafol.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for DNA synthesis and cell growth. Examples of AHAS inhibitors include amidosulfuron, azimsulfuron, bensulfuron-methyl (b2a), chlorimuron-ethyl, chlorsulfuron, cinosulfuron, cyclosulfamuron, ethametsulfuron-methyl, ethoxysulfuron, flazasulfuron, flupyrsulfuron-methyl (b2b), flupyrsulfuron-sodium, foramsulfuron, halosulfuron-methyl, imazosulfuron, iodosulfuron-methyl (including sodium salt), mesosulfuron-methyl, metazosulfuron, metsulfuron-methyl, nicosulfuron, oxasulfuron, primisulfuron-methyl, propyrisulfuron, prosulfuron, pyrazosulfuron-ethyl, rimsulfuron, sulfometuron-methyl, sulfosulfuron, thifensulfuron-methyl (b2c), triasulfuron, tribenuron-methyl, trifloxysulfuron (including sodium salt), triflusulfuron-methyl, tritosulfuron, imazapic, imazamethabenz-methyl, imazamox, imazapyr, imazaquin, imazethapyr, cloransulam-methyl, diclosulam, florasulam, flumetsulam, metosulam, penoxsulam, bispyribac-sodium, pyribenzoxim, pyriftalid, pyrithiobac-sodium, pyriminobac-methyl, thiencarbazone, flucarbazone-sodium and propoxycarbazone-sodium.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include cyclopyrimorate, clodinafop, cyhalofop, diclofop, fenoxaprop, fluazifop, haloxyfop, propaquizafop, quizalofop, alloxydim, butroxydim, clethodim, cycloxydim, pinoxaden, profoxydim, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor and its methyl and ethyl esters and its sodium and potassium salts, aminopyralid benazolin-ethyl, chloramben, clacyfos, clomeprop, clopyralid, dicamba, 2,4-D, 2,4-DB, dichlorprop, fluroxypyr, halauxifen, halauxifen-methyl, mecoprop, MCPA, MCPB, 2,3,6-TBA, picloram, triclopyr, quinclorac and quinmerac.

"EPSP (5-enol-pyruvylshikimate-3-phosphate) synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include paraquat and diquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, saflufencil, azafenidin, carfentrazone carfentrazone-ethyl, sulfentrazone, pentoxazone, benzfendizone, butafenacil, pyraclonil, profluazol, flufenpyr-ethyl and tiafenacil.

"GS (glutamine synthase) inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P and bilanaphos.

"VLCFA (very long chain fatty acid) elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, butachlor, dimethachlor, dimethanamid, metazachlor, metolachlor, pethoxamid, pretilachlor, propachlor, propisochlor, pyroxasulfone, thenylchlor, diphenamid, napropamide, naproanilide, fenoxasulfone, flufenacet, indanofan, mefenacet, fentrazamide, anilofos, cafenstrole, piperophos including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include naptalam (also known as N-(1-naphthyl)phthalamic acid and 2-[(1-naphthalenylamino)carbonyl]benzoic acid) and diflufenzopyr.

"PDS (phytoene desaturase inhibitors) (b11) are chemical compounds that inhibit carotenoid biosynthesis pathway at the phytoene desaturase step. Examples of PDS inhibitors include norflurzon, diflufenican, picolinafen, beflubutamide, fluridone, flurochloridone and flurtamone.

"HPPD (4-hydroxyphenyl-pyruvate dioxygenase) inhibitors" (b12) are chemical substances that inhibit the biosynthesis of synthesis of 4-hydroxyphenyl-pyruvate dioxygenase. Examples of HPPD inhibitors include mesotrione, sulcotrione, topramezone, tembotrione, tefuryltrione, isoxachlortole, isoxaflutole, benzofenap, pyrasulfatole, pyrazolynate, pyrazoxyfen, bicyclopyrone, benzobicyclon, fenquinotrione and 5-[(2-hydroxy-6-oxo-1-cyclohexen-1-yl)carbonyl]-2-(3-methoxyphenyl)-3-(3-methoxypropyl)-4(3H)-pyrimidinone (b12a).

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor and the compounds of Formulae A, B and C.

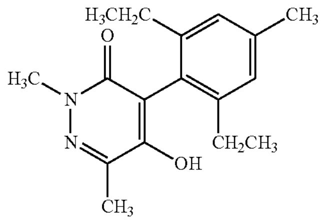

A

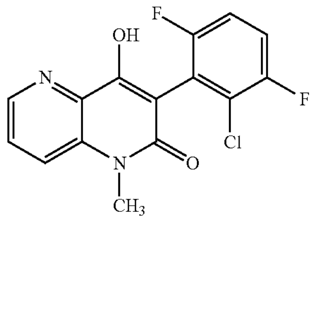

B

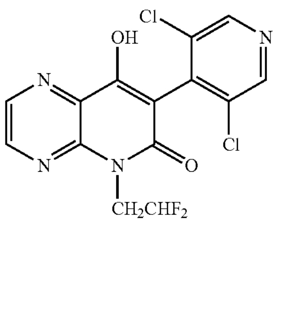

C

HST inhibitors also include compounds of Formulae D and E.

D

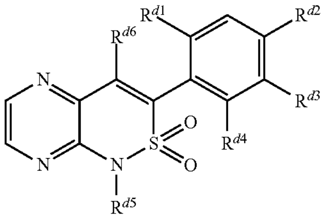

E

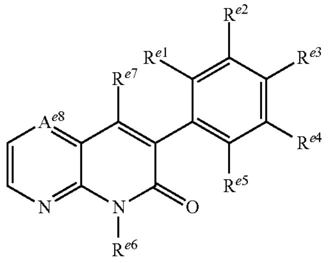

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

Cellulose biosynthesis inhibitors (b14) inhibit the biosynthesis of cellulose in certain plants. They are most effective when using a pre-application or early post-application on young or rapidly growing plants. Examples of cellulose biosynthesis inhibitors include chlorthiamid, diclobenil, flupoxam, indaziflam, isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, clomezone, fluometuron, difenzoquat, bromobutide, flurenol, cinmethylin, cumyluron, dazomet, dymron, methyldymron, methiozolon, ipfencarbazone, etobenzanid, fosamine, fosamine-ammonium, metam, oxaziclomefone, oleic acid, pelargonic acid and pyributicarb.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, 1-bromo-4-[(chloromethyl)sulfonyl]benzene, cloquintocet-mexyl, cumyluron, cyometrinil, cyprosulfamide, daimuron, dichlormid, dicyclonon, 4-(dichloroacetyl)-1-oxa-4-azospiro[4.5]decane (MON 4660), 2-(dichloromethyl)-2-methyl-1,3-dioxolane (MG 191), dimepiperate, fenchlorazole-ethyl, fenclorim, flurazole, fluxofenim, furilazole, isoxadifen-ethyl, mefenpyr-diethyl, mephenate, methoxyphenone, naphthalic anhydride and oxabetrinil.

One or more of the following methods and variations as described in Schemes 1-23 can be used to prepare the compounds of Formula 1. The definitions of A, Q, J, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the compounds of Formulae 1 through 32 below are as defined above in the Summary of the Invention unless otherwise noted. Formulae 1a-1f, 11a-b, 17a, 19a, 21a, 26a, and 27a and are various subsets of a compound of Formulae 1, 11, 17, 19, 21, 26 and 27, respectively. All substituents for Formulae 1a-1f are as defined above for Formula 1 unless otherwise noted.

Compounds of Formula 1a, 1b or 1c wherein Q is O, S or $NR^6$ respectively can be synthesized from compounds of Formula 2 by the reaction shown in Scheme 1 using an electron-deficient aromatic or heteroaromatic compound of Formula 3 wherein X (bound though carbon) is a suitable leaving group, for example, a halogen, sulfonate or alkoxide, in the presence of an appropriate base such as potassium carbonate, cesium carbonate or potassium hydroxide. Typically the reaction is conducted in a polar aprotic solvent such as dimethylsulfoxide, N,N-dimethylformamide, N,N-dimethylacetamide, N-methylpyrrolidinone or acetonitrile at temperatures ranging from ambient temperature to the reflux temperature of the solvent. Compounds of Formula 3 are commercially available or their preparation is known in the art. For reaction conditions for this general coupling methodology, see Carey, F. A., Sundberg, R. J., *Advanced Organic Chemistry Part B, 4th Edition;* Kluwer Academic/Plenum Publishers, New York, 2001; Chapter 11.2.2 and references cited therein.

Scheme 1

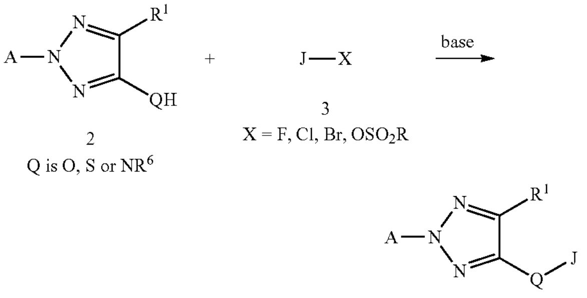

2

Q is O, S or $NR^6$

3

X = F, Cl, Br, $OSO_2R$

1a Q is O;

1b Q is S; or

1c Q is $NR^6$

Compounds of Formula 1d wherein Q is $CH_2$ can be synthesized from a compound of Formula 4 by the reaction shown in Scheme 2. Halomethyl compounds of Formula 4 are reacted with a suitable boronic acid or boronate ester in the presence of a palladium salt or complex such as palladium(II) acetate, tetrakis(triphenylphosphine)palladium(0) or bis(triphenylphosphine)palladium(II) chloride, an appropriate ligand and an inorganic base such as potassium phosphate, potassium carbonate or sodium carbonate. Typically the reaction is conducted in solvent such as 1,2-dimethoxyethane, 1,4-dioxane, toluene, tetrahydrofuran (or a mixture thereof) or t-butanol and water at temperatures ranging from ambient temperature to the reflux temperature of the solvent. Typical procedures using bromomethyl intermediates are disussed in *Eur. J. Chem.* 2011, 46(2), 488-496 and in PCT Patent Publication WO 2012/004714. A typical procedure using a chloromethyl intermediate is discussed in *Angew. Chem., Int. Ed.* 2011, 50(46), 10913-10916. Compounds of Formula 5 are commercially available or their preparation is known in the art.

Scheme 2

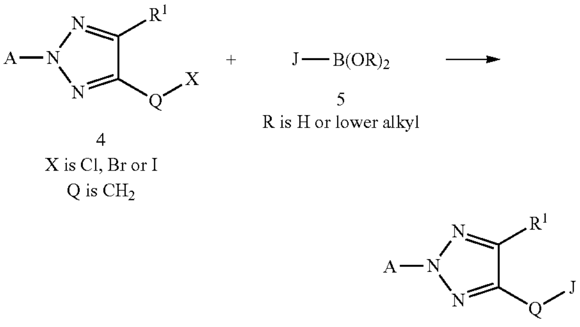

4
X is Cl, Br or I
Q is $CH_2$

5
R is H or lower alkyl

1d
Q is $CH_2$

Compounds of Formula 1d can also be synthesized from a compound of Formula 6 by the reaction shown in Scheme 3. Hydroxymethyl derivatives of Formula 6 are reacted with a suitable organomagnesium halide in the presence of a nickel salt or complex such as nickel(II) chloride, nickel(II) bromide, nickel(II) acetoacetate or bis(tricyclohexylphosphine) nickel(II) chloride and an appropriate ligand such as tricyclohexylphosphine, 1,2-bis(diphenylphosphino)ethane or 1,3-bis(2,6-diisopropylphenyl)-1,3-dihydro-2H-imidazol-2-ylidene. Typically the reaction is conducted in a mixture of solvents including but not limited to dibutyl ether, diisopropyl ether and toluene at temperatures ranging from ambient temperature to the reflux temperature of the solvent. For the discovery and optimization of these types of reactions, see D-G. Yu et al. in *J.A.C.S.* 2012, ASAP, available at http://pubs.acs.org/doi/pdf/10.1021/ja307045r. Compounds of Formula 7 are commercially available or their preparation is known in the art.

Scheme 3

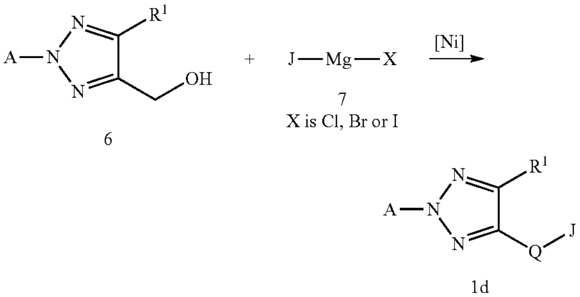

6

7
X is Cl, Br or I

1d
Q is $CH_2$

Compounds of Formula 1d (wherein Q is $CH_2$ and J is directly bound to Q through a nitrogen atom) can be synthesized from a compound of Formula 4 by the reaction shown in Scheme 4 wherein X is a suitable leaving group, for example, a halogen or sulfonate, and wherein J is a nitrogen-containing heterocycle. The reaction is typically conducted in the presence of an appropriate base such as potassium carbonate, cesium carbonate or potassium hydroxide. Typically the reaction is conducted in a solvent such as dimethylsulfoxide, N,N-dimethylformamide, N,N-dimethylacetamide, N-methylpyrrolidinone or acetonitrile at temperatures ranging from ambient temperature to the reflux temperature of the solvent. Compounds of Formula 8 are commercially available or their preparation is known in the art. A typical procedure is discussed in *Nature Chemical Biology* 2008, 4(11), 691-699.

Scheme 4

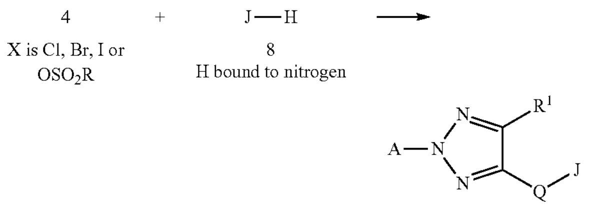

4
X is Cl, Br, I or $OSO_2R$

8
H bound to nitrogen

1d
Q is $CH_2$

As shown in Scheme 5, compounds of Formula 1e wherein Q is C(═O) can be synthesized from a compound of Formula 9 and an organolithium or organomagnesium compound of Formula 10. Typically, these reactions are conducted in a solvent mixture containing tetrahydrofuran, diethyl ether or toluene at a temperature ranging from −78° C. to ambient temperature. Compounds of Formula 10 are commercially available or their preparation is known in the art. A typical procedure is disclosed in PCT Patent publication WO 2009/121939.

Scheme 5

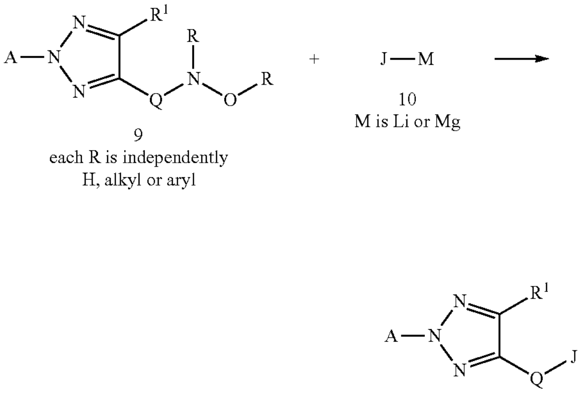

9
each R is independently H, alkyl or aryl

10
M is Li or Mg

1e
Q is C═O

As shown in Scheme 6, a compound of Formula 1f can be prepared from esters of Formula 11 by general methods well known to one skilled in the art. Esters of Formula 11 can be reduced to the corresponding alcohols using a wide variety of reagents, but metal hydride reagents such as lithium aluminum hydride, diisobuyl aluminum hydride or lithium borohydride are particularly general and effective. Typically, these reductions are performed in an ethereal solvent such as diethyl ether, tetrahydrofuran or 1,2-dimethoxyethane at temperatures ranging from −78° C. to the reflux temperature of the solvent. For a comprehensive overview of the methodologies available to reduce esters to alcohols, see Larock, R. C.,

*Comprehensive Organic Transformations: A Guide to Functional Group* Preparations, 2*nd Ed.*, Wiley-VCH, New York, 1999; and references cited therein.

Scheme 6

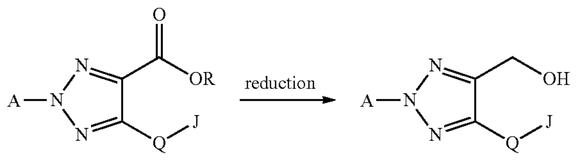

11
R is alkyl

1f

Compounds of Formula 1a, 1b or 1c can alternatively be synthesized by the reaction of N-alkoxy triazolium salts of Formula 12 with a compound of Formula 13 in the presence of a base as shown in Scheme 7. The counterion is typically a non-nucleophilic anion such as tetrafluoroborane or trifluoromethanesufonate. Appropriate solvents for these substitution reactions include acetonitrile, methanol and tetrahydrofuran either alone or mixtures thereof. These reactions are usually conducted at temperatures ranging from 0° C. to the reflux temperature of the solvent. Bases such as potassium carbonate, sodium hydride, sodium carbonate, potassium tert-butoxide, and many others can be employed. The use of an exogenous base is not necessary when anilines are used as the nucleophile. A typical procedure using a phenol is disclosed in UK Patent Application GB 2193493. A typical procedure using a thiophenol is disclosed in *Pest. Sci.* 1996, 48(2), 189-196. A typical procedure using an aniline is disclosed in *J. Chem. Soc., Perkin Transactions* 1 1981, 503-513. Compounds of Formula 13 are commercially available or their preparation is known in the art.

Scheme 7

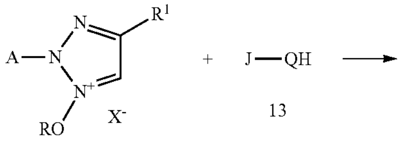

12
R = lower alkyl

13

-continued

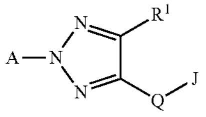

1a, 1b or 1c

Compounds of Formula 1a, 1b or 1c can also be synthesized from a compound of Formula 14 by the reaction shown in Scheme 8 of an electron-deficient aromatic or heteroaromatic compound of Formula 15 wherein X is a suitable leaving group, for example, a halogen, sulfonyl (such as alkylsulfonyl, trifluoromethanesulfonyl, phenylsulfonyl or p-toluenesulfonyl) or lower alkoxide, in the presence of an appropriate base such as potassium carbonate, cesium carbonate or potassium hydroxide. Typically the reaction is conducted in a solvent such as dimethylsulfoxide, N,N-dimethylformamide, N,N-dimethylacetamide, N-methylpyrrolidinone or acetonitrile at temperatures ranging from ambient temperature to the reflux temperature of the solvent. Compounds of Formula 15 are commercially available or their preparation is known in the art. For reaction conditions for this general coupling methodology, see Carey, F. A.; Sundberg, R. J., *Advanced Organic Chemistry Part B, 4th Edition*; Kluwer Academic/Plenum Publishers, New York, 2001; Chapter 11.2.2 and references cited therein. In cases where a compound of Formula 15 lacks sufficiently electron-withdrawing substituents to enable the aromatic substitution in a practical time frame, a suitable nitro-containing aromatic or heteroaromatic compound of Formula 16 can be used to enhance the reaction rate. It is obvious to one skilled in the art that reduction of the nitro group followed by diazotization/reduction of the resulting aniline will satisfactorily remove the activating nitro group. A typical procedure for this series of steps is disclosed in *Angew. Chem., Int. Ed.* 2010, 49(11), 2018-2022. Compounds of Formulae 15 and 16 are commercially available or their preparation is known in the art.

Scheme 8

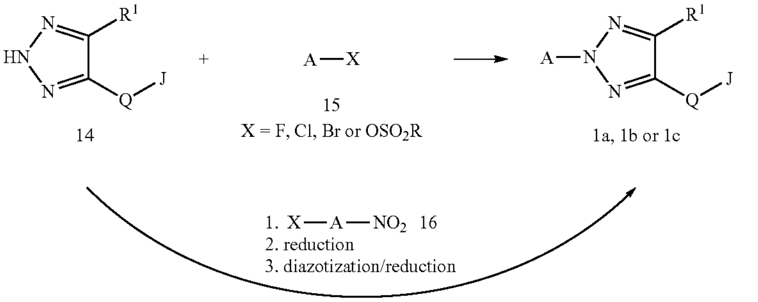

14

15
X = F, Cl, Br or $OSO_2R$ 1a, 1b or 1c

As shown in Scheme 9, a compound of Formula 2a can be synthesized by the reaction of triazole N-oxides of Formula 17 with a suitable activator such as an acid halide, acid anhydride or silyl halide followed by acidic or basic hydrolysis. The activator is selected from acetyl chloride, acetic anhydride (which can also act as the solvent) or trimethylsilyl iodide. Other solvents appropriate for this reaction include chloroform and dichloromethane. These reactions are usually conducted at temperatures ranging from 0° C. to the reflux temperature of the solvent. Basic hydrolysis is typically conducted with a base such as sodium hydroxide, potassium hydroxide or potassium carbonate in a solvent such as water, methanol, ethanol or a mixture tetrahydrofuran and water at temperatures ranging from 0° C. to the reflux temperature of the solvent. Acidic hydrolysis is typically conducted with, but not limited to, an acid such as hydrochloric acid, hydrobromic acid, sulfuric acid, phosphoric acid or acetic acid in a solvent such as chloroform, toluene, methanol, ethanol or water (or a mixture of said solvents) at temperatures ranging from 0° C. to the reflux temperature of the solvent. A typical procedure using acetyl chloride as the activator followed by basic hydrolysis is disclosed in *Bull. Chim. Belg.* 1997, 106(11), 717-728. A typical procedure using trimethylsilyl iodide as the activator followed by acidic hydrolysis is discussed in *Acta Chem. Scan.* 1996, 50(6), 549-555.

Scheme 9

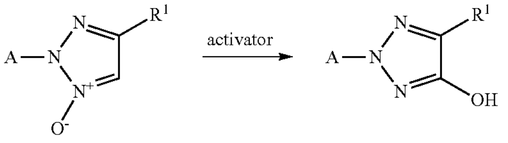

17 2a

As shown in Scheme 10, a compound of Formula 4 is a particularly useful intermediate for use in the preparation of a compound of Formula 1 and can be prepared from several different precursors. Using reaction conditions similar to those discussed in the method of Scheme 6, esters of Formula 18 can be converted to alcohols of Formula 6. Alcohols of Formula 6 can then be converted to the compounds of Formula 4 using a wide range of reagents such as thionyl chloride, phosphorus trichloride, phosphorus tribromide, triphenylphosphine/bromine, triphenylphosphine/iodine. Alternatively, halogenation methods using hydrohalides in solvents such as acetic acid, acetonitrile, diethyl ether, tetrahydrofuran, dichloromethane, water or a mixture of water with the aforementioned solvents, at temperatures ranging from 0° C. to the reflux temperature of the solvent can be used. Typical procedures for the production of a bromomethyl compound are disclosed in PCT Patent Publication WO 2005/115383. Alternatively, a compound of Formula 6 can be prepared by the reaction of a compound of Formula 19 using trifluoroacetic anhydride as described in *Bull. Soc. Chim. Belg.* 1997, 106(11), 717-727. Alcohols of Formula 6 can subsequently be converted to a compound of Formula 4 by the methods described above for Scheme 10.

Scheme 10

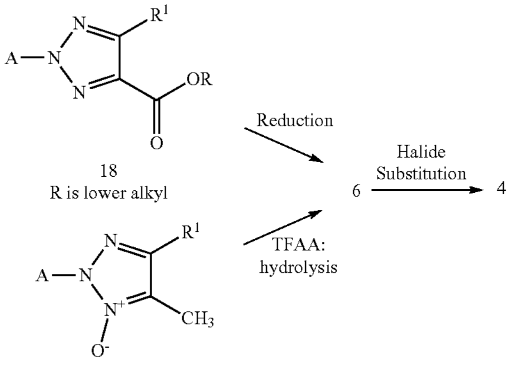

18
R is lower alkyl
19
6
4

Alternatively, a compound of Formula 4 can be prepared from triazole N-oxides of Formula 19 by the one-step procedure shown in Scheme 11. Reaction of a compound of Formula 19 with halogenating agent such as phosphorus oxybromide or phosphorus oxychloride, in solvents such as 1,4-dioxane, 1,2-dichloroethane, chloroform or toluene, at temperatures ranging from ambient to the reflux temperature of the solvent affords compounds of Formula 4 directly.

Scheme 11

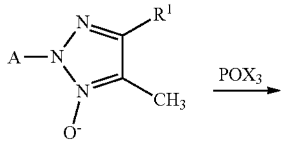

19
4
X = Cl or Br

As shown in Scheme 12, bromides of Formula 4 can also be prepared by radical bromination of a compound of Formula 20 using a brominating agent such as N-bromosuccinimide or bromine, a radical initiator such as azobisisobutyronitrile, benzoyl peroxide or a UV light source, in solvents such as carbon tetrachloride or trifluoromethylcyclohexane at temperatures ranging from ambient to the reflux temperature of the solvent. A typical procedure for the synthesis of a bromomethyl compound is disclosed in PCT Patent publication WO 2007/071900.

Scheme 12

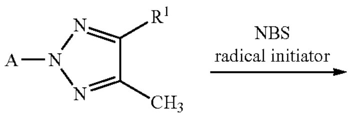

20
4
X = Br

As illustrated in Scheme 13, using reaction conditions similar to those discussed in the method of Scheme 8, triazoles of Formula 21 can be converted into N-aryl triazoles of Formula 11a which are useful for preparing alcohols of Formula 1f as depicted in Scheme 6. Compounds of Formulae 15 (where R is lower alkyl) and 16 are commercially available or their preparation is known in the art.

Scheme 13

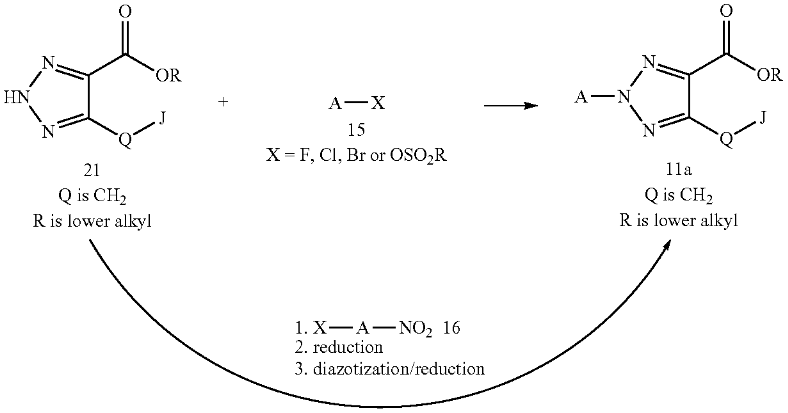

21
Q is $CH_2$
R is lower alkyl

15

11a
Q is $CH_2$
R is lower alkyl

Compounds of Formula 18 can be prepared as shown in Scheme 14. Reaction of a dicarbonyl compound of Formula 22 with a diazonium salt in the presence of an acid acceptor results in a coupling reaction to form a compound of Formula 23. Suitable solvents include lower carboxylic acids such as acetic acid, lower alcohols such as methanol or ethanol, water, and mixtures thereof. Acid acceptors such as, but not limited to, alkali carbonates, bicarbonates, phosphates and acetates can be employed in this reaction. Compounds of Formula 23 can be cyclized to compounds of Formula 18 by reaction with an ammonium salt in the presence of an oxidizing agent. Suitable ammonium salts include halides, acetate, and sulfate among others. The oxidizing agent is preferably, but not limited to, a Cu(II) salt such as copper(II) sulfate, copper(II) chloride or copper(II) bromide or N-iodosuccinimide. Typical conditions for this procedure are described in U.S. Patent Application 20060014785.

Scheme 14

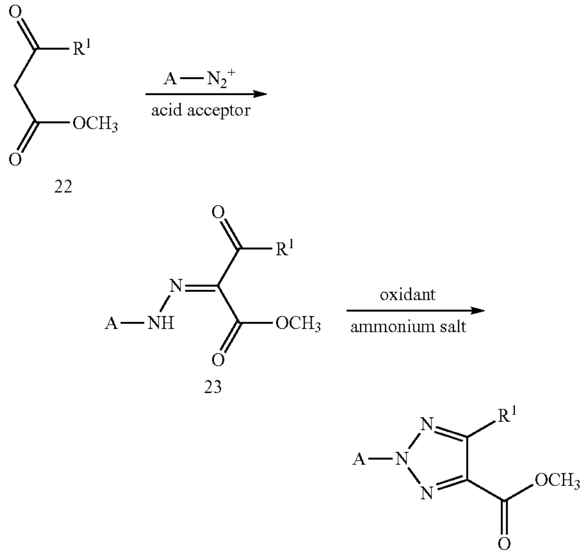

22

23

18

Similarly, Compounds of Formula 11b can be prepared as shown in Scheme 15. The coupling reaction of a dicarbonyl compound of Formula 24 with a diazonium salt in the presence of an acid acceptor can form a compound of Formula 25. Suitable solvents include lower carboxylic acids such as acetic acid, lower alcohols such as methanol or ethanol, water, and mixtures thereof. Acid acceptors such as, but not limited to, alkali carbonates, bicarbonates, phosphates and acetates can be employed in this reaction. Compounds of Formula 25 can be cyclized to compounds of Formula 11b by reaction with an ammonium salt in the presence of an oxidizing agent. Suitable ammonium salts include halides, acetate, and sulfate among others. The oxidizing agent is preferably, but not limited to, a Cu(II) salt such as copper(II) sulfate, copper(II) chloride or copper(II) bromide or N-iodosuccinimide. Typical conditions for this procedure are described in U.S. Patent Application 20060014785.

Scheme 15

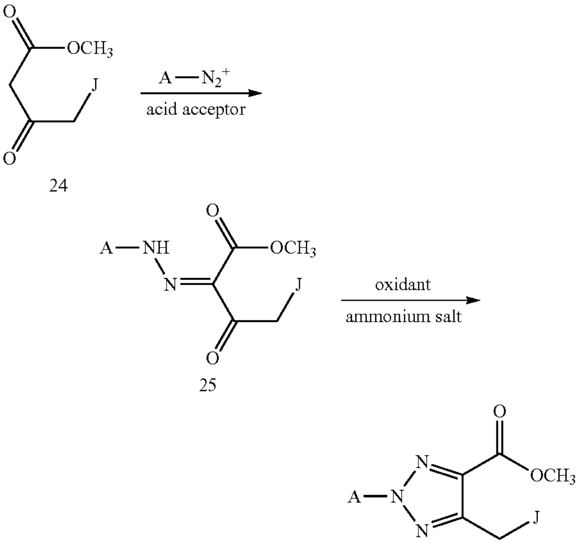

24

25

11b

As shown in Scheme 16, compounds of Formula 12 can be synthesized by the reaction of triazole N-oxides of Formula 17 with strong alkylating reagents such as trimethyloxonium tetrafluoroborate or methyl trifluoromethanesulfonate. Preferred solvents for this substitution reaction include dichloromethane, chloroform and 1,2-dichloroethane. The reactions are usually conducted at temperatures ranging from 0° C. to the reflux temperature of the solvent. Typical procedures are disclosed in *J. Chem. Soc., Perkin Transactions* 1 1982, 2749-2756 and references cited therein.

Scheme 16

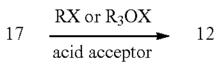

R = lower alkyl or benzyl

As shown in Scheme 17, a compound of Formula 21 can be obtained by removal of an appropriate protecting group such as a trialkylsilyl group, (i.e. trimethylsilyl), or an optionally substituted benzyl group (i.e. benzyl or p-methoxybenzyl) from compounds of Formula 26. The p-methoxybenzyl group is of particular value as an intermediate to prepare a compound of Formula 1 via a compound of Formula 4 as shown in Scheme 2. Deprotection of a compound of Formula 26 wherein PG is p-methoxybenzyl is typically performed via one of the following two methods. First, acid-catalyzed deprotection is usually conducted in neat trifluoroacetic acid or as a mixture with a solvent such as dichloromethane or 1,2-dichloroethane at temperatures ranging from 0° C. to the reflux temperature of the solvent. A typical procedure is disclosed in PCT Patent publication WO 2005/073192. Second, the p-methoxybenzyl group can be removed using an oxidant such as ceric ammonium nitrate or 2,3-dichloro-5,6-dicyano-1,4-benzoquinone in a mixture of acetonitrile and water or a mixture of dichloromethane and water, respectively. The useful temperature range for these reactions is from ambient to the reflux temperature of the solvent. A typical procedure is disclosed in PCT Patent Publication WO 2007/071900.

Scheme 17

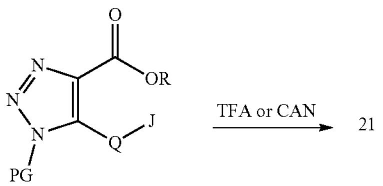

26
R is lower alkyl
PG is a protection group

As illustrated in Scheme 18, a compound of Formula 23 can be prepared from a compound of Formula 27 using reaction conditions similar to those discussed in the method of Scheme 17. For an exemplary preparation of a compound of Formula 27 wherein $R^1$ is either a lower alkoxy group or a haloalkoxy group, see PCT Patent Publication WO 2007/096576.

Scheme 18

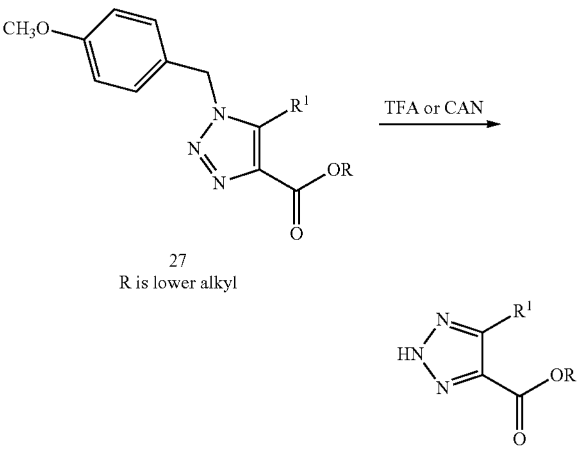

27
R is lower alkyl

23
R is lower alkyl

A compound of Formula 19a wherein $R^1$ can independently be H or $C_1$-$C_4$ alkyl can be synthesized by the reaction of a compound of Formula 28 with a suitable oxidant as shown in Scheme 19. Suitable oxidants include a Cu(II) salt, such as copper(II) sulfate, copper(II) chloride or copper(II) bromide, or N-iodosuccinimide. The preferred solvents for the reaction are pyridine, carbon tetrachloride, methanol, ethanol, water and aqueous mixtures of the aforementioned solvents. The reactions are usually conducted at temperatures ranging from 0° C. to the reflux temperature of the solvent. A typical procedure is disclosed in *J. Chem. Soc., Perkin Transactions* 1 1981, 503-513. Compounds of Formula 28 are commercially available or their preparation is known in the art.

Scheme 19

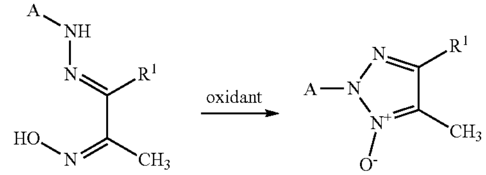

28
$R^1$ is H or $C_1$-$C_4$ alkyl

19a
$R^1$ is H or $C_1$-$C_4$ alkyl

In a similar fashion, a compound of Formula 17a wherein $R^1$ is H or $C_1$-$C_4$ alkyl can be synthesized by the reaction of a compound of Formula 29 with a suitable oxidant as shown in Scheme 20. Suitable oxidants and solvents include those discussed for Scheme 19. The reactions are usually conducted at temperatures ranging from 0° C. to the reflux temperature of the solvent. A typical procedure is disclosed in *J. Chem. Soc., Perkin Transactions* 1 1981, 503-513. Compounds of Formula 29 are commercially available or their preparation is known in the art. A typical procedure is disclosed in *J. Chem. Soc., Perkin Transactions* 1 1981, 503-513.

Scheme 20

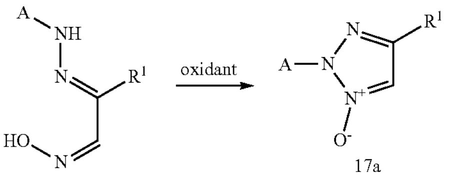

29

17a $R^1$ is H or $C_1$-$C_4$ alkyl

A compound of Formula 26a can be synthesized by the reaction of triazoles of Formula 30 with a wide range of carbon, oxygen, sulfur and nitrogen nucleophiles including cyanide, dialkyl malonates, aryl acetonitriles, aryl acetic acids, aryl acetic esters, amines, phenols, alcohols, thiophenols, alkyl thiols and anilines, optionally in the presence of a base, as shown in Scheme 21. Typical bases including sodium hydride, sodium methoxide, sodium ethoxide, cesium carbonate, potassium carbonate or potassium tert-butoxide can be employed. Solvents suitable for this substitution reaction are dimethylsulfoxide, N,N-dimethylformamide, tetrahydrofuran, lower alkyl alcohols and acetonitrile at temperatures ranging from ambient temperature to the reflux temperature of the solvent. For the preparation of compounds of Formula 30, see *J. Het. Chem.* 1981, 18(6), 1117-1122.

Scheme 21

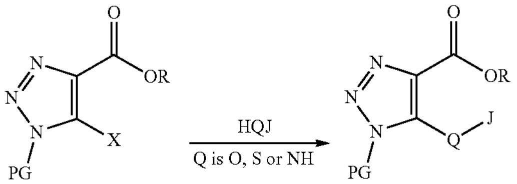

30

R = lower alkyl

PG is a protection group

26a

R = lower alkyl

Q is O or S

Similarly, a compound of Formula 27a can be synthesized by the reaction of triazoles of Formula 31 with a wide range of carbon, nitrogen, oxygen and sulfur nucleophiles including cyanide, dialkyl malonates, aryl acetonitriles, aryl acetic acids, aryl acetic esters, amines, phenols, alcohols, thiophenols, alkyl thiols and anilines, optionally in the presence of a base, as shown in Scheme 22. Typical bases including sodium hydride, sodium methoxide, sodium ethoxide, cesium carbonate, potassium carbonate or potassium tert-butoxide can be employed. Solvents suitable for this substitution reaction are dimethylsulfoxide, N,N-dimethylformamide, tetrahydrofuran, lower alkyl alcohols and acetonitrile at temperatures ranging from ambient temperature to the reflux temperature of the solvent. For the preparation of compounds of Formula 31, see *J. Het. Chem.* 1981, 18(6), 1117-1122.

Scheme 22

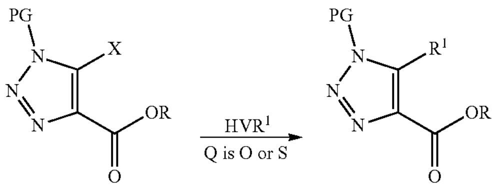

31

R = lower alkyl

PG is p-methoxybenzyl

27a

R = lower alkyl

Q is O or S

As shown in Scheme 23, a compound of Formulae 21a or 14a wherein Q is C═O or $CH_2$ respectively can be synthesized by the reaction of compounds of Formula 32 with an inorganic azide salt, typically sodium azide. The preferred solvents for the substitution reaction are dimethylsulfoxide, N,N-dimethylformamide, tetrahydrofuran, lower alkyl alcohols, acetonitrile and water or a mixture thereof at temperatures ranging from 0° C. to the reflux temperature of the solvent. A typical procedure is disclosed in *J. Org. Chem.* 2008, 73(11), 4317-4319. A compound of Formula 32 is commercially available or its preparation is known in the art.

Scheme 23

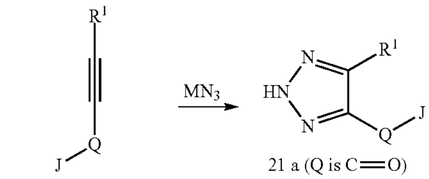

32

Q is C═O or $CH_2$ 21 a (Q is C═O)

or 14a (Q is $CH_2$)

The synthesis of 1,2,3-triazoles and derivatives thereof are well known in the literature. For a general discussion of their synthesis, see Rachwal, A. R, Katritzky, A. R., 1,2,3-Triazoles, *Comprehensive Heterocyclic Chemistry III* 2008, 5, 1-158 and Tome, A. C., Product class 13: 1,2,3-Triazoles, *Science of Synthesis* 2004, 13, 415-601.

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations, 2nd Ed.*, Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular order presented to prepare the compounds of Formula 1.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ unless otherwise noted; "s" means singlet, "m" means multiplet, "br s" means broad singlet. Mass spectra (MS) are reported as the molecular weight of the highest isotopic abundance parent ion (M+1) formed by addition of H+(molecular weight of 1) to the molecule, observed by mass spectrometry using atmospheric pressure chemical ionization ($AP^+$) where "amu" stands for atomic mass units. The presence of molecular ions containing one or more higher atomic weight isotopes of lower abundance (e.g., $^{37}$Cl, $^{81}$Br) is not reported.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet and "br s" means broad singlet.

Synthesis Example 1

Preparation of 4-[[5-methoxy-2-[4-(trifluoromethyl)phenyl]-2H-1,2,3-triazol-4-yl]methyl]-2-(trifluoromethyl)pyridine (Compound 15)

Step A: Preparation of 4-Methyl-2-[4-(trifluoromethyl)phenyl]-2H-1,2,3-triazole 1-oxide To a stirred solution of anti-pyruvic aldehyde 1-oxime (2.67 g, 30.7 mmol) in diethyl ether (50 mL) was added 4-(trifluoromethyl)phenylhydrazine (5.40 g, 30.7 mmol). The reaction mixture was stirred at 23° C. for 2 h, then concentrated under reduced pressure. The crude residue was dissolved in 15% aqueous pyridine (150 mL). A solution of copper(II) sulfate pentahydrate (15.31 g, 61.3 mmol) in water (75 mL) was added at once. The resulting mixture was stirred at reflux for 17 h, then cooled to 0° C. Ethyl acetate (100 mL) was added and the mixture was filtered through Celite® diatomaceaous filter aid. The layers were separated, and the aqueous layer was extracted with ethyl acetate (2×100 mL). The combined organic layers were washed with 1.0 M aqueous hydrochloric acid (3×50 mL). The organic layer was dried ($MgSO_4$), filtered, and evaporated under reduced pressure. The residue was purified by chromatography on silica gel, eluting with 0 to 50% ethyl acetate in hexanes, to afford the title compound (5.84 g) as a colorless solid.

$^1$H NMR δ 2.37 (s, 3H), 7.32 (s, 1H), 7.75-7.79 (m, 2H), 8.15-8.20 (m, 2H).

Step B: Preparation of 1-Methoxy-4-methyl-2-[4-(trifluoromethyl)phenyl]-2H-1,2,3-triazolium tetrafluoroborate (1:1)

To a stirred solution of 4-methyl-2-[4-(trifluoromethyl)phenyl]-2H-1,2,3-triazole 1-oxide (i.e. the product of Step A, 5.22 g, 21.5 mmol) in dichloromethane (100 mL) was added trimethyloxonium tetrafluoroborate (4.13 g, 27.9 mmol). The reaction mixture was stirred at 23° C. for 65 h, then concentrated under reduced pressure to afford a crude mixture of the title compound as a brown oil which was used directly in the next step without further purification.

$^1$H NMR δ 2.60 (s, 3H), 4.47 (s, 3H), 7.90-7.98 (m, 4H), 9.01 (s, 1H).

Step C: Preparation of 4-methoxy-5-methyl-2-[4-(trifluoromethyl)phenyl]-2H-1,2,3-triazole Sodium metal (0.25 g, 11.0 mmol) was stirred at 23° C. in methanol (10 mL) until a clear solution was obtained. This sodium methoxide solution was added to crude 1-methoxy-4-methyl-2-[4-(trifluoromethyl)phenyl]-2H-1,2,3-triazolium tetrafluoroborate (1:1) (i.e. the product of Step B, 1.1 g, 3.2 mmol). The reaction mixture was stirred at 23° C. for 6 h, during which time a white precipitate formed. The reaction mixture was diluted with water (20 mL) and extracted with ethyl acetate (40 mL, 10 mL). The organic layer was dried ($MgSO_4$) and concentrated under reduced pressure. The crude residue was purified by chromatography on silica gel eluting with 0 to 10% ethyl acetate in hexanes to afford the title compound (0.82 g) as a colorless solid.

$^1$H NMR δ 2.28 (s, 3H), 4.05 (s, 3H), 7.64-7.68 (m, 2H), 7.96-8.00 (m, 2H).

Step D: Preparation of 4-(bromomethyl)-5-methoxy-2-[4-(trifluoromethyl)phenyl]-2H-1,2,3-triazole To a solution of 4-methoxy-5-methyl-2-[4-(trifluoromethyl)phenyl]-2H-1,2,3-triazole (i.e. the product of Step C, 0.82 g, 3.2 mmol) in carbon tetrachloride (10 mL) was added N-bromosuccinimide (0.62 g, 3.5 mmol) and 2,2'-azobis(2-methylpropionitrile) (0.026 g, 0.2 mmol). The reaction mixture was heated at reflux for 2 h, then an additional portion of 2,2'-azobis(2-methylpropionitrile) (0.026 g, 0.2 mmol) was added. The reaction mixture was heated at reflux for 2.5 h, cooled to room temperature, diluted with water (10 mL) and extracted with dichloromethane (2×10 mL). The organic layers were dried ($Na_2SO_4$) and concentrated under reduced pressure to afford a crude material containing approximately 66% (by weight) of the title compound as determined by $^1$H NMR. The crude material was used directly in the next step without further purification.

$^1$H NMR δ 4.11 (s, 3H), 4.53 (s, 2H), 7.67-7.72 (m, 2H), 8.02-8.07 (m, 2H).

Step E: Preparation of 4-[[5-methoxy-2-[4-(trifluoromethyl)phenyl]-2H-1,2,3-triazol-4-yl]methyl]-2-(trifluoromethyl)pyridine To a solution of 4-(bromomethyl)-5-methoxy-2-[4-(trifluoromethyl)phenyl]-2H-1,2,3-triazole (i.e. the product of Step D, 0.525 g, 66 weight %, 1.0 mmol) in tetrahydrofuran/water (3:1, 4 mL total), was added tetrakis(triphenylphosphine)palladium(0) (0.059 g, 0.05 mmol), potassium phosphate tribasic (0.43 g, 2.0 mmol) and 2-(trifluoromethyl)pyridine-4-boronic acid pinacol ester (0.42 g, 1.5 mmol). The mixture was heated to reflux and stirred for 17 h. The reaction mixture was diluted with water (20 mL) and extracted twice with ethyl acetate (25 mL, 15 mL). The organic layer was dried ($MgSO_4$) and concentrated under reduced pressure. The crude residue was purified by chromatography on silica gel eluting with 10% ethyl acetate in hexanes to afford the title compound (0.12 g) as a pale yellow solid.

$^1$H NMR δ 4.06 (s, 3H), 4.09 (s, 2H), 7.42-7.45 (m, 1H), 7.63-7.72 (m, 3H), 8.00-8.04 (m, 2H), 8.64-8.67 (m, 1H).

Synthesis Example 2

Preparation of 4-methoxy-2-[4-(trifluoromethyl)phenyl]-5-[[3-(trifluoromethyl)-1H-pyrazol-1-yl]methyl]-2H-1,2,3-triazole (Compound 17)

Step A: Preparation of 4-methoxy-2-[4-(trifluoromethyl)phenyl]-5-[[3-(trifluoromethyl)-1H-pyrazol-1-yl]methyl]-2H-1,2,3-triazole To a solution of 4-(bromomethyl)-5-methoxy-2-[4-(trifluoromethyl)phenyl]-2H-1,2,3-triazole (i.e. the product of Example 1, Step D) (0.25 g, 66 weight %, 0.5 mmol) in N,N-dimethylformamide (2 mL total), was added 3-(trifluoromethyl)pyrazole (0.082 g, 0.6 mmol) and anhydrous potassium carbonate (0.21 g, 1.5 mmol). The mixture was heated to 55° C. and stirred for 75 min. The reaction mixture was cooled to 23° C., diluted with water (20 mL) and extracted with ethyl acetate (15 mL). The organic layer was washed with water (10 mL) and saturated aqueous sodium chloride solution (10 mL), dried ($MgSO_4$) and concentrated under reduced pressure. The crude residue was purified by chromatography on silica gel eluting with 0 to 40% ethyl acetate in hexanes to afford the title compound (0.098 g) as a colorless oil.

$^1$H NMR δ 4.07 (s, 3H), 5.44 (s, 2H), 6.53-6.55 (m, 1H), 7.55-7.59 (m, 1H), 7.67-7.72 (m, 2H), 8.02-8.07 (m, 2H).

Synthesis Example 3

Preparation of 4-methyl-2-[4-(trifluoromethyl)phenyl]-5-[[5-(trifluoromethyl)-3-thienyl]oxy]-2H-1,2,3-triazole (Compound 1)

Step A: Preparation of 4-methyl-2-[4-(trifluoromethyl)phenyl]-5-[[5-(trifluoromethyl)-3-thienyl]oxy]-2H-1,2,3-triazole Potassium tert-butoxide (0.30 g, 2.6 mmol) and 5-trifluoromethylthiophene-3-one (0.44 g, 2.6 mmol) were dissolved in acetonitrile (4 mL). A solution of crude 1-methoxy-4-methyl-2-[4-(trifluoromethyl)phenyl]-2H-1,2,3-triazolium tetrafluoroborate (1:1) (i.e., the product of Example 1, Step B, 0.70 g, 2.0 mmol) in acetonitrile (4 mL) was added at once. The reaction mixture was stirred at 23° C. for 27 h. The reaction mixture was diluted with water (20 mL) and extracted with diethyl ether (2×25 mL). The organic layer was dried ($MgSO_4$) and concentrated under reduced pressure. The crude residue was purified by chromatography on silica gel eluting with 0 to 5% ethyl acetate in hexanes to afford the title compound (0.105 g) as a colorless solid.

$^1$H NMR δ 2.37 (s, 3H), 7.35-7.37 (m, 1H), 7.41-7.43 (m, 1H), 7.67-7.73 (m, 2H), 8.02-8.06 (m, 2H).

Synthesis Example 4

Preparation of 4-[[2-(4-fluorophenyl)-5-methyl-2H-1,2,3-triazol-4-yl]oxy]-2-(trifluoromethyl)pyridine (Compound 129)

Step A: Preparation of 2-(4-fluorophenyl)-4-methyl-2H-1,2,3-triazole 1-oxide

To a stirred solution of anti-pyruvic aldehyde 1-oxime (3.4 g, 39 mmol) in diethyl ether (75 mL) was added 4-fluorophenylhydrazine hydrochloride (5.85 g, 36 mmol). The reaction mixture was stirred at 23° C. for 16 h, and then concentrated under reduced pressure. The crude residue was dissolved in pyridine (120 mL). A solution of copper(II) sulfate pentahydrate (18 g, 72 mmol) in water (55 mL) was added dropwise over 4 min. The resulting mixture was stirred at reflux for 2 h. The mixture was concentrated under reduced pressure to remove excess pyridine. To the mixture was added 1.0 M aqueous hydrochloric acid. The mixture was extracted with ethyl acetate and the organic layer was separated and washed with 1.0 M aqueous hydrochloric acid until a clear amber organic layer was obtained. The organic layer was dried ($MgSO_4$), filtered, and evaporated under reduced pressure to afford the title compound (6.6 g) as a colorless solid. The title compound was used directly in the next step without further purification.

$^1$H NMR δ 2.35 (s, 3H), 7.17-7.22 (m, 2H), 7.29 (s, 1H), 7.86-7.91 (m, 2H).

Step B: Preparation of 2-(4-fluorophenyl)-5-methyl-2H-1,2,3-triazol-4-yl acetate 2-(4-Fluorophenyl)-4-methyl-2H-1,2,3-triazole 1-oxide (i.e. the product of Step A, 6.6 g, 34 mmol) was added to acetic anhydride (47 mL, 500 mmol), and the reaction mixture was stirred at reflux for 28 h. The reaction was concentrated under reduced pressure. The residue was taken up in ethyl acetate, washed successively with water and saturated aqueous sodium chloride solution, dried with magnesium sulfate and concentrated under reduced pressure to afford the title compound (7.8 g) as a beige solid. The title compound was used directly in the next step without further purification.

$^1$H NMR δ 2.26 (s, 3H), 2.38 (s, 3H), 7.10-7.16 (m, 2H), 7.88-7.94 (m, 2H).

Step C: Preparation of 2-(4-fluorophenyl)-2,3-dihydro-5-methyl-4H-1,2,3-triazol-4-one 2-(4-Fluorophenyl)-5-methyl-2H-1,2,3-triazol-4-yl acetate (i.e. the product of Step B, 7.8 g, 33 mmol) was suspended in methanol (150 mL). A solution of sodium hydroxide (7 M, 22 mL, 140 mmol) was added over several minutes with stirring during which time the mixture became homogeneous and then stirred at 23° C. for 18 h. The reaction was concentrated under reduced pressure to remove excess methanol. The remaining residue was diluted with water (200 mL) and washed with hexanes. The aqueous layer was acidified with concentrated hydrochloric acid during which time a thick creamy precipitate formed. The mixture was diluted with water and stirred for 30 min. The precipitate was filtered and washed well with water. The moist solid was dissolved in ethyl acetate, dried ($MgSO_4$) and concentrated under reduced pressure to afford the title compound (6.1 g) as a beige solid. The title compound was used directly in the next step without further purification.

$^1$H NMR δ 2.33 (s, 3H), 7.12-7.19 (m, 2H), 7.73-7.80 (m, 2H), 9.73 (s, 1H).

Step D: Preparation of 4-[[2-(4-fluorophenyl)-5-methyl-2H-1,2,3-triazol-4-yl]oxy]-2-(trifluoromethyl)pyridine To a solution of 2-(4-fluorophenyl)-2,3-dihydro-5-methyl-4H-1,2,3-triazol-4-one (i.e. the product of Step C, 3.1 g, 16 mmol) in N,N-dimethylformamide (70 mL) was added anhydrous potassium carbonate (6.2 g, 45 mmol) under an atmosphere of nitrogen. 4-Chloro-2-trifluoromethyl-pyridine (2.9 g, 16 mmol) was added and the mixture was heated to 100° C. for 20 h. The reaction mixture was diluted with water, then extracted with diethyl ether. The organic layer was washed successively with water and saturated aqueous sodium chloride solution, dried ($MgSO_4$), filtered, and concentrated under reduced pressure. The crude material was purified by chromatography on silica gel eluting with 0 to 20% ethyl acetate in hexanes to obtain the title compound (4.2 g) as a viscous light yellow oil that solidified upon standing to form an off-white solid.

$^1$H NMR δ 2.32 (s, 3H), 7.14-7.19 (m, 2H). 7.28-7.32 (m, 1H), 7.50-7.54 (m, 1H), 7.90-7.96 (m, 2H), 8.65-8.69 (m, 1H).

Synthesis Example 5

Preparation of 5-[3-(trifluoromethoxy)phenoxy]-2-[4-(trifluoromethyl)phenyl]-2H-1,2,3-triazole-4-methanol (Compound 114)

Step A: Preparation of 1-(azidomethyl)-4-methoxybenzene

To a stirred solution of 4-methoxybenzyl chloride (25.0 g, 156 mmol) in N,N-dimethylformamide (75 mL) was added sodium azide (11.5 g, 177 mmol). The reaction mixture was stirred at 23° C. for 15 h, then diluted with water (300 mL). The mixture was extracted with diethyl ether (3×75 mL) and the combined organic layers were washed with water (2×100 mL). The organic layer was dried ($MgSO_4$), filtered, and evaporated under reduced pressure to afford the title compound (25.5 g) as a pale yellow oil. The title compound was used directly in the next step without further purification.

$^1$H NMR δ 3.82 (s, 3H), 4.27 (s, 2H), 6.88-6.93 (m, 2H), 7.22-7.27 (m, 2H).

Step B: Preparation of ethyl 5-hydroxy-1-[(4-methoxyphenyl)methyl]-1H-1,2,3-triazole-4-carboxylate Sodium metal (3.8 g, 164 mmol) was added to absolute ethanol (200 mL). The mixture was stirred under reflux until a clear solution was obtained. Diethyl malonate (26.3 g, 164 mmol) was added to this solution which was again heated to reflux, and a solution of 1-(azidomethyl)-4-methoxybenzene (i.e. the product of Step A, 25.5 g, 156 mmol) in ethanol (50 mL) was added at once. The reaction mixture was stirred at reflux for 24 h then the reaction mixture was concentrated to dryness under reduced pressure. The residue was diluted with water (100 mL) and acidified to pH 2 with 1 M aqueous hydrochloric acid, stirred for 30 min, and the solid was filtered off and washed with water. The solid was dried over phosphorus pentoxide. The solid was stirred in chloroform (500 mL) and the insoluble solids were filtered off. Hexanes (400 mL) were added to precipitate the product, which was removed by filtration and dried to afford the title compound (12.0 g) as a beige solid.

$^1$H NMR δ 1.35-1.40 (m, 3H), 3.78 (s, 3H), 4.36-4.43 (m, 2H), 5.30 (s, 2H), 6.15 (br s, 1H) 6.83-6.88 (m, 2H), 7.27-7.32 (m, 2H).

Step C: Preparation of ethyl 5-chloro-1-[(4-methoxyphenyl)methyl]-1H-1,2,3-triazole-4-carboxylate Ethyl 5-hydroxy-1-[(4-methoxyphenyl)methyl]-1H-1,2,3-triazole-4-carboxylate (i.e. the product of Step B, 10.0 g, 36.1 mmol) was suspended in anhydrous toluene (300 mL) under a nitrogen atmosphere. Phosphorus pentachloride (8.3 g, 39.8 mmol) was added and the mixture was stirred at 40° C. for 90 min. during which time a clear yellow solution was formed. The reaction was concentrated under reduced pressure to remove most of the toluene. The resulting residue was diluted with diethyl ether (150 mL) and washed with saturated aqueous sodium bicarbonate solution (70 mL) and water (70 mL). The organic layer was dried ($MgSO_4$) and concentrated under reduced pressure to afford the crude product which was recrystallized twice from hexanes (200 mL, 100 mL) to afford the title compound (6.0 g) as a pale yellow solid.

$^1$H NMR δ 1.38-1.43 (m, 3H), 3.79 (s, 3H), 4.40-4.46 (m, 2H), 5.50 (s, 2H), 6.85-6.89 (m, 2H), 7.24-7.29 (m, 2H).

Step D: Preparation of ethyl-1-[(4-methoxyphenyl)methyl]-5-[(3-(trifluoromethoxy)phenoxy]-1H-1,2,3-triazole-4-carboxylate To a solution of 3-(trifluoromethoxy)phenol (0.99 g, 5.6 mmol) in N,N-dimethylformamide (10 mL) was added sodium hydride (0.23 g, 5.8 mmol, 60% dispersion in oil). The mixture was stirred at 23° C. for 45 min. then ethyl 5-chloro-1-[(4-methoxyphenyl)methyl]-1H-1,2,3-triazole-4-carboxylate (i.e. the product of Step C, 1.50 g, 5.1 mmol) was added. The reaction mixture was heated to 75° C. for 90 h. Additional sodium hydride (0.06 g, 1.5 mmol) and 3-(trifluoromethoxy)phenol (0.25 g, 1.4 mmol) were added and the mixture was stirred at 75° C. for 45 h. The reaction mixture was concentrated to dryness under reduced pressure. The resulting residue was taken up in ethyl acetate (50 mL) and washed successively with water (2×50 mL) and saturated aqueous sodium chloride solution (50 mL). The organic layer was dried ($MgSO_4$) and concentrated under reduced pressure to afford the crude product. The crude material was purified by chromatography on silica gel eluting with 0 to 60% ethyl acetate in hexanes to obtain the title compound (1.52 g) as a yellow oil.

$^1$H NMR δ 1.07-1.11 (m, 3H), 3.74 (s, 3H), 4.15-4.21 (m, 2H), 5.38 (s, 2H), 6.60-6.65 (m, 2H), 6.73-6.78 (m, 2H), 6.94-6.99 (m, 1H), 7.15-7.20 (m, 2H), 7.22-7.26 (m, 1H).

Step E: Preparation of ethyl 5-[3-(trifluoromethoxy)phenoxy]-2H-1,2,3-triazole-4-carboxylate A solution of ethyl-1-[(4-methoxyphenyl)methyl]-5-[(3-(trifluoromethoxy)phenoxy]-1H-1,2,3-triazole-4-carboxylate (i.e. the product of Step D, 1.50 g, 3.4 mmol) in trifluoroacetic acid (35 mL) was heated to 65° C. with stirring for 5 h. The reaction mixture was concentrated to dryness under reduced pressure. The residue was taken up in ethyl acetate (50 mL) and washed with saturated aqueous sodium bicarbonate solution (30 mL). The organic layer was dried ($MgSO_4$) and concentrated under reduced pressure to afford the crude product. The crude material was purified by chromatography on silica gel eluting with 0 to 40% ethyl acetate in 1-chlorobutane to obtain the title compound (0.90 g) as a beige solid.

$^1$H NMR δ 1.28-1.32 (m, 3H), 4.36-4.42 (m, 2H), 7.02-7.12 (m, 3H), 7.35-7.40 (m, 1H), 12.62 (br s, 1H).

Step F: Preparation of ethyl 2-[2-nitro-4-(trifluoromethyl)phenyl]-5-[3-(trifluoromethoxy)phenoxy]-2H-1,2,3-triazole-4-carboxylate To a solution of ethyl 5-[3-(trifluoromethoxy)phenoxy]-2H-1,2,3-triazole-4-carboxylate (i.e. the product of Step E, 0.55 g, 1.7 mmol) in N,N-dimethylformamide (5 mL) was added anhydrous potassium carbonate (0.48 g, 3.5 mmol) and 4-fluoro-3-nitrobenzotrifluoride (0.29 mL, 2.1 mmol). The mixture was heated to 80° C. with stirring for 90 min. The reaction mixture was concentrated to dryness under reduced pressure. The resulting residue was diluted with water (10 mL) and extracted with ethyl acetate (30 mL, 15 mL). The organic layer was dried ($MgSO_4$) and concentrated under reduced pressure to afford the crude product. The crude material was purified by chromatography on silica gel eluting with 0 to 20% ethyl acetate in hexanes to obtain the title compound (0.76 g) as a pale yellow oil.

$^1$H NMR δ 1.36-1.41 (m, 3H), 4.42-4.48 (m, 2H), 7.07-7.21 (m, 3H), 7.41-7.45 (m, 1H), 7.96-7.99 (m, 1H), 8.10-8.14 (m, 1H).

Step G: Preparation of 2-(2-amino-4-trifluoromethyl-phenyl)-5-(3-trifluoromethoxy-phenoxy)-2H-[1,2,3]triazole-4-carboxylic acid ethyl ester To a solution of ethyl 2-[2-nitro-4-(trifluoromethyl)phenyl]-5-[3-(trifluoromethoxy)phenoxy]-2H-1,2,3-triazole-4-carboxylate (i.e. the product of Step F, 0.76 g, 1.5 mmol) in acetonitrile (30 mL) was added a solution of sodium hydrosulfite (1.31 g, 7.5 mmol) in water (20 mL). The mixture was stirred at 23° C. for 2.5 h. The reaction mixture was diluted with saturated aqueous sodium chloride solution (30 mL) and extracted with ethyl acetate (2×50 mL). The organic layer was dried ($MgSO_4$) and concentrated under reduced pressure to afford the title compound (0.70 g) as a pale yellow solid. The title compound was used directly in the next step without further purification.

$^1$H NMR δ 1.31-1.36 (m, 3H), 4.38-4.44 (m, 2H), 7.00-7.18 (m, 5H), 7.39-7.44 (m, 1H), 7.98-8.01 (m, 1H).

Step H: Preparation of ethyl 5-[3-(trifluoromethoxy)phenoxy]-2-[4-(trifluoromethyl)phenyl]-2H-1,2,3-triazole-4-carboxylate To a solution of ethyl 2-[2-amino-4-(trifluoromethyl)phenyl]-5-[3-(trifluoromethoxy)phenoxy]-2H-1,2,3-triazole-4-carboxylate (i.e. the product of Step G, 0.70 g, 1.5 mmol) in ethanol (20 mL) was added concentrated sulfuric acid (2 mL). The stirring mixture was cooled to −20° C., and then isopentyl nitrite (0.91 g, 8.8 mmol) was added dropwise over 5 min. The reaction mixture was stirred at −20° C. for 1 h, after which an aqueous solution of hypophosphorus acid (3.9 g, 29.4 mmol, 50% in water) was added. The solution was stirred at 23° C. for 14 h. The reaction mixture was diluted with saturated aqueous sodium chloride solution (20 mL), extracted with ethyl acetate (2×40 mL), and washed with saturated aqueous sodium bicarbonate solution (2×20 mL). The organic layer was dried ($MgSO_4$) and concentrated under reduced pressure to afford the crude residue which was purified by chromatography on silica gel eluting with 0 to 15% ethyl acetate in hexanes to obtain the title compound (0.55 g) as a colorless solid.

$^1$H NMR δ 1.33-1.38 (m, 3H), 4.40-4.46 (m, 2H), 7.07-7.12 (m, 1H), 7.17-7.21 (m, 2H), 7.39-7.44 (m, 1H), 7.73-7.78 (m, 2H), 8.15-8.19 (m, 2H).

Step I: Preparation of 5-[3-(trifluoromethoxy)phenoxy]-2-[4-(trifluoromethyl)phenyl]-2H-1,2,3-triazole-4-methanol To a solution of ethyl 5-[3-(trifluoromethoxy)phenoxy]-2-[4-(trifluoromethyl)phenyl]-2H-1,2,3-triazole-4-carboxylate (i.e. the product of Step H, 0.39 g, 0.8 mmol) in anhydrous tetrahydrofuran (6 mL) that was cooled to 0° C. was added a solution of lithium aluminum hydride in tetrahydrofuran (1.0 M, 0.8 mL, 0.8 mmol). The reaction mixture was stirred at 0° C. for 20 min., after which the reaction was quenched with the addition of ethyl acetate (5 mL). The mixture was stirred at 23° C. for 5 min., and then water (6 drops) was added. The mixture was stirred for 5 min., and then sodium sulfate was added. The mixture was stirred for 5 min., and then the mixture was filtered and concentrated under reduced pressure to obtain the title compound (0.35 g, 100%) as a pale yellow oil. The title compound was used directly in the next step without further purification.

$^1$H NMR δ 1.90-1.95 (m, 1H), 4.80-4.84 (m, 2H), 7.05-7.09 (m, 1H), 7.18-7.23 (m, 2H), 7.38-7.44 (m, 1H), 7.70-7.74 (m, 2H), 8.05-8.09 (m, 2H).

Synthesis Example 6

Preparation of 4-methyl-5-[3-(trifluoromethoxy)phenoxy]-2-[(4-(trifluoromethyl)phenyl]-2H-1,2,3-triazole (Compound 119)

Step A: Preparation of 4-(Bromomethyl)-5-[3-(trifluoromethoxy)phenoxy]-2-[4-(trifluoromethyl)phenyl)-2H-1,2,3-triazole 5-[3-(Trifluoromethoxy)phenoxy]-2-[4-(trifluoromethyl)phenyl]-2H-1,2,3-triazole-4-methanol (i.e. the product of Example 5, Step I, 0.17 g, 0.4 mmol) was suspended in 33% hydrobromic acid in acetic acid (2 mL) and 48% hydrobromic acid in water (2 mL). The mixture was heated to reflux with stirring for 4 h. The reaction mixture was cooled to 0° C. and basified with 50% aqueous sodium hydroxide solution. The reaction mixture was diluted with water (20 mL), extracted with ethyl acetate (3×15 mL), and washed with saturated aqueous sodium bicarbonate solution (10 mL). The organic layer was dried ($MgSO_4$) and concentrated under reduced pressure to obtain the title compound (0.19 g) as a pale yellow solid. The title compound was used directly in the next step without further purification.

$^1$H NMR δ 4.56 (s, 2H), 7.07-7.11 (m, 1H), 7.22-7.26 (m, 2H), 7.40-7.45 (m, 1H), 7.70-7.74 (m, 2H), 8.04-8.08 (m, 2H).

Step B: Preparation of 4-methyl-5-[3-(trifluoromethoxy)phenoxy]-2-[(4-(trifluoromethyl)phenyl]-2H-1,2,3-triazole A reaction vial was charged with a magnetic stir bar, 4-(bromomethyl)-5-[3-(trifluoromethoxy)phenoxy]-2-[4-(trifluoromethyl)phenyl)-2H-1,2,3-triazole (i.e. the product of Step A, 0.075 g, 0.16 mmol) and palladium on carbon (5 weight %, 0.033 g, 0.03 mmol). The vial was purged with nitrogen gas, and then absolute ethanol (5 mL) was added. The vial was purged and backfilled with hydrogen gas 10 times. The solution was stirred at 23° C. for 6 h under a balloon of hydrogen gas. The reaction mixture was quenched with triethylamine (0.1 mL), stirred for 5 min., filtered, and concentrated under reduced pressure. The residue was diluted with water (5 mL) and extracted with ethyl acetate (2×5 mL). The organic layer was dried ($MgSO_4$) and concentrated under reduced pressure to obtain the title compound (0.046 g,) as a beige solid.

$^1$H NMR δ 2.32 (s, 3H), 7.02-7.06 (m, 1H), 7.12-7.17 (m, 2H), 7.37-7.42 (m, 1H), 7.68-7.73 (m, 2H), 8.02-8.07 (m, 2H).

Synthesis Example 7

Preparation of 4-(methoxymethyl)-5-[3-(trifluoromethoxy)phenoxy]-2-[4-(trifluoromethyl)phenyl]-2H-1,2,3-triazole (Compound 115)

Step A: Preparation of 4-(methoxymethyl)-5-[3-(trifluoromethoxy)phenoxy]-2-[4-(trifluoromethyl)phenyl]-2H-1,2,3-triazole To a stirred solution of 5-[3-(trifluoromethoxy)phenoxy]-2-[4-(trifluoromethyl)phenyl]-2H-1,2,3-triazole-4-methanol (i.e. the product of Example 5, Step I, 0.075 g, 0.18 mmol) in anhydrous tetrahydrofuran (2 mL) was added sodium hydride (0.011 g, 0.28 mmol, 60% dispersion in oil). After 15 min., iodomethane (0.017 mL, 0.27 mmol) was added. The mixture was stirred at 23° C. for 1.75 h. The reaction mixture was diluted with water (20 mL), extracted with diethyl ether (3×15 mL), and washed with saturated aqueous sodium chloride solution (10 mL). The organic layer was dried ($MgSO_4$) and concentrated under reduced pressure to afford the crude product which was purified by chromatography on silica gel eluting with 0 to 10% ethyl acetate in hexanes to obtain the title compound (0.045 g.) as a clear, colorless oil.

$^1$H NMR δ 3.43 (s, 3H), 4.56 (s, 3H), 7.04-7.08 (m, 1H), 7.17-7.22 (m, 2H), 7.38-7.43 (m, 1H), 7.69-7.74 (m, 2H), 8.06-8.11 (m, 2H).

Synthesis Example 8

Preparation of 4-(fluoromethyl)-5-[3-(trifluoromethoxy)phenoxy]-2-[4-(trifluoromethyl)phenyl]-2H-1,2,3-triazole (Compound 116)

Step A: Preparation of 4-(fluoromethyl)-5-[3-(trifluoromethoxy)phenoxy]-2-[4-(trifluoromethyl)phenyl]-2H-1,2,3-triazole To a stirred solution of 5-[3-(trifluoromethoxy)phenoxy]-2-[4-(trifluoromethyl)phenyl]-2H-1,2,3-triazole-4-methanol (i.e. the product of Example 5, Step I, 0.075 g, 0.18 mmol) in anhydrous dichloromethane (4 mL) cooled to −78° C. was added (diethylamino)sulfur trifluoride (0.032 mL, 0.24 mmol). The mixture was stirred for 2 h during which time the temperature increase to −30° C. The reaction mixture was diluted with saturated aqueous sodium bicarbonate solution (5 mL), extracted with ethyl acetate (3×15 mL), and washed with saturated aqueous sodium chloride solution (10 mL). The organic layer was dried ($MgSO_4$) and concentrated under reduced pressure to afford the crude product which was purified by chromatography on silica gel eluting with 0 to 10% ethyl acetate in hexanes to obtain the title compound (0.052 g) as a yellow solid.

$^1$H NMR δ 5.44-5.46 (m, 2H), 7.07-7.11 (m, 1H), 7.21-7.25 (m, 2H), 7.40-7.45 (m, 1H), 7.71-7.76 (m, 2H), 8.07-8.12 (m, 2H).

Synthesis Example 9

Preparation of 4-ethyl-5-[3-(trifluoromethoxy)phenoxy]-2-[4-(trifluoromethyl)phenyl]-2H-1,2,3-triazole (Compound 125)

Step A: Preparation of 4-ethyl-5-[3-(trifluoromethoxy)phenoxy]-2-[4-(trifluoromethyl)phenyl]-2H-1,2,3-triazole To a suspension of copper(I) cyanide (0.037 g, 0.41 mmol) in anhydrous tetrahydrofuran (2 mL) at −78° C. under a nitrogen atmosphere was added a solution of methyllithium in diethyl ether (1.6 M, 0.54 mL, 0.86 mmol). The mixture was stirred at 0° C. until a clear, colorless solution formed, and then the solution was cooled back to −78° C. To the methylcuprate solution was added a solution of 4-(bromomethyl)-5-[3-(trifluoromethoxy)phenoxy]-2-[4-(trifluoromethyl)phenyl)-2H-1,2,3-triazole (i.e. the product of Example 6, Step A, 0.100 g, 0.21 mmol) in anhydrous tetrahydrofuran (4 mL). The mixture was stirred for 1 h. The reaction mixture was quenched with saturated aqueous ammonium chloride solution (5 mL) and stirred vigorously at 23° C. until the solution turned deep blue in color. The reaction mixture was extracted with ethyl acetate (2×10 mL). The organic layer was dried ($MgSO_4$) and concentrated under reduced pressure to afford the crude product which was purified by chromatography on silica gel eluting with 0 to 10% ethyl acetate in hexanes to obtain the title compound (0.038 g) as a clear, colorless oil.

$^1$H NMR δ 1.29-1.35 (m, 3H), 2.68-2.75 (m, 2H), 7.01-7.06 (m, 1H), 7.11-7.17 (m, 2H), 7.36-7.42 (m, 1H), 7.68-7.72 (m, 2H), 8.03-8.07 (m, 2H).

Synthesis Example 10

Preparation of 4-[[2-(2,4-difluorophenyl)-5-methyl-2H-1,2,3-triazol-4-yl]methyl]-2-(trifluoromethyl) pyridine (Compound 54)

Step A: Preparation of 2-(2,4-difluorophenyl)-4,5-dimethyl-2H-1,2,3-triazole 1-oxide To a stirred solution of anti-pyruvic aldehyde 1-oxime (2.2 g, 22.2 mmol) in diethyl ether (50 mL) was added 2,4-difluorophenylhydrazine hydrochloride (4.0 g, 22.2 mmol) and pyridine (2 mL). The reaction mixture was stirred at 23° C. for 64 h. The solid that formed was removed by filtration and washed with diethyl ether. The filtrate was concentrated under reduced pressure. The crude residue was dissolved in pyridine (100 mL). A solution of copper(II) sulfate pentahydrate (11.1 g, 44.4 mmol) in water (60 mL) was added at once and the resulting mixture was stirred at reflux for 20 h. The mixture was diluted with water and extracted with diethyl ether. The combined organic layers were washed with 1.0 M aqueous hydrochloric acid, dried ($MgSO_4$) and concentrated under reduced pressure to afford the crude product. The crude material was purified by chromatography on silica gel eluting with 0 to 100% ethyl acetate in hexanes to obtain the title compound (1.98 g) as an orange solid.

$^1$H NMR δ 2.26 (s, 3H), 2.33 (s, 3H), 7.01-7.07 (m, 2H), 7.48-7.54 (m, 1H).

Step B: Preparation of [2-(2,4-difluoro-phenyl)-5-methyl-2H-[1,2,3]triazol-4-yl]-methanol To a solution of 2-(2,4-difluorophenyl)-4,5-dimethyl-2H-1,2,3-triazole 1-oxide (i.e. the product of Step A, 1.78 g, 7.0 mmol) in tetrahydrofuran (14 mL) was added trifluoroacetic anhydride (2.5 mL, 17.5 mmol). The reaction mixture was stirred at 110° C. in the microwave for 75 min. The mixture was diluted with ethyl acetate, washed successively with 1.0 M aqueous sodium hydroxide and 50% aqueous sodium hydroxide, dried ($MgSO_4$) and concentrated under reduced pressure to afford the crude product. The crude material was purified by chromatography on silica gel eluting with 0 to 100% ethyl acetate in hexanes to obtain the title compound (0.59 g) as a colorless solid.

$^1$H NMR δ 1.79 (br s, 1H), 2.43 (s, 3H), 4.82 (s, 2H), 6.96-7.05 (m, 2H), 7.70-7.76 (m, 1H).

Step C: Preparation of 4-(bromomethyl)-2-(2,4-difluorophenyl)-5-methyl-2H-1,2,3-triazole 2-(2,4-Difluorophenyl)-5-methyl-2H-1,2,3-triazole-4-methanol (i.e. the product of Step B, 0.70 g, 3.1 mmol) was suspended in 48% hydrobromic acid in water (16 mL). The mixture was heated to reflux with stirring for 2 h. The reaction mixture was diluted with water, cooled to 0° C. and basified with 50% aqueous sodium hydroxide solution. The reaction mixture was extracted with ethyl acetate, dried ($MgSO_4$) and concentrated under reduced pressure to obtain the title compound (0.75 g) as a pale yellow oil. The title compound was used directly in the next step without further purification.

$^1$H NMR δ 2.43 (s, 3H), 4.58 (s, 2H), 6.96-7.05 (m, 2H), 7.72-7.78 (m, 1H).

Step D: Preparation of 4-[[2-(2,4-difluorophenyl)-5-methyl-2H-1,2,3-triazol-4-yl]methyl]-2-(trifluoromethyl)pyridine To a solution of 4-(bromomethyl)-2-(2,4-difluorophenyl)-5-methyl-2H-1,2,3-triazole (i.e. the product of Step C, 0.30 g, 1.0 mmol) in tetrahydrofuran/water (3:1, 4 mL total), was added tetrakis(triphenylphosphine)palladium(0) (0.058 g, 0.05 mmol), potassium phosphate tribasic (0.43 g, 2.0 mmol) and 2-(trifluoromethyl)pyridine-4-boronic acid pinacol ester (0.31 g, 1.15 mmol). The mixture was heated to 70° C. and stirred for 96 h. The reaction mixture was diluted with water and extracted with ethyl acetate. The organic layer was dried ($MgSO_4$) and concentrated under reduced pressure. The crude residue was purified by twice by chromatography on silica gel eluting with 0 to 100% ethyl acetate in hexanes, and then was purified by reverse-phase chromatography on C18 silica gel to afford the title compound (0.18 g) as a colorless solid.

$^1$H NMR δ 2.30 (s, 3H), 4.17 (s, 2H), 6.97-7.06 (m, 2H), 7.37-7.41 (m, 1H), 7.60-7.63 (m, 1H), 7.72-7.78 (m, 1H), 8.64-8.68 (m, 1H).

Synthesis Example 11

Preparation of 4-[[5-ethoxy-2-(4-fluorophenyl)-2H-1,2,3-triazol-4-yl]methyl]-2-(trifluoromethyl)pyridine (Compound 196)

Step A: Preparation of ethyl 5-ethoxy-2-(4-fluorophenyl)-2H-1,2,3-triazole-4-carboxylate A stirred mixture of 4-fluoroaniline (11.1 g, 100 mmol) in water (50 mL) and concentrated hydrochloric acid (19 mL) was cooled to −15° C. To this mixture was added a previously cooled (0° C.) solution of sodium nitrite (7.6 g, 110 mmol) in water (25 mL) over 5 min. Ice was added directly to the reaction to maintain the temperature below 5° C. After the addition was complete, the reaction was stirred at 0° C. for 15 min. Sodium acetate (41.0 g, 500 mmol) was added followed by ethyl 3-ethoxy-3-iminopropionate (15.9 g, 100 mmol). A yellow precipitate formed immediately. The suspension was stirred at 23° C. for 30 min., and then the solid was filtered and washed with water (40 mL). The still wet hydrazone was dissolved in pyridine (150 mL). A solution of copper (II) sulfate (49.7 g, 199 mmol) in water (150 mL) was added at once. The dark mixture was heated to 90° C. for 4 h. The majority of the pyridine (~100 mL) was removed under vacuum. The residue was diluted with ethyl acetate (200 mL), water (100 mL) and 2 M sulfuric acid (80 mL). The resulting emulsion was filtered through Celite® diatomaceous earth filter aid. The organic layer was washed with 2 M sulfuric acid (2×100 mL), dried ($MgSO_4$) and concentrated under reduced pressure. The resulting crude mixture was recrystallized from ethanol (80 mL) to obtain the title compound (15.1 g) as a pale red solid.

$^1$H NMR δ 1.40-1.45 (m, 3H), 1.49-1.54 (m, 3H), 4.41-4.51 (m, 4H), 7.13-7.18 (m, 2H), 7.99-8.04 (m, 2H).

Step B: Preparation of 5-ethoxy-2-(4-fluorophenyl)-N-methoxy-N-methyl-2H-1,2,3-triazole-4-carboxamide To an oven-dried flask under a nitrogen atmosphere was added N,O-dimethylhydroxylamine hydrochloride (2.8 g, 28.6 mmol) to which a solution of trimethylaluminum (2.0 M in toluene, 14.3 mL, 28.6 mmol) was added at 0° C. and stirred for 30 min. Ethyl 5-ethoxy-2-(4-fluorophenyl)-2H-1,2,3-triazole-4-carboxylate (i.e. the product of Step A, 4.0 g, 14.3 mmol) was added and the resulting solution was stirred at 23° C. for 4 h. The reaction mixture was cooled to 0° C. and carefully quenched by the dropwise addition of water (2 mL). Dichloromethane, (50 mL), sodium sulfate and water (3 mL) were added sequentially to the mixture which was then stirred for 20 min. at 23° C. The mixture was dried ($Na_2SO_4$ and $MgSO_4$) and concentrated under reduced pressure to obtain the title compound (3.7 g) as an orange solid.

$^1$H NMR δ 1.46-1.51 (m, 3H), 3.39 (s, 3H), 3.86 (s, 3H), 4.43-4.49 (m, 2H), 7.12-7.18 (m, 2H), 7.93-7.98 (m, 2H).

Step C: Preparation of [5-ethoxy-2-(4-fluorophenyl)-2H-1,2,3-triazol-4-yl][2-(trifluoromethyl)-4-pyridinyl]methanone A solution of isopropylmagnesium chloride lithium chloride complex (1.3 M in THF, 8.5 mL, 11.0 mmol) was added to a solution of 4-iodo-2-(trifluoromethyl)pyridine (3.0 g, 11.0 mmol) in tetrahydrofuran (10 mL) cooled to 0° C. After 10 minutes, the solution was stirred at 23° C. for 35 min. The dark reddish brown solution was then cooled to −78° C. A solution of 5-ethoxy-2-(4-fluorophenyl)-N-methoxy-N-methyl-2H-1,2,3-triazole-4-carboxamide (i.e. the product of Step B, 2.5 g, 8.5 mmol) in tetrahydrofuran (25 mL) was added. The solution was stirred at 23° C. for 22 h. The reaction was quenched by the addition of a saturated aqueous ammonium chloride solution (10 mL) and water (10 mL). The mixture was extracted with ethyl acetate (2×40 mL), dried ($MgSO_4$) and concentrated under reduced pressure to obtain the crude product. The crude residue was purified by chromatography on silica gel eluting with 0 to 20% ethyl acetate in hexanes to afford the title compound (1.8 g) as a colorless solid.

$^1$H NMR δ 1.53-1.58 (t, 3H), 4.54-4.60 (m, 2H), 7.19-7.24 (m, 2H), 8.00-8.04 (m, 2H), 8.22-8.26 (m, 1H), 8.45-8.47 (m, 1H), 8.94-8.98 (m, 1H).

Step D: Preparation of 4-[[5-ethoxy-2-(4-fluorophenyl)-2H-1,2,3-triazol-4-yl]methyl]-2-(trifluoromethyl)pyridine To a solution of [5-ethoxy-2-(4-fluorophenyl)-2H-1,2,3-triazol-4-yl][2-(trifluoromethyl)-4-pyridinyl]methanone (i.e. the product of Step C, 2.7 g, 7.1 mmol) in acetic acid (15 mL) was added iodine (1.8 g, 7.1 mmol) and hypophosphorous acid (50% in water, 3.1 mL, 28.4 mmol). The mixture was heated to 110° C. under a nitrogen atmosphere for 6 h. The reaction mixture was cooled to 23° C. and neutralized to ~pH 7 with 1 M NaOH and a saturated aqueous sodium bicarbonate solution. The mixture was extracted with ethyl acetate (2×15 mL), dried ($MgSO_4$) and concentrated under reduced pressure. The crude residue was purified by chromatography on silica gel eluting with 0 to 20% ethyl acetate in hexanes to afford the title compound (2.1 g) as an off-white solid.

$^1$H NMR δ 1.39-1.44 (t, 3H), 4.08 (s, 2H), 4.33-4.39 (m, 2H), 7.09-7.15 (m, 2H), 7.42-7.46 (m, 1H), 7.66-7.68 (m, 1H), 7.84-7.88 (m, 2H), 8.63-8.66 (m, 1H).

By the procedures described herein together with methods known in the art, the following compounds of Tables 1 to 126 can be prepared. The following abbreviations are used in the Tables which follow: n means normal, i means iso, Me means methyl, Et means ethyl, Pr means propyl, i-Pr means isopropyl, Ph means phenyl, OMe means methoxy, OEt means ethoxy and SMe means methylthio.

In the following Tables 1 to 125, J-1A, J-2A, J-10A, J-17A, J-17B, J-18A, J-18B, J-20A, J-22A and J-29A refer to the following structures:

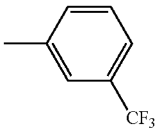
J-1A

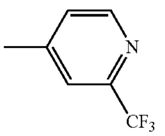
J-2A

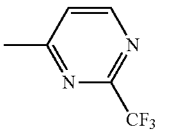
J-10A

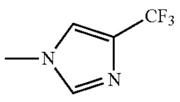
J-17A

-continued

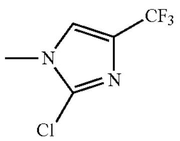
J-17B

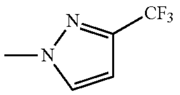
J-18A

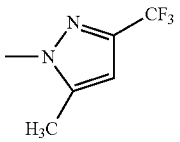
J-18B

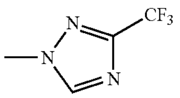
J-20A

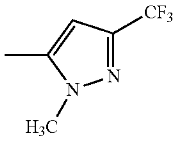
J-22A

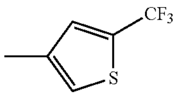
J-29A

TABLE 1

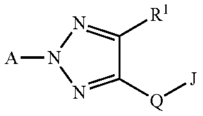

1

J is J-2A; Q is O; $R^1$ is Me; and A is

| A |
|---|
| Ph(4-F) |
| Ph(4-$CF_3$) |
| Ph(4-Cl) |
| Ph(4-Br) |
| Ph(4-$SF_5$) |
| Ph(4-$OCF_3$) |
| Ph(4-$SCH_3$) |
| Ph(4-$OCH_3$) |
| Ph(4-CN) |
| Ph(4-Me) |
| Ph |
| Ph(3-F) |
| Ph(3-$CF_3$) |
| Ph(3-Cl) |
| Ph(3-Br) |
| Ph(3-$SF_5$) |
| Ph(3-$OCF_3$) |
| Ph(3-SMe) |
| Ph(3-OMe) |
| Ph(3-CN) |
| Ph(3-Me) |
| Ph(2-F) |

-continued

| A |
|---|
| Ph(2-$CF_3$) |
| Ph(2-Cl) |
| Ph(2-Br) |
| Ph(2,4-di-F) |
| Ph(3,4-di-F) |
| Ph(2,5-di-F) |
| Ph(2,4,6-tri-F) |
| Ph(2-Cl,4-F) |
| Ph(3-Cl,4-F) |
| Ph(4-F,3-$CF_3$) |
| Ph(2-F,4-$CF_3$) |
| Ph(3-F,4-$CF_3$) |
| Ph(3-Cl,4-$CF_3$) |
| Ph(2-Cl,4-$CF_3$) |
| Ph(4-Cl,3-$CF_3$) |
| 2-Pyridinyl |
| 3-Pyridinyl |
| 4-Pyridinyl |
| 2-Pyridinyl(5-$CF_3$) |
| 2-Pyridinyl(5-Cl) |
| 4-Pyridinyl(2-$CF_3$) |
| 4-Pyridinyl(2-Cl) |
| 2-Pyridinyl(6-$CF_3$) |
| 3-Pyridinyl(5-$CF_3$) |
| 5-Pyridinyl(2-$CF_3$) |
| 2-Pyrazinyl(5-$CF_3$) |
| 3-Pyridazinyl(6-$CF_3$) |
| 2-Pyridinyl(5-F) |
| 4-Pyridinyl(2-F) |
| 2-Pyridinyl(6-F) |
| 3-Pyridinyl(5-F) |
| 3-Pyridinyl(6-F) |
| 2-Pyrimidinyl(5-Cl) |
| 2-Pyrimidinyl(5-$CF_3$) |
| 4-Pyrimidinyl(2-$CF_3$) |
| 2-Pyrimidinyl(4-$CF_3$) |
| 2-Thienyl(5-Cl) |
| 2-Thienyl(5-$CF_3$) |
| 2-Thiazolyl(4-$CF_3$) |
| 1,2,4-Thiadiazol-5-yl(3-$CF_3$) |

Table 2 is constructed in the same manner except that the Row Heading "J is J-2A; Q is O, $R^1$ is Me; and A is" is replaced with the Row Heading listed for Table 2 below (i.e. "J is J-2A; Q is O; $R^1$ is Et; and A is"). Therefore the first entry in Table 2 is a compound of Formula 1 wherein $R^1$ is Et; Q is O; A is Ph(4-F) (i.e. 4-fluorophenyl); and J is J-2A. Tables 3 through 125 are constructed similarly.

| Table | Row Heading |
|---|---|
| 2 | J is J-2A; Q is O; $R^1$ is Et; and A is |
| 3 | J is J-2A; Q is O; $R^1$ is n-Pr; and A is |
| 4 | J is J-2A; Q is O; $R^1$ is i-Pr; and A is |
| 5 | J is J-2A; Q is O; $R^1$ is OMe; and A is |
| 6 | J is J-2A; Q is O; $R^1$ is SMe; and A is |
| 7 | J is J-2A; Q is O; $R^1$ is $OCHF_2$; and A is |
| 8 | J is J-2A; Q is O; $R^1$ is $CH_2OCH_3$; and A is |
| 9 | J is J-2A; Q is O; $R^1$ is OEt; and A is |
| 10 | J is J-2A; Q is O; $R^1$ is $OCH_2CF_3$; and A is |
| 11 | J is J-2A; Q is $CH_2$; $R^1$ is Me; and A is |
| 12 | J is J-2A; Q is $CH_2$; $R^1$ is Et; and A is |
| 13 | J is J-2A; Q is $CH_2$; $R^1$ is n-Pr; and A is |
| 14 | J is J-2A; Q is $CH_2$; $R^1$ is i-Pr; and A is |
| 15 | J is J-2A; Q is $CH_2$; $R^1$ is OMe; and A is |
| 16 | J is J-2A; Q is $CH_2$; $R^1$ is SMe; and A is |
| 17 | J is J-2A; Q is $CH_2$; $R^1$ is $OCHF_2$; and A is |
| 18 | J is J-2A; Q is $CH_2$; $R^1$ is $CH_2OCH_3$; and A is |
| 19 | J is J-2A; Q is $CH_2$; $R^1$ is OEt; and A is |
| 20 | J is J-2A; Q is $CH_2$; $R^1$ is $OCH_2CF_3$; and A is |
| 21 | J is J-1A; Q is O; $R^1$ is Me; and A is |
| 22 | J is J-1A; Q is O; $R^1$ is Et; and A is |
| 23 | J is J-1A; Q is O; $R^1$ is n-Pr; and A is |
| 24 | J is J-1A; Q is O; $R^1$ is i-Pr; and A is |
| 25 | J is J-1A; Q is O; $R^1$ is OMe; and A is |
| 26 | J is J-1A; Q is O; $R^1$ is SMe; and A is |
| 27 | J is J-1A; Q is O; $R^1$ is OCHF2; and A is |
| 28 | J is J-1A; Q is O; $R^1$ is $CH_2OCH_3$; and A is |
| 29 | J is J-1A; Q is O; $R^1$ is OEt; and A is |
| 30 | J is J-1A; Q is O; $R^1$ is $OCH_2CF_3$; and A is |
| 31 | J is J-1A; Q is $CH_2$; $R^1$ is Me; and A is |
| 32 | J is J-1A; Q is $CH_2$; $R^1$ is Et; and A is |
| 33 | J is J-1A; Q is $CH_2$; $R^1$ is n-Pr; and A is |
| 34 | J is J-1A; Q is $CH_2$; $R^1$ is i-Pr; and A is |
| 35 | J is J-1A; Q is $CH_2$; $R^1$ is OMe; and A is |
| 36 | J is J-1A; Q is $CH_2$; $R^1$ is SMe; and A is |
| 37 | J is J-1A; Q is $CH_2$; $R^1$ is $OCHF_2$; and A is |
| 38 | J is J-1A; Q is $CH_2$; $R^1$ is $CH_2OCH_3$; and A is |
| 39 | J is J-1A; Q is $CH_2$; $R^1$ is OEt; and A is |
| 40 | J is J-1A; Q is $CH_2$; $R^1$ is $OCH_2CF_3$; and A is |
| 41 | J is J-10A; Q is O; $R^1$ is Me; and A is |
| 42 | J is J-10A; Q is O; $R^1$ is Et; and A is |
| 43 | J is J-10A; Q is O; $R^1$ is OMe; and A is |
| 44 | J is J-10A Q is O; $R^1$ is $OCHF_2$; and A is |
| 45 | J is J-10A; Q is $CH_2$; $R^1$ is Me; and A is |
| 46 | J is J-10A; Q isCH2; $R^1$ is Et; and A is |
| 47 | J is J-10A; Q is $CH_2$; $R^1$ is OMe; and A is |
| 48 | J is J-10A; Q is $CH_2$; $R^1$ is $OCHF_2$; and A is |
| 49 | J is J-29A; Q is O; $R^1$ is Me; and A is |
| 50 | J is J-29A; Q is O; $R^1$ is Et; and A is |
| 51 | J is J-29A; Q is O; $R^1$ is OMe; and A is |
| 52 | J is J-29A; Q is O; $R^1$ is $OCHF_2$; and A is |
| 53 | J is J-29A; Q is $CH_2$; $R^1$ is Me; and A is |
| 54 | J is J-29A; Q is $CH_2$; $R^1$ is Et; and A is |
| 55 | J is J-29A; Q is $CH_2$; $R^1$ is OMe; and A is |
| 56 | J is J-29A; Q is $CH_2$; $R^1$ is $OCHF_2$; and A is |
| 57 | J is J-2A; Q is C=O; $R^1$ is Me; and A is |
| 58 | J is J-2A; Q is C=O; $R^1$ is Et; and A is |
| 59 | J is J-2A; Q is C=O; $R^1$ is OMe; and A is |
| 60 | J is J-2A; Q is C=O; $R^1$ is $OCHF_2$; and A is |
| 61 | J is J-1A; Q is C=O; $R^1$ is Me; and A is |
| 62 | J is J-1A; Q is C=O; $R^1$ is Et; and A is |
| 63 | J is J-1A; Q is C=O; $R^1$ is OMe; and A is |
| 64 | J is J-JA; Q is C=O; $R^1$ is $OCHF_2$; and A is |
| 65 | J is J-2A; Q is S; $R^1$ is Me; and A is |
| 66 | J is J-2A; Q is S; $R^1$ is Et; and A is |
| 67 | J is J-2A; Q is S; $R^1$ is OMe; and A is |
| 68 | J is J-2A; Q is S; $R^1$ is $OCHF_2$; and A is |
| 69 | J is J-1A; Q is S; $R^1$ is Me; and A is |
| 70 | J is J-1A; Q is S; $R^1$ is Et; and A is |
| 71 | J is J-1A; Q is S; $R^1$ is OMe; and A is |
| 72 | J is J-1A; Q is S; $R^1$ is $OCHF_2$; and A is |
| 73 | J is J-2A; Q is NH; $R^1$ is Me; and A is |
| 74 | J is J-2A; Q is NH; $R^1$ is Et; and A is |
| 75 | J is J-2A; Q is NH; $R^1$ is OMe; and A is |
| 76 | J is J-2A; Q is NH; $R^1$ is $OCHF_2$; and A is |
| 77 | J is J-1A; Q is NH; $R^1$ is Me; and A is |
| 78 | J is J-1A; Q is NH; $R^1$ is Et; and A is |
| 79 | J is J-1A; Q is NH; $R^1$ is OMe; and A is |
| 80 | J is J-1A; Q is NH; $R^1$ is $OCHF_2$; and A is |
| 81 | J is J-2A; Q is CHF; $R^1$ is Me; and A is |
| 82 | J is J-2A; Q is CHF; $R^1$ is Et; and A is |
| 83 | J is J-2A; Q is CHF; $R^1$ is OMe; and A is |
| 84 | J is J-2A; Q is CHF; $R^1$ is $OCHF_2$; and A is |
| 85 | J is J-1A; Q is CHF; $R^1$ is Me; and A is |
| 86 | J is J-1A; Q is CHF; $R^1$ is Et; and A is |
| 87 | J is J-1A; Q is CHF; $R^1$ is OMe; and A is |
| 88 | J is J-1A; Q is CHF; $R^1$ is $OCHF_2$; and A is |
| 89 | J is J-22A; Q is O; $R^1$ is Me; and A is |
| 90 | J is J-22A; Q is O; $R^1$ is Et; and A is |
| 91 | J is J-22A; Q is O; $R^1$ is OMe; and A is |
| 92 | J is J-22A; Q is O; $R^1$ is $OCHF_2$; and A is |
| 93 | J is J-22A; Q is $CH_2$; $R^1$ is Me; and A is |
| 94 | J is J-22A; Q is $CH_2$; $R^1$ is Et; and A is |
| 95 | J is J-22A; Q is $CH_2$; $R^1$ is OMe; and A is |
| 96 | J is J-22A; Q is $CH_2$; $R^1$ is $OCHF_2$; and A is |
| 97 | J is J-2A; Q is O; $R^1$ is Cl; and A is |
| 98 | J is J-2A; Q is $CH_2$; $R^1$ is Cl; and A is |
| 99 | J is J-1A; Q is O; $R^1$ is Br; and A is |
| 100 | J is J-1A; Q is $CH_2$; $R^1$ is Br; and A is |

-continued

| Table | Row Heading |
|---|---|
| 101 | J is J-18A; Q is $CH_2$; $R^1$ is Et; and A is |
| 102 | J is J-18A; Q is $CH_2$; $R^1$ is Me; and A is |
| 103 | J is J-18A; Q is $CH_2$; $R^1$ is OMe; and A is |
| 104 | J is J-18A; Q is $CH_2$; $R^1$ is $OCHF_2$; and A is |
| 105 | J is J-18A; Q is $CH_2$; $R^1$ is Cl; and A is |
| 106 | J is J-20A; Q is $CH_2$; $R^1$ is Et; and A is |
| 107 | J is J-20A; Q is $CH_2$; $R^1$ is Me; and A is |
| 108 | J is J-20A; Q is $CH_2$; $R^1$ is OMe; and A is |
| 109 | J is J-20A; Q is $CH_2$; $R^1$ is $OCHF_2$; and A is |
| 110 | J is J-20A; Q is $CH_2$; $R^1$ is Cl; and A is |
| 111 | J is J-17A; Q is $CH_2$; $R^1$ is Et; and A is |
| 112 | J is J-17A; Q is $CH_2$; $R^1$ is Me; and A is |
| 113 | J is J-17A; Q is $CH_2$; $R^1$ is OMe; and A is |
| 114 | J is J-17A; Q is $CH_2$; $R^1$ is $OCHF_2$; and A is |
| 115 | J is J-17A; Q is $CH_2$; $R^1$ is Cl; and A is |
| 116 | J is J-17B; Q is $CH_2$; $R^1$ is Et; and A is |
| 117 | J is J-17B; Q is $CH_2$; $R^1$ is Me; and A is |
| 118 | J is J-17B; Q is $CH_2$; $R^1$ is OMe; and A is |
| 119 | J is J-17B; Q is $CH_2$; $R^1$ is $OCHF_2$; and A is |
| 120 | J is J-17B; Q is $CH_2$; $R^1$ is Cl; and A is |
| 121 | J is J-18B; Q is $CH_2$; $R^1$ is Et; and A is |
| 122 | J is J-18B; Q is $CH_2$; $R^1$ is Me; and A is |
| 123 | J is J-18B; Q is $CH_2$; $R^1$ is OMe; and A is |
| 124 | J is J-18B; Q is $CH_2$; $R^1$ is $OCHF_2$; and A is |
| 125 | J is J-18B; Q is $CH_2$; $R^1$ is Cl; and A is |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and*

*Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A and B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 129 | 98.5% |
| silica aerogel | 0.5% |
| synthetic amorphous fine silica | 1.0% |

Example B

Wettable Powder

| | |
|---|---|
| Compound 14 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 15 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 16 | 25.0% |
| anhydrous sodium sulfate | 10.0% |
| crude calcium ligninsulfonate | 5.0% |

-continued

| | |
|---|---|
| sodium alkylnaphthalenesulfonate | 1.0% |
| calcium/magnesium bentonite | 59.0% |

Example E

Emulsifiable Concentrate

| | |
|---|---|
| Compound 47 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 129 | 5.0% |
| polyvinylpyrrolidone-vinyl copolymer acetate | 30.0% |
| alkylpolyglycoside | 30.0% |
| glyceryl monooleate | 15.0% |
| water | 20.0% |

Test results indicate that the compounds of the present invention are highly active preemergent and/or postemergent herbicides and/or plant growth regulants. The compounds of the intention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), *sorghum*, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, cyclopyrimorate (6-chloro-3-(2-cyclopropyl-6-methylphenoxy)-4-pyridazinyl 4-morpholinecarboxylate), clodinafop-propargyl, clomazone, clomeprop, clopyralid, clopyralid-olamine, cloransulam-methyl, cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione (2-[[8-chloro-3,4-dihydro-4-(4-methoxyphenyl)-3-oxo-2-quinoxalinyl]carbonyl]-1,3-cyclohexanedione), fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methiozolin, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate), tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, N-(aminocarbonyl)-2-methylbenzenesulfonamide, benoxacor, BCS (1-bromo-4-[(chloromethyl)sulfonyl]benzene), cloquintocet-mexyl, cyometrinil, cyprosulfonamide, dichlormid, 4-(dichloroacetyl)-1-oxa-4-azospiro[4.5]decane (MON 4660), 2-(dichloromethyl)-2-methyl-1,3-dioxolane (MG 191), dicyclonon, dietholate, ethyl 1,6-dihydro-1-(2-methoxyphenyl)-6-oxo-2-phenyl-5-pyrimidinecarboxylate, fenchlorazole-ethyl, fenclorim, flurazole, fluxofenim, furilazole, 2-hydroxy-N,N-dimethyl-6-(trifluoromethyl)pyridine-3-carboxamide, isoxadifen-ethyl, mefenpyr-diethyl, mephenate, methoxyphenone ((4-methoxy-3-methylphenyl)(3-methylphenyl)methanone), naphthalic anhydride (1,8-naphthalic anhydride) oxabetrinil and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with another herbicide. Table A1 lists specific combinations of a Component (a) with Component (b) illustrative of the mixtures, compositions and methods of the present invention. Compound 1 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192 to 6:1. The remaining lines of Table A1 are to be construed similarly.

TABLE A1

| Component (a) | Component (b) | Typical Weight Ratio | More Typical Weight Ratio | Most Typical Weight Ratio |
|---|---|---|---|---|
| Compound 129 | 2,4-D | 1:192 to 6:1 | 1:64 to 2:1 | 1:24 to 1:3 |
| Compound 129 | 4-amino-3-chloro-6-(4-chloro-2-fluoro-3-methoxyphenyl)-2-pyridinecarboxylic acid (halauxifen) | 1:20 to 56:1 | 1:6 to 19:1 | 1:2 to 4:1 |
| Compound 129 | 4-amino-3-chloro-6-(4-chloro-2-fluoro-3-methoxyphenyl)-2-pyridinecarboxylic acid methyl ester (halauxifen methyl) | 1:20 to 56:1 | 1:6 to 19:1 | 1:2 to 4:1 |
| Compound 129 | Acetochlor | 1:768 to 2:1 | 1:256 to 1:2 | 1:96 to 1:11 |
| Compound 129 | Acifluorfen | 1:96 to 12:1 | 1:32 to 4:1 | 1:12 to 1:2 |
| Compound 129 | Aclonifen | 1:857 to 2:1 | 1:285 to 1:3 | 1:107 to 1:12 |
| Compound 129 | Alachlor | 1:768 to 2:1 | 1:256 to 1:2 | 1:96 to 1:11 |
| Compound 129 | Ametryn | 1:384 to 3:1 | 1:128 to 1:1 | 1:48 to 1:6 |
| Compound 129 | Amicarbazone | 1:192 to 6:1 | 1:64 to 2:1 | 1:24 to 1:3 |
| Compound 129 | Amidosulfuron | 1:6 to 168:1 | 1:2 to 56:1 | 1:1 to 11:1 |
| Compound 129 | Aminocyclopyrachlor | 1:48 to 24:1 | 1:16 to 8:1 | 1:6 to 2:1 |
| Compound 129 | Aminopyralid | 1:20 to 56:1 | 1:6 to 19:1 | 1:2 to 4:1 |
| Compound 129 | Amitrole | 1:768 to 2:1 | 1:256 to 1:2 | 1:96 to 1:11 |
| Compound 129 | Anilofos | 1:96 to 12:1 | 1:32 to 4:1 | 1:12 to 1:2 |
| Compound 129 | Asulam | 1:960 to 2:1 | 1:320 to 1:3 | 1:120 to 1:14 |
| Compound 129 | Atrazine | 1:192 to 6:1 | 1:64 to 2:1 | 1:24 to 1:3 |
| Compound 129 | Azimsulfuron | 1:6 to 168:1 | 1:2 to 56:1 | 1:1 to 11:1 |
| Compound 129 | Beflubutamid | 1:342 to 4:1 | 1:114 to 2:1 | 1:42 to 1:5 |
| Compound 129 | Benfuresate | 1:617 to 2:1 | 1:205 to 1:2 | 1:77 to 1:9 |
| Compound 129 | Bensulfuron-methyl | 1:25 to 45:1 | 1:8 to 15:1 | 1:3 to 3:1 |
| Compound 129 | Bentazone | 1:192 to 6:1 | 1:64 to 2:1 | 1:24 to 1:3 |
| Compound 129 | Benzobicyclon | 1:85 to 14:1 | 1:28 to 5:1 | 1:10 to 1:2 |
| Compound 129 | Benzofenap | 1:257 to 5:1 | 1:85 to 2:1 | 1:32 to 1:4 |
| Compound 129 | Bicyclopyrone | 1:42 to 27:1 | 1:14 to 9:1 | 1:5 to 2:1 |
| Compound 129 | Bifenox | 1:257 to 5:1 | 1:85 to 2:1 | 1:32 to 1:4 |
| Compound 129 | Bispyribac-sodium | 1:10 to 112:1 | 1:3 to 38:1 | 1:1 to 7:1 |
| Compound 129 | Bromacil | 1:384 to 3:1 | 1:128 to 1:1 | 1:48 to 1:6 |
| Compound 129 | Bromobutide | 1:384 to 3:1 | 1:128 to 1:1 | 1:48 to 1:6 |
| Compound 129 | Bromoxynil | 1:96 to 12:1 | 1:32 to 4:1 | 1:12 to 1:2 |
| Compound 129 | Butachlor | 1:768 to 2:1 | 1:256 to 1:2 | 1:96 to 1:11 |
| Compound 129 | Butafenacil | 1:42 to 27:1 | 1:14 to 9:1 | 1:5 to 2:1 |
| Compound 129 | Butylate | 1:1542 to 1:2 | 1:514 to 1:5 | 1:192 to 1:22 |
| Compound 129 | Carfenstrole | 1:192 to 6:1 | 1:64 to 2:1 | 1:24 to 1:3 |
| Compound 129 | Carfentrazone-ethyl | 1:128 to 9:1 | 1:42 to 3:1 | 1:16 to 1:2 |
| Compound 129 | Chlorimuron-ethyl | 1:8 to 135:1 | 1:2 to 45:1 | 1:1 to 9:1 |
| Compound 129 | Chlorotoluron | 1:768 to 2:1 | 1:256 to 1:2 | 1:96 to 1:11 |
| Compound 129 | Chlorsulfuron | 1:6 to 168:1 | 1:2 to 56:1 | 1:1 to 11:1 |
| Compound 129 | Cincosulfuron | 1:17 to 68:1 | 1:5 to 23:1 | 1:2 to 5:1 |
| Compound 129 | Cinidon-ethyl | 1:384 to 3:1 | 1:128 to 1:1 | 1:48 to 1:6 |
| Compound 129 | Cinmethylin | 1:34 to 34:1 | 1:11 to 12:1 | 1:4 to 3:1 |
| Compound 129 | Clacyfos | 1:34 to 34:1 | 1:11 to 12:1 | 1:4 to 3:1 |
| Compound 129 | Clethodim | 1:48 to 24:1 | 1:16 to 8:1 | 1:6 to 2:1 |
| Compound 129 | Clodinafop-propargyl | 1:20 to 56:1 | 1:6 to 19:1 | 1:2 to 4:1 |
| Compound 129 | Clomazone | 1:384 to 3:1 | 1:128 to 1:1 | 1:48 to 1:6 |
| Compound 129 | Clomeprop | 1:171 to 7:1 | 1:57 to 3:1 | 1:21 to 1:3 |
| Compound 129 | Clopyralid | 1:192 to 6:1 | 1:64 to 2:1 | 1:24 to 1:3 |
| Compound 129 | Cloransulam-methyl | 1:12 to 96:1 | 1:4 to 32:1 | 1:1 to 6:1 |
| Compound 129 | Cumyluron | 1:384 to 3:1 | 1:128 to 1:1 | 1:48 to 1:6 |
| Compound 129 | Cyanazine | 1:384 to 3:1 | 1:128 to 1:1 | 1:48 to 1:6 |
| Compound 129 | Cyclopyrimorate | 1:17 to 68:1 | 1:5 to 23:1 | 1:2 to 5:1 |
| Compound 129 | Cyclosulfamuron | 1:17 to 68:1 | 1:5 to 23:1 | 1:2 to 5:1 |
| Compound 129 | Cycloxydim | 1:96 to 12:1 | 1:32 to 4:1 | 1:12 to 1:2 |
| Compound 129 | Cyhalofop | 1:25 to 45:1 | 1:8 to 15:1 | 1:3 to 3:1 |
| Compound 129 | Daimuron | 1:192 to 6:1 | 1:64 to 2:1 | 1:24 to 1:3 |
| Compound 129 | Desmedipham | 1:322 to 4:1 | 1:107 to 2:1 | 1:40 to 1:5 |
| Compound 129 | Dicamba | 1:192 to 6:1 | 1:64 to 2:1 | 1:24 to 1:3 |
| Compound 129 | Dichlobenil | 1:1371 to 1:2 | 1:457 to 1:4 | 1:171 to 1:20 |
| Compound 129 | Dichlorprop | 1:925 to 2:1 | 1:308 to 1:3 | 1:115 to 1:13 |
| Compound 129 | Diclofop-methyl | 1:384 to 3:1 | 1:128 to 1:1 | 1:48 to 1:6 |
| Compound 129 | Diclosulam | 1:10 to 112:1 | 1:3 to 38:1 | 1:1 to 7:1 |
| Compound 129 | Difenzoquat | 1:288 to 4:1 | 1:96 to 2:1 | 1:36 to 1:4 |
| Compound 129 | Diflufenican | 1:857 to 2:1 | 1:285 to 1:3 | 1:107 to 1:12 |
| Compound 129 | Diflufenzopyr | 1:12 to 96:1 | 1:4 to 32:1 | 1:1 to 6:1 |
| Compound 129 | Dimethachlor | 1:768 to 2:1 | 1:256 to 1:2 | 1:96 to 1:11 |
| Compound 129 | Dimethametryn | 1:192 to 6:1 | 1:64 to 2:1 | 1:24 to 1:3 |
| Compound 129 | Dimethenamid-P | 1:384 to 3:1 | 1:128 to 1:1 | 1:48 to 1:6 |

TABLE A1-continued

| Component (a) | Component (b) | Typical Weight Ratio | More Typical Weight Ratio | Most Typical Weight Ratio |
|---|---|---|---|---|
| Compound 129 | Dithiopyr | 1:192 to 6:1 | 1:64 to 2:1 | 1:24 to 1:3 |
| Compound 129 | Diuron | 1:384 to 3:1 | 1:128 to 1:1 | 1:48 to 1:6 |
| Compound 129 | EPTC | 1:768 to 2:1 | 1:256 to 1:2 | 1:96 to 1:11 |
| Compound 129 | Esprocarb | 1:1371 to 1:2 | 1:457 to 1:4 | 1:171 to 1:20 |
| Compound 129 | Ethalfluralin | 1:384 to 3:1 | 1:128 to 1:1 | 1:48 to 1:6 |
| Compound 129 | Ethametsulfuron-methyl | 1:17 to 68:1 | 1:5 to 23:1 | 1:2 to 5:1 |
| Compound 129 | Ethoxyfen | 1:8 to 135:1 | 1:2 to 45:1 | 1:1 to 9:1 |
| Compound 129 | Ethoxysulfuron | 1:20 to 56:1 | 1:6 to 19:1 | 1:2 to 4:1 |
| Compound 129 | Etobenzanid | 1:257 to 5:1 | 1:85 to 2:1 | 1:32 to 1:4 |
| Compound 129 | Fenoxaprop-ethyl | 1:120 to 10:1 | 1:40 to 4:1 | 1:15 to 1:2 |
| Compound 129 | Fenoxasulfone | 1:85 to 14:1 | 1:28 to 5:1 | 1:10 to 1:2 |
| Compound 129 | Fenquinotrione | 1:17 to 68:1 | 1:5 to 23:1 | 1:2 to 5:1 |
| Compound 129 | Fentrazamide | 1:17 to 68:1 | 1:5 to 23:1 | 1:2 to 5:1 |
| Compound 129 | Flazasulfuron | 1:17 to 68:1 | 1:5 to 23:1 | 1:2 to 5:1 |
| Compound 129 | Florasulam | 1:2 to 420:1 | 1:1 to 140:1 | 2:1 to 27:1 |
| Compound 129 | Fluazifop-butyl | 1:192 to 6:1 | 1:64 to 2:1 | 1:24 to 1:3 |
| Compound 129 | Flucarbazone | 1:8 to 135:1 | 1:2 to 45:1 | 1:1 to 9:1 |
| Compound 129 | Flucetosulfuron | 1:8 to 135:1 | 1:2 to 45:1 | 1:1 to 9:1 |
| Compound 129 | Flufenacet | 1:257 to 5:1 | 1:85 to 2:1 | 1:32 to 1:4 |
| Compound 129 | Flumetsulam | 1:24 to 48:1 | 1:8 to 16:1 | 1:3 to 3:1 |
| Compound 129 | Flumiclorac-pentyl | 1:10 to 112:1 | 1:3 to 38:1 | 1:1 to 7:1 |
| Compound 129 | Flumioxazin | 1:25 to 45:1 | 1:8 to 15:1 | 1:3 to 3:1 |
| Compound 129 | Fluometuron | 1:384 to 3:1 | 1:128 to 1:1 | 1:48 to 1:6 |
| Compound 129 | Flupyrsulfuron-methyl | 1:3 to 336:1 | 1:1 to 112:1 | 2:1 to 21:1 |
| Compound 129 | Fluridone | 1:384 to 3:1 | 1:128 to 1:1 | 1:48 to 1:6 |
| Compound 129 | Fluroxypyr | 1:96 to 12:1 | 1:32 to 4:1 | 1:12 to 1:2 |
| Compound 129 | Flurtamone | 1:857 to 2:1 | 1:285 to 1:3 | 1:107 to 1:12 |
| Compound 129 | Fluthiacet-methyl | 1:48 to 42:1 | 1:16 to 14:1 | 1:3 to 3:1 |
| Compound 129 | Fomesafen | 1:96 to 12:1 | 1:32 to 4:1 | 1:12 to 1:2 |
| Compound 129 | Foramsulfuron | 1:13 to 84:1 | 1:4 to 28:1 | 1:1 to 6:1 |
| Compound 129 | Glufosinate | 1:288 to 4:1 | 1:96 to 2:1 | 1:36 to 1:4 |
| Compound 129 | Glyphosate | 1:288 to 4:1 | 1:96 to 2:1 | 1:36 to 1:4 |
| Compound 129 | Halosulfuron-methyl | 1:17 to 68:1 | 1:5 to 23:1 | 1:2 to 5:1 |
| Compound 129 | Haloxyfop-methyl | 1:34 to 34:1 | 1:11 to 12:1 | 1:4 to 3:1 |
| Compound 129 | Hexazinone | 1:192 to 6:1 | 1:64 to 2:1 | 1:24 to 1:3 |
| Compound 129 | Imazamox | 1:13 to 84:1 | 1:4 to 28:1 | 1:1 to 6:1 |
| Compound 129 | Imazapic | 1:20 to 56:1 | 1:6 to 19:1 | 1:2 to 4:1 |
| Compound 129 | Imazapyr | 1:85 to 14:1 | 1:28 to 5:1 | 1:10 to 1:2 |
| Compound 129 | Imazaquin | 1:34 to 34:1 | 1:11 to 12:1 | 1:4 to 3:1 |
| Compound 129 | Imazethabenz-methyl | 1:171 to 7:1 | 1:57 to 3:1 | 1:21 to 1:3 |
| Compound 129 | Imazethapyr | 1:24 to 48:1 | 1:8 to 16:1 | 1:3 to 3:1 |
| Compound 129 | Imazosulfuron | 1:27 to 42:1 | 1:9 to 14:1 | 1:3 to 3:1 |
| Compound 129 | Indanofan | 1:342 to 4:1 | 1:114 to 2:1 | 1:42 to 1:5 |
| Compound 129 | Indaziflam | 1:25 to 45:1 | 1:8 to 15:1 | 1:3 to 3:1 |
| Compound 129 | Iodosulfuron-methyl | 1:3 to 336:1 | 1:1 to 112:1 | 2:1 to 21:1 |
| Compound 129 | Ioxynil | 1:192 to 6:1 | 1:64 to 2:1 | 1:24 to 1:3 |
| Compound 129 | Ipfencarbazone | 1:85 to 14:1 | 1:28 to 5:1 | 1:10 to 1:2 |
| Compound 129 | Isoproturon | 1:384 to 3:1 | 1:128 to 1:1 | 1:48 to 1:6 |
| Compound 129 | Isoxaben | 1:288 to 4:1 | 1:96 to 2:1 | 1:36 to 1:4 |
| Compound 129 | Isoxaflutole | 1:60 to 20:1 | 1:20 to 7:1 | 1:7 to 2:1 |
| Compound 129 | Lactofen | 1:42 to 27:1 | 1:14 to 9:1 | 1:5 to 2:1 |
| Compound 129 | Lenacil | 1:384 to 3:1 | 1:128 to 1:1 | 1:48 to 1:6 |
| Compound 129 | Linuron | 1:384 to 3:1 | 1:128 to 1:1 | 1:48 to 1:6 |
| Compound 129 | MCPA | 1:192 to 6:1 | 1:64 to 2:1 | 1:24 to 1:3 |
| Compound 129 | MCPB | 1:288 to 4:1 | 1:96 to 2:1 | 1:36 to 1:4 |
| Compound 129 | Mecoprop | 1:768 to 2:1 | 1:256 to 1:2 | 1:96 to 1:11 |
| Compound 129 | Mefenacet | 1:384 to 3:1 | 1:128 to 1:1 | 1:48 to 1:6 |
| Compound 129 | Mefluidide | 1:192 to 6:1 | 1:64 to 2:1 | 1:24 to 1:3 |
| Compound 129 | Mesosulfuron-methyl | 1:5 to 224:1 | 1:1 to 75:1 | 1:1 to 14:1 |
| Compound 129 | Mesotrione | 1:42 to 27:1 | 1:14 to 9:1 | 1:5 to 2:1 |
| Compound 129 | Metamifop | 1:42 to 27:1 | 1:14 to 9:1 | 1:5 to 2:1 |
| Compound 129 | Metazachlor | 1:384 to 3:1 | 1:128 to 1:1 | 1:48 to 1:6 |
| Compound 129 | Metazosulfuron | 1:25 to 45:1 | 1:8 to 15:1 | 1:3 to 3:1 |
| Compound 129 | Methabenzthiazuron | 1:768 to 2:1 | 1:256 to 1:2 | 1:96 to 1:11 |
| Compound 129 | Metolachlor | 1:768 to 2:1 | 1:256 to 1:2 | 1:96 to 1:11 |
| Compound 129 | Metosulam | 1:8 to 135:1 | 1:2 to 45:1 | 1:1 to 9:1 |
| Compound 129 | Metribuzin | 1:192 to 6:1 | 1:64 to 2:1 | 1:24 to 1:3 |
| Compound 129 | Metsulfuron-methyl | 1:2 to 560:1 | 1:1 to 187:1 | 3:1 to 35:1 |
| Compound 129 | Molinate | 1:1028 to 2:1 | 1:342 to 1:3 | 1:128 to 1:15 |
| Compound 129 | Napropamide | 1:384 to 3:1 | 1:128 to 1:1 | 1:48 to 1:6 |
| Compound 129 | Naptalam | 1:192 to 6:1 | 1:64 to 2:1 | 1:24 to 1:3 |
| Compound 129 | Nicosulfuron | 1:12 to 96:1 | 1:4 to 32:1 | 1:1 to 6:1 |
| Compound 129 | Norflurazon | 1:1152 to 1:1 | 1:384 to 1:3 | 1:144 to 1:16 |
| Compound 129 | Orbencarb | 1:1371 to 1:2 | 1:457 to 1:4 | 1:171 to 1:20 |
| Compound 129 | Orthosulfamuron | 1:20 to 56:1 | 1:6 to 19:1 | 1:2 to 4:1 |
| Compound 129 | Oryzalin | 1:514 to 3:1 | 1:171 to 1:2 | 1:64 to 1:8 |
| Compound 129 | Oxadiargyl | 1:384 to 3:1 | 1:128 to 1:1 | 1:48 to 1:6 |

TABLE A1-continued

| Component (a) | Component (b) | Typical Weight Ratio | More Typical Weight Ratio | Most Typical Weight Ratio |
|---|---|---|---|---|
| Compound 129 | Oxadiazon | 1:548 to 3:1 | 1:182 to 1:2 | 1:68 to 1:8 |
| Compound 129 | Oxasulfuron | 1:27 to 42:1 | 1:9 to 14:1 | 1:3 to 3:1 |
| Compound 129 | Oxaziclomefone | 1:42 to 27:1 | 1:14 to 9:1 | 1:5 to 2:1 |
| Compound 129 | Oxyfluorfen | 1:384 to 3:1 | 1:128 to 1:1 | 1:48 to 1:6 |
| Compound 129 | Paraquat | 1:192 to 6:1 | 1:64 to 2:1 | 1:24 to 1:3 |
| Compound 129 | Pendimethalin | 1:384 to 3:1 | 1:128 to 1:1 | 1:48 to 1:6 |
| Compound 129 | Penoxsulam | 1:10 to 112:1 | 1:3 to 38:1 | 1:1 to 7:1 |
| Compound 129 | Penthoxamid | 1:384 to 3:1 | 1:128 to 1:1 | 1:48 to 1:6 |
| Compound 129 | Pentoxazone | 1:102 to 12:1 | 1:34 to 4:1 | 1:12 to 1:2 |
| Compound 129 | Phenmedipham | 1:102 to 12:1 | 1:34 to 4:1 | 1:12 to 1:2 |
| Compound 129 | Picloram | 1:96 to 12:1 | 1:32 to 4:1 | 1:12 to 1:2 |
| Compound 129 | Picolinafen | 1:34 to 34:1 | 1:11 to 12:1 | 1:4 to 3:1 |
| Compound 129 | Pinoxaden | 1:25 to 45:1 | 1:8 to 15:1 | 1:3 to 3:1 |
| Compound 129 | Pretilachlor | 1:192 to 6:1 | 1:64 to 2:1 | 1:24 to 1:3 |
| Compound 129 | Primisulfuron-methyl | 1:8 to 135:1 | 1:2 to 45:1 | 1:1 to 9:1 |
| Compound 129 | Prodiamine | 1:384 to 3:1 | 1:128 to 1:1 | 1:48 to 1:6 |
| Compound 129 | Profoxydim | 1:42 to 27:1 | 1:14 to 9:1 | 1:5 to 2:1 |
| Compound 129 | Prometryn | 1:384 to 3:1 | 1:128 to 1:1 | 1:48 to 1:6 |
| Compound 129 | Propachlor | 1:1152 to 1:1 | 1:384 to 1:3 | 1:144 to 1:16 |
| Compound 129 | Propanil | 1:384 to 3:1 | 1:128 to 1:1 | 1:48 to 1:6 |
| Compound 129 | Propaquizafop | 1:48 to 24:1 | 1:16 to 8:1 | 1:6 to 2:1 |
| Compound 129 | Propoxycarbazone | 1:17 to 68:1 | 1:5 to 23:1 | 1:2 to 5:1 |
| Compound 129 | Propyrisulfuron | 1:17 to 68:1 | 1:5 to 23:1 | 1:2 to 5:1 |
| Compound 129 | Propyzamide | 1:384 to 3:1 | 1:128 to 1:1 | 1:48 to 1:6 |
| Compound 129 | Prosulfocarb | 1:1200 to 1:2 | 1:400 to 1:4 | 1:150 to 1:17 |
| Compound 129 | Prosulfuron | 1:6 to 168:1 | 1:2 to 56:1 | 1:1 to 11:1 |
| Compound 129 | Pyraclonil | 1:42 to 27:1 | 1:14 to 9:1 | 1:5 to 2:1 |
| Compound 129 | Pyraflufen-ethyl | 1:5 to 224:1 | 1:1 to 75:1 | 1:1 to 14:1 |
| Compound 129 | Pyrasulfotole | 1:13 to 84:1 | 1:4 to 28:1 | 1:1 to 6:1 |
| Compound 129 | Pyrazolynate | 1:857 to 2:1 | 1:285 to 1:3 | 1:107 to 1:12 |
| Compound 129 | Pyrazosulfuron-ethyl | 1:10 to 112:1 | 1:3 to 38:1 | 1:1 to 7:1 |
| Compound 129 | Pyrazoxyfen | 1:5 to 224:1 | 1:1 to 75:1 | 1:1 to 14:1 |
| Compound 129 | Pyribenzoxim | 1:10 to 112:1 | 1:3 to 38:1 | 1:1 to 7:1 |
| Compound 129 | Pyributicarb | 1:384 to 3:1 | 1:128 to 1:1 | 1:48 to 1:6 |
| Compound 129 | Pyridate | 1:288 to 4:1 | 1:96 to 2:1 | 1:36 to 1:4 |
| Compound 129 | Pyriftalid | 1:10 to 112:1 | 1:3 to 38:1 | 1:1 to 7:1 |
| Compound 129 | Pyriminobac-methyl | 1:20 to 56:1 | 1:6 to 19:1 | 1:2 to 4:1 |
| Compound 129 | Pyrimisulfan | 1:17 to 68:1 | 1:5 to 23:1 | 1:2 to 5:1 |
| Compound 129 | Pyrithiobac | 1:24 to 48:1 | 1:8 to 16:1 | 1:3 to 3:1 |
| Compound 129 | Pyroxasulfone | 1:85 to 14:1 | 1:28 to 5:1 | 1:10 to 1:2 |
| Compound 129 | Pyroxsulam | 1:5 to 224:1 | 1:1 to 75:1 | 1:1 to 14:1 |
| Compound 129 | Quinclorac | 1:192 to 6:1 | 1:64 to 2:1 | 1:24 to 1:3 |
| Compound 129 | Quizalofop-ethyl | 1:42 to 27:1 | 1:14 to 9:1 | 1:5 to 2:1 |
| Compound 129 | Rimsulfuron | 1:13 to 84:1 | 1:4 to 28:1 | 1:1 to 6:1 |
| Compound 129 | Saflufenacil | 1:25 to 45:1 | 1:8 to 15:1 | 1:3 to 3:1 |
| Compound 129 | Sethoxydim | 1:96 to 12:1 | 1:32 to 4:1 | 1:12 to 1:2 |
| Compound 129 | Simazine | 1:384 to 3:1 | 1:128 to 1:1 | 1:48 to 1:6 |
| Compound 129 | Sulcotrione | 1:120 to 10:1 | 1:40 to 4:1 | 1:15 to 1:2 |
| Compound 129 | Sulfentrazone | 1:147 to 8:1 | 1:49 to 3:1 | 1:18 to 1:3 |
| Compound 129 | Sulfometuron-methyl | 1:34 to 34:1 | 1:11 to 12:1 | 1:4 to 3:1 |
| Compound 129 | Sulfosulfuron | 1:8 to 135:1 | 1:2 to 45:1 | 1:1 to 9:1 |
| Compound 129 | Tebuthiuron | 1:384 to 3:1 | 1:128 to 1:1 | 1:48 to 1:6 |
| Compound 129 | Tefuryltrione | 1:42 to 27:1 | 1:14 to 9:1 | 1:5 to 2:1 |
| Compound 129 | Tembotrione | 1:31 to 37:1 | 1:10 to 13:1 | 1:3 to 3:1 |
| Compound 129 | Tepraloxydim | 1:25 to 45:1 | 1:8 to 15:1 | 1:3 to 3:1 |
| Compound 129 | Terbacil | 1:288 to 4:1 | 1:96 to 2:1 | 1:36 to 1:4 |
| Compound 129 | Terbuthylatrazine | 1:857 to 2:1 | 1:285 to 1:3 | 1:107 to 1:12 |
| Compound 129 | Terbutryn | 1:192 to 6:1 | 1:64 to 2:1 | 1:24 to 1:3 |
| Compound 129 | Thenylchlor | 1:85 to 14:1 | 1:28 to 5:1 | 1:10 to 1:2 |
| Compound 129 | Thiazopyr | 1:384 to 3:1 | 1:128 to 1:1 | 1:48 to 1:6 |
| Compound 129 | Thiencarbazone | 1:3 to 336:1 | 1:1 to 112:1 | 2:1 to 21:1 |
| Compound 129 | Thifensulfuron-methyl | 1:5 to 224:1 | 1:1 to 75:1 | 1:1 to 14:1 |
| Compound 129 | Tiafenacil | 1:17 to 68:1 | 1:5 to 23:1 | 1:2 to 5:1 |
| Compound 129 | Thiobencarb | 1:768 to 2:1 | 1:256 to 1:2 | 1:96 to 1:11 |
| Compound 129 | Topramazone | 1:6 to 168:1 | 1:2 to 56:1 | 1:1 to 11:1 |
| Compound 129 | Tralkoxydim | 1:68 to 17:1 | 1:22 to 6:1 | 1:8 to 2:1 |
| Compound 129 | Triallate | 1:768 to 2:1 | 1:256 to 1:2 | 1:96 to 1:11 |
| Compound 129 | Triasulfuron | 1:5 to 224:1 | 1:1 to 75:1 | 1:1 to 14:1 |
| Compound 129 | Triaziflam | 1:171 to 7:1 | 1:57 to 3:1 | 1:21 to 1:3 |
| Compound 129 | Tribenuron-methyl | 1:3 to 336:1 | 1:1 to 112:1 | 2:1 to 21:1 |
| Compound 129 | Triclopyr | 1:192 to 6:1 | 1:64 to 2:1 | 1:24 to 1:3 |
| Compound 129 | Trifloxysulfuron | 1:2 to 420:1 | 1:1 to 140:1 | 2:1 to 27:1 |
| Compound 129 | Trifluralin | 1:288 to 4:1 | 1:96 to 2:1 | 1:36 to 1:4 |
| Compound 129 | Triflusulfuron-methyl | 1:17 to 68:1 | 1:5 to 23:1 | 1:2 to 5:1 |
| Compound 129 | Tritosulfuron | 1:13 to 84:1 | 1:4 to 28:1 | 1:1 to 6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 and A4 are constructed similarly.

| Table Number | Component (a) Column Entries |
|---|---|
| A2 | Compound 14 |
| A3 | Compound 15 |
| A4 | Compound 16 |
| A5 | Compound 47 |
| A6 | Compound 129 |
| A7 | Compound 164 |
| A8 | Compound 196 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group glyphosate, chlorimuron-ethyl, nicosulfuron, mesotrione, thifensulfuron-methyl, flupyrsulfuron-methyl, tribenuron, pyroxasulfone. pinoxaden, tembotrione, florasulam, pyroxsulam, metolachlor and S-metolachlor.

The following Tests demonstrate the control efficacy of the compounds of this invention against specific weeds. The weed control afforded by the compounds is not limited, however, to these species. See Index Tables A-B for compound descriptions. The following abbreviations are used in the Index Tables which follow: t is tertiary, s is secondary, n is normal, i is iso, c is cyclo, Pr is propyl, Bu is butyl, c-Pr is cyclopropyl, t-Bu is tert-butyl, Ph is phenyl, thiene means thiophene, 4-pyridinyl(2-$CF_3$) corresponds to structure J-2A, and —$NO_2$ is nitro. The abbreviation "Ex." stands for "Example" and is followed by a number indicating in which example the compound is prepared.

INDEX TABLE A

| Compd. No. | $R^1$ | A | Q | J | M.P. (° C.) or M.S. (AP+) |
|---|---|---|---|---|---|
| 1 (Ex. 3) | $CH_3$ | phenyl(4-$CF_3$) | O | 3-thienyl(5-$CF_3$) | 392 # ** |
| 2 | $CH_3$ | phenyl(4-F) | $CH_2$ | 1H-pyrazol-1-yl(3-$CF_3$) | 40-42 |
| 3 | $CH_3$ | 4-pyridinyl(2-F) | C═O | phenyl(3-$CF_3$) | 351 |
| 4 | $CH_3$ | 4-pyridinyl(2-Cl) | C═O | phenyl(3-$CF_3$) | 367 |
| 5 | $CH_3$ | phenyl(2-Cl) | C═O | phenyl(3-$CF_3$) | 366 |
| 6 | $CH_3$ | phenyl(2-$SCH_3$) | C═O | phenyl(3-$CF_3$) | 378 |
| 7 | $CH_3$ | 2-pyridinyl(5-$CF_3$) | $CH_2$ | 1H-pyrazol-1-yl(3-$CF_3$) | 377 |
| 8 | $CH_3$ | 2-pyridinyl(5-$CF_3$) | $CH_2$ | 1H-1,2,4-triazol-1-yl(3-$CF_3$) | 378 |
| 9 | $CH_3$ | phenyl(4-$CF_3$) | $CH_2$ | 1H-imidazol-1-yl(2-Cl,4-$CF_3$) | 119-121 |
| 10 | $CH_2CH_3$ | phenyl(4-F) | $CH_2$ | 1H-pyrazol-1-yl(3-$CF_2CF_3$) | * |
| 11 | $CH_3$ | phenyl(4-$CF_3$) | $CH_2$ | 1H-imidazol-1-yl(2,5-di-Cl,4-$CF_3$) | 118-120 |
| 12 | $CH_3$ | phenyl(4-$CF_3$) | $CH_2$ | 1H-pyrazol-1-yl(3-$CF_2CF_3$) | 54-57 |
| 13 | $CH_3$ | phenyl(4-$CF_3$) | $CH_2$ | 1H-imidazol-1-yl(5-Cl,4-$CF_3$) | 124-126 |
| 14 | $OCH_2CF_3$ | phenyl(4-$CF_3$) | $CH_2$ | 4-pyridinyl(2-$CF_3$) | 471 |
| 15 (Ex. 1) | $OCH_3$ | pheny(4-$CF_3$) | $CH_2$ | 4-pyridinyl(2-$CF_3$) | 403 ** |
| 16 | $CH_3$ | phenyl(4-F) | $CH_2$ | 4-pyridinyl(2-$CF_3$) | 337 |
| 17 (Ex. 2) | $OCH_3$ | phenyl(4-$CF_3$) | $CH_2$ | 1H-pyrazol-1-yl(3- | 392 ** |
| 18 | $OCH_3$ | phenyl(4-$CF_3$) | $CH_2$ | 1H-1,2,4-triazol-1-yl(3-$CF_3$) | 393 |
| 19 | $OCH_3$ | phenyl(4-$CF_3$) | $CH_2$ | 1H-imidazol-1-yl(3-$CF_3$) | 392 |
| 20 | $CH_3$ | phenyl(4-F) | $CH_2$ | 1H-imidazol-1-yl(2,5-di-Cl,4-$CF_3$) | 126-128 |
| 21 | $CH_3$ | 2-pyridinyl(5-$CF_3$) | $CH_2$ | 1H-pyrazol-1-yl(3-$CF_3$,5-$CH_3$) | 391 |
| 22 | $CH_3$ | 4-pyridinyl | C═O | phenyl(3-$CF_3$) | 333 |
| 23 | $CH_3$ | 2-pyridinyl(5-$CF_3$) | O | 4-pyridinyl(2-$CF_3$) | ** |
| 24 | $OCH_3$ | phenyl(4-F) | C═O | 4-pyridinyl(2-$CF_3$) | 367 |
| 25 | $OCHF_2$ | phenyl(4-F) | $CH_2$ | 4-pyridinyl(2-$CF_3$) | 389 |
| 26 | $OCHF_2$ | phenyl(4-$CF_3$) | $CH_2$ | 4-pyridinyl(2-$CF_3$) | 439 |
| 27 | $SCH_3$ | phenyl(4-F) | $CH_2$ | 4-pyridinyl(2-$CF_3$) | 369 |
| 28 | Cl | phenyl(4-$CF_3$) | $CH_2$ | 4-pyridinyl(2-$CF_3$) | 407 |
| 29 | $OCH_3$ | phenyl(4-$CF_3$) | $CH_2$ | phenyl(3-$CF_3$) | 402 |
| 30 | $OCH_3$ | phenyl(4-$CF_3$) | $CH_2$ | 1H-pyrazol-1-yl(3,5-di-$CF_3$) | * |
| 31 | $CH_3$ | phenyl(4-$CF_3$) | $CH_2$ | 4-pyridinyl(2-$OCH_3$) | * |
| 32 | $CH_3$ | phenyl(4-$CF_3$) | $CH_2$ | 1H-pyrazol-1-yl(4-$CF_3$) | * |
| 33 | $CH_3$ | phenyl(4-F) | $CH_2$ | 4-pyridinyl(2-$OCH_2CF_3$) | 367 |

INDEX TABLE A-continued

| Compd. No. | $R^1$ | A | Q | J | M.P. (° C.) or M.S. ($AP^+$) |
|---|---|---|---|---|---|
| 34 | $OCH_3$ | phenyl(4-F) | O | 4-pyridinyl(2-$CF_3$) | 355 |
| 35 | $CH_3$ | phenyl(4-F) | $CH_2$ | 1H-imidazol-1-yl(2-Cl,4-$CF_3$) | 124-126 |
| 36 | $CH_3$ | phenyl(4-F) | $CH_2$ | 1H-imidazol-1-yl(5-Cl,4-$CF_3$) | 93-95 |
| 37 | $CH_3$ | phenyl(4-$CF_3$) | O | 3-pyridinyl(5-$CF_3$) | 389 |
| 38 | $CH_3$ | phenyl(3-$CF_3$) | O | 4-pyrimidinyl(6-$CF_3$) | 390 |
| 39 | $CH_3$ | 2-pyridinyl(5-F) | C═O | phenyl(3-$CF_3$) | 321 |
| 40 | $CH_3$ | phenyl(3-$CF_3$) | O | 4-pyridinyl(2-$CF_3$) | 389 |
| 41 | $CH_3$ | phenyl(4-$NO_2$) | C═O | phenyl(3-$CF_3$) | * |
| 42 | $CH_3$ | phenyl(4-Cl) | C═O | phenyl(3-$CF_3$) | * |
| 43 | $CH_3$ | phenyl | C═O | phenyl(3-$CF_3$) | 332 |
| 44 | $CH_3$ | phenyl(4-$CH_3$) | C═O | phenyl(3-$CF_3$) | 346 |
| 45 | $CH_3$ | phenyl(4-$CF_3$) | C═O | phenyl(3-$CF_3$) | * |
| 47 | $CH_3$ | phenyl(4-$CF_3$) | $CH_2$ | 4-pyridinyl(2-$CF_3$) | 387 |
| 48 | $CH_3$ | phenyl(4-$CF_3$) | O | 4-pyridinyl(2-$OCHF_2$) | 387 |
| 49 | $CH_3$ | 4-pyridinyl(2-$CF_3$) | C═O | phenyl(3-$CF_3$) | 401 |
| 50 | $CH_3$ | 5-pyrazinyl(2-Cl) | C═O | phenyl(3-$CF_3$) | 368 |
| 51 | $CH_3$ | phenyl(4-$CF_3$) | $CH_2$ | 1H-pyrazol-4-yl(1-$CH_2CF_3$) | 390 |
| 52 | $CH_3$ | phenyl(4-Cl) | O | 4-pyridinyl(2-$CF_3$) | 355 |
| 53 | $CH_3$ | phenyl(4-Br) | O | 4-pyridinyl(2-$CF_3$) | 400 |
| 54 (Ex. 10) | $CH_3$ | phenyl(2,4-di-F) | $CH_2$ | 4-pyridinyl(2-$CF_3$) | 355 ** |
| 55 | $CH_3$ | phenyl(3,4-di-F) | $CH_2$ | 4-pyridinyl(2-$CF_3$) | 355 |
| 56 | $CH_3$ | phenyl(4-F) | O | phenyl(4-F,3-$CF_3$) | 356 |
| 57 | $CH_3$ | 2-pyridinyl(6-$CF_3$) | C═O | phenyl(3-$CF_3$) | 400 |
| 58 | $CH_3$ | 3-pyridazinyl(6-$CF_3$) | C═O | phenyl($CF_3$) | * |
| 59 | $CH_3$ | 1H-1,2,4-thiadiazol-5-yl(3-Cl) | C═O | phenyl(3-$CF_3$) | 374 |
| 60 | $CH_3$ | 2-pyridinyl | C═O | phenyl(3-$CF_3$) | 333 |
| 61 | $CH_3$ | phenyl(4-I) | C═O | phenyl(3-$CF_3$) | * |
| 62 | $CH_3$ | phenyl(3-$NO_2$) | C═O | phenyl(3-$CF_3$) | |
| 63 | $CH_3$ | phenyl(2-$NO_2$) | C═O | phenyl(3-$CF_3$) | |
| 64 | $CH_3$ | phenyl(3-$CF_3$) | O | 1H-pyrazol-5-yl(3-$CF_3$,1-$CH_3$) | 392 |
| 65 | $CH_3$ | phenyl(2-Cl,4-F) | $CH_2$ | 4-pyridinyl(2-$CF_3$) | 371 |
| 66 | $CH_3$ | 3-pyridinyl(5-$CF_3$) | C═O | phenyl(3-$CF_3$) | 401 |
| 68 | $CH_3$ | 2-pyridinyl(5-$CHF_2$) | C═O | phenyl(3-$CF_3$) | 383 |
| 69 | $CH_3$ | phenyl(4-$CF_3$) | NH | phenyl(3-$CF_3$) | 101-104 |
| 70 | $CH_3$ | phenyl(3-$CF_3$) | O | phenyl(3-$CF_3$) | 388 |
| 71 | $CH_3$ | phenyl(4-F) | O | 4-pyridinyl(2-$OCH_2CF_3$) | 369 |
| 72 | $CH_3$ | 3-pyridinyl(6-Cl) | C═O | phenyl(3-$CF_3$) | 367 |
| 73 | $CH_3$ | 3-pyridinyl(6-$CF_3$) | C═O | phenyl(3-$CF_3$) | 401 |
| 74 | $CH_3$ | phenyl(4-$CF_3$) | O | 1H-pyrazol-4-yl(1-$CH_2CF_3$) | 392 |
| 75 | $OCH_3$ | phenyl(4-$CF_3$) | C═O | 4-pyridinyl(2-$CF_3$) | 417 |
| 76 | $CH_3$ | phenyl(3-Cl) | C═O | phenyl(3-$CF_3$) | * |
| 77 | $CH_3$ | phenyl(4-$CF_3$) | O | 4-pyridinyl(2-$OCH_2CF_3$) | 419 |
| 78 | $OCH_3$ | phenyl(4-$CF_3$) | CH(OH) | 4-pyridinyl(2-$CF_3$) | * |
| 79 | $OCH_3$ | phenyl(4-$CF_3$) | $CCH_3$(OH) | 4-pyridinyl(2-$CF_3$) | * |
| 80 | $OCH_3$ | phenyl(4-$CF_3$) | CHF | 4-pyridinyl(2-$CF_3$) | 421 |
| 82 | $CH_3$ | phenyl(4-$CF_3$) | O | phenyl(2-Cl) | 354 |
| 83 | $CH_3$ | phenyl(4-$CF_3$) | O | phenyl(4-$CF_3$) | 69-71 |
| 84 | $CH_3$ | phenyl(4-$CF_3$) | O | phenyl(3-Cl) | 73-75 |
| 86 | $CH_3$ | phenyl(4-F) | O | phenyl(4-F,3-$CH_3$) | 302 |
| 87 | $CH_3$ | phenyl(4-F) | O | 4-pyridinyl(3-$CH_3$) | 285 |
| 88 | $CH_3$ | phenyl(4-$CF_3$) | S | phenyl(3-$CF_3$) | 404 |
| 90 | $CH_3$ | phenyl(3-I) | C═O | phenyl(3-$CF_3$) | * |
| 91 | $CH_3$ | phenyl(2-I) | C═O | phenyl(3-$CF_3$) | * |
| 92 | $CH_3$ | phenyl(4-Br) | C═O | phenyl(3-$CF_3$) | * |
| 93 | $CH_3$ | phenyl(4-$SCH_3$) | C═O | phenyl(3-$CF_3$) | 378 |
| 94 | $CH_3$ | phenyl(4-F) | $CH_2$ | 1H-1,2,4-triazol-1-yl(3-$CF_3$) | 327 |
| 95 | $CH_3$ | phenyl(4-F) | $CH_2$ | 1H-pyrazol-1-yl(3-$CF_3$) | 83-85 |
| 96 | $CH_3$ | phenyl(4-$CF_3$) | $CH_2$ | 1H-imidazol-1-yl(4-$CF_3$) | 106-109 |
| 97 | $CH_3$ | phenyl(4-F) | $CH_2$ | 1H-pyrazol-1-yl(3-$CF_3$,5-$CH_3$) | 91-93 |
| 98 | $CH_3$ | phenyl(4-F) | O | phenyl(3-$CF_3$) | * |
| 99 | $CH_3$ | phenyl(4-F) | O | phenyl(4-Cl,3-$CF_3$) | * |
| 100 | $CH_3$ | phenyl(4-F) | O | phenyl(3-$OCF_3$) | * |
| 101 | $CH_3$ | phenyl(4-F) | O | 4-pyrimidinyl(2-$CF_3$) | * |
| 102 | $CH_3$ | phenyl(4-F) | O | 2-pyrimidinyl(4-$CF_3$) | * |

INDEX TABLE A-continued

| Compd. No. | $R^1$ | A | Q | J | M.P. (° C.) or M.S. ($AP^+$) |
|---|---|---|---|---|---|
| 103 | $CH_3$ | phenyl(4-$CF_3$) | O | phenyl(4-Cl,3-$CF_3$) | * |
| 104 | $CH_3$ | phenyl(4-$CF_3$) | O | 1H-pyrazol-5-yl(1-$CH_3$,3-$CF_3$) | * |
| 105 | Br | 2-pyridinyl(5-$CF_3$) | $CH_2$ | phenyl(3-$CF_3$) | 453 |
| 106 | $CH_3$ | 2-pyridinyl(5-$CF_3$) | $CH_2$ | phenyl(3-$CF_3$) | 387 |
| 107 | $CH_3$ | 2-pyridinyl(5-$CF_3$) | C═O | phenyl(3-$CF_3$) | 401 |
| 108 | $CH_2CH_3$ | 2-pyridinyl(5-$CF_3$) | $CH_2$ | phenyl(3-$CF_3$) | * |
| 109 | $CH_3$ | 2-pyridinyl(5-$CF_3$) | O | phenyl(3-$CF_3$) | 389 |
| 110 | $CH_2OH$ | phenyl(4-$CF_3$) | O | phenyl(3-$CF_3$) | * |
| 111 | $CH_3$ | phenyl(4-CF3) | O | phenyl(3-$CF_3$) | * |
| 112 | $CH_3$ | phenyl(4-F) | $CH_2$ | 1H-imidazol-1-yl(4-$CF_3$) | 76-79 |
| 113 | $CH_2CH_3$ | phenyl(4-$CF_3$) | O | phenyl(3-$CF_3$) | * |
| 114 (Ex. 5) | $CH_2OH$ | phenyl(4-$CF_3$) | O | phenyl(3-$OCF_3$) | ** |
| 115 (Ex. 7) | $CH_2OCH_3$ | phenyl(4-$CF_3$) | O | phenyl(3-$OCF_3$) | ** |
| 116 (Ex. 8) | $CH_2F$ | phenyl(4-$CF_3$) | O | phenyl(3-$OCF_3$) | ** |
| 117 | $CH_3$ | phenyl(4-$CF_3$) | $CH_2$ | 1H-pyrazol-1-yl(3-$CF_3$) | 60-63 |
| 118 | $CH_2CH_3$ | phenyl(4-$CF_3$) | $CH_2$ | 1H-pyrazol-1-yl(3-$CF_3$) | 390 |
| 119 (Ex. 6) | $CH_3$ | phenyl(4-$CF_3$) | O | phenyl(3-$OCF_3$) | ** |
| 120 | $CH_3$ | phenyl(4-$CF_3$) | O | 4-pyridinyl(2-$CF_3$) | 78.3-78.8 |
| 121 | $CH_2CH_3$ | phenyl(4-$CF_3$) | $CH_2$ | 1H-imidazol-1-yl(5-Cl,4-$CF_3$) | 98-100 |
| 122 | $CH_2CH_3$ | phenyl(4-$CF_3$) | $CH_2$ | 1H-imidazol-1-yl(2-Cl,4-$CF_3$) | 82-84 |
| 123 | Br | phenyl(4-$CF_3$) | $CH_2$ | phenyl(3-$CF_3$) | * |
| 124 | $CH_3$ | phenyl(4-$CF_3$) | $CH_2$ | phenyl(3-$CF_3$) | * |
| 125 (Ex. 9) | $CH_2CH_3$ | phenyl(4-$CF_3$) | O | phenyl(3-$OCF_3$) | ** |
| 126 | $CH_3$ | phenyl(4-F) | O | 1H-pyrazol-5-yl(3-$CF_3$,1-$CH_3$) | 342 |
| 127 | $CH_3$ | phenyl(4-F) | O | 2-pyridinyl(6-$CF_3$) | * |
| 128 | $CH_3$ | phenyl(4-F) | O | 2-pyridinyl(4-$CF_3$) | * |
| 129 (Ex. 4) | $CH_3$ | phenyl(4-F) | O | 4-pyridinyl(2-$CF_3$) | 43.5-44.1 |
| 130 | $CH_2CH_3$ | phenyl(4-$CF_3$) | $CH_2$ | 1H-1,2,4-triazol-1-yl(3-$CF_3$) | 391 |
| 131 | $CH_2CH_3$ | phenyl(4-$CF_3$) | $CH_2$ | 1H-pyrazol-1-yl(3-$CF_3$,5-$CH_3$) | 74-76 |
| 132 | $CH_3$ | phenyl(4-$CF_3$) | $CH_2$ | 1H-1,2,4-triazol-1-yl(3-$CF_3$) | 377 |
| 133 | $CH_2CH_3$ | phenyl(4-$CF_3$) | $CH_2$ | 1H-imidazol-1-yl(4-$CF_3$) | 84-86 |
| 134 | $CH_3$ | phenyl(4-$CF_3$) | $CH_2$ | 1H-pyrazol-1-yl(3-$CF_3$,5-$CH_3$) | 101-103 |
| 135 | $CH_3$ | phenyl(4-F) | O | 4-pyridinyl(2-$CH_3$) | 285 |
| 136 | $CH_3$ | phenyl(3,4-di-F) | $CH_2$ | 4-pyridinyl(2-$CHF_2$) | 337, 335 # |
| 137 | $CH_3$ | 4-pyridinyl(2-$CF_3$) | $CH_2$ | 4-pyridinyl(2-$CF_3$) | 386 # |
| 138 | $OCH_3$ | phenyl(4-$CF_3$) | $CH_2$ | 4-pyridinyl(2-$CHF_2$) | 385, 383 # |
| 139 | $OCH_3$ | phenyl(5-F) | $CH_2$ | 4-pyridinyl(2-$CF_3$) | 353 |
| 140 | $CH_3$ | 4-pyridinyl(2-$CF_3$) | C═N—OMe | phenyl(3-$CF_3$) | 430 |
| 141 | $CH_3$ | 4-pyridinyl(2-Cl) | $CH_2$ | 4-pyridinyl(2-$CF_3$) | 354, 352 # |
| 142 | $OCH_2CF_3$ | phenyl(4-F) | $CH_2$ | 4-pyridinyl(2-$CF_3$) | 421 |
| 143 | $CH_2CH_3$ | phenyl(3-$CF_3$) | $CH_2$ | phenyl(3-$CF_3$) | 44-46 |
| 144 | $CH_2CH_3$ | phenyl(4-F) | $CH_2$ | phenyl(3-$CF_3$) | 45-47 |
| 145 | $CH_3$ | phenyl(3,4-di-F) | O | 4-pyridinyl(2-$CF_3$) | 357 |
| 146 | $CH_3$ | phenyl(2,4-di-F) | O | 4-pyridinyl(2-$CF_3$) | 357 |
| 147 | $CH_3$ | phenyl(4-F,3-$CF_3$) | O | 4-pyridinyl(2-$CF_3$) | 407 |
| 148 | $CH_3$ | phenyl(3-F,4-$CF_3$) | O | 4-pyridinyl(2-$CF_3$) | 407 |
| 149 | n-Pr | phenyl(4-F) | $CH_2$ | phenyl(3-$CF_3$) | 59-62 |
| 150 | $CH(CH_3)_2$ | phenyl(4-F) | $CH_2$ | phenyl(3-$CF_3$) | 364 |
| 151 | $CH(CH_3)_2$ | phenyl(4-F) | $CH_2$ | 4-pyridinyl(2-$CF_3$) | 365 |
| 152 | $OCH_3$ | phenyl(4-F) | $CH(CH_3)$ | 4-pyridinyl(2-$CF_3$) | 418 |
| 153 | n-Pr | phenyl(4-F) | $CH_2$ | 4-pyridinyl(2-$CF_3$) | 365 |
| 154 | $CH_2CH_3$ | phenyl(4-F) | $CH_2$ | 4-pyridinyl(2-$CF_3$) | 351 |
| 155 | $CH_2CH_3$ | phenyl(4-$CF_3$) | $CH_2$ | 4-pyridinyl(2-$CF_3$) | 401 |
| 156 | $CH_3$ | phenyl(4-F,3-$CF_3$) | $CH_2$ | 4-pyridinyl(2-$CF_3$) | 405 |
| 157 | $CH_3$ | phenyl(4-F) | $CH_2$ | phenyl(3-$CF_3$) | 336 |
| 158 | F | phenyl(4-F) | C═O | 4-pyridinyl(2-$CF_3$) | * |
| 159 | F | phenyl(4-F) | $CH_2$ | 4-pyridinyl(2-$CF_3$) | * |
| 160 | $CH_2F$ | phenyl(4-F) | O | 4-pyridinyl(2-$CF_3$) | * |
| 161 | $CH_2OCH_3$ | phenyl(4-F) | O | 4-pyridinyl(2-$CF_3$) | * |
| 162 | $CH_3$ | phenyl(3-F,4-$CF_3$) | $CH_2$ | 4-pyridinyl(2-$CF_3$) | 405 |
| 163 | $CH_2OCH_2CH_3$ | phenyl(4-F) | O | 4-pyridinyl(2-$CF_3$) | * |
| 164 | $OCH_2CH_3$ | phenyl(3-$CF_3$) | $CH_2$ | 4-pyridinyl(2-$CF_3$) | * |
| 165 | $OCH_3$ | phenyl(2,4-di-F) | $CH_2$ | 4-pyridinyl(2-$CF_3$) | 371 |
| 166 | $CH_2CH_3$ | phenyl(4-F) | O | 4-pyridinyl(2-$CF_3$) | * |
| 167 | $CH_3$ | phenyl(4-F) | C═O | 4-pyridinyl(2-$CF_3$) | * |

INDEX TABLE A-continued

| Compd. No. | $R^1$ | A | Q | J | M.P. (° C.) or M.S. ($AP^+$) |
|---|---|---|---|---|---|
| 168 | n-Pr | phenyl(4-F) | O | 4-pyridinyl(2-$CF_3$) | * |
| 169 | $CH_2CH_3$ | phenyl(4-$CF_3$) | O | 4-pyridinyl(2-$CF_3$) | * |
| 170 | n-Pr | phenyl(4-$CF_3$) | O | 4-pyridinyl(2-$CF_3$) | 417 |
| 171 | $CH_2CH_3$ | phenyl(3,4-di-F) | O | 4-pyridinyl(2-$CF_3$) | 371 |
| 172 | n-Pr | phenyl(3,4-di-F) | O | 4-pyridinyl(2-$CF_3$) | 385 |
| 173 | $CH_2CH_3$ | phenyl(3,4-di-F) | O | 4-pyridinyl(2-$CH_2F$) | 353 |
| 174 | n-Pr | phenyl(3,4-di-F) | O | 4-pyridinyl(2-$CH_2F$) | 367 |
| 175 | t-Bu | phenyl(4-F) | C═O | 4-pyridinyl(2-$CF_3$) | * |
| 176 | t-Bu | phenyl(4-F) | $CH_2$ | 4-pyridinyl(2-$CF_3$) | * |
| 177 | $OCH_2CH_3$ | phenyl(4-F) | C═O | 4-pyridinyl(2-$CF_3$) | * |
| 178 | $CH_2CH_3$ | phenyl(2,4-di-F) | O | 4-pyridinyl(2-$CF_3$) | 371 |
| 179 | n-Pr | phenyl(2,4-di-F) | O | 4-pyridinyl(2-$CF_3$) | 385 |
| 180 | $CH_2CH_3$ | phenyl(4-F,3-$CF_3$) | O | 4-pyridinyl(2-$CF_3$) | 421 |
| 181 | $CH_2CH_3$ | phenyl(2,4-di-F) | O | 4-pyridinyl(2-$CHF_2$) | 353 |
| 182 | n-Pr | phenyl | O | 4-pyridinyl(2-$CHF_2$) | 367 |
| 183 | CH2CH3 | phenyl(3-F,4-$CF_3$) | O | 4-pyridinyl(2-$CF_3$) | 421 |
| 184 | n-Bu | phenyl(4-CF3) | O | 4-pyridinyl(2-$CF_3$) | * |
| 185 | n-Pr | phenyl(3-F,4-$CF_3$) | O | 4-pyridinyl(2-$CF_3$) | * |
| 186 | $CH_2CH(CH_3)_2$ | phenyl(4-$CF_3$) | O | 4-pyridinyl(2-$CF_3$) | 431 |
| 187 | $CH_2$CH(CH3)$_2$ | phenyl(4-$CF_3$) | O | 4-pyridinyl(2-$CHF_2$) | 413 |
| 188 | $OCH_2CH_3$ | phenyl(4-Cl) | $CH_2$ | 4-pyridinyl(2-$CF_3$) | * |
| 189 | $OCH_2CH_3$ | phenyl(4-Br) | $CH_2$ | 4-pyridinyl(2-$CF_3$) | * |
| 190 | $OCH_2CH_3$ | phenyl(2,4-di-F) | $CH_2$ | 4-pyridinyl(2-$CF_3$) | * |
| 191 | O-n-Pr | phenyl(4-$CF_3$) | $CH_2$ | 4-pyridinyl(2-$CF_3$) | * |
| 192 | $OCH(CH_3)_2$ | phenyl(4-$CF_3$) | $CH_2$ | 4-pyridinyl(2-$CF_3$) | * |
| 193 | $OCH_2CH(CH_3)_2$ | phenyl(4-$CF_3$) | $CH_2$ | 4-pyridinyl(2-$CF_3$) | * |
| 194 | O-n-Bu | phenyl(4-$CF_3$) | $CH_2$ | 4-pyridinyl(2-$CF_3$) | * |
| 195 | $OCH_2CH_3$ | phenyl(4-F) | $CH_2$ | 4-pyridinyl(2-$CHF_2$) | * |
| 196 (Ex. 11) | $OCH_2CH_3$ | phenyl(4-F) | $CH_2$ | 4-pyridinyl(2-$CF_3$) | 59-60 |
| 197 | OC(═O)$CH_3$ | phenyl(4-$CF_3$) | $CH_2$ | 4-pyridinyl(2-$CF_3$) | * |
| 198 | OH | phenyl(4-$CF_3$) | $CH_2$ | 4-pyridinyl(2-$CF_3$) | 389 |
| 199 | c-Pr | phenyl(3-$CF_3$) | O | 4-pyridinyl(2-$CF_3$) | 397 |
| 200 | c-Pr | phenyl(3-$CF_3$) | O | 4-pyridinyl(2-$CF_3$) | 415 |
| 201 | $CH_3$ | 2-pyridinyl(5-$CF_3$) | C═N—OH | phenyl(3-$CF_3$) | 416 |

* See Index Table B for $^1$H NMR data.
** See Synthesis Example for $^1$H NMR data.
\# reported as $AP^-$.

INDEX TABLE B

| Compd. No. | $^1$H NMR data[a] |
|---|---|
| 10 | 1.21 (t, 3H), 2.70 (q, 2H), 5.53 (s, 2H), 6.55 (d, 1H), 7.55 (t, 1H), 7.73 (d, 2H), 8.15 (d, 2H) |
| 23 | 2.42 (s, 3H), 7.39 (m, 1H), 7.57 (m, 1H), 8.06 (m, 1H), 8.13 (m, 1H), 8.69 (m, 1H), 8.84 (s, 1H) |
| 30 | 4.04 (s, 3H), 5.55 (s, 2H), 6.93 (s, 1H), 7.66-7.71 (m, 2H), 8.00-8.04 (m, 2H) |
| 31 | 2.26 (s, 3H), 3.92 (s, 3H), 4.02 (s, 2H), 6.58-6.61 (m, 1H), 6.75-6.79 (m, 1H), 7.69-7.73 (m, 2H), 8.07-8.14 (m, 3H) |
| 32 | 2.36 (s, 3H), 5.46 (s, 2H), 7.72-7.75 (m, 3H), 7.77 (s, 1H), 8.12-8.16 (m, 2H) |
| 41 | 2.73 (s, 3H), 7.67-7.73 (m, 1H), 7.89-7.93 (m, 1H), 8.25-8.30 (m, 2H), 8.37-8.42 (m, 2H), 8.46-8.50 (m, 1H), 8.60-8.63 (m, 1H) |
| 42 | 2.71 (s, 3H), 7.47-7.51 (m, 2H), 7.65-7.70 (m, 1H), 7.86-7.91 (m, 1H), 8.03-8.07 (m, 2H), 8.46-8.50 (m, 1H), 8.61-8.64 (m, 1H) |
| 45 | 2.73 (s, 3H), 7.66-7.72 (m, 1H), 7.77-7.82 (m, 2H), 7.88-7.92 (m, 1H), 8.22-8.26 (m, 2H), 8.47-8.50 (m, 1H), 8.63-8.65 (m, 1H) |
| 58 | 2.80 (s, 3H), 7.68-7.73 (m, 1H), 7.89-7.93 (m, 1H), 8.04-8.08 (m, 1H), 8.42-8.45 (m, 1H), 8.55-8.59 (m, 2H) |
| 61 | 2.71 (s, 3H), 7.64-7.69 (m, 1H), 7.82-7.90 (m, 5H), 8.45-8.49 (m, 1H), 8.61-8.64 (m, 1H) |
| 62 | 2.74 (s, 3H), 7.68-7.75 (m, 2H), 7.89-7.93 (m, 1H), 8.25-8.29 (m, 1H), 8.42-8.51 (m, 2H), 8.61-8.64 (m, 1H), 8.96-8.98 (m, 1H) |
| 63 | 2.71 (s, 3H), 7.58-7.69 (m, 2H), 7.72-7.77 (m, 1H), 7.83-7.90 (m, 2H), 7.95-7.99 (m, 1H), 8.37-8.41 (m, 1H), 8.45-8.48 (m, 1H) |
| 76 | 2.71 (s, 3H), 7.36-7.47 (m, 2H), 7.66-7.71 (m, 1H), 7.86-7.91 (m, 1H), 7.97-8.01 (m, 1H), 8.12-8.16 (m, 1H), 8.47-8.51 (m, 1H), 8.61-8.63 (m, 1H) |
| 78 | 2.89-2.91 (m, 1H), 4.07 (s, 3H), 6.07-6.10 (m, 1H), 7.60-7.63 (m, 1H), 7.68-7.72 (m, 2H), 7.85-7.87 (m, 1H), 8.00-8.04 (m, 2H), 8.72-8.75 (m, 1H) |
| 79 | 1.54 (s, 3H), 3.38 (s, 1H), 4.05 (s, 3H), 7.58-7.62 (m, 1H), 7.69-7.73 (m, 2H), 7.87-7.89 (m, 1H), 8.02-8.06 (m, 2H), 8.68-8.70 (m, 1H) |
| 90 | 2.71 (s, 3H), 7.22-7.27 (m, 1H), 7.66-7.77 (m, 2H), 7.88-7.91 (m, 1H), 8.05-8.09 (m, 1H), 8.46-8.50 (m, 2H), 8.61-8.64 (m, 1H) |
| 91 | 2.74 (s, 3H), 7.21-7.26 (m, 1H), 7.48-7.67 (m, 3H), 7.83-7.87 (m, 1H), 8.02-8.06 (m, 1H), 8.55-8.59 (m, 1H), 8.65-8.68 (m, 1H) |
| 92 | 2.71 (s, 3H), 7.62-7.70 (m, 3H), 7.86-7.91 (m, 1H), 7.96-8.01 (m, 2H), 8.46-8.50 (m, 1H), 8.61-8.64 (m, 1H) |

INDEX TABLE B-continued

| Compd. No. | $^1$H NMR data[a] |
|---|---|
| 98 | 2.29 (s, 3H), 7.14 (m, 2H), 7.42 (m, 4H), 7.91 (m, 2H) |
| 99 | 2.31 (s, 3H), 7.13 (m, 2H), 7.33 (m, 1H), 7.49 (m, 1H), 7.57 (m, 1H), 7.90 (m, 2H) |
| 100 | 2.29 (s, 3H), 7.02 (m, 1H), 7.13 (m, 3H), 7.33 (m, 1H), 7.92 (m, 2H) |
| 101 | 2.28 (s, 3H), 7.16 (m, 2H), 7.30 (m, 1H), 7.94 (m, 2H), 8.84 (m, 1H) |
| 102 | 2.27 (s, 3H), 7.15 (m, 2H), 7.47 (m, 1H), 7.95 (m, 2H), 8.82 (m, 1H) |
| 103 | 2.34 (s, 3H), 7.35-7.39 (m, 1H), 7.49-7.53 (m, 1H), 7.59-7.62 (m, 1H), 7.68-7.73 (m, 2H), 8.01-8.05 (m, 2H) |
| 104 | 2.38 (m, 3H), 3.89-3.91 (m, 3H), 6.73-6.74 (m, 1H), 7.89-7.94 (m, 2H), 8.09-8.13 (m, 2H) (dmso $d_6$) |
| 108 | 1.18-1.24 (m, 3H), 2.60-2.66 (m, 2H), 4.21 (s, 2H), 7.40-7.54 (m, 4H), 8.05-8.16 (m, 2H), 8.80-8.85 (m, 1H) |
| 110 | 1.96 (br s, 1H), 4.81-4.85 (m, 2H), 7.44-7.58 (m, 4H), 7.70-7.74 (m, 2H), 8.04-8.08 (m, 2H) |
| 111 | 2.33 (s, 3H), 7.39-7.53 (m, 4H), 7.68-7.72 (m, 2H), 8.02-8.06 (m, 2H) |
| 113 | 1.30-1.35 (m, 3H), 2.69-2.75 (m, 2H), 7.39-7.53 (m, 4H), 7.68-7.72 (m, 2H), 8.03-8.07 (m, 2H) |
| 123 | 4.16 (s, 2H), 7.42-7.60 (m, 3H), 7.72-7.76 (m, 2H), 8.12-8.16 (m, 2H) |
| 124 | 2.25 (s, 3H), 4.14 (s, 2H), 7.42-7.53 (m, 3H), 7.69-7.73 (m, 2H), 8.10-8.14 (m, 2H) |
| 127 | 2.25 (s, 3H), 7.14 (m, 2H), 7.30 (m, 2H), 7.58 (m, 1H), 7.95 (m, 3H) |
| 128 | 2.25 (s, 3H), 7.14 (m, 2H), 7.29 (m, 1H), 7.34 (s, 1H), 7.93 (m, 2H), 8.33 (m, 1H) |
| 158 | 7.23-7.29 (m, 2H), 8.02-8.06 (m, 2H), 8.31-8.33 (m, 1H), 8.51-8.53 (m, 1H), 9.01-9.04 (m, 1H) |
| 159 | 4.16 (s, 2H), 7.13-7.19 (m, 2H), 7.43-7.46 (m, 1H), 7.63-7.66 (m, 1H), 7.87-7.94 (m, 2H), 8.67-8.71 (m, 1H) |
| 160 | 5.43-5.56 (m, 2H), 7.17-7.23 (m, 2H), 7.37-7.42 (m, 1H), 7.59-7.62 (m, 1H), 7.95-8.02 (m, 2H), 8.68-8.72 (m, 1H) |
| 161 | 3.40 (s, 3H), 4.55 (s, 2H), 7.14-7.21 (m, 2H), 7.33-7.36 (m, 1H), 7.54-7.57 (m, 1H), 7.95-8.00 (m, 2H), 8.66-8.70 (m, 1H) |
| 163 | 1.13-1.18 (m, 3H), 3.53-3.59 (m, 2H), 4.59 (s, 2H), 7.15-7.21 (m, 2H), 7.32-7.35 (m, 1H), 7.52-7.55 (m, 1H), 7.95-8.00 (m, 2H), 8.66-8.70 (m, 1H) |
| 164 | 1.40-1.45 (m, 3H), 4.10 (s, 2H), 4.36-4.40 (m, 2H), 7.43-7.46 (m, 1H), 7.66-7.70 (m, 3H), 7.99-8.02 (m, 2H), 8.64-8.67 (m, 1H) |
| 166 | 1.29-1.35 (m, 3H), 2.66-2.75 (m, 2H), 7.13-7.20 (m, 2H), 7.28-7.32 (m, 1H), 7.51-7.53 (m, 1H), 7.91-7.98 (m, 2H), 8.65-8.68 (m, 1H) |
| 167 | 2.73 (s, 3H), 7.24 (m, 2H), 8.15 (m, 1H), 8.31 (d, 1H), 8.51 (s, 1H), 9.00 (d, 1H) |
| 168 | 0.97-1.00 (m, 3H), 1.79-1.69 (m, 2H), 2.63-2.68 (m, 2H), 7.13-7.20 (m, 2H), 7.28-7.32 (m, 1H), 7.51-7.53 (m, 1H), 7.91-7.98 (m, 2H), 8.65-8.68 (m, 1H) |
| 169 | 1.31-1.37 (m, 3H), 2.71-2.77 (m, 2H), 7.34-7.37 (m, 1H), 7.54-7.57 (m, 1H), 7.72-7.76 (m, 2H), 8.07-8.11 (m, 2H), 8.68-8.71 (m, 1H) |
| 175 | 1.53 (s, 9H), 7.24 (m, 2H), 8.00 (m, 2H), 8.10 (m, 1H), 8.35(s, 1H), 8.95 (m, 1H) |
| 176 | 1.35 (s, 9H), 4.31 (s, 2H), 7.24(m, 2H), 7.35 (m, 1H), 7.61 (m, 1H), 8.00 (m, 2H), 8.65 (m, 1H) |
| 177 | 1.53-1.58 (m, 3H), 4.54-4.60 (m, 2H), 7.18-7.25 (m, 2H), 7.99-8.06 (m, 2H), 8.23-8.26 (m, 1H), 8.45-8.47 (m, 1H), 8.95-8.98 (m, 1H) |
| 184 | 0.92-0.97 (m, 3H), 1.36-1.45 (m, 2H), 1.67-1.75 (m, 2H), 2.68-2.73 (m, 2H), 7.34-7.37 (m, 1H), 7.54-7.57 (m, 1H), 7.72-7.76 (m, 2H), 8.11-8.07 (m, 2H), 8.68-8.71 (m, 1H) |
| 185 | 0.99-1.04 (m, 3H), 1.72-1.81 (m, 2H), 2.65-2.72 (m, 2H), 7.35-7.39 (m, 1H), 7.55-7.57 (m, 1H), 7.68-7.73 (m, 1H), 7.81-7.87 (m, 2H), 8.69-8.72 (m, 1H) |
| 188 | 1.39-1.44 (m, 3H), 4.08 (s, 2H), 4.32-4.40 (m, 2H), 7.36-7.41 (m, 2H), 7.41-7.45 (m, 1H), 7.66-7.68 (m, 1H), 7.81-7.86 (m, 2H), 8.63-8.66 (m, 1H) |
| 189 | 1.38-1.44 (m, 3H), 4.08 (s, 2H), 4.32-4.40 (m, 2H), 7.42-7.45 (m, 1H), 7.51-7.57 (m, 2H), 7.66-7.68 (m, 1H), 7.75-7.81 (m, 2H), 8.63-8.66 (m, 1H) |
| 190 | 1.38-1.43 (m, 3H), 4.10 (s, 2H), 4.32-4.38 (m, 2H), 6.94-7.03 (m, 2H), 7.65-7.72 (m, 2H), 7.43-7.46 (m, 1H), 8.63-8.66 (m, 1H) |
| 191 | 0.97-1.02 (m, 3H), 1.77-1.87 (m, 2H), 4.11 (s, 2H), 4.26-4.30 (m, 2H), 7.43-7.47 (m, 1H), 7.65-7.71 (m, 3H), 7.99-8.03 (m, 2H), 8.64-8.67 (m, 1H) |
| 192 | 1.37-1.40 (m, 6H), 4.09 (s, 2H), 4.93-5.01 (m, 1H), 7.43-7.46 (m, 1H), 7.66-7.70 (m, 3H), 7.98-8.02 (m, 2H), 8.63-8.66 (m, 1H) |
| 193 | 0.95-0.99 (m, 6H), 2.05-2.14 (m, 1H), 4.07-4.10 (m, 2H), 4.11 (s, 2H), 7.43-7.47 (m, 1H), 7.66-7.70 (m, 3H), 7.99-8.03 (m, 2H), 8.64-8.67 (m, 1H) |
| 194 | 0.94-0.99 (m, 3H), 1.37-1.47 (m, 2H), 1.73-1.80 (m, 2H), 4.10 (s, 2H), 4.30-4.34 (m, 2H), 7.42-7.46 (m, 1H), 7.64-7.71 (m, 3H), 7.99-8.02 (m, 2H), 8.63-8.66 (m, 1H) |
| 195 | 1.38-1.44 (m, 3H), 4.06 (s, 2H), 4.32-4.40 (m, 2H), 6.50-6.74 (m, 1H), 7.07-7.15 (m, 2H), 7.33-7.37 (m, 1H), 7.61 (s, 1H), 7.83-7.90 (m, 2H), 8.54-8.57 (m, 1H) |
| 197 | 2.28 (s, 3H), 4.11-4.13 (m, 2H), 7.38-7.41 (m, 1H), 7.60-7.63 (m, 1H), 7.72-7.76 (m, 2H), 8.06-8.10 (m, 2H), 8.67-8.70 (m, 1H) |

[a] $^1$H NMRH data are in ppm downfield from tetramethylsilane, in $CDCl_3$ unless otherwise indicated. Couplings are designated by (s)-singlet, (d)-doublet, (t)-triplet, (m)-multiplet, (t)-triplet, (q)-quartet and (br s)-broad singlet.

BIOLOGICAL EXAMPLES OF THE INVENTION

Test A

Seeds of barnyardgrass (*Echinochloa crus-galli*), crabgrass, large (large crabgrass, *Digitaria sanguinalis*), foxtail, giant (giant foxtail, *Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant. At the same time these species were also treated with postemergence applications of test chemicals formulated in the same manner.

Plants ranged in height from two to ten cm and were in the one- to two-leaf stage for the postemergence treatment. Treated plants and untreated controls were maintained in a greenhouse for approximately ten days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

Compounds

| 1000 g ai/ha | 94 | 95 | 96 | 97 | 105 | 106 | 109 | 117 | 118 | 123 | 124 | 130 | 131 | 132 |
|---|---|---|---|---|---|---|---|---|---|---|---|---|---|---|
| Postemergence | | | | | | | | | | | | | | |
| Barnyardgrass | 40 | 60 | 40 | 30 | 10 | 40 | 90 | 80 | 30 | 10 | 70 | 50 | 30 | 80 |
| Corn | 40 | 30 | 30 | 10 | 10 | 10 | 90 | 40 | 30 | 40 | 60 | 30 | 30 | 30 |
| Crabgrass, Large | 80 | 80 | 70 | 60 | 50 | 80 | 90 | 90 | 90 | 80 | 90 | 90 | 90 | 90 |
| Foxtail, Giant | 70 | 60 | 60 | 20 | — | — | 90 | 90 | 60 | 60 | 90 | 80 | 50 | 90 |
| Morningglory | 100 | 60 | 80 | 40 | 90 | 100 | 90 | 90 | 100 | 100 | 100 | 100 | 70 | 100 |
| Pigweed | 100 | 100 | 90 | 60 | 100 | 100 | 100 | 100 | 100 | 100 | 100 | 100 | 100 | 100 |
| Velvetleaf | 80 | 70 | 70 | 50 | 40 | 70 | 80 | 100 | 70 | 100 | 100 | 100 | 40 | 90 |
| Wheat | 30 | 0 | 30 | 0 | 0 | 10 | 50 | 20 | 20 | 20 | 40 | 30 | 0 | 30 |

| | Compounds | | | | Compound |
|---|---|---|---|---|---|
| 1000 g ai/ha | 133 | 134 | 167 | 31 g ai/ha | 34 |
| Postemergence | | | | | |
| Barnyardgrass | 40 | 30 | 100 | Barnyardgrass | 0 |
| Corn | 20 | 20 | 30 | Corn | 10 |
| Crabgrass, Large | 80 | 90 | 100 | Crabgrass, Large | 10 |
| Foxtail, Giant | 70 | 50 | 100 | Foxtail, Giant | 10 |
| Morningglory | 90 | 100 | 100 | Morningglory | 20 |
| Pigweed | 100 | 100 | 100 | Pigweed | 20 |
| Velvetleaf | 90 | 50 | 50 | Velvetleaf | 0 |
| Wheat | 30 | 0 | 40 | Wheat | 0 |

| | Compounds | | | | | | | | | | | | | |
|---|---|---|---|---|---|---|---|---|---|---|---|---|---|---|
| 500 g ai/ha | 1 | 2 | 3 | 4 | 5 | 6 | 7 | 8 | 9 | 10 | 11 | 12 | 13 | 14 |
| Postemergence | | | | | | | | | | | | | | |
| Barnyardgrass | 20 | 10 | 50 | 30 | 0 | 0 | 90 | 80 | 60 | 50 | 0 | 80 | 0 | 90 |
| Corn | 20 | 10 | 30 | 30 | 0 | 0 | 50 | 40 | 30 | 20 | 0 | 30 | 0 | 40 |
| Crabgrass, Large | 90 | 20 | 90 | 70 | 0 | 20 | 90 | 80 | 70 | 60 | 0 | 90 | 0 | 90 |
| Foxtail, Giant | 70 | 20 | 90 | 40 | 0 | 10 | 90 | 80 | 70 | 50 | 0 | 70 | 10 | 90 |
| Morningglory | 100 | 20 | 100 | 40 | 0 | 0 | 90 | 90 | 100 | 100 | 0 | 100 | 10 | 100 |
| Pigweed | 100 | 90 | 100 | 100 | 30 | 30 | 100 | 100 | 100 | 100 | 20 | 100 | 0 | 100 |
| Velvetleaf | 70 | 0 | 60 | 30 | 0 | 0 | 70 | 80 | 80 | 50 | 0 | 100 | 0 | 100 |
| Wheat | 20 | 10 | 40 | 40 | 0 | 0 | 20 | 20 | 20 | 10 | 0 | 30 | 0 | 50 |

| | Compounds | | | | | | | | | | | | | |
|---|---|---|---|---|---|---|---|---|---|---|---|---|---|---|
| 500 g ai/ha | 15 | 16 | 17 | 18 | 19 | 20 | 21 | 22 | 23 | 24 | 25 | 26 | 27 | 28 |
| Postemergence | | | | | | | | | | | | | | |
| Barnyardgrass | 90 | 100 | 90 | 60 | 50 | 0 | 10 | 20 | 90 | 20 | 90 | 90 | 20 | 90 |
| Corn | 50 | 50 | 30 | 30 | 20 | 10 | 10 | 20 | 50 | 20 | 30 | 40 | 20 | 50 |
| Crabgrass, Large | 90 | 90 | 90 | 80 | 70 | 10 | 40 | 60 | 90 | 20 | 90 | 90 | 40 | 90 |
| Foxtail, Giant | 90 | 90 | 80 | 70 | 50 | 10 | 10 | 50 | 90 | 20 | 90 | 90 | 40 | 90 |
| Morningglory | 100 | 100 | 90 | 90 | 80 | 10 | 40 | 20 | 100 | 20 | 100 | 100 | 90 | 100 |
| Pigweed | 100 | 100 | 100 | 100 | 100 | 30 | 80 | 80 | 100 | 90 | 100 | 100 | 100 | 100 |

TABLE A-continued

| | Compounds | | | | | | | | | | | | | |
|---|---|---|---|---|---|---|---|---|---|---|---|---|---|---|
| Velvetleaf | 100 | 100 | 100 | 80 | 70 | 20 | 20 | 30 | 100 | 20 | 100 | 100 | 50 | 100 |
| Wheat | 50 | 30 | 40 | 30 | 30 | 0 | 0 | — | 50 | 10 | 60 | 80 | 40 | 50 |
| | Compounds | | | | | | | | | | | | | |
| 500 g ai/ha | 29 | 30 | 31 | 32 | 33 | 35 | 36 | 37 | 38 | 39 | 40 | 41 | 42 | 43 |
| | Postemergence | | | | | | | | | | | | | |
| Barnyardgrass | 40 | 0 | 10 | 10 | 0 | 90 | 0 | 20 | 0 | 10 | 40 | 10 | 10 | 20 |
| Corn | 20 | 0 | 20 | 10 | 10 | 50 | 0 | 20 | 0 | 10 | 30 | 20 | 10 | 30 |
| Crabgrass, Large | 90 | 0 | 50 | 30 | 10 | 90 | 0 | 70 | 50 | 10 | 90 | 30 | 30 | 40 |
| Foxtail, Giant | 90 | 0 | 50 | 20 | 10 | 90 | 0 | 80 | 0 | 10 | 90 | 20 | 20 | 30 |
| Morningglory | 100 | 0 | 100 | 50 | 10 | 100 | 0 | 90 | 0 | 0 | 100 | 10 | 50 | 40 |
| Pigweed | 100 | 0 | 90 | 100 | 50 | 100 | 20 | 100 | 30 | 50 | 100 | 80 | 90 | 70 |
| Velvetleaf | 80 | 0 | 20 | 20 | 0 | 100 | 10 | 50 | 60 | 0 | 100 | 50 | 20 | 20 |
| Wheat | 30 | 0 | 10 | 0 | 0 | 60 | 0 | 10 | 0 | 0 | 30 | 10 | 10 | 30 |
| | Compounds | | | | | | | | | | | | | |
| 500 g ai/ha | 44 | 45 | 47 | 48 | 49 | 50 | 51 | 52 | 53 | 54 | 55 | 56 | 57 | 58 |
| | Postemergence | | | | | | | | | | | | | |
| Barnyardgrass | 20 | 10 | 90 | 30 | 20 | 10 | 10 | 70 | 90 | 90 | 90 | 30 | 0 | 10 |
| Corn | 30 | 20 | 40 | 30 | 20 | 10 | 10 | 20 | 40 | 60 | 50 | 20 | 0 | 10 |
| Crabgrass, Large | 40 | 70 | 90 | 90 | 90 | 10 | 10 | 100 | 90 | 90 | 90 | 80 | 10 | 10 |
| Foxtail, Giant | 30 | 50 | 90 | 70 | 60 | 10 | 10 | 100 | 90 | 90 | 90 | 80 | 0 | 10 |
| Morningglory | 70 | 80 | 90 | 90 | 50 | 10 | 10 | 100 | — | — | — | — | 0 | 10 |
| Pigweed | 90 | 100 | 100 | 100 | 100 | 20 | 60 | 100 | 100 | 100 | 100 | 100 | 10 | 80 |
| Velvetleaf | 70 | 70 | 100 | 50 | 60 | 10 | 10 | 100 | 100 | 100 | 100 | 90 | 0 | 0 |
| Wheat | 30 | 20 | 50 | 20 | 20 | 0 | 0 | 20 | 30 | 30 | 40 | 20 | 0 | 10 |
| | Compounds | | | | | | | | | | | | | |
| 500 g ai/ha | 59 | 60 | 61 | 62 | 63 | 64 | 65 | 66 | 68 | 69 | 70 | 71 | 72 | 73 |
| | Postemergence | | | | | | | | | | | | | |
| Barnyardgrass | 0 | 10 | 10 | 10 | 0 | 0 | 40 | 10 | 10 | 10 | 10 | 10 | 10 | 30 |
| Corn | 0 | 10 | 10 | 0 | 0 | 0 | 20 | 10 | 10 | 20 | 20 | 10 | 10 | 20 |
| Crabgrass, Large | 0 | 10 | 10 | 0 | 0 | 0 | 50 | 10 | 10 | 20 | 30 | 10 | 10 | 60 |
| Foxtail, Giant | 0 | 0 | 10 | 0 | 0 | 0 | 70 | 10 | 10 | 10 | 20 | 10 | 10 | 40 |
| Morningglory | 0 | 0 | 30 | 0 | 0 | 0 | — | 10 | 10 | 30 | 20 | 10 | 10 | 70 |
| Pigweed | 0 | 10 | 80 | 10 | 10 | 0 | 100 | 30 | 50 | 90 | 100 | 40 | 70 | 100 |
| Velvetleaf | 0 | 0 | 30 | 0 | 0 | 0 | 60 | 10 | 0 | 20 | 50 | 10 | 10 | 40 |
| Wheat | 0 | 0 | 0 | 0 | 0 | 0 | 20 | 10 | 10 | 10 | 10 | 0 | 0 | 20 |
| | Compounds | | | | | | | | | | | | | |
| 500 g ai/ha | 74 | 75 | 76 | 77 | 78 | 79 | 80 | 82 | 83 | 84 | 86 | 87 | 88 | 90 |
| | Postemergence | | | | | | | | | | | | | |
| Barnyardgrass | 0 | 10 | 20 | 10 | 10 | 0 | 70 | 0 | 0 | 10 | 0 | 0 | 20 | 10 |
| Corn | 0 | 10 | 20 | 10 | 10 | 0 | 20 | 0 | 0 | 30 | 0 | 0 | 10 | 10 |
| Crabgrass, Large | 0 | 20 | 30 | 20 | 20 | 0 | 80 | 0 | 0 | 50 | 0 | 0 | 80 | 10 |
| Foxtail, Giant | 0 | 20 | 20 | 20 | 30 | 10 | 80 | 0 | 0 | 20 | 0 | 0 | 40 | 10 |
| Morningglory | 0 | 30 | 20 | 10 | 40 | 0 | 90 | 0 | 0 | 30 | 0 | 0 | 50 | 10 |
| Pigweed | 0 | 60 | 60 | 100 | 90 | 0 | 100 | 0 | 0 | 90 | 0 | 0 | 100 | 30 |
| Velvetleaf | 0 | 10 | 10 | 10 | 20 | 0 | 100 | 0 | 0 | 20 | 0 | 0 | 80 | 0 |
| Wheat | 0 | 0 | 20 | 0 | 0 | 0 | 40 | 0 | 0 | 0 | 0 | 0 | 10 | 0 |
| | Compounds | | | | | | | | | | | | | |
| 500 g ai/ha | 91 | 92 | 93 | 98 | 99 | 100 | 101 | 102 | 103 | 104 | 107 | 108 | 110 | 111 |
| | Postemergence | | | | | | | | | | | | | |
| Barnyardgrass | 10 | 10 | 10 | 80 | 30 | 30 | 60 | 0 | 0 | 30 | 60 | 70 | 30 | 30 |
| Corn | 10 | 10 | 10 | 30 | 20 | 20 | 20 | 0 | 0 | 20 | 30 | 30 | 30 | 30 |
| Crabgrass, Large | 10 | 30 | 20 | 90 | 70 | 80 | 90 | 10 | 30 | 70 | 90 | 90 | 70 | 90 |
| Foxtail, Giant | 10 | 20 | 10 | 90 | 80 | 70 | 90 | 0 | 20 | 50 | 90 | 90 | 30 | 90 |
| Morningglory | 0 | 30 | 10 | 100 | 80 | 90 | 40 | 0 | 0 | 90 | 80 | 100 | 100 | 100 |
| Pigweed | 30 | 90 | 20 | 100 | 100 | 90 | 90 | 70 | 70 | 100 | 100 | 100 | 100 | 90 |
| Velvetleaf | 10 | 20 | 20 | 80 | 60 | 70 | 20 | 0 | 10 | 60 | 50 | 80 | 60 | 70 |
| Wheat | 0 | 10 | 0 | 30 | 20 | 20 | 10 | 0 | 0 | 0 | 40 | 30 | 30 | 40 |

TABLE A-continued

Compounds

| 500 g ai/ha | 112 | 114 | 115 | 116 | 119 | 120 | 121 | 122 | 125 | 126 | 127 | 128 | 129 |
|---|---|---|---|---|---|---|---|---|---|---|---|---|---|
| Postemergence | | | | | | | | | | | | | |
| Barnyardgrass | 30 | 30 | 30 | 20 | 20 | 80 | 0 | 70 | 30 | 70 | 20 | 20 | 90 |
| Corn | 20 | 30 | 30 | 30 | 30 | 50 | 10 | 30 | 30 | 30 | 20 | 10 | 40 |
| Crabgrass, Large | 90 | 70 | 80 | 80 | 70 | 90 | 10 | 90 | 90 | 90 | 30 | 20 | 90 |
| Foxtail, Giant | 80 | 40 | 60 | 50 | 60 | 80 | 0 | 90 | 60 | 90 | 20 | 10 | 90 |
| Morningglory | 100 | 90 | 100 | 100 | 70 | 100 | 0 | 100 | 100 | 80 | 30 | 30 | 100 |
| Pigweed | 100 | 90 | 100 | 100 | 100 | 100 | 20 | 100 | 100 | 100 | 60 | 40 | 100 |
| Velvetleaf | 60 | 50 | 30 | 50 | 40 | 80 | 10 | 100 | 70 | 80 | 20 | 30 | 100 |
| Wheat | 30 | 30 | 20 | 10 | 10 | 30 | 0 | 30 | 20 | 20 | 10 | 0 | 30 |

| 500 g ai/ha | 135 | 136 | 137 | 138 | 139 | 140 | 141 | 142 | 143 | 144 | 145 | 146 | 147 | 148 |
|---|---|---|---|---|---|---|---|---|---|---|---|---|---|---|
| Postemergence | | | | | | | | | | | | | | |
| Barnyardgrass | 10 | 90 | 90 | 90 | 100 | 30 | 90 | 100 | 50 | 30 | 90 | 90 | 80 | 90 |
| Corn | 20 | 40 | 30 | 70 | 50 | 30 | 50 | 80 | 50 | 30 | 90 | 80 | 40 | 40 |
| Crabgrass, Large | 20 | 90 | 90 | 90 | 90 | 50 | 90 | 100 | 100 | 90 | 90 | 90 | 90 | 80 |
| Foxtail, Giant | 10 | 90 | 90 | 90 | 100 | 50 | 90 | 100 | 100 | 90 | 100 | 90 | 80 | 80 |
| Morningglory | 10 | 100 | 100 | 100 | 100 | 90 | 90 | 100 | 90 | 90 | 100 | 90 | 90 | 90 |
| Pigweed | 50 | 100 | 100 | 100 | 100 | 100 | 100 | 100 | 100 | 100 | 100 | 100 | 100 | 100 |
| Velvetleaf | 30 | 100 | 100 | 100 | 100 | 70 | 90 | 100 | 80 | 50 | 100 | 100 | 90 | — |
| Wheat | 0 | 30 | 30 | 60 | 40 | 20 | 50 | 80 | 40 | 20 | 50 | 30 | 50 | 40 |

| 500 g ai/ha | 149 | 150 | 151 | 152 | 153 | 154 | 155 | 156 | 157 | 158 | 159 | 160 | 161 | 162 |
|---|---|---|---|---|---|---|---|---|---|---|---|---|---|---|
| Postemergence | | | | | | | | | | | | | | |
| Barnyardgrass | 80 | 0 | 20 | 20 | 90 | 90 | 90 | 90 | 70 | 0 | 80 | 90 | 70 | 90 |
| Corn | 40 | 10 | 20 | 20 | 80 | 80 | 70 | 70 | 40 | 20 | 30 | 60 | 30 | 40 |
| Crabgrass, Large | 90 | 20 | 30 | 30 | 100 | 100 | 100 | 100 | 80 | 20 | 40 | 90 | 90 | 90 |
| Foxtail, Giant | 90 | 0 | 30 | 50 | 100 | 100 | 100 | 100 | 90 | 0 | 90 | 90 | 90 | 90 |
| Morningglory | 100 | 0 | 70 | 60 | 100 | 100 | 100 | 90 | 80 | 10 | 90 | 90 | 50 | 90 |
| Pigweed | 100 | 50 | 80 | 90 | 100 | 100 | 100 | 100 | 100 | 80 | 100 | 100 | 100 | 100 |
| Velvetleaf | 100 | 10 | 50 | 60 | 100 | 100 | 100 | 100 | — | 0 | 60 | 100 | 80 | 100 |
| Wheat | 30 | 0 | 0 | 0 | 70 | 50 | 80 | 60 | 20 | 0 | 30 | 50 | 30 | 30 |

| 500 g ai/ha | 163 | 164 | 165 | 166 | 168 | 169 | 170 | 171 | 172 | 173 | 174 | 175 | 176 | 177 |
|---|---|---|---|---|---|---|---|---|---|---|---|---|---|---|
| Postemergence | | | | | | | | | | | | | | |
| Barnyardgrass | 100 | 90 | 90 | 90 | 90 | 90 | 90 | 90 | 90 | 70 | 90 | 0 | 0 | 20 |
| Corn | 30 | 40 | 30 | 30 | 50 | 50 | 50 | 30 | 50 | 20 | 30 | 0 | 0 | 30 |
| Crabgrass, Large | 100 | 90 | 90 | 90 | 90 | 90 | 100 | 100 | 100 | 90 | 90 | 0 | 0 | 60 |
| Foxtail, Giant | 90 | 90 | 90 | 90 | 90 | 90 | 90 | 90 | 90 | 90 | 90 | 0 | 0 | 70 |
| Morningglory | 80 | 100 | 80 | 100 | — | — | 100 | 100 | 100 | 90 | 100 | 0 | 0 | 100 |
| Pigweed | 100 | 100 | 100 | 100 | 100 | 100 | 100 | 100 | 100 | 100 | 100 | 0 | 0 | 100 |
| Velvetleaf | 100 | 100 | 70 | 100 | 100 | 100 | 100 | 90 | 100 | 70 | 80 | 0 | 0 | 50 |
| Wheat | 40 | 60 | 30 | 40 | 50 | 40 | 50 | 40 | 50 | 30 | 40 | 0 | 0 | 30 |

| 500 g ai/ha | 178 | 179 | 180 | 181 | 182 | 183 | 184 | 185 | 186 | 187 | 188 | 189 | 190 | 191 |
|---|---|---|---|---|---|---|---|---|---|---|---|---|---|---|
| Postemergence | | | | | | | | | | | | | | |
| Barnyardgrass | 80 | 90 | 80 | 30 | 80 | 90 | 30 | 90 | 0 | 0 | 90 | 80 | 100 | 100 |
| Corn | 30 | 30 | 30 | 10 | 20 | 50 | 20 | 50 | 20 | 0 | 50 | 40 | 90 | 80 |
| Crabgrass, Large | 90 | 90 | 90 | 50 | 90 | 90 | 90 | 90 | 0 | 0 | 90 | 90 | 100 | 100 |
| Foxtail, Giant | 90 | 90 | 90 | 80 | 100 | 90 | 80 | 90 | 0 | 0 | 90 | 90 | 100 | 100 |
| Morningglory | 100 | 100 | 100 | 90 | 100 | 100 | 100 | 100 | 10 | 0 | 100 | 80 | 100 | 100 |
| Pigweed | 100 | 100 | 100 | 100 | 100 | 100 | 100 | 100 | 60 | 0 | 100 | 100 | 100 | 100 |

TABLE A-continued

| Compounds | | | | | | | | | | | | | | |
|---|---|---|---|---|---|---|---|---|---|---|---|---|---|---|
| Velvetleaf | 100 | 100 | 100 | 70 | 100 | 100 | 90 | 100 | 20 | 0 | 90 | 90 | 100 | 100 |
| Wheat | 40 | 40 | 40 | 20 | 30 | 40 | 20 | 40 | 0 | 0 | 70 | 60 | 100 | 80 |

| | Compounds | | | | | | | | | |
|---|---|---|---|---|---|---|---|---|---|---|
| 500 g ai/ha | 192 | 193 | 194 | 195 | 196 | 197 | 198 | 199 | 200 | 201 |
| Postemergence | | | | | | | | | | |
| Barnyardgrass | 20 | 20 | 20 | 90 | 90 | 10 | 0 | 10 | 10 | 10 |
| Corn | 30 | 30 | 20 | 60 | 80 | 20 | 10 | 20 | 20 | 20 |
| Crabgrass, Large | 30 | 30 | 20 | 90 | 90 | 20 | 10 | 20 | 40 | 30 |
| Foxtail, Giant | 20 | 20 | 30 | 90 | 90 | 40 | 10 | 20 | 20 | 10 |
| Morningglory | 70 | 40 | 30 | 100 | 100 | 40 | 20 | 20 | 30 | 50 |
| Pigweed | 100 | 100 | 100 | 100 | 100 | 70 | 50 | 60 | 100 | 100 |
| Velvetleaf | 100 | 70 | 50 | 100 | 100 | 30 | 10 | 10 | 40 | 40 |
| Wheat | 10 | 10 | 20 | 30 | 70 | 0 | 0 | 0 | 0 | 10 |

| | Compounds | | | | | | | | | | | | | |
|---|---|---|---|---|---|---|---|---|---|---|---|---|---|---|
| 125 g ai/ha | 1 | 2 | 3 | 4 | 5 | 6 | 7 | 8 | 9 | 10 | 11 | 12 | 13 | 14 |
| Postemergence | | | | | | | | | | | | | | |
| Barnyardgrass | 0 | 0 | 30 | 20 | 0 | 0 | 30 | 10 | 50 | 20 | 0 | 30 | 0 | 80 |
| Corn | 20 | 10 | 20 | 20 | 0 | 0 | 10 | 20 | 20 | 20 | 0 | 20 | 0 | 20 |
| Crabgrass, Large | 70 | 10 | 40 | 30 | 0 | 0 | 70 | 40 | 60 | 40 | 0 | 50 | 0 | 80 |
| Foxtail, Giant | 50 | 10 | 30 | 20 | 0 | 0 | 50 | 30 | 50 | 20 | 0 | 50 | 0 | 80 |
| Morningglory | 50 | 10 | 30 | 20 | 0 | 0 | 90 | 90 | 70 | 100 | 0 | 70 | 10 | 80 |
| Pigweed | 90 | 30 | 90 | 80 | 10 | 0 | 100 | 60 | 90 | 70 | 0 | 100 | 0 | 100 |
| Velvetleaf | 30 | 0 | 50 | 30 | 0 | 0 | 30 | 30 | 60 | 40 | 0 | 70 | 0 | 100 |
| Wheat | 10 | 0 | 30 | 20 | 0 | 0 | 0 | 0 | 0 | 0 | 0 | 10 | 0 | 30 |

| | Compounds | | | | | | | | | | | | | |
|---|---|---|---|---|---|---|---|---|---|---|---|---|---|---|
| 125 g ai/ha | 15 | 16 | 17 | 18 | 19 | 20 | 21 | 22 | 23 | 24 | 25 | 26 | 27 | 28 |
| Postemergence | | | | | | | | | | | | | | |
| Barnyardgrass | 90 | 90 | 30 | 50 | 20 | 0 | 0 | 10 | 70 | 0 | 50 | 80 | 0 | 70 |
| Corn | 30 | 30 | 30 | 20 | 20 | 0 | 0 | 10 | 30 | 10 | 30 | 30 | 20 | 30 |
| Crabgrass, Large | 90 | 90 | 90 | 60 | 60 | 0 | 20 | 40 | 90 | 10 | 90 | 90 | 30 | 70 |
| Foxtail, Giant | 90 | 90 | 60 | 30 | 30 | 0 | 0 | 20 | 90 | 10 | 90 | 90 | 30 | 90 |
| Morningglory | 100 | 80 | 50 | 80 | 50 | 0 | 20 | 10 | 90 | 20 | 100 | 100 | 40 | 100 |
| Pigweed | 100 | 100 | 90 | 100 | 90 | 0 | 60 | 50 | 100 | 40 | 100 | 100 | 90 | 100 |
| Velvetleaf | 100 | 100 | 90 | 70 | 60 | 0 | 10 | 10 | 90 | 20 | 80 | 100 | 40 | 80 |
| Wheat | 30 | 20 | 20 | 20 | 10 | 0 | 0 | 10 | 20 | 10 | 40 | 60 | 20 | 40 |

| | Compounds | | | | | | | | | | | | | |
|---|---|---|---|---|---|---|---|---|---|---|---|---|---|---|
| 125 g ai/ha | 29 | 30 | 31 | 32 | 33 | 34 | 35 | 36 | 37 | 38 | 39 | 40 | 41 | 42 |
| Postemergence | | | | | | | | | | | | | | |
| Barnyardgrass | 20 | 0 | 10 | 10 | 0 | 10 | 40 | 0 | 10 | 0 | 0 | 30 | 10 | 0 |
| Corn | 20 | 0 | 10 | 0 | 0 | 10 | 20 | 0 | 10 | 0 | 0 | 10 | 10 | 10 |
| Crabgrass, Large | 90 | 0 | 10 | 20 | 0 | 20 | 80 | 0 | 20 | 20 | 0 | 80 | 10 | 10 |
| Foxtail, Giant | 60 | 0 | 10 | 10 | 0 | 20 | 60 | 0 | 30 | 0 | 0 | 60 | 10 | 10 |
| Morningglory | 80 | 0 | 20 | 10 | 0 | 30 | 90 | 0 | 20 | 0 | 0 | 70 | 10 | 10 |
| Pigweed | 100 | 0 | 60 | 60 | 10 | 80 | 100 | 0 | 80 | 0 | 30 | 100 | 30 | 50 |
| Velvetleaf | 60 | 0 | 10 | 20 | 0 | 10 | 70 | 0 | 20 | 0 | 0 | 70 | 10 | 10 |
| Wheat | 0 | 0 | 0 | 0 | 0 | 0 | 10 | 0 | 0 | 0 | 0 | 20 | 0 | 0 |

| | Compounds | | | | | | | | | | | | | |
|---|---|---|---|---|---|---|---|---|---|---|---|---|---|---|
| 125 g ai/ha | 43 | 44 | 45 | 47 | 48 | 49 | 50 | 51 | 52 | 53 | 54 | 55 | 56 | 57 |
| Postemergence | | | | | | | | | | | | | | |
| Barnyardgrass | 10 | 20 | 10 | 90 | 10 | 10 | 0 | 0 | 20 | 90 | 70 | 90 | 10 | 0 |
| Corn | 20 | 30 | 10 | 20 | 10 | 10 | 0 | 0 | 10 | 30 | 30 | 20 | 10 | 0 |
| Crabgrass, Large | 30 | 30 | 60 | 80 | 50 | 60 | 0 | 0 | 50 | 90 | 80 | 80 | 50 | 0 |
| Foxtail, Giant | 20 | 20 | 20 | 80 | 30 | 30 | 0 | 0 | 50 | 90 | 80 | 90 | 20 | 0 |
| Morningglory | 0 | 20 | 40 | 90 | 10 | 20 | 0 | 0 | 40 | — | — | — | — | 0 |
| Pigweed | 50 | 70 | 100 | 100 | 100 | 80 | 10 | 10 | 100 | 100 | 100 | 100 | 100 | 0 |
| Velvetleaf | 20 | 60 | 40 | 100 | 30 | 30 | 0 | 0 | 30 | 80 | 90 | 100 | 40 | 0 |
| Wheat | 0 | 20 | 10 | 30 | 10 | 10 | 0 | 0 | 10 | 20 | 20 | 20 | 10 | 0 |

TABLE A-continued

Compounds

| 125 g ai/ha | 58 | 59 | 60 | 61 | 62 | 63 | 64 | 65 | 66 | 68 | 69 | 70 | 71 | 72 |
|---|---|---|---|---|---|---|---|---|---|---|---|---|---|---|
| Postemergence | | | | | | | | | | | | | | |
| Barnyardgrass | 0 | 0 | 0 | 0 | 0 | 0 | 0 | 10 | 0 | 0 | 10 | 0 | 0 | 0 |
| Corn | 0 | 0 | 0 | 10 | 0 | 0 | 0 | 10 | 0 | 0 | 10 | 10 | 0 | 0 |
| Crabgrass, Large | 0 | 0 | 0 | 0 | 0 | 0 | 0 | 20 | 10 | 10 | 10 | 10 | 10 | 0 |
| Foxtail, Giant | 0 | 0 | 0 | 0 | 0 | 0 | 0 | 20 | 0 | 10 | 10 | 10 | 10 | 0 |
| Morningglory | 0 | 0 | 0 | 10 | 0 | 0 | 0 | — | 0 | 0 | 20 | 10 | 10 | 0 |
| Pigweed | 50 | 0 | 0 | 40 | 0 | 0 | 0 | 90 | 10 | 10 | 30 | 40 | 10 | 10 |
| Velvetleaf | 0 | 0 | 0 | 10 | 0 | 0 | 0 | 30 | 0 | — | 10 | 10 | 0 | 0 |
| Wheat | 0 | 0 | 0 | 0 | 0 | 0 | 0 | 0 | 0 | 0 | 0 | 0 | 0 | 0 |

| 125 g ai/ha | 73 | 74 | 75 | 76 | 77 | 78 | 79 | 80 | 82 | 83 | 84 | 86 | 87 | 88 |
|---|---|---|---|---|---|---|---|---|---|---|---|---|---|---|
| Postemergence | | | | | | | | | | | | | | |
| Barnyardgrass | 10 | 0 | 0 | 0 | 0 | 0 | 0 | 30 | 0 | 0 | 0 | 0 | 0 | 10 |
| Corn | 10 | 0 | 0 | 10 | 0 | 0 | 0 | 20 | 0 | 0 | 10 | 0 | 0 | 0 |
| Crabgrass, Large | 20 | 0 | 10 | 10 | 10 | 10 | 0 | 40 | 0 | 0 | 10 | 0 | 0 | 30 |
| Foxtail, Giant | 10 | 0 | 10 | 10 | 10 | 10 | 0 | 30 | 0 | 0 | 10 | 0 | 0 | 10 |
| Morningglory | 20 | 0 | 0 | 10 | 10 | 0 | 0 | 40 | 0 | 0 | 30 | 0 | 0 | 10 |
| Pigweed | 70 | 0 | 30 | 50 | 90 | 50 | 0 | 100 | 0 | 0 | 40 | 0 | 0 | 80 |
| Velvetleaf | 20 | 0 | 10 | 0 | 10 | 10 | 0 | 80 | 0 | 0 | 10 | 0 | 0 | 10 |
| Wheat | 10 | 0 | 0 | 0 | 0 | 0 | 0 | 20 | 0 | 0 | 0 | 0 | 0 | 0 |

| 125 g ai/ha | 90 | 91 | 92 | 93 | 98 | 99 | 100 | 101 | 102 | 103 | 104 | 107 | 108 | 110 |
|---|---|---|---|---|---|---|---|---|---|---|---|---|---|---|
| Postemergence | | | | | | | | | | | | | | |
| Barnyardgrass | 0 | 0 | 0 | 0 | 30 | 10 | 10 | 20 | 0 | 0 | 20 | 30 | 40 | 20 |
| Corn | 0 | 10 | 10 | 10 | 20 | 20 | 10 | 10 | 0 | 0 | 10 | 20 | 20 | 20 |
| Crabgrass, Large | 0 | 0 | 10 | 10 | 90 | 30 | 60 | 70 | 0 | 0 | 50 | 60 | 90 | 50 |
| Foxtail, Giant | 0 | 0 | 10 | 10 | 80 | 20 | 50 | 70 | 0 | 0 | 20 | 40 | 60 | 20 |
| Morningglory | 0 | 0 | 10 | 0 | 80 | 60 | 90 | 40 | 0 | 0 | 60 | 70 | 100 | 90 |
| Pigweed | 0 | 10 | 30 | 10 | 100 | 70 | 80 | 80 | 10 | 50 | 70 | 90 | 90 | 70 |
| Velvetleaf | 0 | 0 | 20 | 10 | 60 | 10 | 30 | 10 | 0 | 0 | 30 | 40 | 60 | 30 |
| Wheat | 0 | 0 | 0 | 0 | 10 | 0 | 0 | 0 | 0 | 0 | 0 | 20 | 20 | 10 |

| 125 g ai/ha | 111 | 112 | 114 | 115 | 116 | 119 | 120 | 121 | 122 | 125 | 126 | 127 | 128 | 129 |
|---|---|---|---|---|---|---|---|---|---|---|---|---|---|---|
| Postemergence | | | | | | | | | | | | | | |
| Barnyardgrass | 20 | 0 | 30 | 20 | 10 | 10 | 60 | 0 | 40 | 0 | 20 | 10 | 0 | 90 |
| Corn | 20 | 20 | 20 | 10 | 20 | 10 | 20 | 0 | 20 | 20 | 20 | 10 | 10 | 30 |
| Crabgrass, Large | 90 | 50 | 30 | 50 | 40 | 40 | 80 | 0 | 80 | 60 | 90 | 10 | 10 | 90 |
| Foxtail, Giant | 80 | 20 | 30 | 30 | 30 | 20 | 80 | 0 | 60 | 50 | 60 | 10 | 0 | 90 |
| Morningglory | 70 | 60 | 60 | 90 | 70 | 20 | 90 | 0 | 90 | 60 | 70 | 20 | 30 | 100 |
| Pigweed | 90 | 90 | 80 | 80 | 50 | 70 | 90 | 0 | 100 | 90 | 100 | 40 | 30 | 100 |
| Velvetleaf | 20 | 50 | 30 | 10 | 20 | 20 | 50 | 0 | 80 | 30 | 40 | 20 | 20 | 70 |
| Wheat | 10 | 10 | 10 | 10 | 10 | 0 | 10 | 0 | 20 | 0 | 10 | 0 | 0 | 20 |

| 1000 g ai/ha | 94 | 95 | 96 | 97 | 105 | 106 | 109 | 117 | 118 | 123 | 124 | 130 | 131 | 132 |
|---|---|---|---|---|---|---|---|---|---|---|---|---|---|---|
| Preemergence | | | | | | | | | | | | | | |
| Barnyardgrass | 70 | 50 | 70 | 30 | 10 | 50 | 100 | 100 | 70 | 10 | 90 | 50 | 20 | 90 |
| Corn | 0 | 10 | 0 | 0 | 0 | 10 | 40 | 50 | 20 | 0 | 10 | 0 | 0 | 0 |
| Crabgrass, Large | 100 | 100 | 100 | 40 | 50 | 90 | 100 | 100 | 100 | 60 | 100 | 90 | 90 | 100 |
| Foxtail, Giant | 100 | 100 | 90 | 20 | — | — | 100 | 100 | 100 | 80 | 100 | 90 | 90 | 100 |
| Morningglory | 60 | 0 | 40 | 0 | 10 | 20 | 50 | 40 | 20 | 0 | 40 | 40 | 10 | 60 |
| Pigweed | 100 | 90 | 100 | 0 | 90 | 90 | 100 | 100 | 100 | 80 | 100 | 90 | 90 | 100 |

TABLE A-continued

| | Compounds | | | | | | | | | | | | | |
|---|---|---|---|---|---|---|---|---|---|---|---|---|---|---|
| Velvetleaf | 20 | 40 | 0 | 0 | 10 | 0 | 30 | 30 | 10 | 10 | 80 | 20 | 0 | 60 |
| Wheat | 0 | 0 | 0 | 0 | 0 | 0 | 20 | 10 | 10 | 0 | 0 | 10 | 0 | 0 |

| | Compounds | | | | | | | | | | | | | |
|---|---|---|---|---|---|---|---|---|---|---|---|---|---|---|
| 125 g ai/ha | 135 | 136 | 137 | 138 | 139 | 140 | 141 | 142 | 143 | 144 | 145 | 146 | 147 | 148 |
| Postemergence | | | | | | | | | | | | | | |
| Barnyardgrass | 0 | 60 | 70 | 90 | 90 | 10 | 80 | 100 | 20 | 10 | 80 | 30 | 80 | 80 |
| Corn | 10 | 20 | 20 | 50 | 30 | 20 | 30 | 50 | 40 | 10 | 40 | 20 | 30 | 20 |
| Crabgrass, Large | 10 | 60 | 90 | 90 | 90 | 20 | 90 | 100 | 80 | 50 | 90 | 80 | 80 | 80 |
| Foxtail, Giant | 0 | 90 | 90 | 90 | 90 | 20 | 90 | 100 | 80 | 30 | 90 | 80 | 70 | 80 |
| Morningglory | 0 | 70 | 80 | 100 | 80 | 50 | 80 | 100 | 50 | 20 | 100 | 90 | 90 | 80 |
| Pigweed | 20 | 100 | 100 | 100 | 100 | 100 | 100 | 100 | 100 | 100 | 100 | 100 | 100 | 100 |
| Velvetleaf | 10 | 90 | 80 | 100 | 90 | 20 | 70 | 100 | 40 | 40 | 100 | 70 | 50 | 100 |
| Wheat | 0 | 30 | 20 | 50 | 30 | 10 | 20 | 80 | 10 | 0 | 20 | 10 | 20 | 20 |

| | Compounds | | | | | | | | | | | | | |
|---|---|---|---|---|---|---|---|---|---|---|---|---|---|---|
| 125 g ai/ha | 149 | 150 | 151 | 152 | 153 | 154 | 155 | 156 | 157 | 158 | 159 | 160 | 161 | 162 |
| Postemergence | | | | | | | | | | | | | | |
| Barnyardgrass | 30 | 0 | 10 | 20 | 90 | 90 | 90 | 90 | 20 | 0 | 50 | 70 | 30 | 80 |
| Corn | 30 | 0 | 10 | 10 | 60 | 30 | 40 | 40 | 20 | 0 | 20 | 30 | 10 | 20 |
| Crabgrass, Large | 80 | 0 | 10 | 20 | 100 | 100 | 100 | 100 | 40 | 0 | 20 | 90 | 70 | 90 |
| Foxtail, Giant | 80 | 0 | 10 | 30 | 90 | 90 | 90 | 90 | 80 | 0 | 40 | 90 | 60 | 90 |
| Morningglory | 90 | 0 | 40 | 50 | 90 | 80 | 90 | 90 | 60 | 0 | 60 | 90 | 30 | 90 |
| Pigweed | 100 | 10 | 60 | 60 | 100 | 100 | 100 | 100 | 100 | 10 | 90 | 100 | 100 | 100 |
| Velvetleaf | 60 | 0 | 30 | 40 | 100 | 100 | 100 | 100 | 40 | 0 | 20 | 90 | 40 | 90 |
| Wheat | 20 | 0 | 0 | 0 | 60 | 20 | 40 | 40 | 0 | 0 | 0 | 40 | 10 | 20 |

| | Compounds | | | | | | | | | | | | | |
|---|---|---|---|---|---|---|---|---|---|---|---|---|---|---|
| 125 g ai/ha | 163 | 164 | 165 | 166 | 168 | 169 | 170 | 171 | 172 | 173 | 174 | 175 | 176 | 177 |
| Postemergence | | | | | | | | | | | | | | |
| Barnyardgrass | 70 | 90 | 40 | 70 | 90 | 80 | 90 | 80 | 90 | 30 | 70 | 0 | 0 | 0 |
| Corn | 20 | 30 | 20 | 20 | 20 | 10 | 30 | 20 | 30 | 20 | 20 | 0 | 0 | 20 |
| Crabgrass, Large | 70 | 90 | 70 | 90 | 90 | 90 | 100 | 90 | 90 | 60 | 90 | 0 | 0 | 10 |
| Foxtail, Giant | 60 | 90 | 60 | 90 | 90 | 80 | 90 | 80 | 90 | 30 | 80 | 0 | 0 | 20 |
| Morningglory | 30 | 100 | 60 | 90 | — | — | 100 | 100 | 100 | 90 | 70 | 0 | 0 | 90 |
| Pigweed | 100 | 100 | 100 | 100 | 100 | 100 | 100 | 100 | 100 | 80 | 100 | 0 | 0 | 60 |
| Velvetleaf | 40 | 100 | 40 | 80 | 100 | 100 | 100 | 70 | 90 | 50 | 70 | 0 | 0 | 20 |
| Wheat | 20 | 50 | 20 | 30 | 40 | 30 | 40 | 30 | 40 | 10 | 30 | 0 | 0 | 20 |

| | Compounds | | | | | | | | | | | | | |
|---|---|---|---|---|---|---|---|---|---|---|---|---|---|---|
| 125 g ai/ha | 178 | 179 | 180 | 181 | 182 | 183 | 184 | 185 | 186 | 187 | 188 | 189 | 190 | 191 |
| Postemergence | | | | | | | | | | | | | | |
| Barnyardgrass | 30 | 90 | 50 | 0 | 30 | 80 | 10 | 70 | 0 | 0 | 90 | 60 | 100 | 60 |
| Corn | 20 | 20 | 20 | 0 | 10 | 20 | 10 | 20 | 10 | 0 | 40 | 20 | 60 | 30 |
| Crabgrass, Large | 90 | 90 | 90 | 50 | 70 | 90 | 50 | 90 | 0 | 0 | 90 | 80 | 100 | 90 |
| Foxtail, Giant | 60 | 90 | 90 | 30 | 50 | 90 | 30 | 90 | 0 | 0 | 90 | 90 | 100 | 90 |
| Morningglory | 90 | 100 | 100 | 90 | 60 | 100 | 30 | 100 | 0 | 0 | 90 | 60 | 100 | 100 |
| Pigweed | 100 | 100 | 100 | 90 | 100 | 100 | 100 | 100 | 20 | 0 | 100 | 100 | 100 | 100 |
| Velvetleaf | 60 | 90 | 70 | 30 | 70 | 100 | 40 | 100 | 0 | 0 | 70 | 70 | 100 | 80 |
| Wheat | 20 | 30 | 30 | 0 | 20 | 30 | 10 | 20 | 0 | 0 | 70 | 50 | 70 | 70 |

| | Compounds | | | | | | | | | |
|---|---|---|---|---|---|---|---|---|---|---|
| 125 g ai/ha | 192 | 193 | 194 | 195 | 196 | 197 | 198 | 199 | 200 | 201 |
| Postemergence | | | | | | | | | | |
| Barnyardgrass | 0 | 10 | 10 | 90 | 80 | 0 | 0 | 10 | 0 | 0 |
| Corn | 10 | 10 | 0 | 30 | 70 | 0 | 0 | 10 | 10 | 10 |
| Crabgrass, Large | 10 | 10 | 10 | 90 | 90 | 10 | 0 | 10 | 10 | 20 |
| Foxtail, Giant | 10 | 10 | 10 | 90 | 90 | 10 | 0 | 10 | 10 | 0 |
| Morningglory | 30 | 10 | 10 | 80 | 100 | 30 | 10 | 10 | 10 | 10 |
| Pigweed | 40 | 70 | 40 | 100 | 100 | 30 | 10 | 20 | 50 | 60 |
| Velvetleaf | 20 | 30 | 30 | 90 | 100 | 20 | 10 | 10 | 10 | 20 |
| Wheat | 0 | 0 | 0 | 30 | 50 | 0 | 0 | 0 | 0 | 0 |

TABLE A-continued

| Compounds | | | | | |
|---|---|---|---|---|---|
| | Compounds | | | | Compound |
| 1000 g ai/ha | 133 | 134 | 167 | 31 g ai/ha | 34 |
| Preemergence | | | | | |
| Barnyardgrass | 40 | 30 | 100 | Barnyardgrass | 0 |
| Corn | 10 | 10 | 30 | Corn | 0 |
| Crabgrass, Large | 90 | 100 | 100 | Crabgrass, Large | 0 |
| Foxtail, Giant | 90 | 100 | 100 | Foxtail, Giant | 0 |
| Morningglory | 40 | 10 | — | Morningglory | 0 |
| Pigweed | 90 | 90 | 100 | Pigweed | 0 |
| Velvetleaf | 40 | 0 | 20 | Velvetleaf | 0 |
| Wheat | 0 | 0 | 80 | Wheat | 0 |

| | Compounds | | | | | | | | | | | | | |
|---|---|---|---|---|---|---|---|---|---|---|---|---|---|---|
| 500 g ai/ha | 1 | 2 | 3 | 4 | 5 | 6 | 7 | 8 | 9 | 10 | 11 | 12 | 13 | 14 |
| Preemergence | | | | | | | | | | | | | | |
| Barnyardgrass | 50 | 10 | 50 | 60 | 0 | 0 | 100 | 80 | 70 | 10 | 0 | 80 | 0 | 90 |
| Corn | 0 | 0 | 10 | 0 | 0 | 0 | 30 | 0 | 10 | 0 | 0 | 10 | 0 | 30 |
| Crabgrass, Large | 100 | 90 | 100 | 90 | 0 | 0 | 100 | 100 | 100 | 90 | 0 | 100 | 0 | 100 |
| Foxtail, Giant | 100 | 50 | 100 | 100 | 0 | 0 | 100 | 90 | 90 | 80 | 0 | 100 | 0 | 100 |
| Morningglory | 20 | 0 | 50 | 40 | 0 | 0 | 80 | 90 | 60 | 10 | 0 | 40 | 0 | 80 |
| Pigweed | 90 | 60 | 100 | 100 | 0 | 0 | 100 | 100 | 100 | 80 | 0 | 100 | 0 | 100 |
| Velvetleaf | 10 | 0 | 10 | 0 | 0 | 0 | 60 | 60 | 50 | 20 | 0 | 70 | 0 | 90 |
| Wheat | 0 | 0 | 40 | 30 | 0 | 0 | 0 | 10 | 0 | 0 | 0 | 0 | 0 | 50 |

| | Compounds | | | | | | | | | | | | | |
|---|---|---|---|---|---|---|---|---|---|---|---|---|---|---|
| 500 g ai/ha | 15 | 16 | 17 | 18 | 19 | 20 | 21 | 22 | 23 | 24 | 25 | 26 | 27 | 28 |
| Preemergence | | | | | | | | | | | | | | |
| Barnyardgrass | 100 | 100 | 90 | 30 | 50 | 0 | 10 | 10 | 100 | 0 | 90 | 90 | 10 | 90 |
| Corn | 50 | 20 | 20 | 0 | 0 | 0 | 0 | 0 | 40 | 0 | 30 | 50 | 0 | 20 |
| Crabgrass, Large | 100 | 100 | 100 | 90 | 80 | 0 | 60 | 40 | 100 | 20 | 100 | 100 | 40 | 90 |
| Foxtail, Giant | 100 | 100 | 100 | 90 | 90 | 0 | 30 | 80 | 100 | 70 | 100 | 100 | 80 | 100 |
| Morningglory | 80 | 80 | 50 | 50 | 50 | 0 | 0 | 0 | 80 | 0 | 80 | 80 | 0 | — |
| Pigweed | 100 | 100 | 100 | 100 | 90 | 0 | 50 | 10 | 100 | 20 | 100 | 100 | 80 | 100 |
| Velvetleaf | 80 | 80 | 40 | 30 | 30 | 0 | 0 | 0 | 100 | 0 | 80 | 90 | 0 | 80 |
| Wheat | 50 | 20 | 0 | 0 | 0 | 0 | 0 | 0 | 70 | 0 | 80 | 80 | 0 | 20 |

| | Compounds | | | | | | | | | | | | | |
|---|---|---|---|---|---|---|---|---|---|---|---|---|---|---|
| 500 g ai/ha | 29 | 30 | 31 | 32 | 33 | 35 | 36 | 37 | 38 | 39 | 40 | 41 | 42 | 43 |
| Preemergence | | | | | | | | | | | | | | |
| Barnyardgrass | 50 | 0 | 0 | 0 | 0 | 90 | 0 | 90 | 0 | 0 | 80 | 20 | 10 | 20 |
| Corn | 0 | 0 | 0 | 0 | 0 | 30 | 0 | — | 0 | 0 | 10 | 0 | 0 | 10 |
| Crabgrass, Large | 100 | 0 | 60 | 30 | 10 | 100 | 10 | 100 | 60 | 50 | 100 | 70 | 50 | 80 |
| Foxtail, Giant | 100 | 0 | 90 | 80 | 0 | 100 | 0 | 100 | 20 | 10 | 100 | 70 | 70 | 90 |
| Morningglory | 10 | 0 | 0 | 0 | 0 | 50 | 0 | 20 | 0 | 0 | 10 | 10 | 10 | — |
| Pigweed | 90 | 0 | 50 | 70 | 0 | 100 | 0 | 100 | 10 | 0 | 100 | 50 | 60 | 60 |
| Velvetleaf | 50 | 0 | 0 | 0 | 0 | 50 | 0 | 10 | 0 | 0 | 20 | 10 | 0 | 0 |
| Wheat | 0 | 0 | 0 | 0 | 0 | 0 | 0 | 0 | 0 | 0 | 20 | 0 | 0 | 0 |

| | Compounds | | | | | | | | | | | | | |
|---|---|---|---|---|---|---|---|---|---|---|---|---|---|---|
| 500 g ai/ha | 44 | 45 | 47 | 48 | 49 | 50 | 51 | 52 | 53 | 54 | 55 | 56 | 57 | 58 |
| Preemergence | | | | | | | | | | | | | | |
| Barnyardgrass | 30 | 10 | 100 | 30 | 30 | 0 | 0 | 90 | 100 | 100 | 100 | 80 | 0 | 0 |
| Corn | 20 | 0 | 30 | 0 | 10 | 0 | 0 | 10 | 20 | 40 | 50 | 10 | 0 | 0 |
| Crabgrass, Large | 90 | 70 | 100 | 100 | 100 | 20 | 0 | 100 | 100 | 100 | 100 | 100 | 0 | 10 |
| Foxtail, Giant | 90 | 60 | 100 | 100 | 100 | 40 | 10 | 100 | 100 | 100 | 100 | 100 | 0 | 10 |
| Morningglory | — | 10 | 80 | 20 | 10 | 0 | 0 | 20 | 40 | 90 | 80 | 10 | 0 | 0 |
| Pigweed | 90 | 20 | 100 | 90 | 100 | 10 | 0 | — | 100 | 100 | 100 | 90 | 0 | 30 |

TABLE A-continued

| | Compounds | | | | | | | | | | | | | |
|---|---|---|---|---|---|---|---|---|---|---|---|---|---|---|
| Velvetleaf | 50 | 10 | 100 | 0 | 10 | 0 | 0 | 10 | 50 | 60 | 70 | 10 | 0 | 0 |
| Wheat | 30 | 0 | 40 | 0 | 20 | 0 | 0 | 0 | 30 | 30 | 40 | 10 | 0 | 0 |
| | Compounds | | | | | | | | | | | | | |
| 500 g ai/ha | 59 | 60 | 61 | 62 | 63 | 64 | 65 | 66 | 68 | 69 | 70 | 71 | 72 | 73 |
| | Preemergence | | | | | | | | | | | | | |
| Barnyardgrass | 0 | 0 | 0 | 0 | 0 | 0 | 70 | 0 | 0 | 0 | 0 | 0 | 0 | 40 |
| Corn | 0 | 0 | 0 | 0 | 0 | 0 | 10 | 0 | 0 | 0 | 0 | 0 | 0 | 0 |
| Crabgrass, Large | 0 | 0 | 10 | 0 | 0 | 0 | 100 | 50 | 0 | 10 | 40 | 10 | 10 | 90 |
| Foxtail, Giant | 0 | 0 | 10 | 0 | 0 | 0 | 100 | 70 | 0 | 0 | 50 | 0 | 20 | 90 |
| Morningglory | 0 | 0 | 0 | 0 | 0 | 0 | 20 | 0 | 0 | 0 | 0 | 0 | 0 | 10 |
| Pigweed | 0 | 0 | 10 | 0 | 0 | 0 | 100 | 10 | 0 | 10 | 10 | 0 | 10 | 100 |
| Velvetleaf | 0 | 0 | 0 | 0 | 0 | 0 | 10 | 0 | 0 | 0 | 0 | 0 | 0 | 10 |
| Wheat | 0 | 0 | 0 | 0 | 0 | 0 | 0 | 0 | 0 | 0 | 0 | 0 | 0 | 10 |
| | Compounds | | | | | | | | | | | | | |
| 500 g ai/ha | 74 | 75 | 76 | 77 | 78 | 79 | 80 | 82 | 83 | 84 | 86 | 87 | 88 | 90 |
| | Preemergence | | | | | | | | | | | | | |
| Barnyardgrass | 0 | 20 | 0 | 0 | 20 | 0 | 70 | 0 | 0 | 0 | 0 | 0 | 10 | 0 |
| Corn | 0 | 0 | 0 | 0 | 0 | 0 | 10 | 0 | 0 | 0 | 0 | 0 | 0 | 0 |
| Crabgrass, Large | 0 | 70 | 40 | 10 | 80 | 0 | 100 | 0 | 0 | 60 | 0 | 0 | 50 | 0 |
| Foxtail, Giant | 0 | 90 | 80 | 10 | 70 | 0 | 100 | 0 | 0 | 30 | 0 | 0 | 40 | 0 |
| Morningglory | 0 | — | 0 | 0 | 10 | 0 | 60 | 0 | 0 | 0 | 0 | 0 | 0 | 0 |
| Pigweed | 0 | 40 | 20 | 10 | 70 | 0 | 100 | 0 | 0 | 50 | 0 | 0 | 50 | 0 |
| Velvetleaf | 0 | 0 | 0 | 0 | 20 | 0 | 70 | 0 | 0 | 0 | 0 | 0 | 0 | 0 |
| Wheat | 0 | 10 | 0 | 0 | 0 | 0 | 40 | 0 | 0 | 0 | 0 | 0 | 0 | 0 |
| | Compounds | | | | | | | | | | | | | |
| 500 g ai/ha | 91 | 92 | 93 | 98 | 99 | 100 | 101 | 102 | 103 | 104 | 107 | 108 | 110 | 111 |
| | Preemergence | | | | | | | | | | | | | |
| Barnyardgrass | 0 | 0 | 0 | 60 | 10 | 20 | 80 | 0 | 0 | 20 | 80 | 80 | 0 | 80 |
| Corn | 0 | 0 | 0 | 10 | 0 | 0 | 10 | 0 | 0 | 0 | 10 | 0 | 0 | 20 |
| Crabgrass, Large | 0 | 40 | 0 | 100 | 60 | 90 | 100 | 0 | 10 | 90 | 100 | 100 | 20 | 100 |
| Foxtail, Giant | 0 | 20 | 0 | 100 | 80 | 70 | 100 | 0 | 0 | 90 | 100 | 100 | 20 | 100 |
| Morningglory | 0 | 0 | 0 | 10 | 0 | 0 | 10 | 0 | 0 | 0 | 30 | 20 | 20 | 30 |
| Pigweed | 0 | 10 | 0 | 100 | 60 | 90 | 100 | 0 | 30 | 90 | 100 | 100 | 50 | 90 |
| Velvetleaf | 0 | 0 | 0 | 50 | 20 | 0 | 0 | 0 | 0 | 30 | 10 | 20 | 10 | 50 |
| Wheat | 0 | 0 | 0 | 20 | 0 | 0 | 0 | 0 | 0 | 0 | 0 | 0 | 0 | 0 |
| | Compounds | | | | | | | | | | | | | |
| 500 g ai/ha | 112 | 114 | 115 | 116 | 119 | 120 | 121 | 122 | 125 | 126 | 127 | 128 | 129 | |
| | Preemergence | | | | | | | | | | | | | |
| Barnyardgrass | 40 | 0 | 60 | 30 | 30 | 100 | 0 | 70 | 50 | 80 | 10 | 0 | 100 | |
| Corn | 0 | 0 | 10 | 10 | 0 | 30 | 0 | 20 | 0 | 20 | 0 | 0 | 60 | |
| Crabgrass, Large | 100 | 30 | 100 | 100 | 100 | 100 | 10 | 100 | 90 | 100 | 40 | 20 | 100 | |
| Foxtail, Giant | 90 | 10 | 100 | 90 | 100 | 100 | 0 | 100 | 90 | 90 | 30 | 20 | 100 | |
| Morningglory | 20 | 30 | 10 | 10 | 10 | 30 | 0 | 50 | 10 | 30 | 0 | 20 | 60 | |
| Pigweed | 100 | 10 | 100 | 100 | 100 | 100 | 0 | 100 | 90 | 100 | 20 | 0 | 100 | |
| Velvetleaf | 20 | 10 | 20 | 20 | 10 | 70 | 0 | 60 | 50 | 40 | 0 | 0 | 70 | |
| Wheat | 0 | 0 | 10 | 10 | 0 | 20 | 0 | 20 | 0 | 0 | 0 | 0 | 50 | |
| | Compounds | | | | | | | | | | | | | |
| 500 g ai/ha | 135 | 136 | 137 | 138 | 139 | 140 | 141 | 142 | 143 | 144 | 145 | 146 | 147 | 148 |
| | Preemergence | | | | | | | | | | | | | |
| Barnyardgrass | 0 | 100 | 70 | 100 | 100 | 30 | 100 | 100 | 90 | 30 | 100 | 100 | 100 | 100 |
| Corn | 0 | 10 | 0 | 60 | 30 | 0 | 30 | 80 | 20 | 0 | 40 | 10 | 30 | 20 |
| Crabgrass, Large | 0 | 100 | 90 | 90 | 100 | 50 | 100 | 100 | 100 | 100 | 100 | 100 | 100 | 100 |
| Foxtail, Giant | 0 | 100 | 90 | 100 | 100 | 70 | 100 | 100 | 100 | 100 | 100 | 100 | 100 | 100 |
| Morningglory | 0 | 60 | 60 | 90 | 70 | 0 | 60 | 80 | 0 | 0 | 60 | 60 | 80 | 90 |
| Pigweed | 0 | 90 | 100 | 100 | 100 | 80 | 100 | 100 | 100 | 100 | 100 | 100 | 100 | 100 |
| Velvetleaf | 0 | 60 | 20 | 100 | 90 | 30 | 60 | 90 | 20 | 0 | 80 | 50 | 50 | 70 |
| Wheat | 0 | 10 | 0 | 60 | 50 | 0 | 20 | 80 | 10 | 0 | 60 | 30 | 50 | 50 |

TABLE A-continued

| 500 g ai/ha | 149 | 150 | 151 | 152 | 153 | 154 | 155 | 156 | 157 | 158 | 159 | 160 | 161 | 162 |
|---|---|---|---|---|---|---|---|---|---|---|---|---|---|---|
| Preemergence | | | | | | | | | | | | | | |
| Barnyardgrass | 90 | 0 | 0 | 0 | 100 | 100 | 100 | 100 | 100 | 0 | 80 | 100 | 60 | 100 |
| Corn | 20 | 0 | 0 | 0 | 80 | 70 | 80 | 70 | 0 | 0 | 0 | 40 | 10 | 30 |
| Crabgrass, Large | 100 | 0 | 10 | 10 | 100 | 100 | 100 | 100 | 90 | 0 | 30 | 100 | 100 | 100 |
| Foxtail, Giant | 100 | 0 | 20 | 20 | 100 | 100 | 100 | 100 | 100 | 0 | 90 | 100 | 100 | 100 |
| Morningglory | 30 | 0 | 0 | 0 | 100 | 80 | 90 | 90 | 0 | 0 | 0 | 70 | 10 | 90 |
| Pigweed | 100 | 0 | 60 | 40 | 100 | 100 | 100 | 100 | 100 | 0 | 90 | 100 | 100 | 100 |
| Velvetleaf | 50 | 0 | 0 | 0 | 100 | 70 | — | — | 0 | 0 | 0 | 70 | 50 | 100 |
| Wheat | 50 | 0 | 0 | 0 | 70 | 20 | 70 | 80 | 0 | 0 | 0 | 50 | 10 | 30 |

| 500 g ai/ha | 163 | 164 | 165 | 166 | 168 | 169 | 170 | 171 | 172 | 173 | 174 | 175 | 176 | 177 |
|---|---|---|---|---|---|---|---|---|---|---|---|---|---|---|
| Preemergence | | | | | | | | | | | | | | |
| Barnyardgrass | 100 | 100 | 100 | 100 | 100 | 90 | — | — | — | — | — | 0 | 0 | 70 |
| Corn | 10 | 30 | 10 | 30 | 40 | 20 | 40 | 30 | 60 | 0 | 20 | 0 | 0 | 0 |
| Crabgrass, Large | 100 | 100 | 100 | 100 | 100 | 100 | 100 | 100 | 100 | 100 | 100 | 0 | 0 | 100 |
| Foxtail, Giant | 100 | 100 | 100 | 100 | 100 | 100 | 100 | 100 | 100 | 100 | 100 | 0 | 0 | 100 |
| Morningglory | 30 | 90 | — | — | 50 | 40 | 90 | 60 | 80 | 10 | 40 | 0 | 0 | 40 |
| Pigweed | 100 | 100 | 100 | 100 | 100 | 100 | 100 | 100 | 100 | 70 | 100 | 0 | 0 | 50 |
| Velvetleaf | 20 | 100 | 10 | 70 | 90 | 90 | 100 | 80 | 90 | 20 | 70 | 0 | 0 | 20 |
| Wheat | 0 | 60 | 0 | 50 | 60 | 50 | 80 | 60 | 70 | 0 | 30 | 0 | 0 | 0 |

| 500 g ai/ha | 178 | 179 | 180 | 181 | 182 | 183 | 184 | 185 | 186 | 187 | 188 | 189 | 190 | 191 |
|---|---|---|---|---|---|---|---|---|---|---|---|---|---|---|
| Preemergence | | | | | | | | | | | | | | |
| Barnyardgrass | 100 | 100 | 80 | 20 | 90 | 100 | 50 | 100 | 0 | 0 | 100 | 90 | 100 | 100 |
| Corn | 10 | 30 | 20 | 0 | 10 | 30 | 0 | 30 | 0 | 0 | 20 | 10 | 90 | 60 |
| Crabgrass, Large | 100 | 100 | 100 | 80 | 100 | 100 | 100 | 100 | 0 | 0 | 100 | 100 | 100 | 100 |
| Foxtail, Giant | 100 | 100 | 100 | 80 | 100 | 100 | 90 | 100 | 0 | 0 | 100 | 100 | 100 | 100 |
| Morningglory | 60 | 70 | 70 | 10 | 10 | 90 | 10 | 100 | 0 | 0 | 90 | 30 | 80 | 30 |
| Pigweed | 100 | 100 | 100 | 90 | 100 | 100 | 100 | 100 | 0 | 0 | 100 | 100 | 100 | 100 |
| Velvetleaf | 60 | 100 | 60 | 0 | 70 | 80 | 30 | 100 | 0 | 0 | 90 | 60 | 100 | 80 |
| Wheat | 10 | 50 | 40 | 0 | 0 | 60 | 0 | 50 | 0 | 0 | 50 | 50 | 80 | 70 |

| 500 g ai/ha | 192 | 193 | 194 | 195 | 196 | 197 | 198 | 199 | 200 | 201 |
|---|---|---|---|---|---|---|---|---|---|---|
| Preemergence | | | | | | | | | | |
| Barnyardgrass | 0 | 0 | 0 | 100 | 100 | 0 | 0 | 0 | 0 | 0 |
| Corn | 0 | 0 | 0 | 30 | 50 | 0 | 0 | 0 | 0 | 0 |
| Crabgrass, Large | 70 | 40 | 10 | 100 | 100 | 0 | 0 | 70 | 100 | 20 |
| Foxtail, Giant | 80 | 70 | 30 | 100 | 100 | 0 | 0 | 50 | 100 | 20 |
| Morningglory | 10 | 0 | 0 | 60 | 90 | 0 | 0 | 0 | 10 | 0 |
| Pigweed | 40 | 20 | 10 | 100 | 100 | 0 | 0 | 30 | 100 | 10 |
| Velvetleaf | 0 | 0 | 0 | 80 | 100 | 0 | 0 | 0 | 0 | 0 |
| Wheat | 0 | 0 | 0 | 50 | 70 | 0 | 0 | 0 | 0 | 0 |

| 125 g ai/ha | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Preemergence | | | | | | | | | | | | | | |
| Barnyardgrass | 20 | 0 | 10 | 10 | 0 | 0 | 40 | 20 | 30 | 0 | 0 | 30 | 0 | 70 |
| Corn | 0 | 0 | 0 | 0 | 0 | 0 | 0 | 0 | 0 | 0 | 0 | 0 | 0 | 20 |
| Crabgrass, Large | 70 | 10 | 90 | 80 | 0 | 0 | 100 | 90 | 90 | 40 | 0 | 90 | 0 | 90 |
| Foxtail, Giant | 60 | 10 | 90 | 80 | 0 | 0 | 90 | 60 | 80 | 20 | 0 | 80 | 0 | 100 |
| Morningglory | 0 | 0 | 0 | 0 | 0 | 0 | 30 | 30 | 50 | 0 | 0 | 10 | 0 | 60 |
| Pigweed | 60 | 0 | 70 | 50 | 0 | 0 | 100 | 90 | 90 | 60 | 0 | 80 | 0 | 90 |

TABLE A-continued

| | Compounds | | | | | | | | | | | | | |
|---|---|---|---|---|---|---|---|---|---|---|---|---|---|---|
| Velvetleaf | 0 | 0 | 0 | 0 | 0 | 0 | 30 | 20 | 30 | 0 | 0 | 60 | 0 | 70 |
| Wheat | 0 | 0 | 0 | 0 | 0 | 0 | 0 | 0 | 0 | 0 | 0 | 0 | 0 | 30 |

| | Compounds | | | | | | | | | | | | | |
|---|---|---|---|---|---|---|---|---|---|---|---|---|---|---|
| 125 g ai/ha | 15 | 16 | 17 | 18 | 19 | 20 | 21 | 22 | 23 | 24 | 25 | 26 | 27 | 28 |
| Preemergence | | | | | | | | | | | | | | |
| Barnyardgrass | 100 | 90 | 30 | 20 | 20 | 0 | 0 | 0 | 70 | 0 | 80 | 90 | 0 | 50 |
| Corn | 20 | 10 | 0 | 0 | 0 | 0 | 0 | 0 | 10 | 0 | 10 | 30 | 0 | 20 |
| Crabgrass, Large | 100 | 90 | 100 | 90 | 60 | 0 | 0 | 10 | 100 | 0 | 90 | 100 | 20 | 30 |
| Foxtail, Giant | 100 | 100 | 90 | 80 | 50 | 0 | 0 | 20 | 100 | 20 | 100 | 100 | 10 | 100 |
| Morningglory | 60 | — | 0 | 10 | 10 | 0 | 0 | 0 | 80 | 0 | 30 | 80 | 0 | 20 |
| Pigweed | 100 | 90 | 90 | 80 | 80 | 0 | 0 | 10 | 100 | 0 | 100 | 100 | 0 | 100 |
| Velvetleaf | 70 | 30 | 30 | 20 | 20 | 0 | 0 | 0 | 50 | 0 | 20 | 80 | 0 | 20 |
| Wheat | 30 | 10 | 0 | 0 | 0 | 0 | 0 | 0 | 0 | 0 | 20 | 50 | 0 | 0 |

| | Compounds | | | | | | | | | | | | | |
|---|---|---|---|---|---|---|---|---|---|---|---|---|---|---|
| 125 g ai/ha | 29 | 30 | 31 | 32 | 33 | 34 | 35 | 36 | 37 | 38 | 39 | 40 | 41 | 42 |
| Preemergence | | | | | | | | | | | | | | |
| Barnyardgrass | 10 | 0 | 0 | 0 | 0 | 0 | 60 | 0 | 30 | 0 | 0 | 30 | 10 | 0 |
| Corn | 0 | 0 | 0 | 0 | 0 | 0 | 10 | 0 | 0 | 0 | 0 | 0 | 0 | 0 |
| Crabgrass, Large | 90 | 0 | 0 | 10 | 0 | 50 | 90 | 0 | 90 | 50 | 0 | 100 | 20 | 10 |
| Foxtail, Giant | 80 | 0 | 30 | 10 | 0 | 30 | 80 | 0 | 90 | 0 | 0 | 100 | 40 | 10 |
| Morningglory | 0 | 0 | 0 | 0 | 0 | 0 | 20 | 0 | 0 | 0 | 0 | 0 | 0 | 0 |
| Pigweed | 50 | 0 | 0 | 0 | 0 | 10 | 90 | 0 | 70 | 0 | 0 | 90 | 20 | 10 |
| Velvetleaf | 0 | 0 | 0 | 0 | 0 | 0 | 30 | 0 | 0 | 0 | 0 | 10 | 10 | 0 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 43 | 44 | 45 | 47 | 48 | 49 | 50 | 51 | 52 | 53 | 54 | 55 | 56 | 57 |
| Preemergence | | | | | | | | | | | | | | |
| Barnyardgrass | 0 | 0 | 0 | 90 | 0 | 10 | 0 | 0 | 20 | 80 | 80 | 90 | 0 | 0 |
| Corn | 0 | 0 | 0 | 20 | 0 | 0 | 0 | 0 | 0 | 0 | 10 | 20 | 0 | 0 |
| Crabgrass, Large | 30 | 60 | 70 | 100 | 30 | 80 | 10 | 0 | 100 | 100 | 100 | 100 | 90 | 0 |
| Foxtail, Giant | 20 | 70 | 50 | 100 | 40 | 80 | 10 | 0 | 100 | 100 | 100 | 100 | 30 | 0 |
| Morningglory | — | — | 0 | 70 | 0 | 0 | 0 | 0 | 10 | 30 | 60 | 50 | 0 | 0 |
| Pigweed | 50 | 20 | 10 | 100 | 40 | 60 | 0 | 0 | 100 | 90 | 100 | 100 | 30 | 0 |
| Velvetleaf | 0 | 0 | 0 | 80 | 0 | 0 | 0 | 0 | 0 | 10 | 30 | 40 | 0 | 0 |
| Wheat | 0 | 0 | 0 | 30 | 0 | 10 | 0 | 0 | 0 | 10 | 10 | 10 | 0 | 0 |

| | Compounds | | | | | | | | | | | | | |
|---|---|---|---|---|---|---|---|---|---|---|---|---|---|---|
| 125 g ai/ha | 58 | 59 | 60 | 61 | 62 | 63 | 64 | 65 | 66 | 68 | 69 | 70 | 71 | 72 |
| Preemergence | | | | | | | | | | | | | | |
| Barnyardgrass | 0 | 0 | 0 | 0 | 0 | 0 | 0 | 10 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 0 | 0 | 0 | 0 | 0 | 0 | 0 | 30 | 10 | 0 | 0 | 0 | 0 | 0 |
| Foxtail, Giant | 0 | 0 | 0 | 0 | 0 | 0 | 0 | 90 | 10 | 0 | 0 | 0 | 0 | 0 |
| Morningglory | 0 | 0 | 0 | 0 | 0 | 0 | 0 | 10 | 0 | 0 | 0 | 0 | 0 | 0 |
| Pigweed | 0 | 0 | 0 | 0 | 0 | 0 | 0 | 80 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 73 | 74 | 75 | 76 | 77 | 78 | 79 | 80 | 82 | 83 | 84 | 86 | 87 | 88 |
| Preemergence | | | | | | | | | | | | | | |
| Barnyardgrass | 0 | 0 | 10 | 0 | 0 | 0 | 0 | 20 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 50 | 0 | 20 | 10 | 0 | 60 | 0 | 90 | 0 | 0 | 0 | 0 | 0 | 0 |
| Foxtail, Giant | 60 | 0 | 50 | 10 | 0 | 20 | 0 | 90 | 0 | 0 | 0 | 0 | 0 | 0 |
| Morningglory | 0 | 0 | — | 0 | 0 | 0 | 0 | 0 | 0 | 0 | 0 | 0 | 0 | 0 |
| Pigweed | 30 | 0 | 30 | 0 | 0 | 60 | 0 | 100 | 0 | 0 | 0 | 0 | 0 | 0 |
| Velvetleaf | 0 | 0 | 0 | 0 | 0 | 10 | 0 | 30 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

TABLE A-continued

Compounds

| 125 g ai/ha | 90 | 91 | 92 | 93 | 98 | 99 | 100 | 101 | 102 | 103 | 104 | 107 | 108 | 110 |
|---|---|---|---|---|---|---|---|---|---|---|---|---|---|---|
| Preemergence | | | | | | | | | | | | | | |
| Barnyardgrass | 0 | 0 | 0 | 0 | 10 | 0 | 0 | 50 | 0 | 0 | 10 | 30 | 30 | 0 |
| Corn | 0 | 0 | 0 | 0 | 0 | 0 | 0 | 0 | 0 | 0 | 0 | 0 | 0 | 0 |
| Crabgrass, Large | 0 | 0 | 10 | 0 | 80 | 30 | 10 | 100 | 0 | 0 | 60 | 100 | 90 | 0 |
| Foxtail, Giant | 0 | 0 | 10 | 0 | 70 | 10 | 20 | 100 | 0 | 0 | 60 | 90 | 80 | 0 |
| Morningglory | 0 | 0 | 0 | 0 | 0 | 0 | 0 | 0 | 0 | 0 | 0 | 20 | 0 | 10 |
| Pigweed | 0 | 0 | 0 | 0 | 60 | 20 | 10 | 100 | 0 | 10 | 30 | 70 | 80 | 0 |
| Velvetleaf | 0 | 0 | 0 | 0 | 0 | 0 | 0 | 0 | 0 | 0 | 0 | 10 | 0 | 0 |
| Wheat | 0 | 0 | 0 | 0 | 0 | 0 | 0 | 0 | 0 | 0 | 0 | 0 | 0 | 0 |

| 125 g ai/ha | 111 | 112 | 114 | 115 | 116 | 119 | 120 | 121 | 122 | 125 | 126 | 127 | 128 | 129 |
|---|---|---|---|---|---|---|---|---|---|---|---|---|---|---|
| Preemergence | | | | | | | | | | | | | | |
| Barnyardgrass | 20 | 0 | 0 | 30 | 0 | 0 | 90 | 0 | 20 | 30 | 70 | 0 | 0 | 100 |
| Corn | 0 | 0 | 0 | 0 | 0 | 0 | 20 | 0 | 10 | 0 | 0 | 0 | 0 | 50 |
| Crabgrass, Large | 80 | 80 | 0 | 80 | 70 | 70 | 100 | 0 | 90 | 80 | 100 | 10 | 0 | 100 |
| Foxtail, Giant | 70 | 60 | 0 | 60 | 60 | 50 | 100 | 0 | 90 | 80 | 70 | 10 | 0 | 100 |
| Morningglory | 0 | 0 | 10 | 0 | 0 | 0 | 10 | 0 | 20 | 0 | 10 | 0 | 0 | 50 |
| Pigweed | 70 | 90 | 0 | 100 | 50 | 60 | 100 | 0 | 90 | 70 | 100 | 0 | 0 | 100 |
| Velvetleaf | 0 | 0 | 0 | 0 | 0 | 0 | 40 | 0 | 30 | 0 | 10 | 0 | 0 | 60 |
| Wheat | 0 | 0 | 0 | 0 | 0 | 0 | 10 | 0 | 0 | 0 | 0 | 0 | 0 | 10 |

| 125 g ai/ha | 135 | 136 | 137 | 138 | 139 | 140 | 141 | 142 | 143 | 144 | 145 | 146 | 147 | 148 |
|---|---|---|---|---|---|---|---|---|---|---|---|---|---|---|
| Preemergence | | | | | | | | | | | | | | |
| Barnyardgrass | 0 | 70 | 50 | 90 | 80 | 0 | 40 | 100 | 30 | 0 | 100 | 90 | 90 | 90 |
| Corn | 0 | 0 | 0 | 30 | 10 | 0 | 0 | 30 | 0 | 0 | 10 | 0 | 10 | 10 |
| Crabgrass, Large | 0 | 80 | 90 | 90 | 100 | 20 | 100 | 100 | 90 | 50 | 100 | 100 | 100 | 100 |
| Foxtail, Giant | 0 | 100 | 90 | 100 | 100 | 20 | 100 | 100 | 90 | 50 | 100 | 100 | 100 | 100 |
| Morningglory | 0 | 20 | 40 | 70 | 50 | 0 | 30 | 50 | 0 | 0 | 10 | 10 | — | 40 |
| Pigweed | 0 | 90 | 100 | 100 | 100 | 30 | 100 | 100 | 100 | 50 | 100 | 100 | 100 | 100 |
| Velvetleaf | 0 | 30 | 20 | 70 | 30 | 20 | 20 | 60 | 0 | 0 | 50 | 10 | 20 | 20 |
| Wheat | 0 | 0 | 0 | 30 | 10 | 0 | 0 | 70 | 0 | 0 | 20 | 0 | 30 | 30 |

| 125 g ai/ha | 149 | 150 | 151 | 152 | 153 | 154 | 155 | 156 | 157 | 158 | 159 | 160 | 161 | 162 |
|---|---|---|---|---|---|---|---|---|---|---|---|---|---|---|
| Preemergence | | | | | | | | | | | | | | |
| Barnyardgrass | 60 | 0 | 0 | 0 | 100 | 100 | 100 | 100 | 20 | 0 | 10 | 100 | 20 | 90 |
| Corn | 10 | 0 | 0 | 0 | 70 | 20 | 60 | 40 | 0 | 0 | 0 | 20 | 10 | 20 |
| Crabgrass, Large | 90 | 0 | 0 | 0 | 100 | 100 | 100 | 100 | 20 | 0 | 10 | 100 | 100 | 100 |
| Foxtail, Giant | 90 | 0 | 0 | 0 | 100 | 100 | 100 | 100 | 90 | 0 | 40 | 100 | 100 | 100 |
| Morningglory | 10 | 0 | 0 | 0 | 80 | 20 | 80 | 80 | 0 | 0 | 0 | 40 | 10 | 30 |
| Pigweed | 90 | 0 | 10 | 0 | 100 | 100 | 100 | 100 | 80 | 0 | 70 | 100 | 100 | 100 |
| Velvetleaf | 20 | 0 | 0 | 0 | 80 | 30 | — | 30 | 0 | 0 | 0 | 50 | 0 | 100 |
| Wheat | 0 | 0 | 0 | 0 | 50 | 0 | 10 | 20 | 0 | 0 | 0 | 30 | 0 | 10 |

| 125 g ai/ha | 163 | 164 | 165 | 166 | 168 | 169 | 170 | 171 | 172 | 173 | 174 | 175 | 176 | 177 |
|---|---|---|---|---|---|---|---|---|---|---|---|---|---|---|
| Preemergence | | | | | | | | | | | | | | |
| Barnyardgrass | 90 | 90 | 30 | 90 | 90 | 80 | — | — | — | — | — | 0 | 0 | 0 |
| Corn | 0 | 30 | 0 | 10 | 20 | 20 | 30 | 10 | 30 | 0 | 10 | 0 | 0 | 0 |
| Crabgrass, Large | 100 | 100 | 100 | 100 | 100 | 100 | 100 | 100 | 100 | 60 | 100 | 0 | 0 | 90 |
| Foxtail, Giant | 100 | 100 | 90 | 100 | 100 | 100 | 100 | 100 | 100 | 80 | 90 | 0 | 0 | 90 |
| Morningglory | 10 | 80 | — | — | 20 | 20 | 70 | 50 | 60 | 0 | 20 | 0 | 0 | 20 |
| Pigweed | 100 | 100 | 100 | 100 | 100 | 100 | 100 | 100 | 100 | 50 | 100 | 0 | 0 | 10 |

TABLE A-continued

| | Compounds | | | | | | | | | | | | | |
|---|---|---|---|---|---|---|---|---|---|---|---|---|---|---|
| Velvetleaf | 0 | 80 | 0 | 30 | 30 | 50 | 90 | 60 | 80 | 0 | 50 | 0 | 0 | 0 |
| Wheat | 0 | 50 | 0 | 10 | 40 | 20 | 60 | 10 | 50 | 0 | 0 | 0 | 0 | 0 |

| | Compounds | | | | | | | | | | | | | |
|---|---|---|---|---|---|---|---|---|---|---|---|---|---|---|
| 125 g ai/ha | 178 | 179 | 180 | 181 | 182 | 183 | 184 | 185 | 186 | 187 | 188 | 189 | 190 | 191 |
| Preemergence | | | | | | | | | | | | | | |
| Barnyardgrass | 20 | 90 | 60 | 0 | 30 | 90 | 0 | 100 | 0 | 0 | 90 | 80 | 100 | 90 |
| Corn | 0 | 20 | 10 | 0 | 0 | 20 | 0 | 10 | 0 | 0 | 10 | 10 | 30 | 20 |
| Crabgrass, Large | 90 | 100 | 100 | 10 | 90 | 100 | 70 | 100 | 0 | 0 | 100 | 100 | 100 | 100 |
| Foxtail, Giant | 90 | 100 | 100 | 10 | 90 | 100 | 70 | 100 | 0 | 0 | 100 | 100 | 100 | 100 |
| Morningglory | 0 | 40 | 40 | 0 | 0 | 70 | 0 | 60 | 0 | 0 | 20 | 20 | 80 | 20 |
| Pigweed | 100 | 100 | 100 | 60 | 80 | 100 | 90 | 100 | 0 | 0 | 100 | 100 | 100 | 100 |
| Velvetleaf | 10 | 80 | 50 | 0 | 60 | 70 | 0 | 90 | 0 | 0 | 40 | 20 | 40 | 30 |
| Wheat | 0 | 20 | 20 | 0 | 0 | 30 | 0 | 30 | 0 | 0 | 30 | 20 | 60 | 40 |

| | Compounds | | | | | | | | | |
|---|---|---|---|---|---|---|---|---|---|---|
| 125 g ai/ha | 192 | 193 | 194 | 195 | 196 | 197 | 198 | 199 | 200 | 201 |
| Preemergence | | | | | | | | | | |
| Barnyardgrass | 0 | 0 | 0 | 90 | 100 | 0 | 0 | 0 | 0 | 0 |
| Corn | 0 | 0 | 0 | 20 | 30 | 0 | 0 | 0 | 0 | 0 |
| Crabgrass, Large | 0 | 0 | 0 | 100 | 100 | 0 | 0 | 20 | 80 | 0 |
| Foxtail, Giant | 0 | 10 | 0 | 100 | 100 | 0 | 0 | 0 | 70 | 0 |
| Morningglory | 0 | 0 | 0 | 50 | 60 | 0 | 0 | 0 | 0 | 0 |
| Pigweed | 10 | 0 | 0 | 100 | 100 | 0 | 0 | 10 | 50 | 0 |
| Velvetleaf | 0 | 0 | 0 | 70 | 80 | 0 | 0 | 0 | 0 | 0 |
| Wheat | 0 | 0 | 0 | 20 | 50 | 0 | 0 | 0 | 0 | 0 |

Test B

Seeds selected from rice (*Oryza sativa*), sedge, umbrella (small-flower umbrella sedge *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test.

Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| | Compounds | | | | | | | | | | | | | |
|---|---|---|---|---|---|---|---|---|---|---|---|---|---|---|
| 250 g ai/ha | 3 | 4 | 5 | 6 | 24 | 25 | 26 | 27 | 28 | 34 | 43 | 44 | 53 | 54 |
| Flood | | | | | | | | | | | | | | |
| Barnyardgrass | 0 | 20 | 0 | 0 | 0 | 30 | 60 | 20 | 90 | 65 | 0 | 0 | 60 | 30 |
| Ducksalad | 0 | 40 | 0 | 0 | 0 | 90 | 40 | 50 | 95 | 75 | 85 | 0 | 85 | 85 |
| Rice | 0 | 0 | 0 | 0 | 0 | 35 | 80 | 10 | 80 | 35 | 0 | 0 | 50 | 30 |
| Sedge, Umbrella | 0 | 70 | 0 | 0 | 0 | 95 | 90 | 20 | 95 | 90 | 100 | 0 | 85 | 85 |

| | Compounds | | | | |
|---|---|---|---|---|---|
| 250 g ai/ha | 55 | 56 | 65 | 86 | 87 |
| Flood | | | | | |
| Barnyardgrass | 70 | 30 | 30 | 0 | 0 |
| Ducksalad | 100 | 80 | 60 | 0 | 0 |

TABLE B-continued

| | | | | | |
|---|---|---|---|---|---|
| Rice | 60 | 40 | 25 | 0 | 0 |
| Sedge, Umbrella | 100 | 80 | 75 | 50 | 50 |

| | Compounds | | | | | | | | | | | | | |
|---|---|---|---|---|---|---|---|---|---|---|---|---|---|---|
| 250 g ai/ha | 135 | 136 | 137 | 138 | 139 | 140 | 141 | 142 | 143 | 144 | 145 | 146 | 147 | 148 |
| | Flood | | | | | | | | | | | | | |
| Barnyardgrass | 0 | 45 | 45 | 80 | 65 | 30 | 20 | 70 | 40 | 30 | 90 | 50 | 55 | 65 |
| Ducksalad | 0 | 75 | 50 | 90 | 70 | 0 | 85 | 90 | 0 | 40 | 60 | 60 | 40 | 85 |
| Rice | 0 | 35 | 40 | 50 | 45 | 0 | 35 | 60 | 30 | 20 | 80 | 35 | 50 | 45 |
| Sedge, Umbrella | 0 | 85 | 70 | 90 | 80 | 0 | 85 | 90 | 75 | 80 | 85 | 80 | 80 | 85 |

| | Compounds | | | | | | | | | | | | | |
|---|---|---|---|---|---|---|---|---|---|---|---|---|---|---|
| 250 g ai/ha | 149 | 150 | 151 | 152 | 153 | 154 | 155 | 156 | 157 | 158 | 159 | 160 | 168 | 169 |
| | Flood | | | | | | | | | | | | | |
| Barnyardgrass | 40 | 20 | 0 | 0 | 80 | 60 | 75 | 75 | 0 | 0 | 30 | 65 | 80 | 75 |
| Ducksalad | 60 | 0 | 0 | 0 | 90 | 80 | 80 | 90 | 20 | 0 | 20 | 90 | 80 | 85 |
| Rice | 30 | 0 | 30 | 0 | 60 | 45 | 50 | 50 | 0 | 75 | 30 | 55 | 60 | 55 |
| Sedge, Umbrella | 60 | 0 | 0 | 0 | 90 | 80 | 80 | 85 | 40 | 0 | 60 | 85 | 85 | 85 |

| | Compounds | | | | | | | | | | | | |
|---|---|---|---|---|---|---|---|---|---|---|---|---|---|
| 250 g ai/ha | 170 | 171 | 172 | 173 | 174 | 184 | 185 | 192 | 195 | 196 | 197 | 198 | 201 |
| | Flood | | | | | | | | | | | | |
| Barnyardgrass | 80 | 70 | 80 | 0 | 70 | 25 | 90 | 0 | 85 | 85 | 0 | 0 | 0 |
| Ducksalad | 35 | 0 | 0 | 0 | 50 | 0 | 65 | 0 | 100 | 100 | 0 | 0 | 0 |
| Rice | 60 | 60 | 50 | 0 | 50 | 25 | 65 | 0 | 60 | 70 | 0 | 0 | 0 |
| Sedge, Umbrella | 90 | 85 | 75 | 0 | 75 | 60 | 95 | 0 | 100 | 100 | 0 | 0 | 0 |

| | Compounds | | | | | | | | | | | | | |
|---|---|---|---|---|---|---|---|---|---|---|---|---|---|---|
| 125 g ai/ha | 161 | 162 | 163 | 164 | 165 | 166 | 167 | 175 | 176 | 177 | 178 | 179 | 180 | 181 |
| | Flood | | | | | | | | | | | | | |
| Barnyardgrass | 0 | 70 | 15 | 60 | 10 | 70 | 0 | 0 | 0 | 0 | 0 | 0 | 0 | 0 |
| Ducksalad | 0 | 0 | 70 | 0 | 40 | 70 | 0 | 0 | 0 | 0 | 30 | 65 | 60 | 0 |
| Rice | 20 | 25 | 15 | 45 | 20 | 80 | 30 | 0 | 0 | 0 | 20 | 35 | 30 | 20 |
| Sedge, Umbrella | 80 | 80 | 80 | 75 | 70 | 70 | 50 | 0 | 0 | 40 | 60 | 75 | 70 | 0 |

| | Compounds | | | | | | | | | | | |
|---|---|---|---|---|---|---|---|---|---|---|---|---|
| 125 g ai/ha | 182 | 183 | 186 | 187 | 188 | 189 | 190 | 191 | 193 | 194 | 199 | 200 |
| | Flood | | | | | | | | | | | |
| Barnyardgrass | 0 | 30 | 0 | 0 | 75 | 0 | 70 | 50 | 0 | 0 | 0 | 0 |
| Ducksalad | 0 | 65 | 0 | 0 | 90 | 20 | 70 | 20 | 0 | 0 | 0 | 0 |
| Rice | 15 | 45 | 0 | 0 | 50 | 35 | 50 | 50 | 0 | 0 | 0 | 0 |
| Sedge, Umbrella | 50 | 95 | 0 | 0 | 100 | 0 | 95 | 50 | 0 | 0 | 0 | 0 |

Test C

Seeds of plant species selected from blackgrass (*Alopecurus myosuroides*), bromegrass, downy (downy bromegrass, *Bromus tectorum*), foxtail, green (green foxtail, *Setaria viridis*), ryegrass, Italian (Italian ryegrass, *Lolium multiflorum*), winter wheat (*Triticum aestivum*), wild oat (*Avena fatua*), *galium* (catchweed bedstraw, *Galium aparine*), bermudagrass (*Cynodon dactylon*), surinam grass (*Brachiaria decumbens*), cocklebur (common cocklebur, *Xanthium strumarium*), corn (*Zea mays*), large crabgrass (*Digitaria sanguinalis*), woolly cupgrass (*Eriochloa villosa*), foxtail, giant (giant foxtail, *Setaria* faberii), goosegrass (*Eleusine indica*), johnsongrass (*Sorghum halepense*), *kochia* (*Kochia scoparia*), lambsquarters (*Chenopodium album*), morningglory (*Ipomoea coccinea*), nightshade (eastern black nightshade, *Solanum* ptycanthum), nutsedge, yellow (yellow nutsedge, *Cyperus esculentus*), pigweed (*Amaranthus retroflexus*), ragweed (common ragweed, *Ambrosia* elation), soybean (*Glycine max*), common (oilseed) sunflower (*Helianthus annuus*), Russian thistle (*Salsola kali*) and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also barley (winter barley, *Hordeum vulgare*), canarygrass (*Phalaris minor*), chickweed (common chickweed, *Stellaria media*) windgrass (*Apera spica-venti*) and deadnettle (henbit deadnettle, *Lamium amplexicaule*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments.

Plant species in the flooded paddy test consisted of rice (*Oryza sativa*), sedge, umbrella (small-flower umbrella sedge, *Cyperus difformis*), ducksalad (*Heteranthera limosa*) and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test.

Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| | Compounds | | | | | | | | | | | | | |
|---|---|---|---|---|---|---|---|---|---|---|---|---|---|---|
| 250 g ai/ha | 1 | 2 | 7 | 8 | 9 | 10 | 11 | 12 | 13 | 14 | 15 | 16 | 17 | 18 |
| Flood | | | | | | | | | | | | | | |
| Barnyardgrass | 0 | 0 | 20 | 0 | 30 | 0 | 0 | 60 | 0 | 70 | 75 | 80 | 45 | 0 |
| Ducksalad | 0 | 0 | 70 | 45 | 0 | 0 | 0 | 70 | 0 | 60 | 60 | 100 | 20 | 0 |
| Rice | 0 | 0 | 15 | 0 | 0 | 0 | 0 | 25 | 0 | 45 | 50 | 50 | 45 | 0 |
| Sedge, Umbrella | 0 | 70 | 85 | 75 | 85 | 0 | 0 | 80 | 0 | 75 | 80 | 95 | 75 | 65 |
| | Compounds | | | | | | | | | | | | | |
| 250 g ai/ha | 19 | 20 | 21 | 22 | 23 | 29 | 30 | 31 | 32 | 33 | 35 | 36 | 37 | 38 |
| Flood | | | | | | | | | | | | | | |
| Barnyardgrass | 0 | 0 | 0 | 0 | 25 | 20 | 0 | 0 | 0 | 0 | 30 | 0 | 35 | 0 |
| Ducksalad | 0 | 0 | 0 | 0 | 85 | 0 | 0 | 0 | 0 | 0 | 75 | 0 | 70 | 0 |
| Rice | 0 | 0 | 0 | 0 | 30 | 0 | 0 | 0 | 0 | 0 | 0 | 0 | 20 | 0 |
| Sedge, Umbrella | 70 | 0 | 0 | 0 | 90 | 75 | 30 | 0 | 0 | 0 | 80 | 0 | 0 | 0 |
| | Compounds | | | | | | | | | | | | | |
| 250 g ai/ha | 39 | 40 | 41 | 42 | 45 | 47 | 48 | 49 | 50 | 51 | 52 | 57 | 58 | 59 |
| Flood | | | | | | | | | | | | | | |
| Barnyardgrass | 0 | 30 | 0 | 0 | 0 | 80 | 30 | 15 | 0 | 0 | 75 | 0 | 0 | 0 |
| Ducksalad | 40 | 70 | 0 | 0 | 0 | 90 | 65 | 40 | 0 | 0 | 95 | 0 | 0 | 0 |
| Rice | 10 | 25 | 0 | 0 | 0 | 60 | 20 | 0 | 0 | 0 | 40 | 0 | 0 | 0 |
| Sedge, Umbrella | 20 | 80 | 0 | 0 | 0 | 90 | 45 | 75 | 0 | 0 | 85 | 0 | 0 | 0 |
| | Compounds | | | | | | | | | | | | | |
| 250 g ai/ha | 60 | 61 | 62 | 63 | 64 | 66 | 68 | 70 | 71 | 72 | 73 | 74 | 75 | 76 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 85 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |
| | Compounds | | | | | | | | | | | | | |
| 250 g ai/ha | 77 | 78 | 79 | 80 | 82 | 83 | 84 | 88 | 90 | 91 | 92 | 93 | 94 | 95 |
| Flood | | | | | | | | | | | | | | |
| Barnyardgrass | 0 | 20 | 0 | 20 | 0 | 0 | 10 | 0 | 0 | 0 | 0 | 0 | 0 | 0 |
| Ducksalad | 0 | 0 | 0 | 0 | 0 | 30 | 40 | 0 | 0 | 0 | 0 | 0 | 60 | 0 |
| Rice | 0 | 0 | 0 | 0 | 0 | 25 | 20 | 0 | 0 | 0 | 0 | 0 | 0 | 0 |
| Sedge, Umbrella | 0 | 0 | 0 | 70 | 0 | 30 | 20 | 0 | 0 | 0 | 0 | 0 | 75 | 0 |
| | Compounds | | | | | | | | | | | | | |
| 250 g ai/ha | 96 | 98 | 101 | 105 | 106 | 107 | 108 | 109 | 111 | 115 | 116 | 117 | 118 | 119 |
| Flood | | | | | | | | | | | | | | |
| Barnyardgrass | 10 | 70 | 60 | 0 | 40 | 25 | 30 | 75 | 35 | 60 | 60 | 80 | 65 | 30 |
| Ducksalad | 50 | 70 | 65 | 0 | 70 | 40 | 45 | 80 | 80 | 20 | 50 | 85 | 70 | 80 |

TABLE C-continued

| | | | | | | | | | | | | | | |
|---|---|---|---|---|---|---|---|---|---|---|---|---|---|---|
| Rice | 0 | 40 | 20 | 0 | 30 | 25 | 20 | 25 | 30 | 40 | 30 | 40 | 20 | 25 |
| Sedge, Umbrella | 80 | 80 | 75 | 0 | 80 | 80 | 85 | 85 | 85 | 80 | 85 | 85 | 75 | 85 |

| | Compounds | | | | | | | | | | | |
|---|---|---|---|---|---|---|---|---|---|---|---|---|
| 250 g ai/ha | 120 | 122 | 123 | 124 | 125 | 126 | 129 | 130 | 131 | 132 | 133 | 134 |
| Flood | | | | | | | | | | | | |
| Barnyardgrass | 80 | 40 | 0 | 50 | 10 | 40 | 85 | 15 | 10 | 0 | 15 | 15 |
| Ducksalad | 85 | 65 | 75 | 90 | 90 | 65 | 90 | 20 | 20 | 20 | 20 | 0 |
| Rice | 80 | 30 | 10 | 20 | 10 | 20 | 50 | 15 | 0 | 0 | 0 | 0 |
| Sedge, Umbrella | 90 | 85 | 75 | 90 | 85 | 80 | 95 | 75 | 0 | 65 | 50 | 0 |

| | Compounds | | | | | | | | | | | | | |
|---|---|---|---|---|---|---|---|---|---|---|---|---|---|---|
| 125 g ai/ha | 7 | 8 | 16 | 17 | 18 | 19 | 20 | 21 | 22 | 23 | 29 | 30 | 31 | 32 |
| Flood | | | | | | | | | | | | | | |
| Barnyardgrass | 0 | 0 | 70 | 40 | 0 | 0 | 0 | 0 | 0 | 20 | 0 | 0 | 0 | 0 |
| Ducksalad | 30 | 0 | 95 | 0 | 0 | 0 | 0 | 0 | 0 | 60 | 0 | 0 | 0 | 0 |
| Rice | 0 | 0 | 40 | 35 | 0 | 0 | 0 | 0 | 0 | 0 | 0 | 0 | 0 | 0 |
| Sedge, Umbrella | 50 | 0 | 95 | 30 | 40 | 0 | 0 | 0 | 0 | 80 | 70 | 20 | 0 | 0 |

| | Compounds | | | | | | | | | | | | | |
|---|---|---|---|---|---|---|---|---|---|---|---|---|---|---|
| 125 g ai/ha | 33 | 35 | 36 | 40 | 41 | 45 | 47 | 49 | 57 | 58 | 59 | 60 | 61 | 62 |
| Flood | | | | | | | | | | | | | | |
| Barnyardgrass | 0 | 0 | 0 | 30 | 0 | 0 | 80 | 10 | 0 | 0 | 0 | 0 | 0 | 0 |
| Ducksalad | 0 | 70 | 0 | 60 | 0 | 0 | 90 | 30 | 0 | 0 | 0 | 0 | 0 | 0 |
| Rice | 0 | 0 | 0 | 20 | 0 | 0 | 60 | 0 | 0 | 0 | 0 | 0 | 0 | 0 |
| Sedge, Umbrella | 0 | 80 | 0 | 80 | 0 | 0 | 90 | 70 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 63 | 64 | 68 | 70 | 71 | 72 | 73 | 74 | 75 | 76 | 77 | 78 | 79 | 80 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 82 | 83 | 84 | 88 | 90 | 91 | 92 | 93 | 94 | 98 | 101 | 105 | 106 | 107 |
| Flood | | | | | | | | | | | | | | |
| Barnyardgrass | 0 | 0 | 0 | 0 | 0 | 0 | 0 | 0 | 0 | 30 | 55 | 0 | 20 | 20 |
| Ducksalad | 0 | 20 | 0 | 0 | 0 | 0 | 0 | 0 | 40 | 30 | 50 | 0 | 70 | 20 |
| Rice | 0 | 20 | 20 | 0 | 0 | 0 | 0 | 0 | 0 | 30 | 15 | 0 | 25 | 0 |
| Sedge, Umbrella | 0 | 20 | 0 | 0 | 0 | 0 | 0 | 0 | 60 | 40 | 50 | 0 | 75 | 60 |

| | Compounds | | | | | | | | | | | | | |
|---|---|---|---|---|---|---|---|---|---|---|---|---|---|---|
| 125 g ai/ha | 108 | 109 | 111 | 115 | 116 | 117 | 118 | 119 | 120 | 122 | 123 | 124 | 125 | 126 |
| Barnyardgrass | 20 | 40 | 20 | 45 | 40 | 65 | 50 | 25 | 80 | 40 | 0 | 50 | 0 | 30 |
| Ducksalad | 30 | 60 | 70 | 0 | 30 | 80 | 70 | 80 | 80 | 60 | 75 | 90 | 75 | 20 |

TABLE C-continued

| | | | | | | | | | | | | | | |
|---|---|---|---|---|---|---|---|---|---|---|---|---|---|---|
| Rice | 15 | 15 | 25 | 30 | 20 | 25 | 15 | 25 | 70 | 25 | 0 | 15 | 0 | 10 |
| Sedge, Umbrella | 75 | 85 | 80 | 75 | 75 | 75 | 70 | 85 | 90 | 85 | 50 | 90 | 80 | 75 |

| 125 g ai/ha | Compound 129 |
|---|---|
| Flood | |
| Barnyardgrass | 80 |
| Ducksalad | 80 |
| Rice | 40 |
| Sedge, Umbrella | 85 |

| | Compounds | | | | | | | | | | | | | |
|---|---|---|---|---|---|---|---|---|---|---|---|---|---|---|
| 62 g ai/ha | 1 | 2 | 7 | 8 | 9 | 10 | 11 | 12 | 13 | 14 | 15 | 16 | 17 | 18 |
| Flood | | | | | | | | | | | | | | |
| Barnyardgrass | 0 | 0 | 0 | 0 | 0 | 0 | 0 | 40 | 0 | 50 | 65 | 65 | 20 | 0 |
| Ducksalad | 0 | 0 | 0 | 0 | 0 | 0 | 0 | 60 | 0 | 40 | 40 | 85 | 0 | 0 |
| Rice | 0 | 0 | 0 | 0 | 0 | 0 | 0 | 0 | 0 | 40 | 45 | 30 | 15 | 0 |
| Sedge, Umbrella | 0 | 0 | 40 | 0 | 40 | 0 | 0 | 50 | 0 | 40 | 75 | 90 | 20 | 0 |

| | Compounds | | | | | | | | | | | | | |
|---|---|---|---|---|---|---|---|---|---|---|---|---|---|---|
| 62 g ai/ha | 19 | 20 | 21 | 22 | 23 | 29 | 30 | 31 | 32 | 33 | 35 | 36 | 37 | 38 |
| Flood | | | | | | | | | | | | | | |
| Barnyardgrass | 0 | 0 | 0 | 0 | 0 | 0 | 0 | 0 | 0 | 0 | 0 | 0 | 10 | 0 |
| Ducksalad | 0 | 0 | 0 | 0 | 60 | 0 | 0 | 0 | 0 | 0 | 65 | 0 | 0 | 0 |
| Rice | 0 | 0 | 0 | 0 | 0 | 0 | 0 | 0 | 0 | 0 | 0 | 0 | 10 | 0 |
| Sedge, Umbrella | 0 | 0 | 0 | 0 | 75 | 60 | 0 | 0 | 0 | 0 | 75 | 0 | 0 | 0 |

| | Compounds | | | | | | | | | | | | | |
|---|---|---|---|---|---|---|---|---|---|---|---|---|---|---|
| 62 g ai/ha | 39 | 40 | 41 | 42 | 45 | 47 | 48 | 49 | 50 | 51 | 52 | 57 | 58 | 59 |
| Flood | | | | | | | | | | | | | | |
| Barnyardgrass | 0 | 20 | 0 | 0 | 0 | 50 | 10 | 0 | 0 | 0 | 40 | 0 | 0 | 0 |
| Ducksalad | 0 | 30 | 0 | 0 | 0 | 90 | 20 | 0 | 0 | 0 | 80 | 0 | 0 | 0 |
| Rice | 0 | 10 | 0 | 0 | 0 | 50 | 10 | 0 | 0 | 0 | 15 | 0 | 0 | 0 |
| Sedge, Umbrella | 0 | 75 | 0 | 0 | 0 | 85 | 0 | 0 | 0 | 0 | 65 | 0 | 0 | 0 |

| | Compounds | | | | | | | | | | | | | |
|---|---|---|---|---|---|---|---|---|---|---|---|---|---|---|
| 62 g ai/ha | 60 | 61 | 62 | 63 | 64 | 66 | 68 | 70 | 71 | 72 | 73 | 74 | 75 | 76 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 62 g ai/ha | 77 | 78 | 79 | 80 | 82 | 83 | 84 | 88 | 90 | 91 | 92 | 93 | 94 | 95 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 20 | 0 | 0 | 0 | 0 | 0 | 0 | 0 | 0 |
| Rice | 0 | 0 | 0 | 0 | 0 | 20 | 0 | 0 | 0 | 0 | 0 | 0 | 0 | 0 |
| Sedge, Umbrella | 0 | 0 | 0 | 0 | 0 | 20 | 0 | 0 | 0 | 0 | 0 | 0 | 50 | 0 |

| | Compounds | | | | | | | | | | | | | |
|---|---|---|---|---|---|---|---|---|---|---|---|---|---|---|
| 62 g ai/ha | 96 | 98 | 101 | 105 | 106 | 107 | 108 | 109 | 111 | 115 | 116 | 117 | 118 | 119 |
| Flood | | | | | | | | | | | | | | |
| Barnyardgrass | 10 | 0 | 0 | 0 | 0 | 15 | 0 | 20 | 0 | 40 | 35 | 60 | 30 | 20 |
| Ducksalad | 40 | 0 | 20 | 0 | 60 | 0 | 0 | 20 | 30 | 0 | 0 | 50 | 30 | 50 |

TABLE C-continued

| | | | | | | | | | | | | | | |
|---|---|---|---|---|---|---|---|---|---|---|---|---|---|---|
| Rice | 0 | 0 | 0 | 0 | 0 | 0 | 0 | 15 | 0 | 20 | 0 | 15 | 0 | 15 |
| Sedge, Umbrella | 75 | 0 | 0 | 0 | 50 | 40 | 20 | 63 | 65 | 70 | 60 | 70 | 65 | 75 |

| | Compounds | | | | | | | | | | | |
|---|---|---|---|---|---|---|---|---|---|---|---|---|
| 62 g ai/ha | 120 | 122 | 123 | 124 | 125 | 126 | 129 | 130 | 131 | 132 | 133 | 134 |
| Flood | | | | | | | | | | | | |
| Barnyardgrass | 65 | 20 | 0 | 40 | 0 | 0 | 75 | 0 | 0 | 0 | 0 | 0 |
| Ducksalad | 70 | 0 | 40 | 90 | 0 | 0 | 75 | 0 | 0 | 0 | 0 | 0 |
| Rice | 60 | 0 | 0 | 0 | 0 | 0 | 30 | 0 | 0 | 0 | 0 | 0 |
| Sedge, Umbrella | 85 | 75 | 0 | 90 | 40 | 40 | 75 | 30 | 0 | 0 | 0 | 0 |

| | Compounds | | | | | | | | | | | | | |
|---|---|---|---|---|---|---|---|---|---|---|---|---|---|---|
| 31 g ai/ha | 7 | 8 | 16 | 17 | 18 | 19 | 20 | 21 | 22 | 23 | 29 | 30 | 31 | 32 |
| Flood | | | | | | | | | | | | | | |
| Barnyardgrass | 0 | 0 | 25 | 0 | 0 | 0 | 0 | 0 | 0 | 0 | 0 | 0 | 0 | 0 |
| Ducksalad | 0 | 0 | 70 | 0 | 0 | 0 | 0 | 0 | 0 | 50 | 0 | 0 | 0 | 0 |
| Rice | 0 | 0 | 20 | 10 | 0 | 0 | 0 | 0 | 0 | 0 | 0 | 0 | 0 | 0 |
| Sedge, Umbrella | 30 | 0 | 80 | 0 | 0 | 0 | 0 | 0 | 0 | 60 | 50 | 0 | 0 | 0 |

| | Compounds | | | | | | | | | | | | | |
|---|---|---|---|---|---|---|---|---|---|---|---|---|---|---|
| 31 g ai/ha | 33 | 35 | 36 | 40 | 41 | 45 | 47 | 49 | 57 | 58 | 59 | 60 | 61 | 62 |
| Flood | | | | | | | | | | | | | | |
| Barnyardgrass | 0 | 0 | 0 | 20 | 0 | 0 | 40 | 0 | 0 | 0 | 0 | 0 | 0 | 0 |
| Ducksalad | 0 | 40 | 0 | 30 | 0 | 0 | 0 | 0 | 0 | 0 | 0 | 0 | 0 | 0 |
| Rice | 0 | 0 | 0 | 0 | 0 | 0 | 30 | 0 | 0 | 0 | 0 | 0 | 0 | 0 |
| Sedge, Umbrella | 0 | 75 | 0 | 70 | 0 | 0 | 75 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 63 | 64 | 68 | 70 | 71 | 72 | 73 | 74 | 75 | 76 | 77 | 78 | 79 | 80 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 82 | 83 | 84 | 88 | 90 | 91 | 92 | 93 | 94 | 98 | 101 | 105 | 106 | 107 |
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 0 | 0 | 0 | 0 | 0 | 0 | 0 | 0 | 0 | 0 |
| Rice | 0 | 10 | 0 | 0 | 0 | 0 | 0 | 0 | 0 | 0 | 0 | 0 | 0 | 0 |
| Sedge, Umbrella | 0 | 10 | 0 | 0 | 0 | 0 | 0 | 0 | 0 | 0 | 0 | 0 | 50 | 0 |

| | Compounds | | | | | | | | | | |
|---|---|---|---|---|---|---|---|---|---|---|---|
| 31 g ai/ha | 108 | 109 | 111 | 117 | 118 | 122 | 123 | 124 | 125 | 126 | 129 |
| Flood | | | | | | | | | | | |
| Barnyardgrass | 0 | 0 | 0 | 50 | 20 | 10 | 0 | 20 | 0 | 0 | 55 |
| Ducksalad | 0 | 0 | 0 | 30 | 0 | 0 | 0 | 20 | 0 | 0 | 70 |
| Rice | 0 | 15 | 0 | 15 | 0 | 0 | 0 | 0 | 0 | 0 | 20 |
| Sedge, Umbrella | 20 | 38 | 45 | 65 | 40 | 70 | 0 | 50 | 0 | 30 | 75 |

| | Compounds | | | | | | | | | |
|---|---|---|---|---|---|---|---|---|---|---|
| 250 g ai/ha | 14 | 16 | 23 | 25 | 26 | 28 | 47 | 106 | 120 | 129 |
| Postemergence | | | | | | | | | | |
| Barley | 50 | 45 | 30 | 30 | 40 | 35 | 55 | 40 | 55 | 50 |
| Bermudagrass | 65 | 65 | 30 | 25 | 30 | 25 | 75 | 80 | 10 | 70 |
| Blackgrass | 85 | 80 | 25 | 60 | 90 | 60 | 90 | 60 | 85 | 80 |
| Bromegrass, Downy | 45 | 25 | 5 | 10 | 50 | 35 | 65 | 40 | — | 40 |
| Canarygrass | 85 | 90 | 15 | 55 | 90 | 90 | 90 | 80 | 90 | 85 |

TABLE C-continued

| | | | | | | | | | | |
|---|---|---|---|---|---|---|---|---|---|---|
| Chickweed | 80 | 100 | 70 | 98 | 100 | 100 | — | 98 | 100 | 98 |
| Cocklebur | 75 | 45 | 50 | 20 | 65 | 25 | 70 | 55 | 65 | 25 |
| Corn | 15 | 15 | 30 | 25 | 25 | 25 | 25 | 55 | 10 | 65 |
| Crabgrass, Large | 60 | 60 | 35 | 65 | 40 | 25 | 50 | 65 | 45 | 85 |
| Cupgrass, Woolly | 65 | 75 | 50 | 45 | 55 | 40 | 90 | 50 | 45 | 70 |
| Deadnettle | 100 | 100 | 98 | 100 | 100 | 100 | 100 | 90 | 100 | 100 |
| Foxtail, Giant | 35 | 50 | 25 | 60 | 60 | 50 | 98 | 55 | 55 | 65 |
| Foxtail, Green | 90 | — | 50 | 70 | 85 | 85 | 100 | 85 | 100 | 95 |
| Galium | 80 | 90 | 90 | 55 | 75 | 80 | 98 | 80 | — | 90 |
| Goosegrass | 75 | 10 | 30 | 40 | 70 | 45 | 75 | 55 | 45 | 55 |
| Johnsongrass | 75 | 45 | 20 | 15 | 40 | 10 | 50 | 55 | 45 | 70 |
| Kochia | 95 | 98 | 85 | 90 | 98 | 95 | — | 90 | 98 | 98 |
| Lambsquarters | 100 | 100 | 98 | 98 | 98 | 95 | — | 100 | 100 | 100 |
| Morningglory | 95 | 80 | 90 | — | — | — | 100 | 40 | 98 | 75 |
| Nutsedge, Yellow | 0 | 0 | 10 | 10 | 15 | 25 | 0 | 0 | 0 | 0 |
| Oat, Wild | 60 | 80 | 35 | 30 | 85 | 70 | 90 | 45 | 90 | 80 |
| Pigweed | 85 | 100 | 95 | 98 | 98 | 98 | 100 | 98 | 100 | 100 |
| Ragweed | 80 | 75 | 20 | 60 | 95 | 85 | 95 | 60 | 85 | 45 |
| Ryegrass, Italian | 40 | 20 | 15 | 5 | 35 | 30 | 85 | 30 | 30 | 60 |
| Soybean | 35 | 35 | 65 | 30 | 55 | 60 | 75 | 65 | 100 | 75 |
| Surinam Grass | 55 | 45 | 15 | 20 | 45 | 15 | 60 | 40 | 20 | 60 |
| Velvetleaf | 90 | 85 | 50 | 50 | 85 | 50 | 90 | 65 | 65 | 100 |
| Wheat | 45 | 30 | 30 | 30 | 35 | 20 | 50 | — | 35 | 40 |
| Windgrass | 95 | 50 | 15 | 40 | 80 | 50 | 100 | 85 | — | 100 |

| | Compounds | | | | | | | | | | | | | |
|---|---|---|---|---|---|---|---|---|---|---|---|---|---|---|
| 250 g ai/ha | 137 | 138 | 139 | 141 | 142 | 145 | 148 | 153 | 154 | 155 | 156 | 162 | 164 | 166 |
| Postemergence | | | | | | | | | | | | | | |
| Barley | 35 | 60 | 40 | 30 | 45 | 45 | 45 | — | — | — | — | — | — | — |
| Barnyardgrass | — | — | — | — | — | — | — | 75 | 40 | 75 | 55 | 95 | 10 | 60 |
| Bermudagrass | 45 | 95 | 80 | 95 | 85 | 90 | 55 | — | — | — | — | — | — | — |
| Blackgrass | 60 | 45 | 70 | 75 | 90 | 70 | 80 | 90 | 70 | 90 | 85 | 90 | 15 | 60 |
| Bromegrass, Downy | 85 | 65 | 30 | 45 | 50 | 25 | 65 | — | — | — | — | — | — | — |
| Canarygrass | 75 | 90 | 80 | 80 | 100 | 90 | 95 | — | — | — | — | — | — | — |
| Chickweed | 98 | 98 | 100 | 100 | 98 | 100 | 98 | 95 | 95 | 100 | 98 | 100 | 45 | 90 |
| Cocklebur | 60 | 85 | — | — | 50 | 65 | — | — | — | — | — | — | — | — |
| Corn | — | — | 60 | 60 | 45 | 50 | 60 | 55 | 20 | 45 | 30 | 40 | 20 | 15 |
| Crabgrass, Large | 65 | 95 | 80 | 95 | 95 | 95 | 80 | 90 | 70 | 85 | 70 | 80 | 10 | 40 |
| Cupgrass, Woolly | 90 | 85 | — | 45 | 85 | 75 | 75 | — | — | — | — | — | — | — |
| Deadnettle | 95 | 100 | 100 | 100 | 100 | 100 | 100 | — | — | — | — | — | — | — |
| Foxtail, Giant | 50 | 95 | 75 | 80 | 90 | 85 | 75 | 95 | 75 | 100 | 50 | 98 | 35 | 40 |
| Foxtail, Green | 95 | 90 | 100 | 100 | 100 | 100 | 100 | — | — | — | — | — | — | — |
| Galium | 70 | 90 | 80 | 90 | 90 | 95 | 90 | 85 | 75 | 95 | 95 | 95 | 60 | 80 |
| Goosegrass | — | 80 | 80 | 60 | 90 | 80 | 40 | — | — | — | — | — | — | — |
| Johnsongrass | 90 | 95 | 80 | 15 | 80 | 75 | 98 | 90 | 85 | 98 | 85 | 98 | 10 | 20 |
| Kochia | 90 | 98 | 90 | 90 | 95 | 95 | 95 | 90 | 95 | 95 | 95 | 95 | 90 | 90 |
| Lambsquarters | 100 | 100 | 98 | 98 | 98 | 95 | 98 | 95 | 98 | 98 | 98 | 98 | 70 | 98 |
| Morningglory | 90 | 98 | 70 | — | 80 | 98 | 98 | 95 | 98 | 98 | 100 | — | 75 | 65 |
| Nutsedge, Yellow | 15 | 20 | 25 | 15 | 20 | 15 | 15 | 15 | 15 | 20 | 10 | 10 | 10 | 10 |
| Oat, Wild | 70 | 98 | 80 | 70 | 70 | 80 | 90 | 85 | 65 | 90 | 70 | 90 | 10 | 30 |
| Oilseed Rape | — | — | — | — | — | — | — | 95 | 95 | 95 | 95 | 95 | 25 | 40 |
| Pigweed | 100 | 100 | 98 | 98 | 98 | 98 | 98 | 98 | 98 | 100 | 100 | 95 | 80 | 98 |
| Ragweed | 85 | 85 | 75 | 85 | 75 | 70 | 85 | 85 | 40 | 85 | 80 | 95 | 60 | 75 |
| Ryegrass, Italian | 90 | 75 | 40 | 70 | 50 | 50 | 65 | 65 | 35 | 70 | 70 | 80 | 5 | 25 |
| Soybean | 60 | 80 | 45 | 65 | 55 | 60 | 90 | 85 | 75 | 80 | 95 | 95 | 50 | 35 |
| Surinam Grass | 45 | — | 40 | 30 | 50 | 75 | 30 | — | — | — | — | — | — | — |
| Velvetleaf | 70 | 90 | 75 | 60 | 75 | 60 | 85 | 95 | 65 | 80 | 80 | 85 | 40 | 30 |
| Waterhemp | — | — | — | — | — | — | — | 98 | 98 | 98 | 98 | 100 | 75 | 98 |
| Wheat | 35 | 35 | 40 | 20 | 45 | 40 | 40 | 30 | 30 | 40 | 30 | 25 | 10 | 10 |
| Windgrass | 90 | 80 | — | 60 | 95 | 90 | 100 | — | — | — | — | — | — | — |

| | Compounds | | | | | | | | | | |
|---|---|---|---|---|---|---|---|---|---|---|---|
| 250 g ai/ha | 168 | 169 | 170 | 171 | 172 | 179 | 183 | 185 | 188 | 195 | 196 |
| Postemergence | | | | | | | | | | | |
| Barley | — | — | — | — | — | — | — | — | — | 35 | 50 |
| Barnyardgrass | 95 | 85 | 95 | 75 | 90 | 75 | 85 | 80 | 100 | — | — |
| Bermudagrass | — | — | — | — | — | — | — | — | — | 95 | 90 |
| Blackgrass | 80 | 50 | 70 | 30 | 60 | 60 | 60 | 50 | 90 | 80 | 80 |
| Bromegrass, Downy | — | — | — | — | — | — | — | — | — | 60 | 80 |
| Canarygrass | — | — | — | — | — | — | — | — | — | 100 | 90 |
| Chickweed | 100 | 100 | 95 | 100 | 90 | 95 | 98 | 95 | 95 | 98 | 100 |
| Cocklebur | — | — | — | — | — | — | — | — | — | 50 | 75 |
| Corn | 45 | 30 | 30 | 15 | 30 | 15 | 30 | 25 | 35 | 80 | 65 |
| Crabgrass, Large | 95 | 80 | 90 | 55 | 95 | 80 | 85 | 80 | 95 | 95 | 95 |

TABLE C-continued

| | | | | | | | | | | | |
|---|---|---|---|---|---|---|---|---|---|---|---|
| Cupgrass, Woolly | — | — | — | — | — | — | — | — | — | 75 | 90 |
| Deadnettle | — | — | — | — | — | — | — | — | — | 100 | 100 |
| Foxtail, Giant | 95 | 90 | 98 | 70 | 95 | 80 | 85 | 98 | 100 | 90 | 90 |
| Foxtail, Green | — | — | — | — | — | — | — | — | — | 100 | 100 |
| Galium | 95 | 95 | 90 | 80 | 90 | 90 | 90 | 90 | 90 | 95 | 95 |
| Goosegrass | — | — | — | — | — | — | — | — | — | 80 | 85 |
| Johnsongrass | 75 | 50 | 98 | 25 | 95 | 55 | 75 | 75 | 98 | 95 | 95 |
| Kochia | 90 | 90 | 90 | 90 | 90 | 90 | 95 | 90 | 90 | 95 | 90 |
| Lambsquarters | 95 | 98 | 98 | 95 | 98 | 90 | 98 | 95 | 98 | 95 | 95 |
| Morningglory | 90 | 100 | 100 | — | 80 | 90 | 100 | 100 | — | 95 | 75 |
| Nutsedge, Yellow | 20 | 10 | 10 | 10 | 15 | 10 | 10 | 15 | 15 | 25 | 20 |
| Oat, Wild | 60 | 50 | 90 | 20 | 80 | 50 | 85 | 60 | 90 | 85 | 90 |
| Oilseed Rape | 95 | 60 | 85 | 30 | 95 | 90 | 50 | 55 | 95 | — | — |
| Pigweed | 98 | 100 | 100 | 98 | 98 | 100 | 100 | 100 | 100 | 98 | 98 |
| Ragweed | 80 | 95 | 90 | 55 | 80 | 75 | 95 | 95 | 85 | 85 | 90 |
| Ryegrass, Italian | 80 | 40 | 70 | 10 | 40 | 40 | 40 | 35 | 90 | 60 | 85 |
| Soybean | 60 | 55 | — | — | 60 | 45 | 90 | 55 | 55 | 65 | 70 |
| Surinam Grass | — | — | — | — | — | — | — | — | — | 60 | 75 |
| Velvetleaf | 90 | 80 | 90 | 75 | 80 | 75 | 75 | 90 | 70 | 65 | 80 |
| Waterhemp | 95 | 95 | 100 | 98 | 98 | 95 | 100 | 100 | 100 | — | — |
| Wheat | 45 | 30 | 35 | 20 | 30 | 15 | 30 | 20 | 50 | 30 | 45 |
| Windgrass | — | — | — | — | — | — | — | — | — | 100 | 95 |

| | Compounds | | | | | | | | | | | |
|---|---|---|---|---|---|---|---|---|---|---|---|---|
| 125 g ai/ha | 14 | 15 | 16 | 23 | 25 | 26 | 28 | 47 | 106 | 120 | 124 | 129 |
| Postemergence | | | | | | | | | | | | |
| Barley | 50 | 50 | 45 | 20 | 30 | 30 | 20 | 50 | 35 | 40 | 30 | 45 |
| Bermudagrass | 55 | 35 | 15 | 15 | 25 | 30 | 20 | 55 | 55 | 5 | 60 | 60 |
| Blackgrass | 60 | 80 | 40 | 20 | 40 | 70 | 55 | 60 | 45 | 60 | 85 | 70 |
| Bromegrass, Downy | 40 | 40 | 25 | 5 | 5 | 40 | 35 | 50 | 40 | 30 | 0 | 40 |
| Canarygrass | 85 | 85 | 60 | 15 | 30 | 90 | 60 | 85 | 70 | 60 | 85 | 50 |
| Chickweed | 75 | 75 | 100 | 60 | 98 | 100 | 95 | — | 95 | 100 | 55 | 80 |
| Cocklebur | 45 | 75 | 45 | 40 | 20 | 55 | 20 | 70 | 40 | 65 | 55 | 15 |
| Corn | 15 | 35 | 15 | 20 | 20 | 20 | 25 | 15 | 15 | 10 | 25 | 40 |
| Crabgrass, Large | 45 | 60 | 20 | 25 | 40 | 40 | 20 | 35 | 65 | 25 | 45 | 65 |
| Cupgrass, Woolly | 35 | 75 | 65 | 15 | 25 | 45 | 35 | 80 | 45 | 40 | 20 | 65 |
| Deadnettle | 100 | 100 | 98 | 85 | 90 | 98 | 90 | 100 | 90 | 100 | 98 | 100 |
| Foxtail, Giant | 30 | 75 | 50 | 15 | 55 | 45 | 35 | 80 | 55 | 50 | 45 | 30 |
| Foxtail, Green | 90 | 85 | 98 | 45 | 35 | 70 | 70 | 100 | 70 | 100 | 95 | 95 |
| Galium | 80 | 80 | 80 | 90 | 55 | 75 | 70 | 95 | 80 | 85 | 85 | 90 |
| Goosegrass | 60 | 65 | 10 | 15 | 25 | 40 | 25 | 70 | 45 | 10 | 65 | 30 |
| Johnsongrass | 55 | 80 | 45 | 10 | 10 | 25 | 5 | 35 | 40 | 25 | 45 | 15 |
| Kochia | 95 | 95 | 98 | 80 | 90 | 95 | 75 | — | 85 | 98 | 85 | 98 |
| Lambsquarters | 100 | 100 | 100 | 98 | 98 | 98 | 95 | — | 100 | 100 | 98 | 98 |
| Morningglory | 80 | 90 | 75 | 90 | — | — | — | 100 | 40 | 65 | 40 | 65 |
| Nutsedge, Yellow | 0 | 0 | 0 | 10 | 10 | 15 | 15 | 0 | 0 | 0 | 0 | 0 |
| Oat, Wild | 50 | 60 | 20 | 35 | 30 | 40 | 40 | 85 | 45 | 80 | 35 | 50 |
| Pigweed | 80 | 90 | 100 | 80 | 95 | 80 | 55 | 100 | 98 | 98 | 98 | 98 |
| Ragweed | 60 | 70 | 75 | 20 | 60 | 90 | — | 75 | 60 | 80 | 65 | 45 |
| Ryegrass, Italian | 35 | 60 | 20 | 10 | 5 | 30 | 25 | 75 | 20 | 5 | 65 | 30 |
| Soybean | 30 | 45 | 35 | 55 | 30 | 50 | 35 | 75 | 60 | 55 | 60 | 70 |
| Surinam Grass | 30 | 50 | 10 | 10 | 20 | 25 | 15 | 60 | 35 | 20 | 20 | 50 |
| Velvetleaf | 85 | 90 | 65 | 40 | 45 | 55 | 35 | 80 | 65 | 55 | 55 | 80 |
| Wheat | 40 | 35 | 25 | 15 | 30 | 30 | 10 | 45 | 30 | 35 | 20 | 30 |
| Windgrass | 95 | 90 | 50 | 15 | 40 | 80 | 50 | 85 | 80 | 90 | 98 | 85 |

| | Compounds | | | | | | | | | | | | | |
|---|---|---|---|---|---|---|---|---|---|---|---|---|---|---|
| 125 g ai/ha | 137 | 138 | 139 | 141 | 142 | 145 | 148 | 153 | 154 | 155 | 156 | 160 | 162 | 164 |
| Postemergence | | | | | | | | | | | | | | |
| Barley | 30 | 35 | 35 | 15 | 40 | 35 | 40 | — | — | — | — | — | — | — |
| Barnyardgrass | — | — | — | — | — | — | — | 45 | 25 | 55 | 40 | 35 | 90 | 10 |
| Bermudagrass | — | 75 | 55 | 55 | 75 | 75 | 50 | — | — | — | — | — | — | — |
| Blackgrass | 35 | 40 | 70 | 35 | 80 | 70 | 70 | 70 | 55 | 85 | 75 | 65 | 85 | 15 |
| Bromegrass, Downy | 60 | 50 | 15 | 30 | 45 | 20 | 60 | — | — | — | — | — | — | — |
| Canarygrass | 70 | 70 | 60 | 50 | 85 | 50 | 95 | — | — | — | — | — | — | — |
| Chickweed | 98 | 95 | 98 | 98 | 98 | 98 | 90 | 95 | 95 | 95 | 95 | 98 | 100 | 45 |
| Cocklebur | — | 85 | — | — | 40 | 65 | 98 | — | — | — | — | — | — | — |
| Corn | — | — | 55 | 55 | 35 | — | 55 | 45 | — | 45 | 25 | 25 | 30 | 20 |
| Crabgrass, Large | 40 | 55 | 55 | 80 | 95 | 85 | 60 | 80 | 45 | 75 | 40 | 40 | 35 | 10 |
| Cupgrass, Woolly | 55 | 55 | 50 | 30 | 75 | 40 | 65 | — | — | — | — | — | — | — |
| Deadnettle | 95 | 100 | 98 | 100 | 100 | 100 | 100 | — | — | — | — | — | — | — |
| Foxtail, Giant | — | 55 | 40 | 45 | 80 | 50 | 35 | 90 | 55 | 75 | 25 | 75 | 65 | 20 |
| Foxtail, Green | 95 | 90 | 100 | 100 | 100 | 100 | 100 | — | — | — | — | — | — | — |
| Galium | 70 | — | 80 | 90 | 90 | 90 | 90 | 85 | 70 | 80 | 90 | 95 | 80 | 60 |

TABLE C-continued

| | | | | | | | | | | | | | | |
|---|---|---|---|---|---|---|---|---|---|---|---|---|---|---|
| Goosegrass | 65 | 50 | 60 | 50 | 70 | 70 | 25 | — | — | — | — | — | — | — |
| Johnsongrass | 80 | 45 | 80 | 15 | 80 | 70 | 55 | 60 | 65 | 98 | 65 | 30 | 80 | 10 |
| Kochia | 90 | 98 | 90 | 90 | 95 | 90 | 85 | 90 | 90 | 95 | 90 | 95 | 95 | 40 |
| Lambsquarters | 100 | 100 | 95 | 98 | 98 | 95 | 98 | 95 | 98 | 98 | 98 | 95 | 98 | 60 |
| Morningglory | 80 | 98 | 60 | 95 | 60 | 95 | 98 | 95 | 75 | 65 | 75 | 98 | — | — |
| Nutsedge, Yellow | 10 | 15 | 10 | 15 | 15 | 15 | 15 | 15 | 15 | 10 | 10 | 15 | 5 | 5 |
| Oat, Wild | 50 | 80 | 60 | 45 | 70 | 60 | 80 | 70 | 65 | 75 | 50 | 60 | 60 | 5 |
| Oilseed Rape | — | — | — | — | — | — | — | 90 | 95 | 95 | 95 | 95 | 90 | 20 |
| Pigweed | 100 | 98 | 98 | 98 | 98 | 98 | 98 | 98 | 98 | 98 | 95 | 98 | 90 | 80 |
| Ragweed | 75 | 85 | 45 | — | 75 | 70 | 85 | 80 | 30 | 85 | 75 | 40 | 85 | — |
| Ryegrass, Italian | 65 | 60 | 30 | 50 | 50 | 40 | 60 | 60 | 30 | 65 | 35 | 45 | 60 | 5 |
| Soybean | 55 | 80 | 45 | 55 | 55 | 55 | 80 | 70 | 65 | 80 | 95 | 30 | 75 | — |
| Surinam Grass | 45 | 65 | 35 | 30 | 45 | 60 | 25 | — | — | — | — | — | — | — |
| Velvetleaf | 55 | 80 | 70 | 60 | 55 | 50 | 80 | 65 | 55 | 75 | 60 | 75 | 60 | 40 |
| Waterhemp | — | — | — | — | — | — | — | 98 | 98 | 98 | 98 | 98 | 100 | 65 |
| Wheat | 30 | 35 | 40 | 20 | 40 | 30 | 40 | 30 | 20 | 35 | 25 | 25 | 25 | 10 |
| Windgrass | 70 | 55 | 80 | 55 | 85 | 90 | 98 | — | — | — | — | — | — | — |

| | Compounds | | | | | | | | | | | |
|---|---|---|---|---|---|---|---|---|---|---|---|---|
| 125 g ai/ha | 166 | 168 | 169 | 170 | 171 | 172 | 179 | 183 | 185 | 188 | 195 | 196 |
| Postemergence | | | | | | | | | | | | |
| Barley | — | — | — | — | — | — | — | — | — | — | 35 | 45 |
| Barnyardgrass | 45 | 90 | 75 | 85 | 60 | 85 | 65 | 80 | 70 | 98 | — | — |
| Bermudagrass | — | — | — | — | — | — | — | — | — | — | 90 | 85 |
| Blackgrass | 40 | 80 | 35 | 60 | 10 | 60 | 55 | 60 | 50 | 85 | 80 | 80 |
| Bromegrass, Downy | — | — | — | — | — | — | — | — | — | — | 50 | 70 |
| Canarygrass | — | — | — | — | — | — | — | — | — | — | 85 | 90 |
| Chickweed | 90 | 90 | 95 | — | 95 | 90 | 85 | 80 | 95 | 90 | 98 | 100 |
| Cocklebur | — | — | — | — | — | — | — | — | — | — | — | 65 |
| Corn | 15 | 30 | 20 | 30 | 15 | 25 | 15 | — | 25 | 20 | — | 65 |
| Crabgrass, Large | 20 | 95 | 40 | 80 | 40 | 65 | 35 | 35 | 60 | 95 | 90 | 85 |
| Cupgrass, Woolly | — | — | — | — | — | — | — | — | — | — | 75 | 85 |
| Deadnettle | — | — | — | — | — | — | — | — | — | — | 100 | 100 |
| Foxtail, Giant | 40 | 95 | 65 | 98 | 55 | 80 | 55 | 65 | 90 | 98 | 75 | 90 |
| Foxtail, Green | — | — | — | — | — | — | — | — | — | — | 100 | 100 |
| Galium | 60 | 90 | 90 | 90 | 80 | 90 | 90 | 90 | 90 | 85 | 95 | 90 |
| Goosegrass | — | — | — | — | — | — | — | — | — | — | 60 | 80 |
| Johnsongrass | 20 | 70 | 35 | 80 | 25 | 65 | 20 | 50 | 65 | 95 | 95 | 90 |
| Kochia | 90 | 90 | 90 | 90 | 90 | 90 | 90 | 90 | 90 | 90 | 90 | 90 |
| Lambsquarters | 95 | 95 | 98 | 95 | 95 | 98 | 85 | 95 | 85 | 98 | 95 | 95 |
| Morningglory | 35 | 90 | 100 | 100 | 98 | — | 80 | 100 | 100 | 100 | 90 | 75 |
| Nutsedge, Yellow | 5 | 15 | 10 | 5 | 10 | 15 | 10 | 10 | 10 | 10 | 25 | 15 |
| Oat, Wild | — | 50 | 30 | 85 | 10 | 45 | 35 | 55 | 55 | 60 | 80 | 85 |
| Oilseed Rape | 5 | 90 | 40 | 50 | 30 | 90 | 90 | 25 | 50 | 90 | — | — |
| Pigweed | 95 | 98 | 100 | 100 | 90 | 98 | 98 | 100 | 100 | 98 | 98 | 98 |
| Ragweed | 25 | 65 | 85 | 90 | 55 | 80 | 60 | 90 | 95 | 85 | 70 | 90 |
| Ryegrass, Italian | 20 | 60 | 25 | 35 | 10 | 35 | 25 | 20 | 25 | 85 | 60 | 85 |
| Soybean | 35 | 60 | 50 | 90 | 40 | 60 | 45 | 55 | 45 | 50 | 65 | 65 |
| Surinam Grass | — | — | — | — | — | — | — | — | — | — | — | 70 |
| Velvetleaf | 20 | 80 | 75 | 85 | 45 | 75 | 75 | 75 | 85 | 70 | 60 | 75 |
| Waterhemp | 98 | 95 | 80 | 98 | 75 | 98 | 95 | 100 | 95 | 100 | — | — |
| Wheat | 5 | 35 | 30 | 35 | 20 | 25 | 15 | 20 | 15 | 45 | 25 | 45 |
| Windgrass | — | — | — | — | — | — | — | — | — | — | 95 | 95 |

| | Compounds | | | | | | | | | | | |
|---|---|---|---|---|---|---|---|---|---|---|---|---|
| 62 g ai/ha | 14 | 15 | 16 | 23 | 25 | 26 | 28 | 47 | 106 | 120 | 124 | 129 |
| Postemergence | | | | | | | | | | | | |
| Barley | 35 | 35 | 35 | 15 | 25 | 30 | 15 | 45 | 25 | 30 | 30 | 35 |
| Bermudagrass | 15 | 15 | 5 | 10 | 20 | 20 | 15 | 20 | 40 | 5 | 45 | 45 |
| Blackgrass | 40 | 60 | 25 | 20 | 35 | 35 | 10 | 45 | 40 | 30 | 50 | 60 |
| Bromegrass, Downy | 40 | 35 | 15 | 5 | 5 | 30 | 25 | 30 | 35 | 15 | 0 | 35 |
| Canarygrass | 80 | 85 | 60 | 10 | 10 | 45 | 50 | 75 | 50 | 35 | 35 | 45 |
| Chickweed | 75 | 70 | 98 | 55 | 60 | 98 | 55 | — | 70 | 100 | 55 | 45 |
| Cocklebur | 5 | 60 | 45 | 25 | 20 | 15 | 15 | 65 | 35 | 50 | 20 | 10 |
| Corn | 10 | 15 | 15 | 15 | 20 | 20 | 20 | 15 | 15 | 10 | 25 | 15 |
| Crabgrass, Large | 45 | 45 | 5 | 15 | 20 | 30 | 15 | 15 | 55 | 25 | 40 | 45 |
| Cupgrass, Woolly | 5 | 5 | 20 | 10 | 25 | 40 | 30 | 65 | 45 | 10 | 10 | 65 |
| Deadnettle | 98 | 100 | 98 | 80 | 55 | 98 | 80 | 100 | 80 | 100 | 98 | 100 |
| Foxtail, Giant | 15 | 10 | 40 | 15 | 45 | 30 | 35 | 65 | 40 | 45 | 25 | 20 |
| Foxtail, Green | — | 85 | 98 | 30 | 35 | 40 | 70 | 98 | 50 | 85 | 90 | 95 |
| Galium | 80 | 55 | 65 | 85 | 50 | 55 | 55 | 80 | 65 | 80 | 80 | 85 |
| Goosegrass | 5 | 40 | 5 | 10 | 20 | 30 | 20 | 35 | 35 | 5 | 55 | 25 |
| Johnsongrass | 20 | 60 | 0 | 10 | 5 | 15 | 5 | 10 | 15 | 5 | 40 | 15 |
| Kochia | 95 | 95 | 98 | 75 | 80 | 95 | 65 | — | 85 | 95 | 80 | 95 |

TABLE C-continued

| | | | | | | | | | | | | |
|---|---|---|---|---|---|---|---|---|---|---|---|---|
| Lambsquarters | 100 | 100 | 100 | 40 | 80 | 95 | 35 | — | 100 | 100 | 98 | 98 |
| Morningglory | 80 | 75 | 75 | 70 | — | — | — | 95 | 20 | 60 | 40 | 55 |
| Nutsedge, Yellow | 0 | 0 | 0 | 10 | 5 | 10 | 5 | 0 | 0 | 0 | 0 | 0 |
| Oat, Wild | 45 | 55 | 10 | 10 | 5 | 30 | 15 | — | 30 | 60 | 25 | 35 |
| Pigweed | 60 | 70 | 95 | — | 95 | 60 | 55 | 100 | 98 | 98 | 95 | 98 |
| Ragweed | 55 | 60 | 25 | 10 | 50 | 55 | 60 | 65 | 55 | 60 | 65 | 40 |
| Ryegrass, Italian | 35 | 45 | 10 | 10 | 5 | 20 | 25 | 65 | 5 | 5 | 35 | 15 |
| Soybean | 25 | 35 | 25 | 55 | 30 | 40 | 35 | 70 | 15 | 25 | 55 | 40 |
| Surinam Grass | 5 | 15 | 5 | 10 | 15 | 20 | 10 | 10 | 25 | 5 | 15 | 45 |
| Velvetleaf | 80 | 60 | 65 | 25 | 15 | 50 | 25 | 70 | 45 | 45 | 50 | 45 |
| Wheat | 35 | 35 | 20 | 10 | 20 | 20 | 10 | 35 | 30 | 10 | 15 | 25 |
| Windgrass | 90 | 85 | 50 | 15 | 35 | 55 | 45 | 80 | 65 | 55 | 95 | 80 |

| | Compounds | | | | | | | | | | | | | |
|---|---|---|---|---|---|---|---|---|---|---|---|---|---|---|
| 62 g ai/ha | 137 | 138 | 139 | 141 | 142 | 145 | 148 | 153 | 154 | 155 | 156 | 160 | 162 | 164 |
| Postemergence | | | | | | | | | | | | | | |
| Barley | 10 | 30 | 10 | 10 | 35 | 20 | 35 | — | — | — | — | — | — | — |
| Barnyardgrass | — | — | — | — | — | — | — | 35 | 25 | 35 | 30 | 30 | 65 | 10 |
| Bermudagrass | 30 | 45 | 40 | — | 70 | 40 | 30 | — | — | — | — | — | — | — |
| Blackgrass | 30 | 40 | 40 | 20 | 60 | 60 | 50 | 60 | 35 | 70 | 60 | 45 | 80 | 5 |
| Bromegrass, Downy | 30 | 45 | 10 | 30 | 45 | 10 | 55 | — | — | — | — | — | — | — |
| Canarygrass | 60 | 55 | 45 | 25 | 80 | 40 | 60 | — | — | — | — | — | — | — |
| Chickweed | 80 | 80 | 98 | 90 | 98 | 85 | 75 | 95 | 85 | 70 | 95 | 95 | 100 | 40 |
| Cocklebur | 50 | 70 | — | — | 30 | 15 | 98 | — | — | — | — | — | — | — |
| Corn | — | — | 25 | 45 | 35 | 45 | 30 | 25 | 20 | 25 | 15 | 20 | 30 | 15 |
| Crabgrass, Large | 40 | 50 | 45 | 55 | 80 | 50 | 60 | 55 | 30 | 45 | 30 | 35 | 35 | 5 |
| Cupgrass, Woolly | 50 | 55 | 30 | 20 | 40 | 25 | 55 | — | — | — | — | — | — | — |
| Deadnettle | 95 | 100 | 95 | 100 | 100 | 100 | 95 | — | — | — | — | — | — | — |
| Foxtail, Giant | 40 | 55 | 30 | 20 | 75 | 20 | 35 | 80 | 20 | 45 | 15 | — | 55 | 20 |
| Foxtail, Green | 85 | 85 | 95 | 100 | 100 | 100 | 98 | — | — | — | — | — | — | — |
| Galium | 70 | 90 | 70 | 85 | 80 | 80 | 90 | 65 | 60 | 75 | 90 | 85 | 75 | 30 |
| Goosegrass | 25 | 25 | 40 | 40 | 35 | 35 | 15 | — | — | — | — | — | — | — |
| Johnsongrass | 40 | 45 | 50 | 10 | 70 | 20 | 20 | — | 30 | 80 | 50 | — | 80 | 10 |
| Kochia | 90 | 95 | 85 | 90 | 90 | 85 | 85 | 90 | 90 | 90 | 90 | 95 | 90 | 40 |
| Lambsquarters | 100 | 100 | 95 | 98 | 98 | 95 | 98 | 95 | 98 | 95 | 98 | 95 | 95 | 55 |
| Morningglory | 60 | 90 | 60 | 85 | — | 90 | 98 | 80 | 75 | 65 | 70 | 98 | — | 60 |
| Nutsedge, Yellow | 10 | 10 | 10 | 10 | 5 | 10 | 10 | 10 | 10 | 10 | 10 | 10 | 5 | 5 |
| Oat, Wild | 50 | 60 | 50 | 15 | 45 | 40 | 45 | 50 | 35 | 45 | 50 | 45 | 60 | 5 |
| Oilseed Rape | — | — | — | — | — | — | — | 90 | 90 | 90 | 90 | 95 | 90 | 5 |
| Pigweed | 100 | 98 | 98 | 95 | 98 | 98 | 98 | 95 | 95 | 90 | 90 | 98 | 85 | 75 |
| Ragweed | — | 80 | 40 | 70 | 70 | — | 85 | 55 | 30 | — | 75 | 40 | — | 50 |
| Ryegrass, Italian | 55 | 55 | 30 | 30 | 40 | 30 | 35 | 35 | 10 | 45 | 35 | 30 | 35 | 5 |
| Soybean | 55 | 70 | 40 | 55 | 55 | 50 | 45 | 70 | 60 | 75 | 80 | 25 | 70 | 40 |
| Surinam Grass | 45 | 50 | 35 | 15 | 40 | 30 | 20 | — | — | — | — | — | — | — |
| Velvetleaf | 55 | 75 | 35 | 55 | 50 | 35 | 50 | 60 | 45 | 60 | 50 | 50 | 55 | 30 |
| Waterhemp | — | — | — | — | — | — | — | 98 | 98 | 98 | 98 | 98 | 100 | 65 |
| Wheat | 15 | 10 | 10 | 15 | 25 | 15 | 25 | 30 | 15 | 30 | 15 | 25 | 20 | 10 |
| Windgrass | 50 | 50 | 70 | 50 | 80 | 70 | 80 | — | — | — | — | — | — | — |

| | Compounds | | | | | | | | | | | |
|---|---|---|---|---|---|---|---|---|---|---|---|---|
| 62 g ai/ha | 166 | 168 | 169 | 170 | 171 | 172 | 179 | 183 | 185 | 188 | 195 | 196 |
| Postemergence | | | | | | | | | | | | |
| Barley | — | — | — | — | — | — | — | — | — | — | 20 | 40 |
| Barnyardgrass | 25 | 75 | 25 | 55 | 15 | 45 | 45 | 35 | 35 | 95 | — | — |
| Bermudagrass | — | — | — | — | — | — | — | — | — | — | 60 | 80 |
| Blackgrass | 20 | 45 | 15 | 10 | 10 | 25 | 50 | 20 | 40 | 55 | 70 | 80 |
| Bromegrass, Downy | — | — | — | — | — | — | — | — | — | — | 30 | 50 |
| Canarygrass | — | — | — | — | — | — | — | — | — | — | 60 | 90 |
| Chickweed | 90 | 80 | 60 | 95 | 70 | 85 | 80 | 75 | 85 | 90 | 95 | 98 |
| Cocklebur | — | — | — | — | — | — | — | — | — | — | — | 60 |
| Corn | 15 | 15 | 15 | 25 | 15 | 20 | 15 | 20 | 20 | 20 | 75 | 60 |
| Crabgrass, Large | 15 | 65 | 35 | 30 | 20 | 55 | 20 | 35 | 40 | 85 | 60 | 85 |
| Cupgrass, Woolly | — | — | — | — | — | — | — | — | — | — | 65 | 80 |
| Deadnettle | — | — | — | — | — | — | — | — | — | — | 100 | 100 |
| Foxtail, Giant | 40 | 65 | 65 | 80 | 35 | 35 | 40 | 45 | 80 | 98 | 35 | 85 |
| Foxtail, Green | — | — | — | — | — | — | — | — | — | — | 100 | 100 |
| Galium | 50 | 90 | 90 | 90 | 75 | 90 | 90 | 70 | 80 | 80 | 95 | 85 |
| Goosegrass | — | — | — | — | — | — | — | — | — | — | 50 | 75 |
| Johnsongrass | 15 | 55 | 30 | 25 | 15 | 60 | 20 | 30 | 30 | 75 | 80 | 90 |
| Kochia | 90 | 90 | 90 | 90 | 90 | 90 | 90 | 90 | 90 | 90 | 85 | 90 |
| Lambsquarters | 95 | 95 | 90 | 95 | 75 | 98 | 80 | 95 | 80 | 95 | 95 | 95 |
| Morningglory | 30 | 80 | — | 98 | 65 | 80 | 80 | 98 | 98 | 100 | 90 | 75 |
| Nutsedge, Yellow | 5 | 10 | 5 | 5 | 5 | 10 | 5 | 10 | 10 | 10 | 20 | 10 |
| Oat, Wild | 20 | 45 | 25 | 65 | 5 | 20 | 20 | 40 | 30 | 60 | 75 | 85 |

TABLE C-continued

| | | | | | | | | | | | | |
|---|---|---|---|---|---|---|---|---|---|---|---|---|
| Oilseed Rape | 5 | 70 | 40 | 50 | 20 | 90 | 40 | 25 | 50 | 90 | — | — |
| Pigweed | 85 | 98 | 95 | 100 | 90 | 98 | 98 | — | 98 | 95 | 95 | 98 |
| Ragweed | 15 | 65 | 60 | 85 | 55 | 75 | 55 | 80 | 90 | 75 | 50 | 85 |
| Ryegrass, Italian | 5 | 35 | 10 | 35 | 5 | 20 | 15 | 15 | 10 | 70 | 55 | 60 |
| Soybean | 35 | 35 | 30 | 70 | 35 | 45 | 35 | 55 | 45 | 50 | 40 | 50 |
| Surinam Grass | — | — | — | — | — | — | — | — | — | — | 50 | 70 |
| Velvetleaf | 20 | 75 | 65 | 85 | 25 | 65 | 75 | — | 80 | 65 | 50 | 65 |
| Waterhemp | — | 90 | 80 | 98 | 75 | 95 | 90 | 100 | 90 | 100 | — | — |
| Wheat | 5 | 20 | 10 | 20 | 10 | 20 | 10 | 20 | 15 | 30 | 20 | 35 |
| Windgrass | — | — | — | — | — | — | — | — | — | — | 80 | 80 |

| | Compounds | | | | | | | | | | | |
|---|---|---|---|---|---|---|---|---|---|---|---|---|
| 31 g ai/ha | 14 | 15 | 16 | 23 | 25 | 26 | 28 | 47 | 106 | 120 | 124 | 129 |
| Postemergence | | | | | | | | | | | | |
| Barley | 30 | 35 | 115 | 5 | 20 | 20 | 10 | 35 | 15 | 20 | 15 | 30 |
| Bermudagrass | 0 | 5 | 5 | 5 | 15 | 20 | 10 | 10 | 40 | 5 | 25 | 40 |
| Blackgrass | 15 | 30 | 10 | 15 | 10 | 30 | 10 | 40 | 30 | 25 | 35 | 40 |
| Bromegrass, Downy | 30 | 25 | 15 | 5 | 5 | 15 | 5 | 10 | 30 | 15 | 0 | 35 |
| Canarygrass | 55 | 60 | 20 | 5 | 5 | 40 | 30 | 60 | 35 | 25 | 20 | 30 |
| Chickweed | 60 | 55 | 85 | 30 | 30 | 40 | 30 | 80 | 60 | 75 | 50 | 15 |
| Cocklebur | 5 | 5 | 35 | 25 | 15 | 10 | 10 | 10 | 35 | 45 | 15 | 5 |
| Corn | 5 | 5 | 5 | 10 | 20 | 20 | 15 | 5 | 10 | 5 | 20 | 10 |
| Crabgrass, Large | 10 | 15 | 5 | 10 | 15 | 20 | 10 | 5 | 40 | 5 | 30 | 20 |
| Cupgrass, Woolly | 5 | 5 | 5 | 10 | 25 | 25 | 20 | 55 | 5 | 10 | 5 | 35 |
| Deadnettle | 98 | 100 | 50 | 80 | 50 | 98 | 40 | 95 | 75 | 100 | 80 | 100 |
| Foxtail, Giant | 10 | 10 | 40 | 15 | 35 | 25 | 35 | 65 | 40 | 5 | 15 | 0 |
| Foxtail, Green | 70 | 40 | 30 | — | 35 | 30 | 30 | 20 | 50 | 15 | 70 | 85 |
| Galium | 60 | 55 | 60 | 85 | 50 | 50 | 40 | 80 | 65 | 80 | 70 | 60 |
| Goosegrass | 5 | 25 | 5 | 10 | 15 | 25 | 20 | 5 | 10 | 5 | 45 | 15 |
| Johnsongrass | 20 | 45 | 0 | 5 | 5 | 15 | 5 | 0 | 0 | 0 | 5 | 5 |
| Kochia | 90 | 95 | 95 | 65 | 75 | 75 | 40 | 65 | 85 | 65 | 80 | 95 |
| Lambsquarters | 100 | 100 | 95 | 40 | 70 | 80 | 35 | 100 | 80 | 100 | 95 | 98 |
| Morningglory | 75 | 75 | 50 | 70 | — | — | — | 75 | 0 | 60 | 15 | 50 |
| Nutsedge, Yellow | 0 | 0 | 0 | 10 | 5 | 10 | 5 | 0 | 0 | 0 | 0 | 0 |
| Oat, Wild | 25 | 45 | 5 | 5 | 5 | 10 | 10 | 35 | 10 | 55 | 20 | 20 |
| Pigweed | 45 | 60 | 75 | 70 | 85 | — | 55 | 100 | 95 | 95 | 90 | 85 |
| Ragweed | 55 | 60 | 5 | 10 | 50 | 40 | 35 | 45 | 10 | 60 | 50 | 40 |
| Ryegrass, Italian | 30 | 30 | 10 | 5 | 5 | 10 | 10 | 35 | 5 | 5 | 15 | 5 |
| Soybean | 25 | 10 | 20 | 30 | 25 | 35 | 30 | 40 | 10 | 25 | 55 | 20 |
| Surinam Grass | 5 | 10 | 5 | 5 | 10 | 15 | 5 | 5 | 20 | 5 | 10 | 45 |
| Velvetleaf | 75 | 60 | 10 | 15 | 15 | 25 | 20 | 65 | 5 | 20 | 45 | 45 |
| Wheat | 30 | 25 | 5 | 10 | 10 | 10 | 5 | 15 | 10 | 10 | 10 | 20 |
| Windgrass | 70 | 20 | 45 | 10 | 30 | 40 | 30 | 60 | 50 | 50 | 80 | 60 |

| | Compounds | | | | | | | | | | | | | |
|---|---|---|---|---|---|---|---|---|---|---|---|---|---|---|
| 31 g ai/ha | 137 | 138 | 139 | 141 | 142 | 145 | 148 | 153 | 154 | 155 | 156 | 160 | 162 | 164 |
| Postemergence | | | | | | | | | | | | | | |
| Barley | 10 | 10 | 5 | 5 | 20 | 15 | 35 | — | — | — | — | — | — | — |
| Barnyardgrass | — | — | — | — | — | — | — | 20 | 15 | 25 | 20 | 20 | 20 | 5 |
| Bermudagrass | 30 | 20 | 35 | 15 | 15 | 10 | 10 | — | — | — | — | — | — | — |
| Blackgrass | 10 | 20 | 35 | 20 | 55 | 10 | 40 | 55 | 15 | 40 | 50 | 35 | 45 | 5 |
| Bromegrass, Downy | 10 | 40 | 5 | 25 | 25 | 5 | 45 | — | — | — | — | — | — | — |
| Canarygrass | 45 | 30 | 40 | 20 | 45 | 15 | 40 | — | — | — | — | — | — | — |
| Chickweed | 70 | — | 75 | 80 | 85 | 75 | 75 | 95 | 85 | 50 | 95 | 90 | 100 | 10 |
| Cocklebur | 45 | 65 | — | 5 | — | 10 | 85 | — | — | — | — | — | — | — |
| Corn | — | — | — | 45 | 30 | 35 | 25 | 20 | 20 | 25 | — | 15 | 15 | 15 |
| Crabgrass, Large | 15 | 45 | 40 | 20 | 65 | 25 | 15 | 50 | 20 | 20 | 10 | 25 | 20 | 5 |
| Cupgrass, Woolly | 45 | 50 | 15 | 15 | 40 | 20 | 55 | — | — | — | — | — | — | — |
| Deadnettle | 80 | 98 | 95 | 100 | 100 | 100 | 95 | — | — | — | — | — | — | — |
| Foxtail, Giant | 10 | 20 | 15 | 10 | 20 | 15 | 10 | 45 | 20 | 15 | 10 | 20 | 45 | 10 |
| Foxtail, Green | 80 | 35 | 95 | 100 | 100 | 98 | 80 | — | — | — | — | — | — | — |
| Galium | 45 | 85 | 60 | 85 | 80 | 80 | 80 | 60 | 45 | 70 | 80 | 80 | 75 | 30 |
| Goosegrass | 20 | 5 | 15 | 35 | 35 | 25 | — | — | — | — | — | — | — | — |
| Johnsongrass | 5 | 45 | 30 | 10 | 55 | 10 | 20 | 40 | 10 | 20 | 45 | 15 | 45 | 10 |
| Kochia | 90 | 95 | 85 | 85 | 80 | 85 | 80 | 90 | 90 | 90 | 90 | 90 | 90 | 40 |
| Lambsquarters | 100 | 100 | 90 | 98 | 80 | 95 | 98 | 95 | 75 | 80 | 98 | 80 | 95 | 50 |
| Morningglory | — | 90 | 55 | 85 | 60 | 90 | 70 | 40 | 40 | 55 | 65 | 60 | — | 50 |
| Nutsedge, Yellow | 5 | 10 | 10 | 0 | 5 | 5 | 10 | 10 | 10 | 5 | 5 | 10 | 5 | 0 |
| Oat, Wild | 45 | 55 | 40 | 10 | 35 | 20 | 15 | 35 | 15 | 40 | 35 | 30 | 40 | 5 |
| Oilseed Rape | — | — | — | — | — | — | — | 90 | 80 | 90 | 80 | 95 | 90 | 5 |
| Pigweed | 98 | 98 | 95 | 95 | 98 | 85 | 65 | 95 | 95 | 90 | 75 | 95 | 85 | 50 |
| Ragweed | 65 | 75 | — | 60 | 65 | 60 | 65 | 55 | 30 | 80 | 75 | 10 | 85 | 50 |
| Ryegrass, Italian | 35 | 40 | 25 | 15 | 10 | 20 | 10 | 30 | 5 | 35 | 15 | 30 | 30 | 5 |
| Soybean | 40 | 55 | 40 | 40 | 50 | 50 | 45 | 55 | 45 | 50 | 55 | 25 | 70 | 30 |

TABLE C-continued

| | | | | | | | | | | | | | | |
|---|---|---|---|---|---|---|---|---|---|---|---|---|---|---|
| Surinam Grass | 40 | 45 | 10 | 15 | 40 | 25 | 20 | — | — | — | — | — | — | — |
| Velvetleaf | 35 | 50 | 20 | 40 | 30 | 35 | 50 | 50 | 35 | 50 | 45 | 30 | 35 | 25 |
| Waterhemp | — | — | — | — | — | — | — | 98 | 90 | 98 | 98 | 95 | 98 | 35 |
| Wheat | 10 | 10 | 10 | 10 | 15 | 5 | 20 | 10 | 10 | 15 | 5 | 5 | 20 | 5 |
| Windgrass | 40 | 50 | 50 | 50 | 80 | 50 | 60 | — | — | — | — | — | — | — |

| | Compounds | | | | | | | | | | | |
|---|---|---|---|---|---|---|---|---|---|---|---|---|
| 31 g ai/ha | 166 | 168 | 169 | 170 | 171 | 172 | 179 | 183 | 185 | 188 | 195 | 196 |
| Postemergence | | | | | | | | | | | | |
| Barley | — | — | — | — | — | — | — | — | — | — | 15 | 30 |
| Barnyardgrass | 10 | 40 | 15 | 20 | 10 | 40 | 40 | 15 | 30 | 75 | — | — |
| Bermudagrass | — | — | — | — | — | — | — | — | — | — | 40 | 80 |
| Blackgrass | 10 | 45 | 5 | 10 | 5 | 10 | 30 | 10 | 20 | 55 | 45 | 70 |
| Bromegrass, Downy | — | — | — | — | — | — | — | — | — | — | 15 | 50 |
| Canarygrass | — | — | — | — | — | — | — | — | — | — | 40 | 80 |
| Chickweed | 55 | 80 | 60 | 75 | 50 | 65 | 75 | 75 | 70 | 80 | 95 | 98 |
| Cocklebur | — | — | — | — | — | — | — | — | — | — | — | 55 |
| Corn | 15 | 15 | 10 | 15 | 15 | 20 | 15 | 10 | 15 | 10 | 60 | 60 |
| Crabgrass, Large | 15 | 30 | 35 | 30 | 15 | 20 | 20 | 25 | 25 | 50 | 55 | 80 |
| Cupgrass, Woolly | — | — | — | — | — | — | — | — | — | — | 50 | 30 |
| Deadnettle | — | — | — | — | — | — | — | — | — | — | 100 | 100 |
| Foxtail, Giant | 20 | 55 | 20 | 55 | 25 | 35 | 35 | 45 | 40 | 98 | 35 | 85 |
| Foxtail, Green | — | — | — | — | — | — | — | — | — | — | 100 | 100 |
| Galium | 50 | 90 | 80 | 80 | 70 | 90 | 90 | 70 | 70 | 60 | 80 | 80 |
| Goosegrass | — | — | — | — | — | — | — | — | — | — | 50 | 75 |
| Johnsongrass | 10 | 30 | 15 | 20 | 15 | 35 | 10 | 20 | 10 | 45 | 55 | 80 |
| Kochia | 90 | 90 | 85 | 90 | 90 | 90 | 80 | 90 | 90 | 70 | 75 | 85 |
| Lambsquarters | 60 | 80 | 90 | 85 | 75 | 98 | 80 | 85 | 80 | 90 | 95 | 95 |
| Morningglory | 30 | 50 | 98 | 75 | 60 | 65 | 65 | 98 | 90 | 70 | 65 | 75 |
| Nutsedge, Yellow | 0 | 10 | 5 | 5 | 5 | 10 | 5 | 10 | 10 | 10 | 10 | 10 |
| Oat, Wild | 15 | 30 | 5 | 30 | 5 | 15 | 10 | 30 | 25 | 45 | 60 | 55 |
| Oilseed Rape | 5 | 40 | 30 | 30 | 5 | 50 | 30 | 20 | 10 | 40 | — | — |
| Pigweed | 35 | 80 | 95 | 100 | 70 | 98 | 95 | 100 | 98 | 95 | 95 | 98 |
| Ragweed | 15 | 65 | 40 | 85 | 55 | 75 | 50 | 65 | 75 | 65 | — | 70 |
| Ryegrass, Italian | 5 | 10 | 10 | 15 | 5 | 10 | 10 | 10 | 10 | 50 | 25 | 35 |
| Soybean | 35 | 30 | 30 | 30 | 25 | 35 | 30 | 35 | 40 | 40 | 40 | 45 |
| Surinam Grass | — | — | — | — | — | — | — | — | — | — | 30 | 35 |
| Velvetleaf | 10 | 60 | 50 | 75 | 25 | 65 | 55 | 75 | 55 | 50 | 45 | 55 |
| Waterhemp | 90 | 80 | 75 | 85 | 70 | 90 | 80 | 85 | 90 | 70 | — | — |
| Wheat | 5 | 20 | 10 | 10 | 5 | 10 | 5 | 10 | 5 | 20 | 10 | 15 |
| Windgrass | — | — | — | — | — | — | — | — | — | — | 55 | 80 |

| | Compounds | | | Compounds | |
|---|---|---|---|---|---|
| 16 g ai/ha | 15 | 124 | 16 g ai/ha | 15 | 124 |
| Postemergence | | | | | |
| Barley | 30 | 5 | Goosegrass | 5 | 25 |
| Bermudagrass | 5 | 5 | Johnsongrass | 0 | 5 |
| Blackgrass | 20 | 0 | Kochia | 90 | 75 |
| Bromegrass, Downy | 10 | 0 | Lambsquarters | 100 | 85 |
| Canarygrass | 35 | 0 | Morningglory | 45 | 15 |
| Chickweed | 55 | 45 | Nutsedge, Yellow | 0 | 0 |
| Cocklebur | — | 10 | Oat, Wild | 40 | 20 |
| Corn | 0 | 5 | Pigweed | 5 | 75 |
| Crabgrass, Large | 5 | 20 | Ragweed | 45 | 45 |
| Cupgrass, Woolly | 5 | 5 | Ryegrass, Italian | 10 | 5 |
| Deadnettle | 90 | 75 | Soybean | 10 | 45 |
| Foxtail, Giant | 5 | 15 | Surinam Grass | 5 | 5 |
| Foxtail, Green | 30 | 65 | Velvetleaf | 60 | 45 |
| Galium | 50 | 70 | Wheat | 15 | 5 |
| Goosegrass | 5 | 25 | Windgrass | 20 | 50 |

| 16 g ai/ha | Compound 160 | 16 g ai/ha | Compound 160 |
|---|---|---|---|
| Postemergence | | | |
| Barnyardgrass | 15 | Nutsedge, Yellow | 5 |
| Blackgrass | 25 | Oat, Wild | 15 |
| Chickweed | 70 | Oilseed Rape | 85 |
| Corn | 15 | Pigweed | 95 |
| Crabgrass, Large | 20 | Ragweed | 10 |
| Foxtail, Giant | 15 | Ryegrass, Italian | 10 |
| Galium | 55 | Soybean | 15 |
| Johnsongrass | 10 | Velvetleaf | 20 |

TABLE C-continued

| | | | |
|---|---|---|---|
| Kochia | 90 | Waterhemp | 95 |
| Lambsquarters | 70 | Wheat | 5 |
| Morningglory | 60 | | |

| | Compounds | | | | | | | | |
|---|---|---|---|---|---|---|---|---|---|
| 250 g ai/ha | 14 | 16 | 23 | 25 | 26 | 47 | 106 | 120 | 129 |
| Preemergence | | | | | | | | | |
| Bermudagrass | 100 | 75 | 100 | 100 | 100 | 100 | 100 | 100 | 98 |
| Blackgrass | 98 | 100 | 100 | 100 | 90 | 100 | 95 | 90 | 90 |
| Bromegrass, Downy | 98 | 100 | 10 | 80 | 85 | 100 | 60 | 90 | 100 |
| Cocklebur | 45 | — | 5 | 30 | 55 | 5 | — | 5 | 0 |
| Corn | 10 | — | 85 | 10 | 5 | 40 | 10 | 50 | 65 |
| Crabgrass, Large | 100 | — | 100 | 100 | 100 | 100 | 100 | 100 | 100 |
| Cupgrass, Woolly | 80 | — | 100 | 98 | 90 | 98 | 90 | 98 | 98 |
| Foxtail, Giant | 100 | — | 100 | 100 | 100 | 100 | 100 | 100 | 98 |
| Foxtail, Green | 100 | 100 | 100 | 95 | 95 | 100 | 95 | 90 | 90 |
| Galium | 100 | 100 | 100 | 98 | 100 | 100 | 90 | 100 | 100 |
| Goosegrass | 100 | — | 100 | 100 | 100 | 100 | 100 | 98 | 98 |
| Johnsongrass | 85 | — | 98 | 98 | 98 | 95 | 85 | 98 | 95 |
| Kochia | 85 | — | 100 | 85 | 98 | 98 | 65 | 100 | 95 |
| Lambsquarters | 100 | — | 100 | 98 | 100 | 100 | 100 | 100 | 100 |
| Morningglory | 65 | — | 100 | — | — | 65 | 60 | 90 | 65 |
| Nightshade | 98 | — | 98 | 95 | 98 | 98 | 100 | 95 | 95 |
| Nutsedge, Yellow | 0 | — | 55 | 0 | 0 | 0 | 0 | 0 | 5 |
| Oat, Wild | 90 | 100 | 100 | 90 | 95 | 100 | 80 | 95 | 95 |
| Pigweed | 100 | — | 100 | 100 | 100 | 100 | 100 | 100 | 100 |
| Ragweed | — | — | 60 | 50 | 75 | 80 | 55 | 65 | 55 |
| Russian Thistle | 95 | 100 | — | 90 | 95 | 100 | 100 | 100 | — |
| Ryegrass, Italian | 85 | 100 | 70 | 90 | 80 | 98 | 50 | 95 | 95 |
| Soybean | 0 | — | 50 | 10 | 15 | 35 | 5 | 20 | 40 |
| Sunflower | 15 | — | 0 | 0 | 15 | 10 | 0 | 5 | 0 |
| Surinam Grass | 85 | — | 100 | 100 | 90 | 65 | 90 | 100 | 98 |
| Velvetleaf | 75 | — | 100 | 70 | 100 | 100 | 10 | 100 | 95 |
| Wheat | 45 | 45 | 35 | 35 | 30 | 40 | 5 | 50 | 60 |

| | Compounds | | | | | | | | | | | | | |
|---|---|---|---|---|---|---|---|---|---|---|---|---|---|---|
| 250 g ai/ha | 138 | 139 | 142 | 145 | 146 | 147 | 148 | 153 | 154 | 155 | 156 | 162 | 163 | 164 |
| Preemergence | | | | | | | | | | | | | | |
| Barnyardgrass | — | — | — | — | — | — | — | 100 | 100 | 100 | 100 | 100 | 100 | 70 |
| Bermudagrass | 100 | 100 | 98 | 98 | 98 | 100 | 100 | — | — | — | — | — | — | — |
| Blackgrass | 95 | 90 | 90 | 90 | 90 | 90 | 90 | 90 | 90 | 90 | 90 | 95 | 95 | 70 |
| Bromegrass, Downy | 80 | 85 | 90 | 85 | 80 | 90 | 80 | — | — | — | — | — | — | — |
| Cocklebur | 15 | 5 | — | — | 0 | — | — | — | — | — | — | — | — | — |
| Corn | 55 | 30 | 30 | 60 | 25 | 35 | 45 | 35 | 15 | 45 | 30 | 35 | 10 | 10 |
| Crabgrass, Large | 100 | 100 | 100 | 100 | 100 | 100 | 100 | 100 | 100 | 100 | 100 | 100 | 100 | 100 |
| Cupgrass, Woolly | 100 | 90 | 98 | 98 | 100 | 98 | 98 | — | — | — | — | — | — | — |
| Foxtail, Giant | 100 | 100 | 100 | 100 | 100 | 100 | 100 | 100 | 100 | 100 | 95 | 100 | 100 | 100 |
| Foxtail, Green | 95 | 90 | 90 | 90 | 90 | 95 | 95 | — | — | — | — | — | — | — |
| Galium | 100 | 95 | 100 | 100 | 100 | 100 | 100 | 100 | 100 | 100 | 100 | 100 | 75 | 80 |
| Goosegrass | 100 | 100 | 100 | 100 | 100 | 100 | 100 | — | — | — | — | — | — | — |
| Johnsongrass | 100 | 100 | 100 | 100 | 100 | 98 | 98 | 98 | 95 | 95 | 95 | 98 | 60 | 40 |
| Kochia | 90 | 100 | 100 | 98 | 85 | 85 | 95 | — | — | — | — | — | — | — |
| Lambsquarters | 98 | 90 | 98 | 98 | 95 | 80 | 85 | 100 | 100 | 100 | 100 | — | — | 95 |
| Morningglory | 98 | 55 | — | 85 | 90 | 35 | 75 | 50 | 25 | 90 | 30 | 85 | 75 | 45 |
| Nightshade | 98 | 98 | 98 | 90 | 98 | 98 | 85 | — | — | — | — | — | — | — |
| Nutsedge, Yellow | 5 | 5 | 0 | 10 | 10 | 15 | — | — | — | — | 0 | 5 | 75 | 0 |
| Oat, Wild | 95 | 85 | 90 | 90 | 90 | 95 | 85 | — | — | — | — | — | — | — |
| Oilseed Rape | — | — | — | — | — | — | — | 98 | 100 | 100 | 98 | 100 | 95 | 30 |
| Pigweed | 100 | 100 | 100 | 100 | 100 | 100 | 100 | 100 | 100 | 100 | 100 | 100 | 100 | 100 |
| Ragweed | 50 | 55 | 80 | 55 | 45 | 80 | 70 | 80 | 70 | 95 | 60 | 95 | 35 | 30 |
| Russian Thistle | 100 | 5 | 90 | 95 | 95 | 90 | 95 | — | — | — | — | — | — | — |
| Ryegrass, Italian | 90 | 90 | 90 | 90 | 90 | 95 | 90 | 90 | 90 | 90 | 90 | 95 | 85 | 75 |
| Soybean | 30 | 25 | 20 | 10 | 40 | 35 | 30 | 35 | 15 | 40 | 25 | 25 | 20 | 5 |
| Sunflower | 30 | 10 | 25 | 25 | 35 | 25 | 10 | — | — | — | — | — | — | — |
| Surinam Grass | 100 | 98 | 98 | 100 | 100 | 95 | 100 | — | — | — | — | — | — | — |
| Velvetleaf | 98 | 40 | 100 | 85 | 60 | 100 | 80 | 100 | 100 | 100 | 100 | 100 | 75 | 70 |

TABLE C-continued

| | | | | | | | | | | | | | | |
|---|---|---|---|---|---|---|---|---|---|---|---|---|---|---|
| Waterhemp | — | — | — | — | — | — | — | 100 | 100 | 100 | 100 | 100 | 100 | — |
| Wheat | 50 | 20 | 50 | 50 | 10 | 45 | 35 | 60 | 55 | 35 | 35 | 35 | 0 | 5 |

| | Compounds | | | | | | | | | | | | |
|---|---|---|---|---|---|---|---|---|---|---|---|---|---|
| 250 g ai/ha | 166 | 168 | 169 | 170 | 171 | 172 | 174 | 179 | 183 | 185 | 188 | 195 | 196 |
| Preemergence | | | | | | | | | | | | | |
| Barnyardgrass | 100 | 100 | 100 | 100 | 98 | 100 | 98 | 100 | 100 | 100 | 100 | — | — |
| Bermudagrass | — | — | — | — | — | — | — | — | — | — | — | 98 | 100 |
| Blackgrass | 95 | 98 | 95 | 100 | 100 | 95 | 100 | 100 | 100 | 98 | 100 | 90 | 90 |
| Bromegrass, Downy | — | — | — | — | — | — | — | — | — | — | — | 90 | 100 |
| Cocklebur | — | — | — | — | — | — | — | — | — | — | — | — | 75 |
| Corn | 20 | 55 | 20 | 60 | 25 | 40 | 10 | 20 | 40 | 35 | 20 | 35 | 50 |
| Crabgrass, Large | 100 | 100 | 100 | 100 | 100 | 100 | 100 | 100 | 100 | 100 | 100 | 100 | 100 |
| Cupgrass, Woolly | — | — | — | — | — | — | — | — | — | — | — | 98 | 100 |
| Foxtail, Giant | 100 | 100 | 100 | 100 | 100 | 100 | 100 | 100 | 100 | 100 | 100 | 100 | 100 |
| Foxtail, Green | — | — | — | — | — | — | — | — | — | — | — | 90 | 90 |
| Galium | 100 | 100 | 100 | 100 | 100 | 100 | 100 | 100 | 100 | 100 | 95 | 95 | 100 |
| Goosegrass | — | — | — | — | — | — | — | — | — | — | — | 100 | 100 |
| Johnsongrass | 100 | 100 | 98 | 95 | 95 | 98 | 95 | 100 | 95 | 100 | 98 | 100 | 100 |
| Kochia | — | — | — | — | — | — | — | — | — | — | — | 95 | 98 |
| Lambsquarters | — | 98 | 90 | 98 | 100 | 95 | 90 | 100 | 100 | 100 | 100 | 95 | 95 |
| Morningglory | 45 | 80 | 85 | 100 | 25 | 70 | 55 | 65 | 95 | 100 | 100 | 90 | 100 |
| Nightshade | — | — | — | — | — | — | — | — | — | — | — | 98 | 100 |
| Nutsedge, Yellow | 15 | 5 | 5 | 5 | 0 | 5 | 0 | 5 | 5 | 5 | 20 | 80 | 10 |
| Oat, Wild | — | — | — | — | — | — | — | — | — | — | — | 90 | 90 |
| Oilseed Rape | 100 | 100 | 100 | 100 | 90 | 100 | 50 | 100 | 100 | 100 | 100 | — | — |
| Pigweed | 100 | 100 | 100 | 100 | 100 | 100 | 100 | 100 | 100 | 100 | 100 | 100 | 98 |
| Ragweed | 55 | 80 | 65 | 95 | 15 | 85 | 55 | 45 | 95 | 95 | — | 55 | 90 |
| Russian Thistle | — | — | — | — | — | — | — | — | — | — | — | 90 | 90 |
| Ryegrass, Italian | 100 | 100 | 95 | 95 | 100 | 100 | 95 | 95 | 95 | 100 | 98 | 90 | 90 |
| Soybean | 35 | 35 | 30 | 45 | — | 35 | 10 | 25 | 30 | 40 | 65 | 25 | 35 |
| Sunflower | — | — | — | — | — | — | — | — | — | — | — | 20 | 40 |
| Surinam Grass | — | — | — | — | — | — | — | — | — | — | — | 98 | 100 |
| Velvetleaf | 60 | 100 | 100 | 100 | 65 | 100 | 100 | 80 | 100 | 100 | 90 | 90 | 100 |
| Waterhemp | 100 | — | — | — | — | — | — | — | — | — | 100 | — | — |
| Wheat | 15 | 60 | 50 | 60 | 45 | 45 | 40 | 55 | 40 | 55 | 40 | 30 | 50 |

| | Compounds | | | | | | | | | |
|---|---|---|---|---|---|---|---|---|---|---|
| 125 g ai/ha | 14 | 15 | 16 | 23 | 25 | 26 | 47 | 106 | 120 | 129 |
| Preemergence | | | | | | | | | | |
| Bermudagrass | 100 | 100 | 75 | 100 | 98 | 100 | 100 | 100 | 98 | 98 |
| Blackgrass | 85 | 95 | 100 | 100 | 95 | 90 | 100 | 90 | 90 | 90 |
| Bromegrass, Downy | 60 | 80 | 50 | 5 | 40 | 50 | 90 | 40 | 90 | 95 |
| Cocklebur | 20 | 65 | — | 5 | 0 | 15 | 0 | — | — | 0 |
| Corn | 5 | 10 | — | 70 | 5 | 5 | 10 | 0 | 25 | 45 |
| Crabgrass, Large | 100 | 100 | — | 100 | 100 | 100 | 100 | 100 | 100 | 100 |
| Cupgrass, Woolly | 75 | 95 | — | 100 | 65 | 70 | 95 | 80 | 98 | 98 |
| Foxtail, Giant | 100 | 100 | — | 100 | 100 | 100 | 100 | 100 | 98 | 98 |
| Foxtail, Green | 100 | 100 | 100 | 100 | 95 | 95 | 100 | 95 | 90 | 90 |
| Galium | 100 | 98 | 100 | 100 | 80 | 100 | 100 | 60 | 100 | 100 |
| Goosegrass | 100 | 100 | — | 100 | 100 | 100 | 100 | 98 | 98 | 98 |
| Johnsongrass | 80 | 90 | — | 95 | 65 | 95 | 60 | 75 | 95 | 85 |
| Kochia | 75 | 85 | — | 95 | 55 | 95 | 98 | 45 | 100 | 90 |
| Lambsquarters | 100 | 100 | — | 98 | 98 | 98 | 100 | 100 | 100 | 98 |
| Morningglory | 55 | 45 | — | 100 | — | — | 50 | 10 | 45 | 60 |
| Nightshade | 95 | 90 | — | 95 | 95 | 98 | 98 | 90 | 95 | 90 |
| Nutsedge, Yellow | 0 | 10 | — | 35 | 0 | 0 | 0 | 0 | 0 | 0 |
| Oat, Wild | 70 | 70 | 100 | 80 | 80 | 70 | 90 | 70 | 95 | 95 |
| Pigweed | 100 | 100 | — | 100 | 100 | 100 | 100 | 100 | 100 | 100 |
| Ragweed | — | — | — | 20 | 20 | 50 | 45 | 0 | 45 | 0 |
| Russian Thistle | 95 | 100 | 100 | — | 90 | 95 | 100 | 30 | 85 | — |
| Ryegrass, Italian | 60 | 80 | 100 | 25 | 45 | 60 | 90 | 45 | 90 | 90 |
| Soybean | 0 | 25 | — | 10 | 0 | 5 | 5 | 5 | 10 | 10 |
| Sunflower | 0 | 25 | — | 0 | 0 | 10 | 0 | 0 | 0 | 0 |
| Surinam Grass | 60 | 90 | — | 100 | 55 | 65 | 65 | 80 | 98 | 98 |

TABLE C-continued

| | | | | | | | | | | |
|---|---|---|---|---|---|---|---|---|---|---|
| Velvetleaf | 70 | 80 | — | 80 | 15 | 75 | 90 | 0 | 35 | 45 |
| Wheat | 35 | 50 | 15 | 20 | 10 | 30 | 35 | 0 | 40 | 30 |

| | Compounds | | | | | | | | | | | | | |
|---|---|---|---|---|---|---|---|---|---|---|---|---|---|---|
| 125 g ai/ha | 138 | 139 | 142 | 145 | 146 | 147 | 148 | 153 | 154 | 155 | 156 | 160 | 162 | 163 |
| Preemergence | | | | | | | | | | | | | | |
| Barnyardgrass | — | — | — | — | — | — | — | 100 | 90 | 98 | 90 | 100 | 100 | 75 |
| Bermudagrass | 100 | 100 | 98 | 98 | 98 | 100 | 100 | — | — | — | — | — | — | — |
| Blackgrass | 95 | 90 | 90 | 90 | 90 | 90 | 90 | 90 | 90 | 90 | 90 | 90 | 90 | 90 |
| Bromegrass, Downy | 60 | — | 90 | 70 | 15 | 85 | 50 | — | — | — | — | — | — | — |
| Cocklebur | 15 | 0 | 10 | 10 | 0 | — | — | — | — | — | — | — | — | — |
| Corn | 40 | 10 | 20 | 25 | 15 | 25 | 15 | 25 | 10 | 10 | 10 | 5 | 20 | — |
| Crabgrass, Large | 100 | 100 | 100 | 100 | 100 | 100 | 100 | 100 | 100 | 100 | 98 | 100 | 100 | 100 |
| Cupgrass, Woolly | 95 | 75 | 95 | 95 | 90 | 95 | 95 | — | — | — | — | — | — | — |
| Foxtail, Giant | 100 | 100 | 100 | 100 | 100 | 100 | 100 | 100 | 100 | 100 | 90 | 100 | 100 | 80 |
| Foxtail, Green | 95 | — | 90 | 90 | 90 | 95 | 95 | — | — | — | — | — | — | — |
| Galium | 100 | 85 | 100 | 100 | 95 | 100 | 100 | 100 | 85 | 100 | 100 | 100 | 100 | 5 |
| Goosegrass | 100 | 100 | 100 | 100 | 100 | 100 | 98 | — | — | — | — | — | — | — |
| Johnsongrass | 98 | 100 | 100 | 100 | 98 | 95 | 98 | 95 | 90 | 90 | 90 | 100 | 98 | 60 |
| Kochia | 85 | 90 | 98 | 98 | 85 | 80 | 90 | — | — | — | — | — | — | — |
| Lambsquarters | 98 | 85 | 95 | 95 | 85 | 80 | 65 | 100 | 100 | 100 | 100 | 100 | — | — |
| Morningglory | 65 | 35 | — | 70 | 45 | — | 55 | 50 | 5 | 60 | 10 | 20 | 80 | 30 |
| Nightshade | 98 | 85 | 98 | 85 | 90 | 98 | 85 | — | — | — | — | — | — | — |
| Nutsedge, Yellow | 5 | 0 | 0 | 5 | — | 0 | 5 | 5 | — | — | 0 | 0 | 5 | 20 |
| Oat, Wild | 95 | — | 85 | 90 | 85 | 85 | 85 | — | — | — | — | — | — | — |
| Oilseed Rape | — | — | — | — | — | — | — | 98 | 90 | 90 | 90 | 80 | 100 | 80 |
| Pigweed | 100 | 100 | 100 | 98 | 100 | 100 | 100 | 100 | 100 | 100 | 100 | 100 | 100 | 100 |
| Ragweed | 50 | 30 | 70 | 40 | 45 | 70 | 55 | 80 | 50 | 85 | 30 | 5 | 80 | 20 |
| Russian Thistle | 90 | — | 90 | 90 | 80 | 90 | 95 | — | — | — | — | — | — | — |
| Ryegrass, Italian | 70 | — | 90 | 90 | 55 | 85 | 60 | 90 | 90 | 85 | 90 | 90 | 90 | 65 |
| Soybean | — | 25 | 5 | 5 | — | 20 | 20 | 35 | 15 | 35 | 25 | 20 | — | 10 |
| Sunflower | 30 | 5 | 15 | 20 | 30 | 15 | 10 | — | — | — | — | — | — | — |
| Surinam Grass | 85 | 85 | 98 | 100 | 100 | 95 | 75 | — | — | — | — | — | — | — |
| Velvetleaf | 55 | 40 | 80 | 75 | 15 | 60 | 70 | 95 | 90 | 85 | 40 | 30 | 100 | 20 |
| Waterhemp | — | — | — | — | — | — | — | 100 | 100 | 100 | 100 | 100 | 100 | 100 |
| Wheat | 10 | 10 | 35 | 5 | 0 | 30 | 30 | 60 | 5 | 10 | 20 | 40 | 20 | 0 |

| | Compounds | | | | | | | | | | | | | |
|---|---|---|---|---|---|---|---|---|---|---|---|---|---|---|
| 125 g ai/ha | 164 | 166 | 168 | 169 | 170 | 171 | 172 | 174 | 179 | 183 | 185 | 188 | 189 | 195 |
| Preemergence | | | | | | | | | | | | | | |
| Barnyardgrass | 25 | 98 | 100 | 98 | 100 | 95 | 100 | 98 | 100 | 100 | 100 | 100 | 100 | — |
| Bermudagrass | — | — | — | — | — | — | — | — | — | — | — | — | — | 98 |
| Blackgrass | 60 | 90 | 95 | 95 | 100 | 100 | 95 | 85 | 100 | 95 | 95 | 100 | 100 | 90 |
| Bromegrass, Downy | — | — | — | — | — | — | — | — | — | — | — | — | — | 85 |
| Cocklebur | — | — | — | — | — | — | — | — | — | — | — | — | — | 0 |
| Corn | 10 | 5 | 25 | 10 | 15 | 5 | 15 | 5 | 20 | 40 | 35 | 10 | 20 | 15 |
| Crabgrass, Large | 98 | 100 | 100 | 100 | 100 | 100 | 100 | 100 | 100 | 100 | 100 | 100 | 100 | 100 |
| Cupgrass, Woolly | — | — | — | — | — | — | — | — | — | — | — | — | — | 95 |
| Foxtail, Giant | 98 | 100 | 100 | 100 | 100 | 100 | 100 | 100 | 100 | 100 | 100 | 100 | 100 | 100 |
| Foxtail, Green | — | — | — | — | — | — | — | — | — | — | — | — | — | 90 |
| Galium | 80 | 90 | 100 | 100 | 100 | 98 | 100 | 80 | 100 | 100 | 100 | 95 | 95 | 90 |
| Goosegrass | — | — | — | — | — | — | — | — | — | — | — | — | — | 100 |
| Johnsongrass | 20 | 75 | 100 | 95 | 95 | 75 | 95 | 50 | 95 | 80 | 80 | 95 | 85 | 98 |
| Kochia | — | — | — | — | — | — | — | — | — | — | — | — | — | — |
| Lambsquarters | 95 | — | 98 | 90 | 98 | — | 95 | 90 | 98 | 100 | 100 | 98 | 90 | 90 |
| Morningglory | 25 | 25 | 55 | 80 | 100 | 25 | 55 | 15 | 55 | 70 | 70 | 85 | 60 | 75 |
| Nightshade | — | — | — | — | — | — | — | — | — | — | — | — | — | 95 |
| Nutsedge, Yellow | 0 | 5 | 5 | 5 | — | 0 | 5 | 0 | 0 | 5 | 0 | 5 | 0 | 5 |
| Oat, Wild | — | — | — | — | — | — | — | — | — | — | — | — | — | — |
| Oilseed Rape | — | 90 | 100 | 100 | 100 | 50 | 98 | 50 | 100 | 100 | 100 | 100 | 85 | — |
| Pigweed | 90 | 100 | 100 | 100 | 100 | 100 | 100 | 100 | 100 | 100 | 100 | 100 | 100 | 100 |
| Ragweed | 25 | 25 | 80 | 30 | 75 | 10 | 80 | 55 | 45 | 95 | 95 | — | — | 20 |
| Russian Thistle | — | — | — | — | — | — | — | — | — | — | — | — | — | 90 |
| Ryegrass, Italian | 55 | 50 | 100 | 90 | 95 | 60 | 100 | 90 | 95 | 90 | 100 | 95 | 100 | 90 |
| Soybean | 5 | 20 | 10 | 10 | 20 | 5 | 10 | 10 | 10 | 10 | 40 | — | 25 | 0 |
| Sunflower | — | — | — | — | — | — | — | — | — | — | — | — | — | 15 |
| Surinam Grass | — | — | — | — | — | — | — | — | — | — | — | — | — | 85 |
| Velvetleaf | 30 | 15 | 100 | 75 | 100 | 55 | 100 | 65 | 80 | 100 | 100 | 85 | 60 | 55 |

TABLE C-continued

| | | | | | | | | | | | | | | |
|---|---|---|---|---|---|---|---|---|---|---|---|---|---|---|
| Waterhemp | — | 100 | — | — | — | — | — | — | — | — | — | 100 | 100 | — |
| Wheat | 0 | 5 | 40 | 20 | 60 | 5 | 45 | 20 | 50 | 35 | 40 | 35 | 30 | 5 |

| 125 g ai/ha | Compound 196 | 62 g ai/ha | Compound 196 |
|---|---|---|---|
| Preemergence | | | |
| Barnyardgrass | — | Barnyardgrass | — |
| Bermudagrass | 100 | Bermudagrass | 98 |
| Blackgrass | 90 | Blackgrass | 90 |
| Bromegrass, Downy | 100 | Bromegrass, Downy | 95 |
| Cocklebur | 45 | Cocklebur | — |
| Corn | 45 | Corn | 35 |
| Crabgrass, Large | 100 | Crabgrass, Large | 100 |
| Cupgrass, Woolly | 100 | Cupgrass, Woolly | 98 |
| Foxtail, Giant | 100 | Foxtail, Giant | 100 |
| Foxtail, Green | 90 | Foxtail, Green | 90 |
| Galium | 98 | Galium | 95 |
| Goosegrass | 100 | Goosegrass | 100 |
| Johnsongrass | — | Johnsongrass | 100 |
| Kochia | 98 | Kochia | 98 |
| Lambsquarters | 95 | Lambsquarters | 90 |
| Morningglory | 100 | Morningglory | 85 |
| Nightshade | 100 | Nightshade | 100 |
| Nutsedge, Yellow | 5 | Nutsedge, Yellow | 0 |
| Oat, Wild | 90 | Oat, Wild | 90 |
| Oilseed Rape | — | Oilseed Rape | — |
| Pigweed | 98 | Pigweed | 98 |
| Ragweed | 80 | Ragweed | 60 |
| Russian Thistle | 90 | Russian Thistle | 90 |
| Ryegrass, Italian | 90 | Ryegrass, Italian | 90 |
| Soybean | 30 | Soybean | 15 |
| Sunflower | 30 | Sunflower | 20 |
| Surinam Grass | 100 | Surinam Grass | 98 |
| Velvetleaf | 80 | Velvetleaf | 70 |
| Waterhemp | — | Waterhemp | — |
| Wheat | 40 | Wheat | 15 |

| | Compounds | | | | | | | | | |
|---|---|---|---|---|---|---|---|---|---|---|
| 62 g ai/ha | 14 | 15 | 16 | 23 | 25 | 26 | 47 | 106 | 120 | 129 |
| Preemergence | | | | | | | | | | |
| Bermudagrass | 100 | 100 | 25 | 100 | 98 | 100 | 100 | 100 | 98 | 98 |
| Blackgrass | 40 | 85 | 100 | 85 | 85 | 90 | 98 | 50 | 90 | 90 |
| Bromegrass, Downy | 35 | 30 | 10 | 0 | 5 | 45 | 40 | 5 | 85 | 80 |
| Cocklebur | — | — | — | 0 | 0 | 5 | 0 | — | 0 | 0 |
| Corn | 0 | 0 | — | 30 | 0 | 5 | 5 | 0 | 5 | 10 |
| Crabgrass, Large | 100 | 100 | — | 100 | 100 | 98 | 98 | 100 | 100 | 100 |
| Cupgrass, Woolly | 75 | 85 | — | 100 | 40 | 65 | 80 | 60 | 95 | 95 |
| Foxtail, Giant | 98 | 100 | — | 100 | 100 | 100 | 100 | 85 | 98 | 98 |
| Foxtail, Green | 100 | 100 | 100 | 100 | 95 | 95 | 100 | 95 | 90 | 90 |
| Galium | 90 | 95 | 100 | 95 | 15 | 75 | 100 | 10 | 100 | 100 |
| Goosegrass | 100 | 100 | — | 100 | 100 | 100 | 100 | 98 | 98 | 98 |
| Johnsongrass | 45 | 85 | — | 75 | 30 | 55 | 10 | 20 | 80 | 75 |
| Kochia | 0 | 70 | — | 95 | 40 | 95 | 90 | 0 | 90 | 90 |
| Lambsquarters | 100 | 100 | — | 98 | 90 | 98 | 100 | 100 | 100 | 95 |
| Morningglory | 10 | 15 | — | 20 | — | — | 20 | 0 | 45 | 20 |
| Nightshade | 80 | 85 | — | 90 | 45 | 90 | 98 | 75 | 95 | 90 |
| Nutsedge, Yellow | 0 | 0 | — | 10 | 0 | 0 | 0 | 0 | 0 | 0 |
| Oat, Wild | 40 | 70 | 100 | 80 | 30 | 70 | 90 | 45 | 90 | 85 |
| Pigweed | 100 | 100 | — | 100 | 100 | 100 | 100 | 98 | 100 | 100 |
| Ragweed | — | — | — | 20 | 5 | 35 | 15 | 0 | 45 | 0 |
| Russian Thistle | 90 | 95 | 100 | — | — | 80 | 100 | 5 | — | — |
| Ryegrass, Italian | 35 | 45 | 95 | 5 | 35 | 60 | 50 | 20 | 90 | 90 |
| Soybean | 0 | 0 | — | 5 | 0 | 5 | 0 | 0 | 5 | 0 |
| Sunflower | 0 | 0 | — | 0 | 0 | — | 0 | 0 | 0 | 0 |
| Surinam Grass | 45 | 55 | — | 60 | 20 | 50 | 20 | 20 | 95 | 95 |

TABLE C-continued

| | | | | | | | | | | |
|---|---|---|---|---|---|---|---|---|---|---|
| Velvetleaf | 10 | 20 | — | 25 | 5 | 35 | 60 | 0 | 15 | 10 |
| Wheat | 15 | 25 | 5 | 0 | 5 | 5 | 5 | 0 | 25 | 20 |

| | Compounds | | | | | | | | | | | | | |
|---|---|---|---|---|---|---|---|---|---|---|---|---|---|---|
| 62 g ai/ha | 138 | 139 | 142 | 145 | 146 | 147 | 148 | 153 | 154 | 155 | 156 | 160 | 162 | 163 |
| Preemergence | | | | | | | | | | | | | | |
| Barnyardgrass | — | — | — | — | — | — | — | 90 | 90 | 90 | 90 | 90 | 100 | 25 |
| Bermudagrass | 100 | 100 | 98 | 98 | 98 | 100 | 100 | — | — | — | — | — | — | — |
| Blackgrass | 95 | 90 | 90 | 90 | 70 | 85 | 85 | 90 | 90 | 90 | 90 | 90 | 90 | 85 |
| Bromegrass, Downy | 30 | 20 | 60 | 20 | 0 | 45 | 40 | — | — | — | — | — | — | — |
| Cocklebur | 5 | 0 | 10 | 0 | 0 | — | — | — | — | — | — | — | — | — |
| Corn | 30 | 0 | 5 | 10 | 0 | 10 | 10 | 25 | 5 | 5 | 5 | 5 | 20 | 10 |
| Crabgrass, Large | 100 | 100 | 100 | 100 | 100 | 100 | 100 | 100 | 100 | 100 | 90 | 100 | 100 | 100 |
| Cupgrass, Woolly | 90 | 40 | 70 | 90 | 45 | 55 | 90 | — | — | — | — | — | — | — |
| Foxtail, Giant | 100 | 100 | 100 | 100 | 100 | 98 | 100 | 100 | 100 | 100 | 90 | 100 | 100 | 60 |
| Foxtail, Green | 95 | 90 | 90 | 90 | 90 | 95 | 95 | — | — | — | — | — | — | — |
| Galium | 100 | 80 | 80 | 98 | 95 | 100 | 100 | 98 | 85 | 100 | 100 | 100 | — | 5 |
| Goosegrass | 100 | 100 | 100 | 100 | 85 | 100 | 95 | — | — | — | — | — | — | — |
| Johnsongrass | 85 | 45 | 98 | 35 | 75 | 55 | 80 | 90 | 40 | 90 | 90 | 100 | 60 | 35 |
| Kochia | 65 | 75 | 80 | 90 | 55 | 40 | 40 | — | — | — | — | — | — | — |
| Lambsquarters | 98 | 70 | 90 | 85 | 40 | 45 | 25 | 100 | 100 | 100 | 100 | 100 | — | — |
| Morningglory | 55 | 15 | 35 | 20 | 40 | 30 | 20 | 30 | 5 | 40 | 10 | 15 | 60 | 25 |
| Nightshade | 95 | 75 | 95 | 80 | 35 | 98 | 60 | — | — | — | — | — | — | — |
| Nutsedge, Yellow | — | 0 | — | — | 0 | 0 | 5 | 0 | — | — | 0 | 0 | 0 | 0 |
| Oat, Wild | 85 | 50 | 85 | 70 | 40 | 70 | 85 | — | — | — | — | — | — | — |
| Oilseed Rape | — | — | — | — | — | — | — | 95 | 90 | 90 | 60 | 80 | 100 | 50 |
| Pigweed | 100 | 98 | 98 | 98 | 90 | 100 | 100 | 100 | 100 | 100 | 100 | 100 | 100 | 98 |
| Ragweed | 45 | 0 | 40 | 10 | 0 | 40 | 45 | 10 | 0 | 40 | 10 | 5 | 75 | 10 |
| Russian Thistle | 90 | — | 80 | — | 0 | 90 | 85 | — | — | — | — | — | — | — |
| Ryegrass, Italian | 40 | 60 | 90 | 35 | 30 | 50 | 60 | 90 | 30 | 85 | 80 | 80 | 80 | 45 |
| Soybean | 20 | 15 | 5 | 5 | 15 | 20 | 10 | 20 | 0 | 35 | 10 | 20 | 15 | 5 |
| Sunflower | 10 | 0 | — | 5 | 20 | 15 | 0 | — | — | — | — | — | — | — |
| Surinam Grass | 80 | 65 | 75 | 55 | 20 | 80 | 75 | — | — | — | — | — | — | — |
| Velvetleaf | — | 10 | 75 | 10 | 5 | 55 | 55 | 85 | 45 | 80 | 40 | 30 | 80 | 10 |
| Waterhemp | — | — | — | — | — | — | — | 100 | 100 | 100 | 100 | 100 | 100 | 100 |
| Wheat | 5 | 0 | 5 | 5 | 0 | 5 | 5 | 35 | 5 | 5 | 5 | 15 | 5 | 0 |

| | Compounds | | | | | | | | | | | | | |
|---|---|---|---|---|---|---|---|---|---|---|---|---|---|---|
| 62 g ai/ha | 164 | 166 | 168 | 169 | 170 | 171 | 172 | 174 | 179 | 183 | 185 | 188 | 189 | 195 |
| Preemergence | | | | | | | | | | | | | | |
| Barnyardgrass | 15 | 75 | 100 | 80 | 98 | 75 | 98 | 20 | 100 | 95 | 98 | 100 | 98 | — |
| Bermudagrass | — | — | — | — | — | — | — | — | — | — | — | — | — | 98 |
| Blackgrass | 10 | 90 | 90 | 90 | 95 | 98 | 95 | 80 | 100 | 95 | 95 | 100 | 100 | 90 |
| Bromegrass, Downy | — | — | — | — | — | — | — | — | — | — | — | — | — | 45 |
| Cocklebur | — | — | — | — | — | — | — | — | — | — | — | — | — | — |
| Corn | 5 | — | 15 | 5 | 10 | 0 | 5 | 5 | 20 | 15 | 5 | 5 | 15 | 5 |
| Crabgrass, Large | 75 | 98 | 100 | 100 | 100 | 100 | 100 | 98 | 100 | 100 | 100 | 100 | 100 | 100 |
| Cupgrass, Woolly | — | — | — | — | — | — | — | — | — | — | — | — | — | 95 |
| Foxtail, Giant | 65 | 100 | 100 | 100 | 100 | 100 | 100 | 85 | 100 | 100 | 100 | 100 | 100 | 98 |
| Foxtail, Green | — | — | — | — | — | — | — | — | — | — | — | — | — | 90 |
| Galium | 50 | 10 | 100 | 100 | 100 | 98 | 100 | 50 | 100 | 100 | 100 | 90 | 80 | 80 |
| Goosegrass | — | — | — | — | — | — | — | — | — | — | — | — | — | 100 |
| Johnsongrass | 15 | 30 | 98 | 75 | 75 | 25 | 75 | 25 | 60 | 35 | 70 | 85 | 85 | — |
| Kochia | — | — | — | — | — | — | — | — | — | — | — | — | — | 75 |
| Lambsquarters | 85 | — | 98 | 90 | 85 | 100 | 90 | 85 | 98 | 100 | 100 | 90 | 90 | 80 |
| Morningglory | 15 | 10 | 55 | 55 | 55 | 20 | 35 | 5 | 40 | 45 | 55 | 60 | 40 | 50 |
| Nightshade | — | — | — | — | — | — | — | — | — | — | — | — | — | 85 |
| Nutsedge, Yellow | 0 | 0 | 0 | 5 | 5 | 0 | 5 | 0 | 0 | 0 | 0 | 5 | 0 | 0 |
| Oat, Wild | — | — | — | — | — | — | — | — | — | — | — | — | — | 90 |
| Oilseed Rape | 5 | 50 | 100 | 98 | 95 | 50 | 90 | 5 | 98 | 80 | 85 | 70 | 70 | — |
| Pigweed | 35 | 100 | 100 | 100 | 100 | 100 | 100 | 100 | 100 | 100 | 100 | 100 | 100 | 98 |
| Ragweed | 20 | 20 | 30 | 15 | 60 | 5 | 40 | 15 | 40 | 50 | 80 | — | — | 20 |
| Russian Thistle | — | — | — | — | — | — | — | — | — | — | — | — | — | 90 |
| Ryegrass, Italian | 10 | 40 | 98 | 90 | 90 | 50 | 100 | 40 | 95 | 80 | 100 | 65 | 85 | 80 |
| Soybean | 0 | 5 | 10 | 5 | 5 | 0 | 10 | 0 | 10 | 5 | 10 | 20 | 15 | 0 |
| Sunflower | — | — | — | — | — | — | — | — | — | — | — | — | — | 15 |
| Surinam Grass | — | — | — | — | — | — | — | — | — | — | — | — | — | 75 |
| Velvetleaf | 10 | 0 | 100 | 75 | 100 | 25 | 75 | 15 | 75 | 55 | 80 | 65 | 40 | 25 |

TABLE C-continued

| | | | | | | | | | | | | | | |
|---|---|---|---|---|---|---|---|---|---|---|---|---|---|---|
| Waterhemp | — | 100 | — | — | — | — | — | — | — | — | — | 100 | 100 | — |
| Wheat | 0 | 0 | 40 | 15 | 40 | 0 | 40 | 0 | 15 | 10 | 40 | 30 | 15 | 5 |

| | Compounds | | | | | | | | | |
|---|---|---|---|---|---|---|---|---|---|---|
| 31 g ai/ha | 14 | 15 | 16 | 23 | 25 | 26 | 47 | 106 | 120 | 129 |
| Preemergence | | | | | | | | | | |
| Bermudagrass | 98 | 100 | 5 | 100 | 85 | 75 | 100 | 100 | 98 | 98 |
| Blackgrass | 5 | 50 | 90 | 5 | 60 | 55 | 90 | 50 | 90 | 90 |
| Bromegrass, Downy | 30 | 25 | 5 | 0 | 5 | 5 | 15 | 0 | 45 | 30 |
| Cocklebur | 0 | 0 | — | 0 | 0 | 0 | 0 | — | 0 | 0 |
| Corn | 0 | 0 | — | 5 | 0 | 0 | 0 | 0 | 0 | 0 |
| Crabgrass, Large | 95 | 100 | — | 100 | 98 | 98 | 45 | 100 | 100 | 98 |
| Cupgrass, Woolly | 5 | 45 | — | 95 | 20 | 10 | 45 | 5 | 90 | 80 |
| Foxtail, Giant | 95 | 95 | — | 98 | 98 | 98 | 95 | 65 | 98 | 95 |
| Foxtail, Green | 80 | 95 | 100 | 100 | 90 | 85 | 100 | 90 | 90 | 90 |
| Galium | 20 | 75 | 100 | 80 | 0 | 50 | 85 | 5 | 98 | 85 |
| Goosegrass | 98 | 100 | — | 95 | 90 | 95 | 98 | 80 | 98 | 98 |
| Johnsongrass | 20 | 55 | — | 55 | 5 | 15 | 5 | 0 | 25 | 25 |
| Kochia | 0 | 70 | — | 95 | 10 | 45 | 85 | 0 | 10 | 5 |
| Lambsquarters | 95 | 100 | — | 95 | 90 | 70 | 100 | 85 | 85 | 95 |
| Morningglory | 10 | 5 | — | 20 | — | — | 5 | 0 | 45 | 0 |
| Nightshade | 55 | 25 | — | 50 | 10 | 55 | 45 | 0 | 95 | 85 |
| Nutsedge, Yellow | 0 | 0 | — | 5 | 0 | 0 | 0 | 0 | 0 | 0 |
| Oat, Wild | 20 | 40 | 98 | 45 | 20 | 45 | 80 | 10 | 85 | 40 |
| Pigweed | 100 | 100 | — | 100 | 100 | 100 | 100 | 85 | 100 | 100 |
| Ragweed | — | — | — | 5 | 5 | 15 | 5 | 0 | 0 | 0 |
| Russian Thistle | 10 | 50 | 45 | — | 0 | — | 85 | 0 | 0 | — |
| Ryegrass, Italian | 10 | 40 | 5 | 0 | 5 | 10 | 35 | 5 | 40 | 60 |
| Soybean | 0 | 0 | — | 0 | 0 | 0 | 0 | 0 | 0 | 0 |
| Sunflower | 0 | 0 | — | 0 | 0 | 0 | 0 | — | 0 | 0 |
| Surinam Grass | 20 | 40 | — | 15 | 15 | 10 | 5 | 5 | 65 | 95 |
| Velvetleaf | 10 | 0 | — | 5 | 0 | 25 | 45 | 0 | 5 | 0 |
| Wheat | 0 | 10 | 0 | 0 | 0 | 0 | 0 | 0 | 5 | 0 |

| | Compounds | | | | | | | | | | | | | |
|---|---|---|---|---|---|---|---|---|---|---|---|---|---|---|
| 31 g ai/ha | 138 | 139 | 142 | 145 | 146 | 147 | 148 | 153 | 154 | 155 | 156 | 160 | 162 | 163 |
| Preemergence | | | | | | | | | | | | | | |
| Barnyardgrass | — | — | — | — | — | — | — | 90 | 45 | 40 | 85 | 35 | 98 | 10 |
| Bermudagrass | 100 | 98 | 98 | 98 | 98 | 100 | 98 | — | — | — | — | — | — | — |
| Blackgrass | 90 | 45 | 90 | 85 | 50 | 50 | 60 | 90 | 90 | 90 | 85 | 40 | 60 | 5 |
| Bromegrass, Downy | 10 | 0 | 20 | 5 | 0 | 10 | 5 | — | — | — | — | — | — | — |
| Cocklebur | 5 | — | 0 | 0 | 0 | 35 | 10 | — | — | — | — | — | — | — |
| Corn | 20 | 0 | 0 | 0 | 0 | 10 | 5 | 10 | 0 | 5 | 5 | 5 | 5 | 10 |
| Crabgrass, Large | 98 | 100 | 100 | 98 | 98 | 98 | 100 | 100 | 90 | 100 | 90 | 100 | 100 | 65 |
| Cupgrass, Woolly | 60 | 30 | 55 | 55 | 40 | 50 | 50 | — | — | — | — | — | — | — |
| Foxtail, Giant | 98 | 95 | 100 | 95 | 40 | 85 | 98 | 100 | 100 | 100 | 90 | 100 | 98 | 40 |
| Foxtail, Green | 90 | 90 | 90 | 90 | 90 | 95 | 95 | — | — | — | — | — | — | — |
| Galium | 95 | 5 | 60 | 60 | 95 | 100 | 80 | 80 | 5 | 98 | 85 | 5 | 100 | 0 |
| Goosegrass | 100 | 98 | 100 | 98 | 70 | 98 | 90 | — | — | — | — | — | — | — |
| Johnsongrass | 45 | 15 | 90 | 0 | 5 | 40 | 15 | 90 | 40 | 80 | 75 | 100 | 35 | 30 |
| Kochia | 55 | 65 | 55 | 50 | 30 | 35 | 40 | — | — | — | — | — | — | — |
| Lambsquarters | 95 | 60 | 80 | 55 | 10 | 35 | 15 | 95 | 100 | 90 | 100 | 100 | — | — |
| Morningglory | 15 | 15 | — | 15 | 35 | 30 | 20 | 20 | 0 | 10 | 5 | 5 | 55 | 20 |
| Nightshade | 90 | — | 95 | 35 | — | 98 | 25 | — | — | — | — | — | — | — |
| Nutsedge, Yellow | 5 | 0 | 0 | — | 0 | 0 | 0 | 0 | 0 | 0 | 0 | 0 | 0 | 0 |
| Oat, Wild | 80 | 10 | 85 | 45 | 5 | 60 | 35 | — | — | — | — | — | — | — |
| Oilseed Rape | — | — | — | — | — | — | — | 90 | 5 | 50 | 10 | 5 | 80 | 0 |
| Pigweed | 98 | 98 | 98 | 90 | 85 | 100 | 100 | 100 | 100 | 100 | 100 | 100 | 100 | 95 |
| Ragweed | 40 | 0 | 40 | 0 | 0 | 25 | 15 | 5 | 0 | 20 | 5 | 0 | 50 | 0 |
| Russian Thistle | 85 | — | — | 0 | 0 | 0 | — | — | — | — | — | — | — | — |
| Ryegrass, Italian | 10 | 35 | 30 | 5 | 0 | 10 | 5 | 60 | 10 | 35 | 45 | 15 | 60 | 10 |
| Soybean | 5 | 5 | 0 | — | 10 | — | 5 | 20 | 0 | 0 | 5 | 5 | 15 | 5 |
| Sunflower | 5 | 0 | 15 | 0 | 10 | 15 | 0 | — | — | — | — | — | — | — |
| Surinam Grass | 55 | 15 | 60 | 35 | 10 | 55 | 60 | — | — | — | — | — | — | — |
| Velvetleaf | 5 | 0 | 35 | 0 | 0 | 25 | 15 | — | 5 | 30 | 5 | 5 | 55 | 0 |

TABLE C-continued

| | | | | | | | | | | | | | | |
|---|---|---|---|---|---|---|---|---|---|---|---|---|---|---|
| Waterhemp | — | — | — | — | — | — | — | 100 | 95 | 100 | 100 | 100 | 100 | 90 |
| Wheat | 5 | 0 | 0 | 0 | 0 | 0 | 0 | 10 | 0 | 5 | 0 | 0 | 0 | 0 |

| | Compounds | | | | | | | | | | | | | |
|---|---|---|---|---|---|---|---|---|---|---|---|---|---|---|
| 31 g ai/ha | 164 | 166 | 168 | 169 | 170 | 171 | 172 | 174 | 179 | 183 | 185 | 188 | 189 | 195 |
| Preemergence | | | | | | | | | | | | | | |
| Barnyardgrass | 5 | 5 | 75 | 40 | 80 | 5 | 85 | 5 | 40 | 40 | 55 | 80 | 45 | — |
| Bermudagrass | — | — | — | — | — | — | — | — | — | — | — | — | — | 98 |
| Blackgrass | 5 | 15 | 90 | 80 | 90 | 5 | 90 | 80 | 80 | 80 | 90 | 80 | 90 | 90 |
| Bromegrass, Downy | — | — | — | — | — | — | — | — | — | — | — | — | — | 15 |
| Cocklebur | — | — | — | — | — | — | — | — | — | — | — | — | — | — |
| Corn | 0 | 0 | 5 | 5 | 5 | 0 | 5 | 0 | 5 | 15 | 5 | 5 | 5 | 0 |
| Crabgrass, Large | 70 | 85 | 100 | 100 | 100 | 85 | 100 | 60 | 100 | 100 | 100 | 98 | 98 | 98 |
| Cupgrass, Woolly | — | — | — | — | — | — | — | — | — | — | — | — | — | 20 |
| Foxtail, Giant | 50 | 100 | 100 | 100 | 98 | 98 | 100 | 40 | 100 | 100 | 100 | 100 | 100 | 98 |
| Foxtail, Green | — | — | — | — | — | — | — | — | — | — | — | — | — | 90 |
| Galium | 0 | 10 | 85 | 100 | 98 | 5 | 80 | 5 | 80 | 60 | 80 | 90 | 80 | 10 |
| Goosegrass | — | — | — | — | — | — | — | — | — | — | — | — | — | 98 |
| Johnsongrass | 5 | 10 | 75 | 20 | 50 | 0 | 60 | 5 | 5 | 10 | 25 | 55 | 50 | — |
| Kochia | — | — | — | — | — | — | — | — | — | — | — | — | — | 60 |
| Lambsquarters | 85 | — | 98 | 90 | 85 | 100 | 90 | 85 | 98 | 80 | 100 | 90 | 85 | 55 |
| Morningglory | 5 | — | 45 | 25 | 35 | 0 | 30 | 0 | 5 | 30 | 45 | — | 10 | 30 |
| Nightshade | — | — | — | — | — | — | — | — | — | — | — | — | — | 60 |
| Nutsedge, Yellow | 0 | 0 | 0 | 0 | 0 | 0 | 0 | 0 | 0 | 0 | 0 | 5 | 0 | 0 |
| Oat, Wild | — | — | — | — | — | — | — | — | — | — | — | — | — | 80 |
| Oilseed Rape | 5 | 50 | 100 | 50 | 95 | 0 | 60 | 0 | 80 | 60 | 60 | 20 | — | — |
| Pigweed | 10 | 100 | 100 | 100 | 100 | 60 | 100 | 98 | 100 | 100 | 100 | 100 | 98 | 98 |
| Ragweed | 20 | 20 | 10 | 15 | 5 | 0 | 35 | 5 | 40 | 50 | 40 | — | — | 15 |
| Russian Thistle | — | — | — | — | — | — | — | — | — | — | — | — | — | 90 |
| Ryegrass, Italian | 5 | 5 | 70 | 85 | 55 | 10 | 100 | 10 | 45 | 65 | 90 | 60 | 60 | 50 |
| Soybean | 0 | 5 | 5 | 0 | 5 | 0 | 5 | 0 | 0 | 5 | 5 | 5 | 5 | 0 |
| Sunflower | — | — | — | — | — | — | — | — | — | — | — | — | — | 0 |
| Surinam Grass | — | — | — | — | — | — | — | — | — | — | — | — | — | 55 |
| Velvetleaf | 10 | 0 | 80 | 50 | 60 | 5 | 60 | 5 | 30 | 45 | 60 | 45 | 15 | 10 |
| Waterhemp | — | 55 | — | — | — | — | — | — | — | — | — | 100 | 98 | — |
| Wheat | 0 | 0 | 5 | 5 | 10 | 0 | 15 | 0 | 5 | 5 | 10 | 30 | 5 | 0 |

| 31 g ai/ha | Compound 196 | 31 g ai/ha | Compound 196 |
|---|---|---|---|
| Preemergence | | | |
| Barnyardgrass | — | Morningglory | 40 |
| Bermudagrass | 98 | Nightshade | 100 |
| Blackgrass | 90 | Nutsedge, Yellow | 0 |
| Bromegrass, Downy | 60 | Oat, Wild | 80 |
| Cocklebur | 5 | Oilseed Rape | — |
| Corn | 25 | Pigweed | 95 |
| Crabgrass, Large | 100 | Ragweed | 40 |
| Cupgrass, Woolly | 90 | Russian Thistle | 90 |
| Foxtail, Giant | 100 | Ryegrass, Italian | 80 |
| Foxtail, Green | 90 | Soybean | 10 |
| Galium | 85 | Sunflower | 5 |
| Goosegrass | 100 | Surinam Grass | 90 |
| Johnsongrass | 98 | Velvetleaf | 60 |
| Kochia | 90 | Waterhemp | — |
| Lambsquarters | 85 | Wheat | 0 |

| 16 g ai/ha | Compound 15 | 16 g ai/ha | Compound 15 |
|---|---|---|---|
| Preemergence | | | |
| Bermudagrass | 100 | Lambsquarters | 95 |
| Blackgrass | 15 | Morningglory | 5 |
| Bromegrass, Downy | 15 | Nightshade | 10 |
| Cocklebur | 0 | Nutsedge, Yellow | 0 |
| Corn | 0 | Oat, Wild | 35 |
| Crabgrass, Large | 98 | Pigweed | 98 |
| Cupgrass, Woolly | 5 | Russian Thistle | 5 |
| Foxtail, Giant | 95 | Ryegrass, Italian | 10 |
| Foxtail, Green | 95 | Soybean | 0 |
| Galium | 50 | Sunflower | 0 |
| Goosegrass | 100 | Surinam Grass | 10 |

TABLE C-continued

| | | | |
|---|---|---|---|
| Johnsongrass | 15 | Velvetleaf | 0 |
| Kochia | 0 | Wheat | 0 |

| | Compounds | | | Compounds | |
|---|---|---|---|---|---|
| 16 g ai/ha | 160 | 189 | 16 g ai/ha | 160 | 189 |
| Preemergence | | | | | |
| Barnyardgrass | 5 | 25 | Nutsedge, Yellow | 0 | 0 |
| Blackgrass | 0 | 75 | Oilseed Rape | 0 | 5 |
| Corn | 5 | 5 | Pigweed | 90 | 85 |
| Crabgrass, Large | 90 | 98 | Ragweed | 0 | — |
| Foxtail, Giant | 80 | 100 | Ryegrass, Italian | 5 | 50 |
| Galium | — | 80 | Soybean | 0 | 5 |
| Johnsongrass | 85 | 30 | Velvetleaf | 0 | 10 |
| Lambsquarters | 95 | 45 | Waterhemp | 100 | 90 |
| Morningglory | 0 | — | Wheat | 0 | 0 |

Test D

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), *galium* (catchweed bedstraw, *Galium aparine*), bromegrass, downy (downy bromegrass, *Bromus tectorum*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Italian (Italian ryegrass, *Lolium multiflorum*), *kochia* (*Kochia scoparia*), lambsquarters (*Chenopodium album*), oilseed rape (*Brassica napus*), pigweed (*Amaranthus retroflexus*), Russian thistle (*Salsola iberica*), chamomile (scentless chamomile, *Matricaria inodora*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), mustard, wild (wild mustard, *Sinapis arvensis*), oat, wild (wild oat, *Avena fatua*), radish, wild (wild radish, *Raphanus raphanistrum*), windgrass (*Apera spica-venti*), barley, winter (winter barley, *Hordeum vulgare*), and wheat, winter (winter wheat, *Triticum aestivum*) were planted into a silt loam soil and treated preemergence with test chemicals formulated in a non-phytotoxic solvent mixture which included a surfactant. At the same time, these same crop and weed species were planted in pots containing the planting medium comprising spaghnum peat moss, vermiculite, wetting agent and starter nutrients and treated with postemergence applications of the test chemicals formulated in the same manner. Plants ranged in height from 2 to 18 cm (1- to 4-leaf stage).

Treated plants and controls were maintained in a controlled growth environment for 14 to 21 days after which time all species were compared to controls and visually evaluated. Plant response ratings, summarized in Table D, are based on a scale of 0 to 100 where 0 is no effect and 100 is complete control. A dash (-) response means no test result.

TABLE D

| | Compounds | | | | | | |
|---|---|---|---|---|---|---|---|
| 250 g ai/ha | 14 | 15 | 16 | 23 | 106 | 120 | 129 |
| Postemergence | | | | | | | |
| Barley, Spring | 40 | 40 | 35 | 15 | 30 | 30 | 10 |
| Barley, Winter | 40 | 40 | 40 | 20 | 10 | 40 | 30 |
| Blackgrass | 85 | 85 | 40 | 30 | 30 | 85 | 70 |
| Bluegrass | 95 | 95 | 70 | 40 | 30 | 95 | 70 |
| Bromegrass, Downy | 40 | 40 | 50 | 25 | 15 | 25 | 30 |
| Buckwheat, Wild | 100 | 100 | 50 | 75 | 100 | 98 | 100 |
| Canarygrass | 80 | 80 | 80 | 30 | 30 | 95 | 80 |
| Chamomile | 100 | 100 | 10 | 5 | 25 | 90 | 35 |
| Chickweed | 98 | 100 | 95 | 90 | 90 | 100 | 100 |
| Deadnettle | 100 | 100 | 90 | 90 | 80 | 100 | 100 |
| Field Poppy | 100 | 100 | 100 | 100 | 100 | 100 | 85 |
| Field Violet | 100 | 100 | 80 | 80 | 100 | 100 | 80 |
| Foxtail, Green | 95 | 100 | 95 | 25 | 40 | 100 | 100 |
| Galium | 70 | 100 | 70 | 90 | 60 | 100 | 98 |
| Kochia | 100 | 100 | 95 | 95 | 100 | 100 | 100 |
| Lambsquarters | 100 | 100 | 100 | 100 | 90 | 100 | 100 |
| Mustard, Wild | 100 | 100 | 100 | 100 | 100 | — | — |
| Oat, Wild | 55 | 40 | 50 | 20 | 20 | 70 | 25 |
| Oilseed Rape | 100 | 100 | 100 | 95 | 95 | 98 | 100 |
| Pigweed | 100 | 100 | 100 | 100 | 90 | 100 | 100 |
| Radish, Wild | 100 | 100 | 100 | 100 | 100 | 100 | 100 |
| Russian Thistle | 100 | 100 | 100 | 100 | 100 | 100 | 100 |
| Ryegrass, Italian | 35 | 20 | 35 | 15 | 20 | 30 | 15 |
| Speedwell | 100 | 100 | 100 | 60 | 90 | 100 | 100 |

TABLE D-continued

| | | | | | | | |
|---|---|---|---|---|---|---|---|
| Wheat, Spring | 40 | 50 | 20 | 15 | 20 | 25 | 20 |
| Wheat, Winter | 25 | 35 | 25 | 15 | 5 | 20 | 20 |
| Windgrass | 100 | 100 | 35 | 30 | 50 | 100 | 95 |

| | Compounds | | | | Compounds | | |
|---|---|---|---|---|---|---|---|
| 250 g ai/ha | 137 | 138 | 195 | 250 g ai/ha | 137 | 138 | 195 |
| Postemergence | | | | | | | |
| Barley, Spring | 40 | 40 | 40 | Kochia | 100 | 100 | 100 |
| Barley, Winter | 10 | 20 | 45 | Lambsquarters | 95 | 100 | 100 |
| Blackgrass | 80 | 85 | 70 | Mustard, Wild | 100 | 100 | 100 |
| Bluegrass | 90 | 85 | 80 | Oat, Wild | 50 | 75 | 45 |
| Bromegrass, Downy | 40 | 50 | 40 | Oilseed Rape | 100 | 100 | 100 |
| Buckwheat, Wild | 80 | 80 | 65 | Pigweed | 100 | 100 | 95 |
| Canarygrass | 75 | 80 | 55 | Radish, Wild | 100 | 100 | — |
| Chamomile | 40 | 80 | 50 | Russian Thistle | 90 | 100 | 100 |
| Chickweed | 90 | 100 | 90 | Ryegrass, Italian | 40 | 50 | 25 |
| Deadnettle | 85 | 95 | 90 | Speedwell | 100 | 100 | 100 |
| Field Poppy | 100 | 100 | 100 | Wheat, Spring | 25 | 35 | 35 |
| Field Violet | 95 | 90 | 95 | Wheat, Winter | 20 | 25 | 40 |
| Foxtail, Green | 95 | 100 | 100 | Windgrass | 80 | 90 | 80 |
| Galium | 75 | 100 | 80 | | | | |

| | Compounds | | | | | | |
|---|---|---|---|---|---|---|---|
| 125 g ai/ha | 14 | 15 | 16 | 23 | 106 | 120 | 129 |
| Postemergence | | | | | | | |
| Barley, Spring | 30 | 30 | 20 | 10 | 20 | 15 | 10 |
| Barley, Winter | 35 | 20 | 25 | 10 | 5 | 20 | 15 |
| Blackgrass | 70 | 50 | 25 | 20 | 20 | 75 | 50 |
| Bluegrass | 70 | 50 | 60 | 30 | 15 | 70 | 60 |
| Bromegrass, Downy | 30 | 20 | 40 | 20 | 15 | 20 | 30 |
| Buckwheat, Wild | 60 | 70 | 20 | 40 | 10 | 95 | 100 |
| Canarygrass | 55 | 50 | 40 | 25 | 20 | 90 | 70 |
| Chamomile | 100 | 25 | 5 | 0 | 0 | 80 | 30 |
| Chickweed | 90 | 100 | 95 | 30 | 90 | 100 | 100 |
| Deadnettle | 100 | 100 | 50 | 60 | 60 | 100 | 98 |
| Field Poppy | 100 | 100 | 100 | 100 | 100 | 100 | 100 |
| Field Violet | 100 | 100 | 70 | 70 | 85 | 100 | 100 |
| Foxtail, Green | 30 | 75 | 90 | 25 | 30 | 95 | 95 |
| Galium | 55 | 100 | 60 | 70 | 40 | 98 | 85 |
| Kochia | 100 | 100 | 75 | 90 | 95 | 100 | 100 |
| Lambsquarters | 100 | 100 | 100 | 100 | 50 | 100 | 100 |
| Mustard, Wild | 100 | 100 | — | 100 | 90 | — | — |
| Oat, Wild | 40 | 30 | 45 | 15 | 5 | 35 | 20 |
| Oilseed Rape | 90 | 100 | 100 | 85 | 80 | 90 | 100 |
| Pigweed | 100 | 100 | 90 | 95 | 90 | 100 | 100 |
| Radish, Wild | 100 | 100 | 100 | 75 | 100 | 100 | 100 |
| Russian Thistle | 100 | 100 | 100 | 90 | 60 | 100 | 100 |
| Ryegrass, Italian | 25 | 10 | 30 | 10 | 10 | 15 | 10 |
| Speedwell | 100 | 100 | 95 | 50 | 90 | 100 | 100 |
| Wheat, Spring | 35 | 40 | 15 | 10 | 10 | 20 | 15 |
| Wheat, Winter | 15 | 25 | 20 | 15 | 5 | 15 | 20 |
| Windgrass | 75 | 75 | 25 | 20 | 35 | 100 | 70 |

| | Compounds | | | | | | | | |
|---|---|---|---|---|---|---|---|---|---|
| 125 g ai/ha | 137 | 138 | 145 | 147 | 148 | 155 | 156 | 195 | 196 |
| Postemergence | | | | | | | | | |
| Barley, Spring | 30 | 35 | 20 | 25 | 25 | 35 | 30 | 30 | 55 |
| Barley, Winter | 1 | 20 | 20 | 30 | 30 | 35 | 30 | 30 | 40 |
| Blackgrass | 70 | 80 | 30 | 60 | 65 | 85 | 60 | 50 | 80 |
| Bluegrass | 80 | 70 | 40 | 70 | 70 | 90 | 80 | 60 | 80 |
| Bromegrass, Downy | 30 | 40 | 10 | 50 | 20 | 55 | 35 | 35 | 65 |
| Buckwheat, Wild | 65 | 80 | 85 | 70 | 70 | 75 | 85 | 35 | 95 |
| Canarygrass | 50 | 50 | 60 | 80 | 70 | 85 | 80 | 40 | 85 |
| Chamomile | 20 | 60 | 30 | 80 | 95 | 85 | 100 | 20 | 85 |
| Chickweed | 85 | 95 | 90 | 80 | 90 | 100 | 95 | 85 | 100 |
| Deadnettle | 80 | 80 | 100 | 100 | 100 | 100 | 100 | 75 | 100 |
| Field Poppy | 100 | 100 | 100 | 100 | 100 | 100 | 100 | 100 | 100 |
| Field Violet | 90 | 85 | 95 | 90 | 95 | 95 | 95 | 85 | 100 |
| Foxtail, Green | 80 | 80 | 100 | 60 | 60 | 80 | 65 | 100 | 95 |
| Galium | 75 | 90 | 70 | 90 | 75 | 75 | 80 | 75 | 90 |
| Kochia | 95 | 100 | 100 | 95 | 85 | 85 | 90 | 100 | 90 |

TABLE D-continued

| | | | | | | | | | |
|---|---|---|---|---|---|---|---|---|---|
| Lambsquarters | 95 | 95 | 100 | 95 | 95 | 95 | 95 | 95 | 95 |
| Mustard, Wild | 95 | 100 | 100 | 100 | 100 | 100 | 100 | 95 | 100 |
| Oat, Wild | 35 | 50 | 35 | 35 | 55 | 75 | 65 | 35 | 70 |
| Oilseed Rape | 100 | 100 | 100 | 100 | 100 | 100 | 100 | 100 | 100 |
| Pigweed | 100 | 100 | 100 | 95 | 95 | 95 | 95 | 80 | 100 |
| Radish, Wild | 100 | 100 | — | 100 | 100 | 100 | 100 | — | 100 |
| Russian Thistle | 85 | 95 | 100 | 80 | 75 | 85 | 80 | 85 | 75 |
| Ryegrass, Italian | 35 | 40 | 30 | 35 | 20 | 60 | 25 | 20 | 75 |
| Speedwell | 95 | 98 | 100 | — | — | — | — | 100 | — |
| Wheat, Spring | 20 | 25 | 25 | 25 | 25 | 50 | 25 | 25 | 35 |
| Wheat, Winter | 15 | 20 | 10 | 20 | 25 | 25 | 20 | 25 | 35 |
| Windgrass | 50 | 60 | 80 | 75 | 80 | 95 | 80 | 70 | 95 |

| | Compounds | | | | | | |
|---|---|---|---|---|---|---|---|
| 62 g ai/ha | 14 | 15 | 16 | 23 | 106 | 120 | 129 |
| Postemergence | | | | | | | |
| Barley, Spring | 25 | 25 | 15 | 10 | 15 | 15 | 5 |
| Barley, Winter | 25 | 15 | 10 | 10 | 5 | 20 | 10 |
| Blackgrass | 35 | 30 | 20 | 10 | 10 | 30 | 10 |
| Bluegrass | 35 | 25 | 40 | 25 | 10 | 40 | 20 |
| Bromegrass, Downy | 20 | 10 | 20 | 15 | 10 | 10 | 20 |
| Buckwheat, Wild | 40 | 30 | 10 | 35 | 10 | 85 | 80 |
| Canarygrass | 40 | 40 | 35 | 20 | 10 | 20 | 15 |
| Chamomile | 60 | 0 | 0 | 0 | 0 | 40 | 30 |
| Chickweed | 80 | 100 | 90 | 15 | 90 | 98 | 100 |
| Deadnettle | 40 | 98 | 45 | 50 | 40 | 90 | 80 |
| Field Poppy | 100 | 100 | 100 | 90 | 100 | 100 | 100 |
| Field Violet | 100 | 100 | 30 | 50 | 70 | 100 | 100 |
| Foxtail, Green | 25 | 80 | 80 | 20 | 20 | 80 | 85 |
| Galium | 55 | 70 | 50 | 50 | 40 | 70 | 75 |
| Kochia | 95 | 90 | 95 | 85 | 70 | 100 | 100 |
| Lambsquarters | 80 | 100 | 100 | 80 | 30 | 100 | 95 |
| Mustard, Wild | 90 | 100 | 90 | 85 | 80 | — | — |
| Oat, Wild | 25 | 10 | 30 | 10 | 5 | 20 | 10 |
| Oilseed Rape | 70 | 70 | 95 | 75 | 10 | 80 | 95 |
| Pigweed | 100 | 80 | 80 | 80 | 60 | 90 | 100 |
| Radish, Wild | 85 | 100 | 100 | 40 | 100 | 90 | 100 |
| Russian Thistle | 75 | 100 | 100 | 70 | 30 | 98 | 100 |
| Ryegrass, Italian | 20 | 5 | 25 | 10 | 5 | 10 | 5 |
| Speedwell | 100 | 100 | 85 | 20 | 0 | 100 | 100 |
| Wheat, Spring | 20 | 30 | 10 | 10 | 5 | 10 | 10 |
| Wheat, Winter | 5 | 15 | 15 | 10 | 5 | 10 | 10 |
| Windgrass | 40 | 25 | 20 | 10 | 25 | 95 | 30 |

| | Compounds | | | | | | | | |
|---|---|---|---|---|---|---|---|---|---|
| 62 g ai/ha | 137 | 138 | 145 | 147 | 148 | 155 | 156 | 195 | 196 |
| Postemergence | | | | | | | | | |
| Barley, Spring | 25 | 25 | 15 | 20 | 20 | 25 | 25 | 20 | 35 |
| Barley, Winter | 5 | 15 | 10 | 25 | 25 | 25 | 25 | 15 | 35 |
| Blackgrass | 50 | 70 | 25 | 30 | 30 | 60 | 35 | 35 | 85 |
| Bluegrass | 40 | 50 | 25 | 55 | 25 | 75 | 70 | 40 | 75 |
| Bromegrass, Downy | 20 | 30 | 10 | 15 | 15 | 35 | 15 | 20 | 50 |
| Buckwheat, Wild | 65 | 50 | 45 | 65 | 75 | 70 | 80 | 30 | 90 |
| Canarygrass | 30 | 30 | 35 | 55 | 20 | 70 | 65 | 20 | 80 |
| Chamomile | 15 | 30 | 10 | 75 | 75 | 80 | 75 | 20 | 75 |
| Chickweed | 80 | 85 | 80 | 80 | 80 | 75 | 90 | 60 | 95 |
| Deadnettle | 70 | 75 | 90 | 90 | 100 | 90 | 100 | 75 | 100 |
| Field Poppy | 100 | 90 | 100 | 100 | 95 | 100 | 100 | 95 | 100 |
| Field Violet | 85 | 75 | 95 | 100 | 95 | 100 | 95 | 75 | 95 |
| Foxtail, Green | 70 | 75 | 100 | 25 | 50 | 70 | 25 | 75 | 85 |
| Galium | 40 | 80 | 40 | 75 | 70 | 70 | 75 | 50 | 70 |
| Kochia | 90 | 100 | 100 | 90 | 85 | 85 | 95 | 95 | 90 |
| Lambsquarters | 80 | 90 | 100 | 90 | 95 | 90 | 85 | 80 | 90 |
| Mustard, Wild | 80 | 95 | 90 | 100 | 100 | 100 | 100 | 80 | 100 |
| Oat, Wild | 20 | 30 | 30 | 30 | 30 | 55 | 20 | 25 | 45 |
| Oilseed Rape | 98 | 100 | 70 | 95 | 80 | 100 | 100 | 95 | 100 |
| Pigweed | 95 | 95 | 100 | 85 | 95 | 95 | 90 | 75 | 95 |
| Radish, Wild | 90 | 95 | — | 95 | 100 | 95 | 100 | — | 100 |
| Russian Thistle | 85 | 90 | 98 | 80 | 85 | 85 | 90 | 80 | 80 |
| Ryegrass, Italian | 25 | 35 | 15 | 15 | 20 | 25 | 10 | 20 | 30 |
| Speedwell | 85 | 90 | 85 | — | — | — | — | 100 | — |
| Wheat, Spring | 10 | 10 | 20 | 20 | 20 | 25 | 20 | 20 | 35 |

TABLE D-continued

| | | | | | | | | | |
|---|---|---|---|---|---|---|---|---|---|
| Wheat, Winter | 10 | 20 | 10 | 15 | 15 | 15 | 15 | 10 | 25 |
| Windgrass | 40 | 50 | 60 | 50 | 60 | 80 | 70 | 30 | 95 |

| | Compounds | | | | | | |
|---|---|---|---|---|---|---|---|
| 31 g ai/ha | 14 | 15 | 16 | 23 | 106 | 120 | 129 |
| Postemergence | | | | | | | |
| Barley, Spring | 25 | 15 | 15 | 0 | 10 | 10 | 5 |
| Barley, Winter | 10 | 10 | 10 | 0 | 5 | 15 | 5 |
| Blackgrass | 25 | 15 | 10 | 10 | 10 | 10 | 10 |
| Bluegrass | 20 | 10 | 20 | 20 | 10 | 10 | 10 |
| Bromegrass, Downy | 15 | 10 | 10 | 10 | 0 | 10 | 10 |
| Buckwheat, Wild | 0 | 30 | 0 | 25 | 0 | 75 | 60 |
| Canarygrass | 25 | 35 | 30 | 15 | 5 | 5 | 10 |
| Chamomile | 20 | 0 | 0 | 0 | 0 | 25 | 30 |
| Chickweed | 50 | 100 | 70 | 10 | 90 | 85 | 90 |
| Deadnettle | 25 | 75 | 25 | 30 | 30 | 90 | 75 |
| Field Poppy | 100 | 100 | 100 | 70 | 100 | 100 | 100 |
| Field Violet | 100 | 100 | 20 | 40 | 70 | 70 | 100 |
| Foxtail, Green | 10 | 30 | 30 | 15 | 10 | 15 | 35 |
| Galium | 45 | 55 | 40 | 30 | 40 | 60 | 50 |
| Kochia | 95 | 90 | 90 | 80 | 60 | 98 | 98 |
| Lambsquarters | 80 | 100 | 80 | 30 | 30 | 98 | 85 |
| Mustard, Wild | 50 | 70 | — | 40 | 80 | — | — |
| Oat, Wild | 15 | 10 | 10 | 10 | 5 | 10 | 10 |
| Oilseed Rape | 30 | 100 | 70 | 50 | 10 | 50 | 80 |
| Pigweed | 100 | 80 | 70 | 50 | 50 | 90 | 100 |
| Radish, Wild | 70 | 100 | 100 | 20 | 100 | 100 | 90 |
| Russian Thistle | 0 | 100 | 95 | 50 | 25 | 95 | 98 |
| Ryegrass, Italian | 5 | 5 | 20 | 10 | 5 | 5 | 5 |
| Speedwell | 100 | 100 | 75 | 10 | 0 | 100 | 100 |
| Wheat, Spring | 15 | 25 | 10 | 5 | 5 | 10 | 10 |
| Wheat, Winter | 5 | 10 | 10 | 5 | 5 | 5 | 5 |
| Windgrass | 30 | 10 | 10 | 5 | 10 | 15 | 20 |

| | Compounds | | | | | | | | |
|---|---|---|---|---|---|---|---|---|---|
| 31 g ai/ha | 137 | 138 | 145 | 147 | 148 | 155 | 156 | 195 | 196 |
| Postemergence | | | | | | | | | |
| Barley, Spring | 15 | 20 | 10 | 15 | 15 | 15 | 20 | 15 | 20 |
| Barley, Winter | 5 | 5 | 5 | 20 | 20 | 20 | 20 | 10 | 20 |
| Blackgrass | 30 | 50 | 20 | 25 | 15 | 50 | 15 | 25 | 65 |
| Bluegrass | 20 | 30 | 20 | 10 | 15 | 35 | 65 | 20 | 70 |
| Bromegrass, Downy | 15 | 20 | 5 | 5 | 5 | 15 | 10 | 15 | 35 |
| Buckwheat, Wild | 30 | 40 | 35 | 50 | 60 | 70 | 75 | 20 | 70 |
| Canarygrass | 20 | 25 | 35 | 35 | 30 | 70 | 30 | 10 | 70 |
| Chamomile | 10 | 10 | 10 | 60 | 70 | 70 | 70 | 20 | 70 |
| Chickweed | 50 | 60 | 60 | 70 | 70 | 70 | 75 | 40 | 85 |
| Deadnettle | 40 | 50 | 70 | 95 | 65 | 75 | 85 | 65 | 100 |
| Field Poppy | 40 | 90 | 100 | 90 | 100 | 95 | 100 | 75 | 100 |
| Field Violet | 70 | 70 | 75 | 95 | 95 | 100 | 95 | 70 | 85 |
| Foxtail, Green | 50 | 40 | 60 | 15 | 15 | 15 | 25 | 50 | 80 |
| Galium | 20 | 75 | 35 | 65 | 70 | 70 | 75 | 30 | 85 |
| Kochia | 85 | 95 | 98 | 85 | 85 | 80 | 80 | 85 | 85 |
| Lambsquarters | 75 | 80 | 90 | 75 | 85 | 95 | 90 | 75 | 90 |
| Mustard, Wild | 60 | 90 | 75 | 100 | 100 | 100 | 95 | 80 | 100 |
| Oat, Wild | 10 | 20 | 20 | 15 | 15 | 20 | 15 | 20 | 50 |
| Oilseed Rape | 90 | 95 | 50 | 60 | 35 | 100 | 100 | 85 | 100 |
| Pigweed | 90 | 95 | 95 | 70 | 85 | 75 | 90 | 65 | 95 |
| Radish, Wild | 40 | 80 | — | 100 | 100 | 95 | 85 | — | 100 |
| Russian Thistle | — | 75 | 95 | 85 | 75 | 80 | 85 | 40 | 90 |
| Ryegrass, Italian | 10 | 25 | 10 | 10 | 15 | 15 | 15 | 10 | 15 |
| Speedwell | 70 | 80 | 70 | — | — | — | — | 100 | — |
| Wheat, Spring | 5 | 5 | 10 | 15 | 10 | 20 | 15 | 10 | 25 |
| Wheat, Winter | 5 | 20 | 10 | 15 | 10 | 10 | 15 | 10 | 20 |
| Windgrass | 20 | 30 | 35 | 25 | 30 | 70 | 50 | 15 | 75 |

| | Compounds | | | | | |
|---|---|---|---|---|---|---|
| 16 g ai/ha | 15 | 16 | 23 | 106 | 120 | 129 |
| Postemergence | | | | | | |
| Barley, Spring | 10 | 5 | 0 | 5 | 5 | 5 |
| Barley, Winter | 10 | 5 | 0 | 0 | 10 | 5 |
| Blackgrass | 15 | 5 | 5 | 5 | 5 | 5 |

TABLE D-continued

| | | | | | | |
|---|---|---|---|---|---|---|
| Bluegrass | 0 | 10 | 20 | 10 | 10 | 10 |
| Bromegrass, Downy | 5 | 0 | 0 | 0 | 5 | 10 |
| Buckwheat, Wild | 0 | 0 | 20 | 0 | 50 | 60 |
| Canarygrass | 25 | 20 | 10 | 5 | 0 | 10 |
| Chamomile | 0 | 0 | 0 | 0 | 10 | 20 |
| Chickweed | 40 | 40 | 5 | 20 | 75 | 75 |
| Deadnettle | 50 | 10 | 20 | 20 | 30 | 60 |
| Field Poppy | 100 | 0 | 75 | 100 | 100 | 100 |
| Field Violet | 80 | 0 | 20 | 70 | 70 | 40 |
| Foxtail, Green | 15 | 30 | 15 | 0 | 5 | 35 |
| Galium | 50 | 20 | 25 | 20 | 50 | 40 |
| Kochia | 20 | 85 | 20 | 60 | 98 | 98 |
| Lambsquarters | 50 | 75 | 30 | 20 | 95 | 85 |
| Mustard, Wild | 0 | 10 | 20 | 20 | — | — |
| Oat, Wild | 10 | 0 | 10 | 0 | 10 | 10 |
| Oilseed Rape | 70 | 40 | 50 | 10 | 20 | 80 |
| Pigweed | 80 | 50 | 50 | 10 | 0 | 100 |
| Radish, Wild | 100 | 90 | 20 | 100 | 100 | 90 |
| Russian Thistle | 60 | 90 | 50 | 20 | 95 | 98 |
| Ryegrass, Italian | 0 | 10 | 5 | 5 | 5 | 5 |
| Speedwell | 100 | 25 | 5 | 0 | 60 | 100 |
| Wheat, Spring | 20 | 5 | 0 | 0 | 10 | 5 |
| Wheat, Winter | 5 | 5 | 0 | 5 | 5 | 5 |
| Windgrass | 5 | 0 | 0 | 5 | 5 | 15 |

| | Compounds | | | | | | | | |
|---|---|---|---|---|---|---|---|---|---|
| 16 g ai/ha | 137 | 138 | 145 | 147 | 148 | 155 | 156 | 195 | 196 |
| Postemergence | | | | | | | | | |
| Barley, Spring | 10 | 10 | 10 | 15 | 10 | 10 | 15 | 10 | 15 |
| Barley, Winter | 0 | 5 | 5 | 15 | 10 | 15 | 10 | 0 | 15 |
| Blackgrass | 10 | 30 | 20 | 15 | 10 | 5 | 10 | 20 | 15 |
| Bluegrass | 5 | 20 | 0 | 5 | 5 | 20 | 15 | 10 | 60 |
| Bromegrass, Downy | 5 | 10 | 5 | 5 | 5 | 5 | 10 | 5 | 15 |
| Buckwheat, Wild | 30 | 40 | 30 | 45 | 60 | 75 | 70 | 15 | 50 |
| Canarygrass | 10 | 10 | 30 | 15 | 10 | 20 | 15 | 10 | 30 |
| Chamomile | 0 | 0 | 0 | 45 | 60 | 60 | 50 | 20 | 60 |
| Chickweed | 40 | 60 | 75 | 60 | 60 | 65 | 60 | 30 | 70 |
| Deadnettle | 20 | 50 | 50 | 65 | 70 | 75 | 70 | 60 | 85 |
| Field Poppy | 30 | 80 | 75 | 90 | 90 | 80 | 85 | 35 | 100 |
| Field Violet | 50 | 60 | 80 | 95 | 90 | 95 | 95 | 70 | 80 |
| Foxtail, Green | 40 | 20 | 5 | 15 | 15 | 20 | 10 | 30 | 55 |
| Galium | 20 | 60 | 30 | 55 | 60 | 65 | 70 | 20 | 70 |
| Kochia | 75 | 95 | 90 | 70 | 75 | 70 | 75 | 70 | 70 |
| Lambsquarters | 40 | 70 | 25 | 75 | 85 | 95 | 85 | 60 | 85 |
| Mustard, Wild | 50 | 75 | 70 | 95 | 55 | 80 | 100 | 60 | 100 |
| Oat, Wild | 0 | 10 | 10 | 10 | 5 | 10 | 10 | 10 | 15 |
| Oilseed Rape | 70 | 85 | 50 | 25 | 30 | 85 | 100 | 70 | 80 |
| Pigweed | 90 | 90 | 70 | 75 | 70 | 70 | 85 | 60 | 85 |
| Radish, Wild | 40 | 80 | — | 85 | 90 | 85 | 65 | — | 65 |
| Russian Thistle | 30 | 50 | 40 | 45 | 65 | 70 | 60 | 15 | 80 |
| Ryegrass, Italian | 0 | 10 | 0 | 5 | 5 | 5 | 5 | 5 | 5 |
| Speedwell | 70 | 80 | 55 | — | — | — | — | 100 | — |
| Wheat, Spring | 0 | 5 | 5 | 10 | 10 | 15 | 10 | 5 | 15 |
| Wheat, Winter | 5 | 10 | 5 | 10 | 10 | 5 | 10 | 5 | 15 |
| Windgrass | 10 | 15 | 10 | 15 | 15 | 20 | 25 | 10 | 60 |

| 8 g ai/ha | Compound 145 | 8 g ai/ha | Compound 145 |
|---|---|---|---|
| Postemergence | | | |
| Barley, Spring | 5 | Galium | 5 |
| Barley, Winter | 0 | Kochia | 80 |
| Blackgrass | 5 | Lambsquarters | 10 |
| Bluegrass | 0 | Mustard, Wild | 25 |
| Bromegrass, Downy | 5 | Oat, Wild | 10 |
| Buckwheat, Wild | 15 | Oilseed Rape | 0 |
| Canarygrass | 20 | Pigweed | 20 |
| Chamomile | 0 | Russian Thistle | 10 |
| Chickweed | 40 | Ryegrass, Italian | 0 |
| Deadnettle | 0 | Speedwell | 50 |
| Field Poppy | 25 | Wheat, Spring | 5 |

TABLE D-continued

| | | | |
|---|---|---|---|
| Field Violet | 70 | Wheat, Winter | 5 |
| Foxtail, Green | 5 | Windgrass | 5 |

| | Compounds | | | | | | |
|---|---|---|---|---|---|---|---|
| 250 g ai/ha | 14 | 15 | 16 | 106 | 120 | 129 | 195 |
| Preemergence | | | | | | | |
| Barley, Spring | 20 | 15 | 5 | 0 | 20 | 20 | 30 |
| Barley, Winter | 35 | 30 | 25 | 20 | 40 | 15 | 20 |
| Blackgrass | 60 | 90 | 100 | 0 | 100 | 100 | 100 |
| Bluegrass | 100 | 100 | 100 | 0 | 100 | 100 | 80 |
| Bromegrass, Downy | 30 | 40 | 40 | 0 | 60 | 30 | 50 |
| Buckwheat, Wild | 40 | 100 | 20 | 100 | 100 | 100 | 40 |
| Canarygrass | 98 | 100 | 100 | 0 | 100 | 100 | 95 |
| Chamomile | — | — | 100 | — | 100 | 100 | 100 |
| Chickweed | 100 | 100 | — | 100 | 100 | 100 | — |
| Deadnettle | 100 | 100 | 100 | 0 | 100 | 100 | 100 |
| Field Poppy | — | — | 100 | — | 100 | 100 | 100 |
| Field Violet | 95 | — | 100 | — | 100 | 100 | — |
| Foxtail, Green | 100 | 100 | 100 | 100 | 100 | 100 | 100 |
| Galium | 100 | 100 | 20 | 80 | 100 | 100 | 80 |
| Kochia | 90 | 100 | 100 | 30 | 100 | 100 | 85 |
| Lambsquarters | 75 | 100 | 100 | 40 | 100 | 100 | 75 |
| Mustard, Wild | 95 | 100 | 100 | 60 | 100 | 100 | 100 |
| Oat, Wild | 50 | 100 | 100 | 10 | 100 | 100 | 75 |
| Oilseed Rape | 40 | 75 | 100 | 20 | 70 | 60 | 20 |
| Pigweed | 100 | 100 | 100 | 40 | 100 | 100 | 95 |
| Radish, Wild | 100 | 100 | — | 30 | 100 | 100 | — |
| Russian Thistle | 40 | 80 | 90 | 0 | 100 | 100 | 30 |
| Ryegrass, Italian | 50 | 70 | 60 | 0 | 100 | 90 | 60 |
| Speedwell | 100 | — | 100 | — | — | — | 100 |
| Wheat, Spring | 15 | 5 | 10 | 0 | 20 | 15 | 0 |
| Wheat, Winter | 20 | 5 | 0 | 0 | 10 | 10 | 10 |
| Windgrass | 85 | 100 | 100 | 80 | 100 | 100 | 100 |

| | Compounds | | | | | |
|---|---|---|---|---|---|---|
| 125 g ai/ha | 14 | 15 | 16 | 106 | 120 | 129 |
| Preemergence | | | | | | |
| Barley, Spring | 15 | 10 | 5 | 0 | 10 | 15 |
| Barley, Winter | 10 | 20 | 10 | 0 | 15 | 10 |
| Blackgrass | 10 | 80 | 70 | 0 | 100 | 100 |
| Bluegrass | 85 | 80 | 30 | 0 | 100 | 100 |
| Bromegrass, Downy | 20 | 0 | 25 | 0 | 25 | 20 |
| Buckwheat, Wild | 35 | 100 | 0 | 100 | 70 | 70 |
| Canarygrass | 90 | 90 | 90 | 0 | 100 | 100 |
| Chamomile | — | — | 70 | — | 100 | 30 |
| Chickweed | 100 | 100 | — | 100 | 100 | 100 |
| Deadnettle | 100 | 95 | 100 | 0 | 100 | 100 |
| Field Poppy | — | — | 100 | — | 100 | 100 |
| Field Violet | 95 | — | 90 | — | 100 | 100 |
| Foxtail, Green | 75 | 100 | 100 | 0 | 100 | 100 |
| Galium | 100 | 100 | 20 | 40 | 100 | 100 |
| Kochia | 80 | 70 | 90 | 30 | 95 | 100 |
| Lambsquarters | 60 | 100 | 95 | 40 | 100 | 90 |
| Mustard, Wild | 90 | 100 | 100 | 50 | 100 | 80 |
| Oat, Wild | 20 | 40 | 100 | 10 | 55 | 55 |
| Oilseed Rape | 30 | 20 | 50 | 10 | 30 | 30 |
| Pigweed | 90 | 98 | 90 | 20 | 100 | 100 |
| Radish, Wild | 100 | 100 | — | 30 | 90 | 100 |
| Russian Thistle | 10 | 80 | — | 0 | 100 | 100 |
| Ryegrass, Italian | 25 | 25 | 60 | 0 | 80 | 70 |
| Speedwell | 100 | — | 100 | — | — | — |
| Wheat, Spring | 5 | 0 | 5 | 0 | 10 | 5 |
| Wheat, Winter | 10 | 0 | 0 | 0 | 5 | 5 |
| Windgrass | 40 | 100 | 100 | 25 | 100 | 75 |

| | Compounds | | | | | |
|---|---|---|---|---|---|---|
| 125 g ai/ha | 147 | 148 | 155 | 156 | 195 | 196 |
| Preemergence | | | | | | |
| Barley, Spring | 10 | 5 | 10 | 15 | 0 | 30 |
| Barley, Winter | 15 | 5 | 10 | 15 | 0 | 40 |
| Blackgrass | 40 | 5 | 70 | 70 | 80 | 100 |

TABLE D-continued

| | | | | | | |
|---|---|---|---|---|---|---|
| Bluegrass | 35 | 50 | 85 | 100 | 50 | 100 |
| Bromegrass, Downy | 15 | 20 | 35 | 95 | 35 | 90 |
| Buckwheat, Wild | 100 | 50 | 70 | 100 | 20 | 95 |
| Canarygrass | 100 | 100 | 100 | 100 | 80 | 100 |
| Chamomile | 95 | 100 | 100 | 100 | 100 | 100 |
| Chickweed | 100 | 100 | 100 | 100 | — | 100 |
| Deadnettle | 100 | 100 | 95 | 100 | 100 | 100 |
| Field Poppy | 100 | 95 | 100 | 100 | 100 | 100 |
| Field Violet | 100 | 100 | 100 | 100 | — | 100 |
| Foxtail, Green | 100 | 100 | 100 | 100 | 100 | 100 |
| Galium | — | — | — | — | 30 | — |
| Kochia | 70 | 75 | 75 | 80 | 80 | 100 |
| Lambsquarters | 85 | 90 | 90 | 100 | 30 | 100 |
| Mustard, Wild | 95 | 95 | 100 | 100 | 100 | 100 |
| Oat, Wild | 70 | 65 | 60 | 90 | 75 | 100 |
| Oilseed Rape | 15 | 20 | 100 | 100 | 10 | 100 |
| Pigweed | 100 | 100 | 100 | 100 | 100 | 100 |
| Radish, Wild | 100 | 100 | 100 | 100 | — | 100 |
| Russian Thistle | — | — | — | — | 0 | — |
| Ryegrass, Italian | 30 | 35 | 65 | 60 | 20 | 100 |
| Speedwell | 100 | 100 | 100 | 100 | 100 | 100 |
| Wheat, Spring | 5 | 5 | 5 | 5 | 0 | 25 |
| Wheat, Winter | 5 | 10 | 5 | 5 | 0 | 15 |
| Windgrass | 100 | 90 | 100 | 100 | 100 | 100 |

| | Compounds | | | | | |
|---|---|---|---|---|---|---|
| 62 g ai/ha | 14 | 15 | 16 | 106 | 120 | 129 |
| Preemergence | | | | | | |
| Barley, Spring | 10 | 0 | 5 | 0 | 5 | 5 |
| Barley, Winter | 0 | 5 | 5 | 0 | 10 | 0 |
| Blackgrass | 0 | 25 | 40 | 0 | 98 | 30 |
| Bluegrass | 30 | 5 | 20 | 0 | 100 | 85 |
| Bromegrass, Downy | 10 | 0 | 25 | 0 | 5 | 10 |
| Buckwheat, Wild | 30 | 100 | 0 | 100 | 10 | 0 |
| Canarygrass | 25 | 80 | 50 | 0 | 100 | 100 |
| Chamomile | — | — | 25 | — | 20 | 30 |
| Chickweed | 100 | 100 | — | 100 | 90 | 100 |
| Deadnettle | 70 | 40 | 60 | 0 | 100 | 100 |
| Field Poppy | — | — | 100 | — | 80 | 70 |
| Field Violet | 90 | — | 80 | — | 95 | 100 |
| Foxtail, Green | 10 | 100 | 100 | 0 | 100 | 100 |
| Galium | 0 | 30 | — | 0 | 65 | 100 |
| Kochia | 40 | 0 | 90 | 0 | 30 | 75 |
| Lambsquarters | 40 | 90 | 80 | 40 | 90 | 90 |
| Mustard, Wild | 50 | 100 | 100 | 50 | 90 | 40 |
| Oat, Wild | 20 | 15 | 10 | 0 | 25 | 5 |
| Oilseed Rape | 0 | 10 | 50 | 10 | 10 | 10 |
| Pigweed | 70 | 70 | 80 | 0 | 100 | 90 |
| Radish, Wild | 40 | 0 | — | 30 | 20 | 10 |
| Russian Thistle | 0 | 0 | 40 | 0 | 100 | 100 |
| Ryegrass, Italian | 25 | 5 | 10 | 0 | 40 | 10 |
| Speedwell | 100 | — | 40 | — | — | — |
| Wheat, Spring | 0 | 0 | 0 | 0 | 5 | 0 |
| Wheat, Winter | 0 | 0 | 0 | 0 | 5 | 0 |
| Windgrass | 20 | 40 | 90 | 5 | 100 | 10 |

| | Compounds | | | | | |
|---|---|---|---|---|---|---|
| 62 g ai/ha | 147 | 148 | 155 | 156 | 195 | 196 |
| Preemergence | | | | | | |
| Barley, Spring | 5 | 5 | 5 | 5 | 0 | 15 |
| Barley, Winter | 5 | 5 | 5 | 10 | 0 | 15 |
| Blackgrass | 30 | 5 | 20 | 15 | 75 | 100 |
| Bluegrass | 20 | 60 | 60 | 40 | 20 | 75 |
| Bromegrass, Downy | 10 | 10 | 10 | 20 | 25 | 70 |
| Buckwheat, Wild | 30 | 65 | 50 | 65 | 20 | 70 |
| Canarygrass | 100 | 60 | 100 | 100 | 40 | 100 |
| Chamomile | 90 | 70 | 95 | 100 | 100 | 100 |
| Chickweed | 70 | 70 | 100 | 100 | — | 100 |
| Deadnettle | 100 | 100 | 80 | 100 | 60 | 100 |
| Field Poppy | 95 | 100 | 95 | 95 | 60 | 100 |
| Field Violet | 95 | 95 | 95 | 100 | — | 100 |
| Foxtail, Green | 75 | 70 | 85 | 30 | 100 | 75 |
| Galium | — | — | — | — | 10 | — |
| Kochia | 50 | 10 | 65 | 65 | 60 | 100 |

TABLE D-continued

| | | | | | | |
|---|---|---|---|---|---|---|
| Lambsquarters | 80 | 80 | 90 | 85 | 0 | 100 |
| Mustard, Wild | 100 | 55 | 100 | 95 | 40 | 100 |
| Oat, Wild | 35 | 30 | 15 | 25 | 0 | 75 |
| Oilseed Rape | 5 | 10 | 100 | 85 | 0 | 100 |
| Pigweed | 80 | 85 | 100 | 100 | 60 | 100 |
| Radish, Wild | 100 | 100 | 100 | 100 | — | 70 |
| Russian Thistle | — | — | — | — | 0 | — |
| Ryegrass, Italian | 15 | 5 | 10 | 5 | 0 | 60 |
| Speedwell | 100 | 50 | 100 | 100 | 100 | 100 |
| Wheat, Spring | 0 | 0 | 0 | 0 | 0 | 5 |
| Wheat, Winter | 0 | 0 | 5 | 0 | 0 | 10 |
| Windgrass | 100 | 35 | 85 | 85 | 75 | 100 |

| | Compounds | | | | | | | Compounds | | |
|---|---|---|---|---|---|---|---|---|---|---|
| 31 g ai/ha | 14 | 15 | 16 | 106 | 120 | 129 | 16 g ai/ha | 16 | 120 | 129 |
| Preemergence | | | | | | | | | | |
| Barley, Spring | 0 | 0 | 0 | 0 | 0 | 0 | Barley, Spring | 0 | 0 | 0 |
| Barley, Winter | 0 | 0 | 0 | 0 | 0 | 0 | Barley, Winter | 0 | 0 | 0 |
| Blackgrass | 0 | 0 | 0 | 0 | 80 | 0 | Blackgrass | 0 | 0 | 0 |
| Bluegrass | 0 | 0 | 20 | — | 100 | 0 | Bluegrass | 0 | 0 | 0 |
| Bromegrass, Downy | 0 | 0 | 20 | 0 | 0 | 10 | Bromegrass, Downy | 0 | 0 | 0 |
| Buckwheat, Wild | 0 | 0 | 0 | 50 | — | 0 | Buckwheat, Wild | 0 | — | 0 |
| Canarygrass | 10 | 25 | 40 | 0 | 90 | 15 | Canarygrass | 20 | 0 | 0 |
| Chamomile | — | — | 0 | — | 10 | 30 | Chamomile | 0 | 0 | 0 |
| Chickweed | 75 | 100 | — | 100 | 90 | 100 | Chickweed | — | 20 | 0 |
| Deadnettle | 60 | 10 | 40 | 0 | 85 | 10 | Deadnettle | 0 | 0 | 0 |
| Field Poppy | — | — | 100 | — | 80 | 75 | Field Poppy | 100 | 0 | 0 |
| Field Violet | 75 | — | 30 | — | 90 | 100 | Field Violet | 0 | 75 | 100 |
| Foxtail, Green | 0 | 70 | 100 | 0 | 100 | 90 | Foxtail, Green | 25 | 70 | 5 |
| Galium | — | — | 0 | 0 | 15 | 0 | Galium | 0 | 0 | — |
| Kochia | 10 | 0 | 30 | 0 | 10 | 25 | Kochia | 30 | 0 | 20 |
| Lambsquarters | 0 | 0 | 50 | 40 | 80 | 80 | Lambsquarters | 30 | — | 0 |
| Mustard, Wild | 0 | 100 | 0 | 20 | — | 5 | Mustard, Wild | 0 | 0 | 0 |
| Oat, Wild | 0 | — | 10 | 0 | 5 | 0 | Oat, Wild | 0 | 0 | 0 |
| Oilseed Rape | 0 | 0 | 0 | 10 | 10 | 0 | Oilseed Rape | 0 | 0 | 0 |
| Pigweed | 20 | 20 | 80 | 0 | 100 | 80 | Pigweed | 25 | 30 | 30 |
| Radish, Wild | — | 0 | — | 0 | — | 0 | Radish, Wild | — | 0 | 0 |
| Russian Thistle | 0 | 0 | 35 | 0 | 100 | 100 | Russian Thistle | 0 | 100 | 80 |
| Ryegrass, Italian | 0 | 0 | 0 | 0 | 5 | 5 | Ryegrass, Italian | 0 | 0 | 0 |
| Speedwell | 100 | — | 20 | — | — | — | Speedwell | — | 0 | — |
| Wheat, Spring | 0 | 0 | 0 | 0 | 0 | 0 | Wheat, Spring | 0 | 0 | 0 |
| Wheat, Winter | 0 | 0 | 0 | 0 | 0 | 0 | Wheat, Winter | 0 | 0 | 0 |
| Windgrass | 10 | 30 | 20 | 5 | 80 | 0 | Windgrass | 20 | 0 | 0 |

| | Compounds | | | | | |
|---|---|---|---|---|---|---|
| 31 g ai/ha | 147 | 148 | 155 | 156 | 195 | 196 |
| Preemergence | | | | | | |
| Barley, Spring | 0 | 0 | 5 | 5 | 0 | 5 |
| Barley, Winter | 0 | 0 | 0 | 5 | 0 | 10 |
| Blackgrass | 0 | 10 | 10 | 5 | 70 | 20 |
| Bluegrass | 15 | 15 | 15 | 5 | 10 | 35 |
| Bromegrass, Downy | 5 | 0 | 5 | 5 | 0 | 15 |
| Buckwheat, Wild | 10 | 30 | 25 | 50 | 0 | 45 |
| Canarygrass | 35 | 50 | 70 | 70 | 25 | 100 |
| Chamomile | 15 | 20 | 80 | 55 | 0 | 85 |
| Chickweed | 85 | 60 | 50 | 100 | — | 65 |
| Deadnettle | 10 | 45 | 5 | 15 | 60 | 40 |
| Field Poppy | 75 | 70 | 95 | 100 | 40 | 90 |
| Field Violet | 100 | 100 | 95 | 95 | — | 95 |
| Foxtail, Green | 25 | 50 | 65 | 10 | 90 | 60 |
| Galium | — | — | — | — | 0 | — |
| Kochia | 15 | 20 | 60 | 30 | 50 | 70 |
| Lambsquarters | 50 | 40 | 55 | 30 | 0 | 65 |
| Mustard, Wild | 60 | 15 | 55 | 85 | 10 | 95 |
| Oat, Wild | 15 | 20 | 50 | 10 | 0 | 30 |
| Oilseed Rape | 0 | 0 | 5 | 0 | 0 | 15 |
| Pigweed | 75 | 70 | 80 | 85 | 60 | 100 |
| Radish, Wild | 10 | 20 | 95 | 10 | — | 20 |
| Russian Thistle | — | — | — | — | 0 | — |
| Ryegrass, Italian | 5 | 5 | 0 | 5 | 0 | 10 |
| Speedwell | 20 | 95 | 100 | 100 | 100 | 100 |
| Wheat, Spring | 0 | 0 | 0 | 0 | 0 | 5 |

TABLE D-continued

| | | | | | | |
|---|---|---|---|---|---|---|
| Wheat, Winter | 0 | 5 | 0 | 0 | 0 | 5 |
| Windgrass | 60 | 10 | 10 | 10 | 40 | 100 |

| | Compounds | | | | | |
|---|---|---|---|---|---|---|
| 16 g ai/ha | 147 | 148 | 155 | 156 | 195 | 196 |
| Preemergence | | | | | | |
| Barley, Spring | 0 | 0 | 0 | 5 | 0 | 5 |
| Barley, Winter | 0 | 0 | 5 | 5 | 0 | 5 |
| Blackgrass | 0 | 0 | 5 | 0 | 0 | 10 |
| Bluegrass | 0 | 0 | 15 | 5 | 0 | 5 |
| Bromegrass, Downy | 0 | 0 | 0 | 0 | 0 | 5 |
| Buckwheat, Wild | 15 | 20 | 10 | 0 | 0 | 60 |
| Canarygrass | 5 | 0 | 10 | 15 | 0 | 40 |
| Chamomile | 25 | 10 | 5 | 10 | 0 | 55 |
| Chickweed | 35 | 25 | 35 | 50 | — | 50 |
| Deadnettle | 5 | 10 | 5 | 5 | 60 | 10 |
| Field Poppy | 55 | 10 | 80 | 85 | 30 | 95 |
| Field Violet | 75 | 90 | 90 | 60 | — | 80 |
| Foxtail, Green | 10 | 15 | 20 | 5 | 15 | 60 |
| Galium | — | — | — | — | 0 | — |
| Kochia | 15 | 10 | 30 | 10 | 40 | 35 |
| Lambsquarters | 5 | 35 | 20 | 25 | 0 | 55 |
| Mustard, Wild | 55 | 20 | 55 | 10 | 0 | 35 |
| Oat, Wild | 5 | 5 | 5 | 5 | 0 | 25 |
| Oilseed Rape | 0 | 5 | 0 | 0 | 0 | 5 |
| Pigweed | 35 | 15 | 60 | 50 | 60 | 65 |
| Radish, Wild | — | 10 | 100 | 5 | — | 50 |
| Russian Thistle | — | — | — | — | 0 | — |
| Ryegrass, Italian | 0 | 0 | 0 | 0 | 0 | 5 |
| Speedwell | 10 | 5 | 100 | 10 | 30 | 5 |
| Wheat, Spring | 0 | 0 | 0 | 0 | 0 | 0 |
| Wheat, Winter | 0 | 0 | 0 | 0 | 0 | 5 |
| Windgrass | 0 | 5 | 5 | 0 | 25 | 20 |

Test E

Seeds of plant species selected from corn (*Zea mays*), soybean (*Glycine max*), velvetleaf (*Abutilon theophrasti*), lambsquarters (*Chenopodium album*), poinsettia, wild (wild poinsettia, *Euphorbia heterophylla*), pigweed, palmer (palmer pigweed, *Amaranthus palmeri*), waterhemp (common waterhemp, *Amaranthus rudis*), smartweed (ladysthumb smartweed, *Polygonum persicaria*), surinam grass (*Brachiaria decumbens*), crabgrass, large (large crabgrass, *Digitaria sanguinalis*), crabgrass, Brazil (Brazilian crabgrass, *Digitaria horizontalis*), *panicum*, fall (fall *panicum, Panicum dichotomiflorum*), foxtail, giant (giant foxtail, *Setaria* faberii), foxtail, green (green foxtail, *Setaria viridis*), goosegrass (*Eleusine indica*), johnsongrass (*Sorghum halepense*), ragweed (common ragweed, *Ambrosia* elation), barnyardgrass (*Echinochloa crus-galli*), sandbur (southern sandbur, *Cenchrus echinatus*), arrowleaf *sida* (*Sida rhombifolia*), ryegrass, Italian (Italian ryegrass, *Lolium multiflorum*), dayflower, (VA) (Virginia dayflower, *Commelina virginica*), field bindweed (*Convolvulus arvensis*), cocklebur (common cocklebur, *Xanthium strumarium*), morningglory (*Ipomoea coccinea*), nightshade (eastern black nightshade, *Solanum* ptycanthum), *kochia* (*Kochia scoparia*), nutsedge, yellow (yellow nutsedge, *Cyperus esculentus*) and beggarticks (hairy beggarticks, *Bidens pilosa*) were planted into a silt loam soil and treated preemergence with test chemicals formulated in a non-phytotoxic solvent mixture which included a surfactant. At the same time, plants selected from these crop and weed species were planted in pots containing a growing medium comprising spaghnum peat moss, vermiculite, wetting agent and starter nutrients and treated with postemergence applications of some of the test chemicals formulated in the same manner. Plants ranged in height from 2 to 18 cm for postemergence treatments (1- to 4-leaf stage).

Treated plants and controls were maintained in a greenhouse for 14 to 21 days, after which time all species were compared to controls and visually evaluated. Plant response ratings, summarized in Table E, are based on a scale of 0 to 100 where 0 is no effect and 100 is complete control. A dash (-) response means no test result.

TABLE E

| | Compound | | Compounds | |
|---|---|---|---|---|
| 250 g ai/ha | 47 | 125 g ai/ha | 47 | 120 |
| Postemergence | | | | |
| Arrowleaf *Sida* | 85 | Arrowleaf *Sida* | 80 | 50 |
| Barnyardgrass | 60 | Barnyardgrass | 45 | 30 |
| Beggarticks | 50 | Beggarticks | 50 | 35 |
| Corn | 20 | Corn | 20 | 20 |
| Crabgrass, Brazil | 50 | Crabgrass, Brazil | 40 | 40 |
| Dayflower, VA | 30 | Dayflower, VA | 25 | 15 |

TABLE E-continued

| | | | | |
|---|---|---|---|---|
| Field Bindweed | 65 | Field Bindweed | — | 35 |
| *Panicum*, Fall | 40 | *Panicum*, Fall | 30 | 25 |
| Pigweed, Palmer | 100 | Pigweed, Palmer | 100 | 100 |
| *Poinsettia*, Wild | 100 | *Poinsettia*, Wild | 98 | 90 |
| Ryegrass, Italian | 80 | Ryegrass, Italian | 50 | 35 |
| Sandbur | 50 | Sandbur | 30 | 35 |
| Smartweed | 85 | Smartweed | 80 | 40 |
| Soybean | 75 | Soybean | 60 | 50 |
| Waterhemp | 95 | Waterhemp | 85 | 75 |

| | Compounds | | | Compounds | |
|---|---|---|---|---|---|
| 62 g ai/ha | 47 | 120 | 31 g ai/ha | 47 | 120 |
| Postemergence | | | | | |
| Arrowleaf *Sida* | 70 | 50 | Arrowleaf *Sida* | 60 | 40 |
| Barnyardgrass | 40 | 25 | Barnyardgrass | 30 | 20 |
| Beggarticks | 40 | 30 | Beggarticks | 30 | 20 |
| Corn | 20 | 20 | Corn | 15 | 10 |
| Crabgrass, Brazil | 40 | 30 | Crabgrass, Brazil | 30 | 25 |
| Dayflower, VA | 20 | 10 | Dayflower, VA | 10 | 10 |
| Field Bindweed | — | 35 | Field Bindweed | 40 | 30 |
| *Panicum*, Fall | 30 | 20 | *Panicum*, Fall | 20 | 10 |
| Pigweed, Palmer | 95 | 95 | Pigweed, Palmer | 90 | 90 |
| *Poinsettia*, Wild | 90 | 60 | *Poinsettia*, Wild | 75 | 13 |
| Ryegrass, Italian | 30 | 20 | Ryegrass, Italian | 20 | 15 |
| Sandbur | 25 | 30 | Sandbur | 25 | 20 |
| Smartweed | 50 | — | Smartweed | 40 | — |
| Soybean | 60 | 40 | Soybean | 50 | 30 |
| Waterhemp | 80 | 75 | Waterhemp | 70 | 65 |

| | Compounds | | | Compound |
|---|---|---|---|---|
| 16 g ai/ha | 47 | 120 | 8 g ai/ha | 120 |
| Postemergence | | | | |
| Arrowleaf *Sida* | 50 | 40 | Arrowleaf *Sida* | 30 |
| Barnyardgrass | 30 | 10 | Barnyardgrass | 10 |
| Beggarticks | 30 | 10 | Beggarticks | 10 |
| Corn | 10 | 10 | Corn | 10 |
| Crabgrass, Brazil | 20 | 15 | Crabgrass, Brazil | 10 |
| Dayflower, VA | 10 | 10 | Dayflower, VA | 10 |
| Field Bindweed | — | 20 | *Panicum*, Fall | 5 |
| *Panicum*, Fall | 10 | 10 | Pigweed, Palmer | 90 |
| Pigweed, Palmer | 70 | 90 | *Poinsettia*, Wild | 25 |
| *Poinsettia*, Wild | 75 | 35 | Ryegrass, Italian | 0 |
| Ryegrass, Italian | 10 | 10 | Sandbur | 10 |
| Sandbur | 20 | 10 | Smartweed | 10 |
| Smartweed | 30 | 10 | Soybean | 15 |
| Soybean | 50 | 20 | Waterhemp | 30 |
| Waterhemp | 60 | 50 | | |

| | Compounds | | | | | | Compounds | | | | |
|---|---|---|---|---|---|---|---|---|---|---|---|
| 250 g ai/ha | 14 | 15 | 23 | 47 | 120 | 250 g ai/ha | 14 | 15 | 23 | 47 | 120 |
| Preemergence | | | | | | | | | | | |
| Arrowleaf *Sida* | 80 | 60 | 35 | 95 | 50 | Morningglory | 75 | 65 | — | 65 | 60 |
| Barnyardgrass | 60 | 100 | 20 | 100 | 100 | Nightshade | 98 | 100 | 98 | 98 | 100 |
| Beggarticks | 100 | 100 | — | — | — | Nutsedge, Yellow | 15 | 0 | 15 | 35 | 25 |
| Cocklebur | — | 20 | 0 | 50 | — | *Panicum*, Fall | 100 | 100 | 100 | 100 | 100 |
| Corn | 0 | 10 | 20 | 25 | 10 | Pigweed, Palmer | 100 | 100 | 100 | 100 | 100 |
| Crabgrass, Brazil | 100 | 100 | 85 | 100 | 100 | *Poinsettia*, Wild | 75 | 80 | 35 | 100 | 50 |
| Crabgrass, Large | 100 | 100 | 100 | 100 | 100 | Ragweed | 90 | 60 | 25 | 90 | 80 |
| Dayflower, VA | 75 | 95 | 5 | — | 50 | Ryegrass, Italian | 100 | 100 | 10 | 100 | 98 |
| Field Bindweed | 75 | 95 | 70 | 100 | 98 | Sandbur | 50 | 100 | 65 | 100 | 75 |
| Foxtail, Giant | 100 | 100 | 100 | 100 | 100 | Smartweed | 80 | 100 | — | — | — |
| Foxtail, Green | 100 | 100 | 95 | 100 | 100 | Soybean | 35 | 35 | 20 | 40 | 35 |
| Goosegrass | 100 | 100 | 60 | 100 | 100 | Surinam Grass | 100 | 100 | 20 | 65 | 100 |

TABLE E-continued

| | | | | | | | | | | | |
|---|---|---|---|---|---|---|---|---|---|---|---|
| Johnsongrass | 95 | 100 | 60 | 100 | 65 | Velvetleaf | 95 | 95 | 65 | 100 | 65 |
| Kochia | 100 | 100 | 100 | 100 | 100 | Waterhemp | 100 | 100 | 100 | 100 | 100 |
| Lambsquarters | 98 | 100 | 98 | 100 | 98 | | | | | | |

| | Compounds | | | | | | |
|---|---|---|---|---|---|---|---|
| 125 g ai/ha | 14 | 15 | 16 | 23 | 47 | 120 | 129 |
| Preemergence | | | | | | | |
| Arrowleaf *Sida* | 65 | 50 | 35 | 0 | 60 | 15 | 30 |
| Barnyardgrass | 60 | 98 | 98 | 20 | 100 | 25 | 35 |
| Beggarticks | 98 | 80 | — | — | — | 80 | — |
| Cocklebur | 50 | — | 0 | 0 | 35 | 90 | 35 |
| Corn | 0 | 5 | 20 | 0 | 20 | 10 | 10 |
| Crabgrass, Brazil | 100 | 100 | 100 | 65 | 100 | 100 | 100 |
| Crabgrass, Large | 100 | 100 | 90 | 70 | 100 | 100 | 100 |
| Dayflower, VA | 70 | 60 | 85 | 5 | — | 50 | — |
| Field Bindweed | 65 | 60 | 50 | 0 | 85 | 40 | 35 |
| Foxtail, Giant | 100 | 100 | 100 | 100 | 100 | 100 | 100 |
| Foxtail, Green | 70 | 100 | 100 | 70 | 100 | 100 | 100 |
| Goosegrass | 100 | 100 | 100 | 35 | 100 | 100 | 100 |
| Johnsongrass | 90 | 98 | 98 | 20 | 40 | 35 | 25 |
| Kochia | 98 | 100 | 100 | 100 | 100 | 90 | 95 |
| Lambsquarters | 98 | 100 | 98 | 98 | 100 | 98 | 98 |
| Morningglory | 75 | 65 | — | — | 40 | 60 | 50 |
| Nightshade | 98 | 98 | 100 | 95 | 98 | 98 | 60 |
| Nutsedge, Yellow | 0 | 0 | 20 | 15 | 10 | 15 | 20 |
| *Panicum*, Fall | 100 | 100 | 100 | 100 | 100 | 100 | 100 |
| Pigweed, Palmer | 100 | 100 | 100 | 100 | 100 | 100 | 100 |
| *Poinsettia*, Wild | 65 | 75 | 98 | 35 | 65 | 35 | 25 |
| Ragweed | 80 | 30 | 30 | 0 | 50 | 35 | 20 |
| Ryegrass, Italian | 95 | 100 | 98 | 0 | 100 | 90 | 60 |
| Sandbur | 50 | 90 | 60 | 25 | — | 20 | 50 |
| Smartweed | — | 98 | — | — | — | — | — |
| Soybean | — | 35 | 20 | 0 | 40 | 35 | 25 |
| Surinam Grass | 65 | 98 | 35 | 20 | 40 | 90 | 60 |
| Velvetleaf | 80 | 65 | 80 | 65 | 75 | 50 | 25 |
| Waterhemp | 100 | 100 | 100 | 98 | 100 | 100 | 100 |

| | Compounds | | | | | | |
|---|---|---|---|---|---|---|---|
| 62 g ai/ha | 14 | 15 | 16 | 23 | 47 | 120 | 129 |
| Preemergence | | | | | | | |
| Arrowleaf *Sida* | 30 | 40 | 0 | 0 | 40 | 0 | 30 |
| Barnyardgrass | 35 | 85 | 98 | 0 | 85 | 5 | 10 |
| Beggarticks | 90 | 50 | — | — | — | — | — |
| Cocklebur | 0 | 0 | 0 | 0 | 20 | 90 | 35 |
| Corn | 0 | 0 | 20 | 0 | 20 | 5 | 10 |
| Crabgrass, Brazil | 100 | 100 | 100 | 65 | 100 | 100 | 95 |
| Crabgrass, Large | 95 | 100 | 90 | 35 | 100 | 98 | 100 |
| Dayflower, VA | 60 | 25 | 50 | 0 | — | 50 | — |
| Field Bindweed | 65 | 40 | 20 | 0 | 50 | 20 | 35 |
| Foxtail, Giant | 98 | 100 | — | 5 | 100 | 100 | 98 |
| Foxtail, Green | 50 | 90 | 100 | 5 | 100 | 100 | 100 |
| Goosegrass | 100 | 100 | 100 | 20 | — | 100 | 60 |
| Johnsongrass | 70 | 65 | 40 | 0 | 35 | 15 | 20 |
| Kochia | 90 | 90 | 100 | 60 | 100 | 50 | 95 |
| Lambsquarters | 98 | 100 | 98 | 0 | 98 | 90 | 75 |
| Morningglory | 35 | 50 | — | — | 35 | 35 | 40 |
| Nightshade | 98 | 98 | 100 | 0 | 98 | 80 | 50 |
| Nutsedge, Yellow | 0 | 0 | 20 | 0 | 10 | 0 | 0 |
| *Panicum*, Fall | 100 | 100 | 100 | 80 | 100 | 100 | 100 |
| Pigweed, Palmer | 100 | 100 | 98 | 100 | 100 | 100 | 100 |
| *Poinsettia*, Wild | 50 | 65 | 40 | 0 | 40 | 0 | 0 |
| Ragweed | 35 | — | 30 | 0 | 10 | 30 | 20 |
| Ryegrass, Italian | 85 | 80 | 50 | 0 | 70 | 35 | 40 |
| Sandbur | 15 | 50 | 50 | 0 | 90 | 5 | 20 |
| Smartweed | 80 | 98 | — | — | — | — | — |
| Soybean | 25 | 20 | 0 | 0 | 40 | 35 | 20 |
| Surinam Grass | 25 | 75 | 30 | 10 | 25 | 35 | 15 |

TABLE E-continued

| | | | | | | | |
|---|---|---|---|---|---|---|---|
| Velvetleaf | 50 | 65 | 80 | 10 | 40 | 35 | 20 |
| Waterhemp | 100 | 100 | 100 | 80 | 100 | 100 | 100 |

| | Compounds | | | | | | |
|---|---|---|---|---|---|---|---|
| 31 g ai/ha | 14 | 15 | 16 | 23 | 47 | 120 | 129 |
| Preemergence | | | | | | | |
| Arrowleaf *Sida* | 30 | 30 | 0 | 0 | 20 | 0 | 0 |
| Barnyardgrass | 15 | 50 | 50 | 0 | 30 | 0 | 5 |
| Beggarticks | 50 | 5 | — | — | — | 0 | — |
| Cocklebur | 0 | 0 | 0 | 0 | 10 | 0 | 0 |
| Corn | 0 | 0 | 0 | 0 | 15 | — | 0 |
| Crabgrass, Brazil | 75 | 98 | 95 | 0 | 80 | 100 | 60 |
| Crabgrass, Large | 75 | 90 | 5 | 5 | 75 | 95 | 80 |
| Dayflower, VA | 50 | 10 | 35 | 0 | — | 0 | — |
| Field Bindweed | 20 | 5 | 0 | 0 | 25 | 10 | 0 |
| Foxtail, Giant | 75 | 98 | 100 | 5 | 100 | 100 | 75 |
| Foxtail, Green | 35 | — | 90 | 0 | 100 | 85 | 100 |
| Goosegrass | 100 | 100 | 98 | — | 100 | 100 | 50 |
| Johnsongrass | 20 | 65 | 20 | 0 | 30 | 15 | 20 |
| Kochia | 50 | 65 | 70 | 0 | 35 | 20 | 50 |
| Lambsquarters | 98 | 100 | 75 | 0 | 95 | 50 | 0 |
| Morningglory | 20 | 50 | — | — | 30 | 30 | 0 |
| Nightshade | 60 | 35 | 50 | 0 | 75 | 0 | 0 |
| Nutsedge, Yellow | 0 | 0 | 0 | 0 | 0 | 0 | 0 |
| *Panicum*, Fall | 80 | 98 | 100 | 15 | 100 | 95 | 98 |
| Pigweed, Palmer | 100 | 100 | 98 | 90 | 100 | 100 | 100 |
| *Poinsettia*, Wild | 25 | 30 | 20 | 0 | 25 | 0 | 0 |
| Ragweed | 20 | 5 | 0 | 0 | 0 | 0 | 5 |
| Ryegrass, Italian | 40 | 75 | 30 | 0 | 40 | 35 | 25 |
| Sandbur | 5 | 25 | 10 | 0 | 20 | 5 | 20 |
| Smartweed | 25 | 60 | — | — | — | — | — |
| Soybean | 10 | 0 | 0 | 0 | 40 | 25 | 15 |
| Surinam Grass | 10 | 50 | 0 | 0 | 20 | 35 | 15 |
| Velvetleaf | 35 | 30 | 30 | 0 | 40 | 30 | 0 |
| Waterhemp | 98 | 100 | 100 | 80 | 100 | 98 | 80 |

| | Compounds | | | | | | |
|---|---|---|---|---|---|---|---|
| 16 g ai/ha | 14 | 15 | 16 | 23 | 47 | 120 | 129 |
| Preemergence | | | | | | | |
| Arrowleaf *Sida* | 10 | — | 0 | 0 | 0 | 0 | 0 |
| Barnyardgrass | 5 | 10 | 10 | 0 | 5 | 0 | 0 |
| Beggarticks | 5 | 5 | — | — | — | 0 | — |
| Cocklebur | 0 | — | 0 | 0 | 0 | 0 | 0 |
| Corn | 0 | 0 | 0 | 0 | 0 | 0 | 0 |
| Crabgrass, Brazil | 60 | 60 | 70 | 0 | 35 | 90 | 15 |
| Crabgrass, Large | 65 | 15 | 5 | 5 | 20 | 75 | 10 |
| Dayflower, VA | 10 | 5 | 0 | 0 | — | 0 | — |
| Field Bindweed | 5 | 5 | 0 | 0 | 25 | 0 | 0 |
| Foxtail, Giant | 50 | 65 | 80 | 0 | 90 | 85 | 20 |
| Foxtail, Green | 25 | 20 | 90 | 0 | 85 | 15 | 60 |
| Goosegrass | 65 | 75 | 40 | 0 | 100 | 95 | 40 |
| Johnsongrass | 10 | 10 | 15 | 0 | 25 | 15 | 20 |
| Kochia | 20 | 35 | 20 | 0 | 25 | 0 | 35 |
| Lambsquarters | 80 | 90 | 0 | — | 95 | 0 | 0 |
| Morningglory | 0 | 10 | — | — | 15 | 0 | 0 |
| Nightshade | 35 | 5 | 0 | 0 | — | 0 | 0 |
| Nutsedge, Yellow | 0 | 0 | 0 | 0 | 0 | 0 | 0 |
| *Panicum*, Fall | 65 | 98 | 70 | 0 | 100 | 95 | 35 |
| Pigweed, Palmer | 75 | 100 | 98 | 90 | 100 | 65 | 80 |
| *Poinsettia*, Wild | 15 | 30 | 0 | 0 | 0 | 0 | 0 |
| Ragweed | 0 | 0 | 0 | 0 | 0 | 0 | 0 |
| Ryegrass, Italian | 0 | 20 | 0 | 0 | 20 | 0 | 25 |
| Sandbur | 5 | 5 | 0 | 0 | 0 | 5 | 0 |
| Soybean | 0 | 0 | 0 | 0 | 0 | 0 | 15 |
| Surinam Grass | 5 | 5 | 0 | 0 | 15 | 0 | 0 |
| Velvetleaf | 20 | 20 | 20 | 0 | 30 | 15 | 0 |
| Waterhemp | 90 | 98 | 70 | 0 | 100 | 95 | 35 |

| | Compounds | |
|---|---|---|
| 8 g ai/ha | 16 | 129 |
| Preemergence | | |
| Arrowleaf *Sida* | 0 | 0 |
| Barnyardgrass | 0 | 0 |
| Cocklebur | — | 0 |
| Corn | 0 | 0 |
| Crabgrass, Brazil | 30 | 10 |
| Crabgrass, Large | 0 | 0 |
| Dayflower, VA | 0 | — |
| Field Bindweed | 0 | 0 |
| Foxtail, Giant | 5 | 0 |
| Foxtail, Green | 60 | 0 |
| Goosegrass | 40 | 40 |
| Johnsongrass | 0 | 0 |
| Kochia | 0 | 35 |
| Lambsquarters | 0 | 0 |
| Morningglory | — | 0 |
| Nightshade | 0 | 0 |
| Nutsedge, Yellow | 0 | 0 |
| *Panicum*, Fall | 0 | 0 |
| Pigweed, Palmer | 95 | 30 |
| *Poinsettia*, Wild | 0 | 0 |
| Ragweed | 0 | 0 |
| Ryegrass, Italian | 0 | 0 |
| Sandbur | 0 | 0 |
| Soybean | 0 | 0 |
| Surinam Grass | 0 | 0 |
| Velvetleaf | 0 | 0 |
| Waterhemp | 60 | 20 |

Test F

Seeds of plant species selected from corn (*Zea mays*), soybean (*Glycine max*), velvetleaf (*Abutilon theophrasti*), lambsquarters (*Chenopodium album*), poinsettia, wild (wild poinsettia, *Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, Brazil (Brazilian crabgrass, *Digitaria horizontalis*), *panicum*, fall (fall *panicum Panicum dichotomiflorum*), crabgrass, large (large crabgrass, *Digitaria sanguinalis*), foxtail, giant (giant foxtail, *Setaria faberii*), foxtail, green (green foxtail *Setaria viridis*), goosegrass (*Eleusine indica*), ragweed (common ragweed, *Ambrosia elatior*), barnyardgrass (*Echinochloa crus-galli*), sandbur (southern sandbur, *Cenchrus echinatus*), arrowleaf *sida* (*Sida rhombifolia*), ryegrass, Italian (Italian ryegrass, *Lolium multiflorum*), dayflower, VA (Virginia (VA) dayflower, *Commelina virginica*), field bindweed (*Convolvulus arvensis*), cocklebur (common cocklebur, *Xanthium strumarium*), morningglory (*Ipomoea coccinea*), nightshade (eastern black nightshade, *Solanum ptycanthum*), *kochia* (*Kochia scoparia*), nutsedge, yellow (yellow nutsedge, *Cyperus esculentus*), johnsongrass (*Sorghum halepense*), smartweed (ladysthumb smartweed, *Polygonum persicaria*), and beggarticks (hairy beggarticks, *Bidens pilosa*), were planted into a silt loam soil and treated preemergence with test chemicals formulated in a non-phytotoxic solvent mixture which included a surfactant. At the same time, plants selected from these crop and weed species and also pigweed (*Amaranthus retroflexus*), waterhemp_RES1 (ALS/Triazine resistant common waterhemp, *Amaranthus rudis*) and waterhemp_RES2 (ALS/HPPD resistant common waterhemp, *Amaranthus rudis*) were planted in pots containing a planting medium comprising spaghnum peat moss, vermiculite, wetting agent and starter nutrients treated with postemergence applications of some of the test chemicals formulated in the same manner. Plants ranged in height from 2 to 18 cm for postemergence treatments (1- to 4-leaf stage).

Treated plants and controls were maintained in a greenhouse for 14 to 21 days, after which time all species were compared to controls and visually evaluated. Plant response ratings, summarized in Table E, are based on a scale of 0 to 100 where 0 is no effect and 100 is complete control. A dash (-) response means no test result.

TABLE F

| | Compounds | |
|---|---|---|
| 250 g ai/ha | 169 | 172 |
| Postemergence | | |
| Arrowleaf *Sida* | 50 | 100 |
| Barnyardgrass | 40 | 85 |
| Beggarticks | 40 | 60 |
| Corn | 10 | 30 |
| Crabgrass, Brazil | 30 | 90 |
| Dayflower, VA | 20 | 50 |
| Field Bindweed | 55 | 60 |
| *Panicum*, Fall | 30 | 50 |
| Pigweed, Palmer | 100 | 100 |
| *Poinsettia*, Wild | 85 | 100 |
| Ryegrass, Italian | 30 | 50 |
| Sandbur | 25 | 40 |
| Smartweed | 35 | 70 |
| Soybean | 50 | 90 |
| Waterhemp | 100 | 100 |
| Waterhemp, Res2 | 100 | — |
| Waterhemp, Res1 | 95 | 95 |

| | Compounds | | | | |
|---|---|---|---|---|---|
| 125 g ai/ha | 141 | 145 | 169 | 172 | 196 |
| Postemergence | | | | | |
| Arrowleaf *Sida* | 75 | 70 | 30 | 90 | 95 |
| Barnyardgrass | 40 | 40 | 25 | 50 | 90 |
| Beggarticks | 75 | 45 | 30 | 50 | 70 |
| Corn | 30 | 10 | 10 | 20 | 25 |
| Crabgrass, Brazil | 95 | 50 | 20 | 70 | 95 |
| Dayflower, VA | 75 | 70 | 10 | 30 | 70 |
| Field Bindweed | 85 | 75 | 35 | 60 | 75 |
| *Panicum*, Fall | 75 | 40 | 25 | 50 | 85 |
| Pigweed | 95 | — | — | — | 95 |
| Pigweed, Palmer | 100 | 90 | 100 | 100 | 100 |
| *Poinsettia*, Wild | 98 | — | 70 | 100 | 95 |
| Ryegrass, Italian | 40 | 40 | 20 | 40 | 80 |
| Sandbur | 35 | 35 | 20 | 30 | 50 |
| Smartweed | — | — | 25 | 60 | — |
| Soybean | 85 | 60 | 40 | 75 | 80 |
| Waterhemp | — | 95 | 100 | 100 | — |
| Waterhemp, Res2 | 100 | 85 | 100 | — | 95 |
| Waterhemp, Res1 | 95 | 90 | 95 | 95 | 100 |

| | Compounds | | | | |
|---|---|---|---|---|---|
| 62 g ai/ha | 141 | 145 | 162 | 169 | 196 |
| Postemergence | | | | | |
| Arrowleaf *Sida* | 70 | 60 | 60 | 20 | 95 |
| Barnyardgrass | 30 | 30 | 35 | 15 | 60 |
| Beggarticks | 60 | 35 | 30 | 25 | 60 |
| Corn | 20 | 10 | 10 | 10 | 20 |
| Crabgrass, Brazil | 95 | 40 | 30 | 20 | 95 |
| Dayflower, VA | 60 | 60 | 25 | 10 | 60 |
| Field Bindweed | 80 | 70 | 50 | 30 | 75 |
| *Panicum*, Fall | 60 | 40 | 30 | 20 | 85 |
| Pigweed | 95 | — | — | — | 95 |
| Pigweed, Palmer | 100 | 85 | 90 | 90 | 100 |
| *Poinsettia*, Wild | 95 | — | 80 | 60 | 95 |
| Ryegrass, Italian | 25 | 30 | 0 | 20 | 70 |
| Sandbur | 30 | 35 | 20 | 20 | 30 |
| Smartweed | — | — | 15 | 15 | — |
| Soybean | — | 50 | 55 | 30 | 70 |
| Waterhemp | — | 95 | 95 | 90 | — |
| Waterhemp, Res2 | 95 | — | 100 | 95 | 95 |
| Waterhemp, Res1 | 95 | — | 95 | 90 | 95 |

| | Compounds | | | | | |
|---|---|---|---|---|---|---|
| 31 g ai/ha | 141 | 145 | 162 | 169 | 172 | 196 |
| Postemergence | | | | | | |
| Arrowleaf *Sida* | 60 | 50 | 35 | 20 | 65 | 90 |
| Barnyardgrass | 20 | 30 | 25 | 0 | 20 | 60 |
| Beggarticks | 50 | 30 | 25 | 25 | 40 | 60 |
| Corn | 20 | 10 | 10 | 5 | 15 | 20 |

TABLE F-continued

| | | | | | | |
|---|---|---|---|---|---|---|
| Crabgrass, Brazil | 95 | 40 | 20 | 20 | 50 | 85 |
| Dayflower, VA | 35 | 50 | 20 | 10 | 20 | 60 |
| Field Bindweed | 70 | — | 30 | 20 | 25 | 70 |
| *Panicum*, Fall | 50 | 40 | 25 | 15 | 20 | 80 |
| Pigweed | 95 | — | — | — | — | 95 |
| Pigweed, Palmer | 95 | — | 90 | 50 | 100 | 100 |
| *Poinsettia*, Wild | 85 | — | 75 | 60 | 80 | 95 |
| Ryegrass, Italian | 15 | 20 | 0 | 0 | 20 | 40 |
| Sandbur | 20 | 30 | 20 | 15 | 20 | 20 |
| Smartweed | — | — | 15 | 10 | 30 | — |
| Soybean | 80 | 40 | 45 | 20 | 50 | 65 |
| Waterhemp | — | 95 | 95 | 90 | 95 | — |
| Waterhemp, Res2 | 95 | — | 95 | 85 | — | 95 |
| Waterhemp, Res1 | 95 | — | 95 | 90 | 70 | 95 |

| | Compounds | | | | | | Compounds | | | | |
|---|---|---|---|---|---|---|---|---|---|---|---|
| 16 g ai/ha | 141 | 145 | 162 | 169 | 196 | 16 g ai/ha | 141 | 145 | 162 | 169 | 196 |
| Postemergence | | | | | | | | | | | |
| Arrowleaf *Sida* | 50 | 40 | 30 | 20 | 90 | Pigweed, Palmer | 95 | 70 | 80 | 50 | 100 |
| Barnyardgrass | 20 | 20 | 10 | 0 | 40 | *Poinsettia*, Wild | 80 | — | 60 | 50 | 85 |
| Beggarticks | 40 | 25 | 25 | 25 | 60 | Ryegrass, Italian | 10 | 10 | 0 | 0 | 20 |
| Corn | 15 | 10 | 10 | 5 | 15 | Sandbur | 10 | 20 | 15 | 15 | 20 |
| Crabgrass, Brazil | 80 | 25 | 15 | 20 | 75 | Smartweed | — | — | 10 | 10 | — |
| Dayflower, VA | 10 | 20 | 20 | 10 | 50 | Soybean | 70 | 35 | 30 | 20 | 60 |
| Field Bindweed | 60 | 60 | 20 | 20 | 60 | Waterhemp | — | 90 | 90 | 75 | — |
| *Panicum*, Fall | 50 | 25 | 20 | 10 | 40 | Waterhemp, Res2 | 95 | — | 90 | 75 | 90 |
| Pigweed | 95 | — | — | — | 95 | Waterhemp, Res1 | 95 | — | 90 | 85 | 95 |

| | Compounds | | | | | Compound |
|---|---|---|---|---|---|---|
| 8 g ai/ha | 141 | 145 | 162 | 196 | 4 g ai/ha | 162 |
| Postemergence | | | | | | |
| Arrowleaf *Sida* | 40 | 30 | 25 | 80 | Arrowleaf *Sida* | 10 |
| Barnyardgrass | 10 | 20 | 10 | 30 | Barnyardgrass | 10 |
| Beggarticks | 40 | 10 | 20 | 50 | Beggarticks | 15 |
| Corn | 15 | 5 | 5 | 15 | Corn | 5 |
| Crabgrass, Brazil | 70 | 15 | 15 | 60 | Crabgrass, Brazil | 15 |
| Dayflower, VA | 10 | 15 | 15 | 30 | Dayflower, VA | 5 |
| Field Bindweed | 50 | 50 | 20 | 50 | Field Bindweed | 20 |
| *Panicum*, Fall | 30 | 10 | 20 | 20 | *Panicum*, Fall | 15 |
| Pigweed | 90 | — | — | 85 | Pigweed, Palmer | 70 |
| Pigweed, Palmer | 95 | 40 | 70 | 95 | *Poinsettia*, Wild | 15 |
| *Poinsettia*, Wild | 60 | — | 30 | 75 | Ryegrass, Italian | 0 |
| Ryegrass, Italian | 10 | 5 | 0 | 15 | Sandbur | 10 |
| Sandbur | 10 | 10 | 10 | 10 | Smartweed | 10 |
| Smartweed | — | — | 10 | — | Soybean | 20 |
| Soybean | 50 | 25 | 30 | 50 | Waterhemp | 80 |
| Waterhemp | — | 90 | 90 | — | Waterhemp, Res2 | 75 |
| Waterhemp, Res2 | 85 | — | 90 | 90 | Waterhemp, Res1 | 70 |
| Waterhemp, Res1 | 90 | — | 90 | 95 | | |

| | Compounds | | | | | | | | | |
|---|---|---|---|---|---|---|---|---|---|---|
| 250 g ai/ha | 139 | 146 | 148 | 153 | 154 | 155 | 169 | 171 | 172 | 174 |
| Preemergence | | | | | | | | | | |
| Arrowleaf *Sida* | 0 | 10 | 0 | 65 | 0 | 75 | 5 | 60 | 100 | 25 |
| Barnyardgrass | 98 | 20 | 98 | 100 | 100 | 100 | 95 | 100 | 100 | 100 |
| Beggarticks | 0 | 0 | 0 | — | 15 | 80 | 5 | 0 | 25 | 0 |
| Cocklebur | — | — | — | — | 0 | 40 | — | — | 5 | 0 |
| Corn | 5 | 0 | 5 | 10 | 5 | 15 | 0 | 5 | 15 | 0 |
| Crabgrass, Brazil | — | — | 100 | 100 | 100 | 100 | 100 | 100 | 100 | 100 |
| Crabgrass, Large | 100 | 100 | 100 | 100 | 100 | 100 | 100 | 100 | 100 | 100 |
| Dayflower, VA | 65 | 35 | 90 | 95 | 90 | 60 | 75 | 30 | 90 | 5 |
| Field Bindweed | 20 | 25 | 50 | 100 | 95 | 100 | 80 | 5 | 95 | 5 |
| Foxtail, Giant | 100 | 100 | 100 | 100 | 100 | 100 | 100 | 100 | 100 | 100 |
| Foxtail, Green | 100 | 100 | 100 | 100 | 100 | 100 | 100 | 100 | 100 | 100 |
| Goosegrass | 100 | 98 | 100 | 100 | 100 | 100 | 100 | 100 | 100 | 100 |
| Johnsongrass | 100 | 100 | 40 | 100 | 98 | 100 | 80 | 75 | 100 | 70 |
| Kochia | 98 | 98 | 98 | 100 | 98 | 100 | 98 | 98 | 100 | 98 |
| Lambsquarters | 98 | 98 | 100 | 98 | 98 | 98 | 100 | 98 | 98 | 98 |
| Morningglory | 20 | 25 | 70 | 65 | — | — | 40 | 65 | 5 | 20 |
| Nightshade | 100 | 100 | 98 | 100 | 100 | 100 | 100 | 5 | 100 | 35 |
| Nutsedge, Yellow | 0 | 0 | 35 | 10 | 0 | 30 | 25 | 0 | 25 | 35 |

TABLE F-continued

| | | | | | | | | | | |
|---|---|---|---|---|---|---|---|---|---|---|
| *Panicum*, Fall | 100 | 100 | 100 | 100 | 100 | 100 | 100 | 100 | 100 | 100 |
| Pigweed, Palmer | — | 100 | 100 | 100 | 100 | 100 | 100 | 100 | 100 | 100 |
| *Poinsettia*, Wild | 80 | 40 | 100 | 98 | 85 | 100 | 98 | 10 | 98 | 30 |
| Ragweed | 0 | 25 | 75 | 80 | 40 | 80 | 100 | — | — | — |
| Ryegrass, Italian | 95 | 25 | 100 | 95 | 100 | 95 | 100 | 50 | 100 | 80 |
| Sandbur | 40 | 70 | 100 | 100 | 100 | 100 | 75 | 50 | 100 | 70 |
| Smartweed | — | — | 90 | — | — | — | 95 | 5 | 98 | 50 |
| Soybean | 35 | 0 | 40 | 25 | 25 | 30 | 20 | 20 | 20 | 0 |
| Surinam Grass | 75 | 35 | 98 | 98 | 90 | 90 | 100 | 30 | 98 | 50 |
| Velvetleaf | 65 | 25 | 65 | 100 | 100 | 98 | 100 | 50 | 100 | 35 |
| Waterhemp | 100 | 100 | 100 | 100 | 100 | 100 | 100 | 100 | 100 | 100 |

| | Compounds | | | | | | | | | | | |
|---|---|---|---|---|---|---|---|---|---|---|---|---|
| 125 g ai/ha | 139 | 142 | 146 | 148 | 153 | 154 | 155 | 169 | 171 | 172 | 174 | 196 |
| Preemergence | | | | | | | | | | | | |
| Arrowleaf *Sida* | 0 | 35 | 0 | 0 | 25 | 0 | 40 | 5 | 30 | 95 | 25 | 15 |
| Barnyardgrass | 10 | 80 | 10 | 20 | 75 | 90 | 30 | 60 | 80 | 100 | 35 | 100 |
| Beggarticks | 0 | 75 | 0 | 0 | 65 | 0 | 70 | 5 | 0 | 25 | 0 | 65 |
| Cocklebur | 0 | — | — | 0 | — | — | 40 | — | — | — | — | 0 |
| Corn | 0 | 0 | 0 | 0 | 0 | 5 | 15 | 0 | 0 | 15 | 0 | 30 |
| Crabgrass, Brazil | — | — | — | 100 | 100 | 100 | 100 | 100 | 100 | 100 | 100 | — |
| Crabgrass, Large | 100 | 100 | 98 | 100 | 100 | 100 | 100 | 100 | 100 | 100 | 95 | 100 |
| Dayflower, VA | 60 | 70 | 35 | 65 | 80 | 70 | 35 | 65 | 30 | 70 | 5 | 65 |
| Field Bindweed | 0 | 98 | 0 | 20 | 100 | 35 | 95 | 20 | 5 | 95 | 5 | 65 |
| Foxtail, Giant | 98 | 100 | 98 | 100 | 100 | 100 | 100 | 100 | 100 | 100 | 90 | 100 |
| Foxtail, Green | 100 | 100 | 100 | 100 | 100 | 100 | 100 | 100 | 100 | 100 | 95 | 100 |
| Goosegrass | 98 | 100 | 75 | 100 | 100 | 100 | 100 | 100 | 100 | 100 | — | 100 |
| Johnsongrass | 98 | 30 | 70 | 30 | 100 | 50 | 90 | 50 | 65 | 75 | 30 | 98 |
| Kochia | 90 | 95 | 50 | 95 | 100 | 95 | 98 | 98 | 15 | 100 | 10 | 100 |
| Lambsquarters | 90 | 98 | 98 | 100 | 98 | 98 | 98 | 98 | 65 | 98 | 65 | 98 |
| Morningglory | 5 | 35 | 0 | 50 | 65 | — | — | 40 | 35 | 5 | 0 | 70 |
| Nightshade | 100 | 98 | 65 | 98 | 100 | 90 | 100 | 100 | 5 | 100 | — | 100 |
| Nutsedge, Yellow | 0 | 0 | 0 | 20 | 10 | 0 | 25 | 25 | 0 | 25 | 20 | 75 |
| *Panicum*, Fall | 100 | 100 | 100 | 100 | 100 | 100 | 100 | 100 | 100 | 100 | 100 | 100 |
| Pigweed, Palmer | — | — | 100 | 100 | 100 | 100 | 100 | 100 | 100 | 100 | 98 | — |
| *Poinsettia*, Wild | 75 | 70 | 40 | 20 | 70 | 25 | 80 | 40 | 10 | 50 | 20 | 75 |
| Ragweed | 0 | 40 | 0 | 75 | 20 | 0 | 50 | 60 | — | — | — | 50 |
| Ryegrass, Italian | 30 | 100 | 20 | 95 | 65 | 70 | 85 | 100 | 25 | 100 | 50 | 100 |
| Sandbur | 35 | 70 | 25 | 70 | 95 | 98 | 100 | 65 | 50 | 70 | 5 | 98 |
| Smartweed | — | — | — | 75 | — | — | — | 40 | 0 | 50 | 0 | — |
| Soybean | 0 | 25 | 0 | 20 | 5 | 25 | 30 | — | 0 | 20 | 0 | 35 |
| Surinam Grass | 75 | 60 | 20 | 98 | 75 | 70 | 90 | 75 | 10 | 35 | 5 | 100 |
| Velvetleaf | 0 | 75 | 0 | 25 | 98 | 40 | 98 | 60 | 15 | 80 | 15 | 95 |
| Waterhemp | 100 | 100 | 100 | 100 | 100 | 100 | 100 | 100 | 100 | 100 | 98 | 100 |

| | Compounds | | | | | | | | | | | |
|---|---|---|---|---|---|---|---|---|---|---|---|---|
| 62 g ai/ha | 139 | 142 | 146 | 148 | 153 | 154 | 155 | 162 | 169 | 171 | 174 | 196 |
| Preemergence | | | | | | | | | | | | |
| Arrowleaf *Sida* | 0 | 30 | 0 | 0 | 25 | 0 | 10 | 0 | 0 | 15 | 0 | 15 |
| Barnyardgrass | 10 | 30 | 10 | 0 | 10 | 85 | 30 | 30 | 20 | 5 | 5 | 70 |
| Beggarticks | 0 | 65 | 0 | 0 | 35 | 0 | 40 | 0 | 0 | 0 | 0 | 50 |
| Cocklebur | 0 | 0 | — | — | 0 | 0 | 0 | 0 | 0 | 0 | — | 0 |
| Corn | 0 | 0 | 0 | 0 | 0 | 0 | 10 | 0 | 0 | 0 | 0 | 5 |
| Crabgrass, Brazil | — | — | — | 100 | 100 | 100 | 100 | 100 | 100 | 100 | 100 | — |
| Crabgrass, Large | 95 | 98 | 98 | 100 | 100 | 100 | 100 | 100 | 100 | 98 | 95 | 100 |
| Dayflower, VA | 30 | 50 | 10 | 40 | 40 | 25 | 20 | 65 | 10 | 0 | 0 | 50 |
| Field Bindweed | 0 | 75 | 0 | 0 | 65 | 5 | 85 | 5 | — | 0 | 0 | — |
| Foxtail, Giant | 85 | 100 | 90 | 100 | 100 | 100 | 98 | 100 | 100 | 100 | 70 | 98 |
| Foxtail, Green | 98 | 98 | 50 | 100 | 100 | 100 | 100 | 100 | 100 | 95 | 75 | 100 |
| Goosegrass | 80 | 100 | 70 | 100 | 98 | 95 | 100 | 100 | 100 | 100 | 98 | 100 |
| Johnsongrass | 90 | — | 60 | 20 | 50 | 25 | 90 | 20 | 20 | 10 | 30 | 95 |
| Kochia | 35 | 85 | 30 | 90 | 95 | 85 | 70 | 98 | 95 | 5 | 0 | 100 |
| Lambsquarters | 65 | 98 | 40 | 98 | 98 | 75 | 98 | 98 | 98 | 35 | 0 | 95 |
| Morningglory | 0 | 25 | 0 | 30 | 30 | — | — | 30 | 30 | 5 | 0 | 70 |
| Nightshade | 75 | 98 | 65 | 0 | 100 | 10 | 98 | 95 | 100 | 5 | 0 | 100 |
| Nutsedge, Yellow | 0 | 0 | 0 | 0 | 0 | 0 | 10 | 35 | — | 0 | 0 | 10 |
| *Panicum*, Fall | 100 | 100 | 90 | 100 | 100 | 100 | 100 | 100 | 100 | 100 | 85 | 100 |
| Pigweed, Palmer | — | — | 100 | 100 | 100 | 100 | 100 | 100 | 100 | 95 | 75 | — |
| *Poinsettia*, Wild | 35 | 35 | 20 | 0 | 40 | 25 | 40 | 10 | 30 | 0 | 0 | 65 |
| Ragweed | 0 | 30 | 0 | 0 | 5 | 0 | 5 | 95 | 5 | — | — | 50 |
| Ryegrass, Italian | 30 | 70 | 15 | 65 | 20 | 10 | 75 | 95 | 5 | 0 | 0 | 75 |
| Sandbur | 5 | 50 | 10 | 15 | 40 | 80 | 95 | 50 | 20 | 10 | 5 | 90 |
| Smartweed | — | — | — | 0 | — | — | — | 95 | 40 | 0 | 0 | — |
| Soybean | 0 | 0 | 0 | 20 | 0 | 20 | 30 | 25 | 20 | 0 | 0 | 20 |

TABLE F-continued

| | | | | | | | | | | | | |
|---|---|---|---|---|---|---|---|---|---|---|---|---|
| Surinam Grass | 5 | 5 | 0 | 75 | 10 | 50 | 70 | 30 | 70 | 5 | 5 | 25 |
| Velvetleaf | 0 | 65 | 0 | 0 | 65 | 30 | 60 | 35 | 0 | 0 | 0 | 75 |
| Waterhemp | 100 | 100 | 98 | 100 | 100 | 98 | 100 | 100 | 98 | — | 98 | 100 |

| | Compounds | | | | | | | | | | | |
|---|---|---|---|---|---|---|---|---|---|---|---|---|
| 31 g ai/ha | 139 | 142 | 146 | 148 | 153 | 154 | 162 | 169 | 171 | 172 | 174 | 196 |
| Preemergence | | | | | | | | | | | | |
| Arrowleaf *Sida* | 0 | 30 | 0 | 0 | 5 | 0 | 0 | 0 | 0 | 30 | 0 | 15 |
| Barnyardgrass | 10 | 5 | 0 | 0 | 10 | 5 | 30 | 0 | 5 | 70 | 0 | 40 |
| Beggarticks | 0 | 40 | 0 | 0 | 25 | 0 | 0 | 0 | 0 | 15 | 0 | 50 |
| Cocklebur | — | 0 | — | 0 | — | — | 0 | 0 | 0 | — | — | 0 |
| Corn | 0 | 0 | 0 | 0 | 0 | 0 | 0 | 0 | 0 | 0 | 0 | 0 |
| Crabgrass, Brazil | — | — | — | 100 | 100 | 100 | 100 | 100 | 98 | 100 | 80 | — |
| Crabgrass, Large | 95 | 20 | 75 | 100 | 95 | 98 | 95 | 98 | 98 | 100 | 85 | 100 |
| Dayflower, VA | 5 | 5 | 0 | 40 | 10 | 0 | 35 | 5 | 0 | 40 | 0 | 35 |
| Field Bindweed | 0 | 50 | 0 | 0 | 65 | 0 | 5 | 0 | 0 | 5 | 0 | 25 |
| Foxtail, Giant | 40 | 75 | 20 | 95 | 85 | 65 | 100 | 100 | 60 | 100 | 5 | 98 |
| Foxtail, Green | 35 | 75 | 20 | 100 | 75 | 75 | 100 | 100 | 50 | 75 | 50 | 85 |
| Goosegrass | 70 | 70 | 40 | 98 | 95 | 95 | 100 | 95 | 80 | 98 | 50 | 75 |
| Johnsongrass | 75 | 5 | 50 | 20 | 10 | 20 | 20 | 0 | 0 | 50 | 0 | 65 |
| Kochia | 0 | 80 | 5 | 90 | 75 | 25 | 70 | 95 | 0 | 20 | 0 | 10 |
| Lambsquarters | 20 | 65 | 0 | 50 | 65 | 30 | 98 | 30 | 0 | 50 | 0 | 80 |
| Morningglory | 0 | 0 | 0 | 30 | 30 | — | 30 | 0 | 0 | 0 | 0 | 30 |
| Nightshade | 35 | 80 | 10 | 0 | 50 | 10 | — | 80 | 0 | 5 | 0 | 95 |
| Nutsedge, Yellow | 0 | 0 | 0 | 0 | 0 | 0 | 35 | 20 | 0 | 25 | 0 | 0 |
| *Panicum*, Fall | 25 | 65 | 5 | 85 | 100 | 90 | 100 | 100 | 65 | 75 | 65 | 98 |
| Pigweed, Palmer | — | — | 100 | 90 | 100 | 100 | 100 | 100 | 0 | 100 | 0 | — |
| *Poinsettia*, Wild | 20 | 10 | 20 | 0 | 25 | 0 | 10 | 0 | 0 | 20 | 0 | 50 |
| Ragweed | 0 | 0 | 0 | 0 | 5 | 0 | 70 | 0 | — | — | — | 0 |
| Ryegrass, Italian | 5 | 65 | 10 | 0 | 5 | 0 | 80 | 0 | 0 | 35 | 0 | 75 |
| Sandbur | 5 | 5 | 0 | 0 | 35 | 30 | 15 | 20 | 5 | 5 | 5 | 5 |
| Smartweed | — | — | — | 0 | — | — | 0 | 0 | 0 | 5 | 0 | — |
| Soybean | 0 | 0 | 0 | 0 | 0 | 0 | 25 | 0 | 0 | 0 | 0 | 20 |
| Surinam Grass | 0 | 5 | 0 | 40 | 5 | 10 | — | 65 | 0 | 20 | 0 | 15 |
| Velvetleaf | 0 | 0 | 0 | 0 | 50 | 20 | 0 | 0 | 0 | 0 | 0 | 20 |
| Waterhemp | 100 | 98 | 75 | 90 | 100 | 60 | 100 | 80 | 95 | 98 | 65 | 98 |

| | Compounds | | | | | | | | | | |
|---|---|---|---|---|---|---|---|---|---|---|---|
| 16 g ai/ha | 139 | 142 | 146 | 148 | 153 | 154 | 162 | 169 | 171 | 174 | 196 |
| Preemergence | | | | | | | | | | | |
| Arrowleaf *Sida* | 0 | 0 | 0 | 0 | 5 | 0 | 0 | 0 | 0 | 0 | 0 |
| Barnyardgrass | 0 | 0 | 0 | 0 | 5 | 0 | 20 | 0 | 0 | 0 | 25 |
| Beggarticks | 0 | 0 | 0 | 0 | 0 | 0 | 0 | 0 | 0 | 0 | 50 |
| Cocklebur | — | 0 | — | — | 0 | 0 | — | 0 | 0 | — | — |
| Corn | 0 | 0 | 0 | 0 | 0 | 0 | 0 | 0 | 0 | 0 | 0 |
| Crabgrass, Brazil | — | — | — | 100 | 98 | 75 | 100 | 100 | 0 | 0 | — |
| Crabgrass, Large | 30 | — | 0 | 95 | 80 | 50 | 0 | 98 | 75 | 50 | 75 |
| Dayflower, VA | 0 | 0 | 0 | 0 | 5 | 0 | 35 | 0 | 0 | 0 | 35 |
| Field Bindweed | 0 | 20 | 0 | 0 | 5 | 0 | 5 | 0 | 0 | 0 | 0 |
| Foxtail, Giant | 0 | 35 | 20 | 25 | 40 | 5 | 70 | 70 | 40 | 0 | 85 |
| Foxtail, Green | 10 | 20 | 20 | 35 | 50 | 40 | 80 | 98 | 20 | 35 | 75 |
| Goosegrass | 5 | 40 | 0 | 25 | 80 | 10 | 95 | 50 | 70 | 35 | 60 |
| Johnsongrass | 0 | 0 | 0 | 0 | 0 | 0 | 20 | 0 | 0 | 0 | 65 |
| Kochia | 0 | 20 | 0 | 0 | 25 | 5 | — | 0 | 0 | 0 | 5 |
| Lambsquarters | 0 | 0 | 0 | 0 | 0 | 0 | 98 | 0 | 0 | 0 | 70 |
| Morningglory | 0 | 0 | 0 | 0 | 0 | — | 20 | 0 | 0 | 0 | 30 |
| Nightshade | 20 | 65 | 0 | 0 | 50 | 0 | 5 | 0 | 0 | 0 | 95 |
| Nutsedge, Yellow | 0 | 0 | 0 | 0 | 0 | 0 | 35 | 0 | 0 | 0 | 0 |
| *Panicum*, Fall | 0 | 25 | 0 | 75 | 5 | 15 | 100 | 65 | 0 | 0 | — |
| Pigweed, Palmer | — | — | 85 | 0 | 98 | 100 | 98 | 35 | 0 | 0 | — |
| *Poinsettia*, Wild | 0 | 0 | 20 | 0 | 0 | 0 | 0 | 0 | 0 | 0 | 50 |
| Ragweed | 0 | 0 | 0 | 0 | 5 | 0 | 0 | 0 | — | — | 0 |
| Ryegrass, Italian | 0 | 5 | 0 | 0 | 5 | 0 | 35 | 0 | 0 | 0 | 40 |
| Sandbur | 0 | 5 | 0 | 0 | 5 | 0 | 5 | 0 | 0 | 0 | 5 |
| Smartweed | — | — | — | 0 | — | — | 0 | 0 | 0 | 0 | — |
| Soybean | 0 | 0 | 0 | 0 | 0 | 0 | 0 | 0 | 0 | 0 | 0 |
| Surinam Grass | 0 | 5 | 0 | 25 | 0 | 0 | — | 0 | 0 | 0 | — |

TABLE F-continued

| | | | | | | | | | | | |
|---|---|---|---|---|---|---|---|---|---|---|---|
| Velvetleaf | 0 | 0 | 0 | 0 | 20 | 0 | 0 | 0 | 0 | 0 | 10 |
| Waterhemp | 70 | 98 | 25 | 30 | 65 | 50 | 90 | 60 | 0 | 0 | 95 |

| | Compounds | | | Compound |
|---|---|---|---|---|
| 8 g ai/ha | 162 | 196 | 4 g ai/ha | 162 |
| Preemergence | | | | |
| Arrowleaf *Sida* | 0 | 0 | Arrowleaf *Sida* | 0 |
| Barnyardgrass | 20 | 0 | Barnyardgrass | 0 |
| Beggarticks | 0 | 0 | Beggarticks | 0 |
| Cocklebur | 0 | — | Cocklebur | 0 |
| Corn | 0 | 0 | Corn | 0 |
| Crabgrass, Brazil | 100 | — | Crabgrass, Brazil | 0 |
| Crabgrass, Large | 0 | — | Dayflower, VA | 0 |
| Dayflower, VA | 35 | 5 | Field Bindweed | 0 |
| Field Bindweed | 0 | 0 | Foxtail, Giant | 0 |
| Foxtail, Giant | 20 | 5 | Foxtail, Green | 0 |
| Foxtail, Green | 15 | 75 | Goosegrass | 0 |
| Goosegrass | 0 | 40 | Johnsongrass | 20 |
| Johnsongrass | 20 | — | Kochia | 30 |
| Kochia | — | 5 | Lambsquarters | 0 |
| Lambsquarters | 0 | 60 | Morningglory | 0 |
| Morningglory | 0 | 0 | Nightshade | 0 |
| Nightshade | 0 | 95 | Nutsedge, Yellow | 0 |
| Nutsedge, Yellow | 0 | 0 | *Panicum*, Fall | 0 |
| *Panicum*, Fall | 0 | 25 | Pigweed, Palmer | 0 |
| Pigweed, Palmer | 25 | — | *Poinsettia*, Wild | 0 |
| *Poinsettia*, Wild | 0 | 0 | Ragweed | 0 |
| Ragweed | 0 | 0 | Ryegrass, Italian | 0 |
| Ryegrass, Italian | 0 | 0 | Sandbur | 0 |
| Sandbur | 0 | 5 | Smartweed | 0 |
| Smartweed | 0 | — | Soybean | 0 |
| Soybean | 0 | 0 | Surinam Grass | 0 |
| Surinam Grass | 0 | 0 | Velvetleaf | 0 |
| Velvetleaf | 0 | 0 | Waterhemp | 50 |
| Waterhemp | 85 | 50 | | |

Test G

Seeds of smallflower umbrella sedge (CYPDI, *Cyperus difformis*) and ducksalad (HETLI, *Heteranthera limosa*) were sown on the soil surface in two separate quadrants of 11 cm tubs filled with steam pasteurized Tama soil. Simultaneously, plantings of barnyardgrass (ECHCG, *Echinochloa crus-galli*) and *japonica* rice (ORYSP, *Oryza sativa*) were established in separate "plug" flats. Plants were grown in a greenhouse using supplemental lighting to maintain a photoperiod of approximately 16 h; daytime and nighttime temperatures were approximately 27-30° C. and 19-22° C., respectively. After 8 days, barnyardgrass plants were transplanted to one of the remaining quadrants of the tub, and the water level was adjusted to a final depth of 3 cm. Herbicide application timing was targeted at the 2.0 to 2.5 leaf stage and the plants were treated with test chemicals formulated in a non-phytotoxic solvent. Treated plants and controls were maintained in a greenhouse for 14 days, after which time all species were compared to controls and visually evaluated. Plant response ratings are summarized in Tables G1 through G3, and are based on a scale of 0 to 100 where 0 is no effect and 100 is complete control. A dash (-) response means no test result.

TABLE G1

Results from Compd. No. 16 Alone and in Combination with Bensulfuron-Methyl (b2a)

| Treatment | Rate (g/ha) | ORYSP | ECHCG | CYPDI | HETLI |
|---|---|---|---|---|---|
| b2a | 16 | 0 | 60 | 90 | 90 |
| b2a | 31 | 0 | 68 | 90 | 95 |
| b2a | 62 | 0 | 75 | 93 | 98 |

TABLE G1-continued

Results from Compd. No. 16 Alone and in Combination with Bensulfuron-Methyl (b2a)

| Treatment | Rate (g/ha) | ORYSP | ECHCG | CYPDI | HETLI |
|---|---|---|---|---|---|
| Compd. No. 16 | 8 | 10 | 25 | 85 | 0 |
| Compd. No. 16 | 16 | 15 | 35 | 85 | 60 |
| b2a + Compd. No. 16 | 16 + 8 | 0 | 40 | 93 | 99 |
| b2a + Compd. No. 16 | 31 + 8 | 8 | 58 | 97 | 100 |
| b2a + Compd. No. 16 | 62 + 8 | 13 | 73 | 98 | 100 |
| b2a + Compd. No. 16 | 16 + 16 | 18 | 45 | 95 | 99 |
| b2a + Compd. No. 16 | 31 + 16 | 25 | 52 | 96 | 98 |
| b2a + Compd. No. 16 | 62 + 16 | 18 | 67 | 98 | 99 |

TABLE G2

Results from Compd. No. 129 Alone and in Combination with Bensulfuron-Methyl (b2a)

| Treatment | Rate (g/ha) | ORYSP | ECHCG | CYPDI | HETLI |
|---|---|---|---|---|---|
| b2a | 32 | 0 | 60 | 90 | 90 |
| b2a | 64 | 0 | 68 | 90 | 95 |
| b2a | 125 | 0 | 75 | 93 | 98 |
| Compd. No. 129 | 16 | 0 | 0 | 0 | 0 |

TABLE G2-continued

| Results from Compd. No. 129 Alone and in Combination with Bensulfuron-Methyl (b2a) | | | | | |
|---|---|---|---|---|---|
| Treatment | Rate (g/ha) | ORYSP | ECHCG | CYPDI | HETLI |
| Compd. No. 129 | 32 | 10 | 5 | 48 | 25 |
| b2a + Compd. No. 129 | 32 + 16 | 0 | 47 | 99 | 99 |
| b2a + Compd. No. 129 | 64 + 16 | 5 | 60 | 98 | 99 |
| b2a + Compd. No. 129 | 125 + 16 | 13 | 72 | 99 | 100 |
| b2a + Compd. No. 129 | 32 + 32 | 3 | 40 | 98 | 98 |
| b2a + Compd. No. 129 | 64 + 32 | 10 | 55 | 93 | 95 |
| b2a + Compd. No. 129 | 125 + 32 | 17 | 68 | 94 | 98 |

TABLE G3

| Results from Compd. No. 129 Alone and in Combination with 5-[(2-hydroxy-6-oxo-1-cyclohexen-1-yl)carbonyl]-2-(3-methoxyphenyl)-3-(3-methoxypropyl)-4(3H)-pyrimidinone (b12a) | | | | | |
|---|---|---|---|---|---|
| Treatment | Rate (g/ha) | ORYSP | ECHCG | CYPDI | HETLI |
| Compd. No. 129 | 31 | 5 | 15 | 75 | 40 |
| b12a | 125 | 5 | 35 | 80 | 80 |
| Cmpd. No. 129 + b12a | 31 + 125 | 13 | 93 | 95 | 100 |

Test H

Seeds of plant species selected from wheat (TRZAW, *Triticum aestivum*), barley (HORBW, *Hordeum vulgare*), *Kochia* (KCHSC, *Kochia caoparia*) blackgrass (ALOMY, *Alopecurus myosuroides*), canarygrass (PHAMI, *Phalaris minor*), Italian ryegrass (LOLMU, *Lolium multiflorum*) common lambsquarter (CHEAL, *Chenopodium album*), pigweed (AMARE, *Amaranthus retroflexus*), Common Chickweed (STEME, *Stellaria media*), Russian thistle (SASKR, *Salsola iberica*), Wild Buckwheat (POLCO, *Polygonum convolvulus*), Catchweed Bedstraw (GALAP, *Galium aparine*), Mustard (SINAR, *Sinapisar arvensis*), Henbit Deadnettle (LAMAM, *Lamium amplexicaule*), Wild Radish (RAPRA, *Raphanus raphanistrum*), Field Poppy (PAPRH, *Papaver rhoeas*), Field Violet (VIOAR, *Viola arvennsis*), Scentless Chamomile (MATIN *Matricaria inodora*) were planted into soil and treated post-emergence with test chemicals formulated in a non-phytotoxic solvent mixture. Plants were grown in a greenhouse using supplemental lighting to maintain a photoperiod of approximately 14 hours; daytime and nighttime temperatures were approximately 23°-29° and 16°-19° Celsius, respectively. Balanced fertilizer was applied through the watering system. Treated plants and controls were maintained in a greenhouse for 20 days, after which time all species were compared to controls and visually evaluated. Plant response ratings were calculated as the mean of three replicates (unless otherwise indicated), are summarized in Table G, and are based on a scale of 0 to 100 where 0 is no effect and 100 is complete control. A dash (-) response means no test result.

TABLE H1

| Results from Compd. No. 129 Alone and in Combination with Flupyrsulfuron-methyl (b2b) and in Combination with Thifensulfuron-methyl (b2c) | | | | | | | |
|---|---|---|---|---|---|---|---|
| Treatment | Rate | TRZAW | HORBW | KCHSC | SASKR | STEME | CHEAL |
| Compd. No. 129 | 31 | 10 | 10 | 80 | 65 | 50 | 85 |
| Compd. No. 129 | 62 | 15 | 15 | 85 | 80 | 70 | 80 |
| Compd. No. 129 | 125 | 15 | 15 | 95 | 90 | 80 | 90 |
| b2b | 8 | 0 | 20 | 75 | 50 | 90 | 60 |
| b2b | 16 | 5 | 30 | 100 | 50 | 100 | 85 |
| b2b | 31 | 5 | 60 | 80 | 50 | 100 | 75 |
| b2b | 62 | 25 | 70 | 95 | 60 | 100 | 80 |
| b2c | 8 | 0 | 0 | 70 | 100 | 85 | 85 |
| b2c | 16 | 0 | 5 | 85 | 100 | 100 | 70 |
| b2c | 31 | 0 | 5 | 95 | 100 | 100 | 100 |
| b2c | 62 | 5 | 5 | 100 | 100 | 100 | 95 |
| Compd. No. 129 + b2b | 31 + 8 | 10 | 35 | 90 | 50 | 95 | 80 |
| Compd. No. 129 + b2b | 31 + 16 | 10 | 35 | 95 | 50 | 100 | 85 |
| Compd. No. 129 + b2b | 31 + 31 | 15 | 70 | 90 | 95 | 100 | 95 |
| Compd. No. 129 + b2b | 31 + 62 | 25 | 75 | 95 | 60 | 100 | 95 |
| Compd. No. 129 + b2b | 62 + 8 | 15 | 35 | 90 | 65 | 100 | 90 |
| Compd. No. 129 + b2b | 62 + 16 | 20 | 40 | 100 | 100 | 100 | 95 |
| Compd. No. 129 + b2b | 62 + 31 | 20 | 60 | 100 | 70 | 100 | 95 |
| Compd. No. 129 + b2b | 62 + 62 | 25 | 75 | 100 | 65 | 100 | 100 |
| Compd. No. 129 + b2b | 125 + 8 | 15 | 35 | 90 | 90 | 100 | 95 |
| Compd. No. 129 + b2b | 125 + 16 | 15 | 65 | 90 | 90 | 100 | 75 |
| Compd. No. 129 + b2b | 125 + 31 | 25 | 75 | 95 | 90 | 95 | 95 |
| Compd. No. 129 + b2b | 125 + 62 | 40 | 80 | 100 | 95 | 100 | — |
| Compd. No. 129 + b2c | 31 + 16 | 10 | 10 | 100 | 95 | 95 | 80 |
| Compd. No. 129 + b2c | 31 + 31 | 10 | 10 | 90 | 100 | 95 | 95 |
| Compd. No. 129 + b2c | 62 + 16 | 10 | 10 | 85 | 100 | 90 | 95 |
| Compd. No. 129 + b2c | 62 + 31 | 10 | 10 | 95 | 100 | 100 | 95 |
| Compd. No. 129 + b2c | 62 + 62 | 10 | 10 | 95 | 95 | 95 | 95 |
| Compd. No. 129 + b2c | 125 + 16 | 15 | 20 | 100 | 100 | 100 | 100 |

TABLE H1-continued

Results from Compd. No. 129 Alone and in Combination with Flupyrsulfuron-methyl (b2b) and in Combination with Thifensulfuron-methyl (b2c)

| | | | | | | | |
|---|---|---|---|---|---|---|---|
| Compd. No. 129 + b2c | 125 + 31 | 15 | 20 | 100 | 95 | 100 | 95 |
| Compd. No. 129 + b2c | 125 + 62 | 15 | 20 | 100 | 95 | 100 | — |

| Treatment | Rate | POLCO | AMARI | SINAR | GALAP | LAMAM | RAPRA |
|---|---|---|---|---|---|---|---|
| Compd. No. 129 | 31 | 30 | 80 | 80 | 65 | 60 | 60 |
| Compd. No. 129 | 62 | 25 | 90 | 95 | 60 | 70 | 85 |
| Compd. No. 129 | 125 | 70 | 95 | 95 | 70 | 80 | 90 |
| b2b | 8 | 100 | 100 | 100 | 90 | 90 | 100 |
| b2b | 16 | 85 | 100 | 95 | 95 | 95 | 100 |
| b2b | 31 | 100 | 100 | 100 | 90 | 95 | 100 |
| b2b | 62 | 100 | 100 | 100 | 100 | 90 | 100 |
| b2c | 8 | 95 | 100 | 80 | 80 | 60 | 95 |
| b2c | 16 | 95 | 100 | 90 | 90 | 70 | 75 |
| b2c | 31 | 95 | 100 | 85 | 75 | 75 | 100 |
| b2c | 62 | 95 | 100 | 95 | 95 | 75 | 95 |
| Compd. No. 129 + b2b | 31 + 8 | 100 | 100 | 95 | 95 | 95 | 100 |
| Compd. No. 129 + b2b | 31 + 16 | 90 | 100 | 100 | 95 | 95 | 100 |
| Compd. No. 129 + b2b | 31 + 31 | 100 | 100 | 100 | 100 | 95 | 100 |
| Compd. No. 129 + b2b | 31 + 62 | 100 | 100 | 100 | 100 | 90 | 100 |
| Compd. No. 129 + b2b | 62 + 8 | 95 | 100 | 100 | 95 | 85 | 100 |
| Compd. No. 129 + b2b | 62 + 16 | 100 | 100 | 100 | 100 | 90 | 100 |
| Compd. No. 129 + b2b | 62 + 31 | 95 | 100 | 100 | 100 | 90 | 100 |
| Compd. No. 129 + b2b | 62 + 62 | 100 | 100 | 100 | 100 | 100 | 95 |
| Compd. No. 129 + b2b | 125 + 8 | 95 | 100 | 100 | 100 | 85 | 100 |
| Compd. No. 129 + b2b | 125 + 16 | 95 | 100 | 95 | 95 | 90 | 100 |
| Compd. No. 129 + b2b | 125 + 31 | 95 | 100 | 100 | 100 | 90 | 100 |
| Compd. No. 129 + b2b | 125 + 62 | 100 | 100 | 95 | 95 | 90 | 100 |
| Compd. No. 129 + b2c | 31 + 16 | 90 | 100 | 85 | 65 | 70 | 95 |
| Compd. No. 129 + b2c | 31 + 31 | 95 | 100 | 90 | 80 | 70 | 95 |
| Compd. No. 129 + b2c | 62 + 16 | 95 | 100 | 85 | 85 | 70 | 100 |
| Compd. No. 129 + b2c | 62 + 31 | 100 | 100 | 90 | 85 | 90 | 100 |
| Compd. No. 129 + b2c | 62 + 62 | 100 | 100 | 95 | 95 | 90 | 100 |
| Compd. No. 129 + b2c | 125 + 16 | 95 | 100 | 95 | 80 | 85 | 95 |
| Compd. No. 129 + b2c | 125 + 31 | 95 | 100 | 90 | 95 | 85 | 95 |
| Compd. No. 129 + b2c | 125 + 62 | 100 | 100 | 95 | 100 | 85 | 95 |

| Treatment | Rate | PAPRH | VIOAR | MATIN | LOLMU | PHAMI | ALOMY |
|---|---|---|---|---|---|---|---|
| Compd. No. 129 | 31 | 85 | 60 | 0 | 10 | 15 | 5 |
| Compd. No. 129 | 62 | 90 | 75 | 5 | 10 | 20 | 10 |
| Compd. No. 129 | 125 | 90 | 90 | 10 | 15 | 60 | 30 |
| b2b | 8 | 100 | 50 | 90 | 60 | 40 | 100 |
| b2b | 16 | 90 | 75 | 95 | 60 | 55 | 100 |
| b2b | 31 | 100 | 70 | 100 | 65 | 85 | 100 |
| b2b | 62 | 95 | 95 | 95 | 80 | 90 | 100 |
| b2c | 8 | 70 | 80 | 95 | 20 | 10 | 10 |
| b2c | 16 | 75 | 85 | 90 | 50 | 60 | 45 |
| b2c | 31 | 100 | 75 | 100 | 70 | 70 | 60 |
| b2c | 62 | 100 | 95 | 100 | 90 | 90 | 65 |
| Compd. No. 129 + b2b | 31 + 8 | 90 | 60 | 100 | 65 | 55 | 95 |
| Compd. No. 129 + b2b | 31 + 16 | 90 | 65 | 100 | 70 | 65 | 95 |
| Compd. No. 129 + b2b | 31 + 31 | 100 | 80 | 100 | 75 | 70 | 100 |
| Compd. No. 129 + b2b | 31 + 62 | 100 | 100 | 100 | 75 | 95 | 100 |
| Compd. No. 129 + b2b | 62 + 8 | 85 | 95 | 95 | 50 | 25 | 95 |
| Compd. No. 129 + b2b | 62 + 16 | 90 | 70 | 95 | 60 | 55 | 95 |
| Compd. No. 129 + b2b | 62 + 31 | 90 | 85 | 95 | 65 | 70 | 100 |
| Compd. No. 129 + b2b | 62 + 62 | 95 | 85 | 95 | 85 | 95 | 95 |
| Compd. No. 129 + b2b | 125 + 8 | 75 | 65 | 90 | 60 | 55 | 90 |
| Compd. No. 129 + b2b | 125 + 16 | 85 | 70 | 95 | 70 | 60 | 95 |
| Compd. No. 129 + b2b | 125 + 31 | 100 | 80 | 90 | 60 | 70 | 95 |
| Compd. No. 129 + b2b | 125 + 62 | 90 | 85 | 95 | 90 | 85 | 95 |
| Compd. No. 129 + b2c | 31 + 16 | 70 | 75 | 80 | 10 | 25 | 15 |
| Compd. No. 129 + b2c | 31 + 31 | 75 | 75 | 90 | 20 | 35 | 45 |
| Compd. No. 129 + b2c | 62 + 16 | 80 | 90 | 90 | 20 | 60 | 40 |
| Compd. No. 129 + b2c | 62 + 31 | 80 | 75 | 95 | 65 | 75 | 50 |
| Compd. No. 129 + b2c | 62 + 62 | 95 | 80 | 95 | 65 | 90 | 60 |
| Compd. No. 129 + b2c | 125 + 16 | 95 | 80 | 95 | 60 | 60 | 60 |
| Compd. No. 129 + b2c | 125 + 31 | 95 | 80 | 100 | 60 | 75 | 65 |
| Compd. No. 129 + b2c | 125 + 62 | 95 | 80 | 95 | 70 | 85 | 70 |

What is claimed is:

1. A compound selected from Formula 1, N-oxides and salts thereof,

1

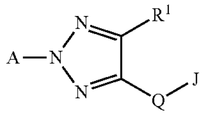

wherein $R^1$ is halogen, cyano, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_n(R^{12})$, $C_2$-$C_4$ alkylthioalkyl, $C_2$-$C_4$ alkylsulfonylalkyl, $C_1$-$C_4$ alkylamino, $C_2$-$C_4$ dialkylamino, $C_3$-$C_6$ cycloalkyl or hydroxy;

A is a radical selected from the group consisting of

A-1

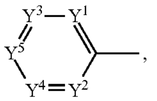

,

A-2

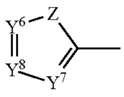

and

A-3

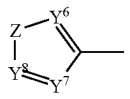

each $Y^1$, $Y^2$, $Y^3$, $Y^4$ and $Y^5$ is independently N or $CR^2$, provided no more than 3 of $Y^1$, $Y^2$, $Y^3$, $Y^4$ and $Y^5$ are N;

each $Y^6$, $Y^7$ and $Y^8$ is independently N or $CR^3$, provided no more than 2 of $Y^6$, $Y^7$ and $Y^8$ are N;

Z is O or S;

Q is $C(R^4)(R^5)$, O, S or $NR^6$;

J is phenyl substituted with 1 $R^7$ and optionally substituted with up to 2 $R^8$; or J is a 6-membered aromatic heterocyclic ring substituted with 1 $R^7$ and optionally substituted with up to 2 $R^8$ on carbon ring members; or J is a 5-membered aromatic heterocyclic ring substituted with 1 $R^9$ on carbon ring members and $R^{11}$ on nitrogen ring members; and optionally substituted with 1 $R^{10}$ on carbon ring members;

each $R^2$ is independently H, halogen, cyano, nitro, $SF_5$, $C_1$-$C_4$ alkoxy, $C_1$-$C_4$ haloalkoxy, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy or $S(O)_nR^{12}$;

each $R^3$ is independently H, halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^2$;

$R^4$ is H, F, Cl, Br, cyano, $C_1$-$C_4$ alkyl, $C_1$-$C_4$ haloalkyl or $CO_2R^{13}$;

$R^5$ is H, F, $C_1$-$C_4$ alkyl, OH or $OR^{13}$; or $R^4$ and $R^5$ are taken together with the carbon to which they are attached to form C(=O), C(=$NOR^{13}$) or C(=N—$N(R^{14})(R^{15})$);

$R^6$ is H, $C_1$-$C_4$ alkyl or $C_1$-$C_4$ haloalkyl;

$R^7$ is halogen, cyano, $SF_5$, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

each $R^8$ is independently halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^{12}$; or $R^7$ and $R^8$ are taken together with two adjacent carbon atoms to form a 5-membered carbocyclic ring containing ring members selected from up to two O atoms and up to two S atoms, and optionally substituted on carbon atom ring members with up to five halogen atoms;

$R^9$ is halogen, cyano, $SF_5$, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

$R^{10}$ is halogen, cyano, $C_1$-$C_4$ alkyl, $C_1$-$C_4$ haloalkyl, $C_1$-$C_4$ alkoxy, $C_1$-$C_4$ haloalkoxy or $S(O)_nR^{12}$;

$R^{11}$ is $C_1$-$C_4$ alkyl or $C_1$-$C_4$ haloalkyl;

each $R^{12}$ is independently $C_1$-$C_4$ alkyl or $C_1$-$C_4$ haloalkyl;

each $R^{13}$ is independently H or $C_1$-$C_4$ alkyl;

$R^{14}$ is $C_1$-$C_4$ alkyl or $C_1$-$C_4$ haloalkyl;

$R^{15}$ is $C_1$-$C_4$ alkyl or $C_1$-$C_4$ haloalkyl; and each n is independently 0, 1 or 2;

provided i) when $R^1$ is $CH_3$; A is A-1; $Y^1$, $Y^2$, $Y^3$ and $Y^4$ are each CH; and $Y^5$ is $CCF_3$ then J is other than 3-chloro-1H-1,2,4-thiadiazol-5-$Y^{1,4}$-fluoro-2-pyridinyl, 4-chlorophenyl or 2,4-dichlorophenyl; and ii) when $R^1$ is $CH_3$; A is A-1; $Y^1$, $Y^2$, $Y^3$ and $Y^4$ are each CH; and $Y^5$ is CF then J is other than 4-fluoro-3-methylphenyl.

2. The compound of claim 1 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl, $C_2$-$C_4$ alkenyl, $C_2$-$C_4$ alkynyl, $C_3$-$C_4$ alkenyloxy, $C_3$-$C_4$ alkynyloxy, $C_2$-$C_6$ alkylcarbonyloxy, $C_1$-$C_4$ hydroxyalkyl, $SO_n(R^{12})$, $C_2$-$C_4$ alkylthioalkyl or $C_2$-$C_4$ alkylsulfonylalkyl;

A is a radical selected from the group consisting of A-1 and A-2;

each $Y^1$, $Y^3$, $Y^4$ and $Y^5$ is independently N or $CR^2$; and $Y^2$ is $CR^2$;

each $Y^6$ and $Y^7$ is independently N or $CR^3$; and $Y^8$ is $CR^3$;

Z is S;

Q is $C(R^4)(R^5)$, O or S;

J is selected from the group consisting of

J-1

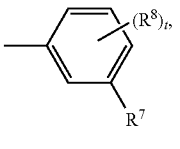

J-2

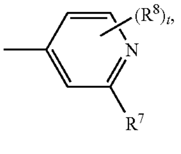

J-3

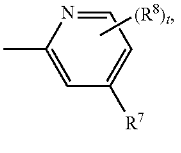

-continued
J-4
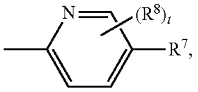
J-5
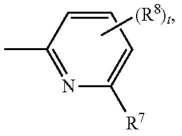
J-6
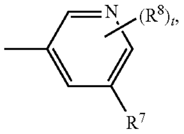
J-7
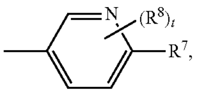
J-8
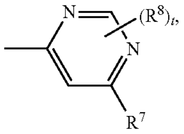
J-9
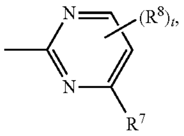
J-12
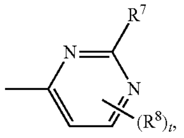
J-13
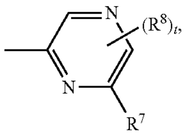
J-14
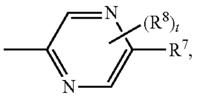
J-15
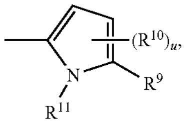
J-16
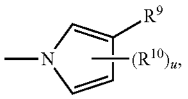
J-17
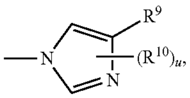
-continued
J-18
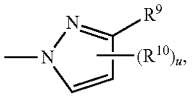
J-19
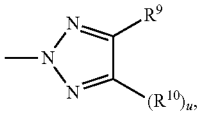
J-20
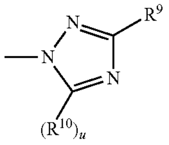
J-21
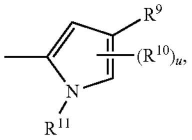
J-22
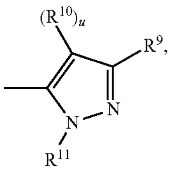
J-23
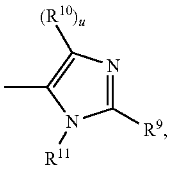
J-24
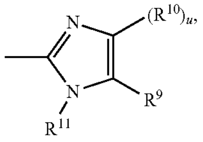
J-25
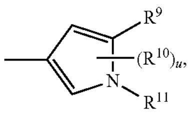
J-26
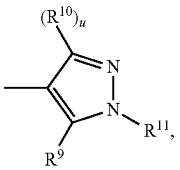
J-27
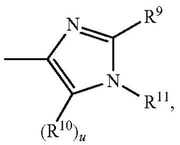

-continued

J-28

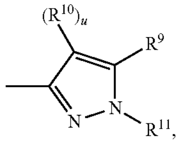

J-29

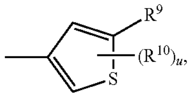

J-30

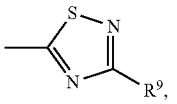

J-31

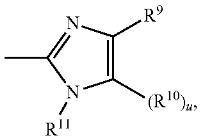

J-32

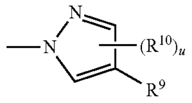 and

J-33

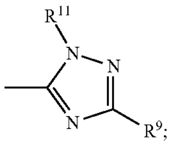

t is 0, 1 or 2;

u is 0 or 1;

each $R^2$ is independently H, halogen, $C_1$-$C_4$ alkoxy, $C_1$-$C_4$ alkyl or $C_1$-$C_4$ haloalkyl;

each $R^3$ is independently H, halogen or $C_1$-$C_4$ haloalkyl;

$R^4$ is H, F, Cl, Br or $C_1$-$C_4$ alkyl;

$R^5$ is H, F or OH; or $R^4$ and $R^5$ are taken together with the carbon to which they are attached to form C(=O);

$R^7$ is halogen, $C_1$-$C_4$ alkyl, $C_1$-$C_4$ haloalkyl, $C_1$-$C_4$ alkoxy or $C_1$-$C_4$ haloalkoxy;

$R^8$ is independently halogen or $C_1$-$C_4$ haloalkyl; or $R^7$ and $R^8$ are taken together with two adjacent carbon atoms to form a 2,2-difluorodioxolane ring;

$R^9$ is halogen, $C_1$-$C_4$ alkyl, $C_1$-$C_4$ haloalkyl, $C_1$-$C_4$ alkoxy or $C_1$-$C_4$ haloalkoxy;

$R^{10}$ is halogen, $C_1$-$C_4$ alkyl, $C_1$-$C_4$ haloalkyl, $C_1$-$C_4$ alkoxy or $C_1$-$C_4$ haloalkoxy;

$R^{11}$ is $C_1$-$C_4$ alkyl or $C_1$-$C_4$ haloalkyl;

each $R^{12}$ is independently $C_1$-$C_4$ alkyl;

each $R^{13}$ is independently $CH_3$ or $CH_2CH_3$;

$R^{14}$ is $C_1$-$C_4$ alkyl;

$R^{15}$ is $C_1$-$C_4$ alkyl; and n is 0 or 2.

3. The compound of claim 2 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl, $C_1$-$C_4$ haloalkyl or $C_2$-$C_4$ alkenyl;

each $Y^1$ and $Y^5$ is independently N or $CR^2$; and each $Y^2$, $Y^3$ and $Y^4$ is $CR^2$;

each $Y^6$ and $Y^7$ is N; and $Y^8$ is $CR^3$;

Q is $C(R^4)(R^5)$ or O;

J is selected from J-1, J-2, J-3, J-4, J-5, J-6, J-7, J-9, J-12, J-17, J-18, J-20, J-22, J-26, J-29 and J-30;

t is 0 or 1;

u is 0;

each $R^2$ is independently H, halogen, $C_1$-$C_4$ alkyl or $C_1$-$C_4$ haloalkyl;

each $R^3$ is independently H, F, Cl or $CF_3$;

$R^4$ is H, F or $CH_3$;

$R^5$ is H or F;

$R^7$ is F, $CH_3$ or $CF_3$;

$R^8$ is independently F, Cl or $CF_3$;

$R^9$ is halogen, $C_1$-$C_4$ alkyl or $C_1$-$C_4$ haloalkyl;

$R^{10}$ is halogen, $C_1$-$C_4$ alkyl or $C_1$-$C_4$ haloalkyl;

$R^{11}$ is $C_1$-$C_4$ alkyl;

each $R^{12}$ is $CH_3$; and each $R^{13}$ is $CH_3$.

4. The compound of claim 2 wherein $R^1$ is halogen, $C_1$-$C_4$ alkoxy, $C_1$-$C_4$ haloalkoxy, $C_2$-$C_4$ alkoxyalkyl, $C_1$-$C_4$ alkyl or $C_1$-$C_4$ haloalkyl;

A is A-1;

$Y^1$ is N or $CR^2$; and each $Y^2$, $Y^3$, $Y^4$ and $Y^5$ is independently $CR^2$;

Q is $C(R^4)(R^5)$;

J is selected from J-1, J-2, J-10, J-17, J-18 and J-20;

t is 0;

each $R^2$ is independently H, F, Cl, $CH_3$ or $CF_3$;

$R^4$ is H;

$R^5$ is H; and $R^7$ is F or $CF_3$.

5. The compound of claim 3 wherein $R^1$ is $C_1$-$C_4$ alkoxy, $C_1$-$C_4$ haloalkoxy or $C_1$-$C_4$ alkyl;

A is A-1;

$Y^1$ is N or $CR^2$; and each $Y^2$, $Y^3$, $Y^4$ and $Y^5$ is independently $CR^2$;

Q is O;

J is selected from J-1, J-2, J-17 and J-18;

each $R^2$ is independently H, F, Cl or $CF_3$; and $R^7$ is $CF_3$.

6. The compound of claim 3 wherein $R^1$ is $CH_3$;

each $Y^1$, $Y^2$, $Y^3$, $Y^4$ and $Y^5$ is independently $CR^2$;

J is J-2; and each $R^2$ is independently H or F.

7. The compound of claim 1 selected from the group consisting of

4-[[2-(4-fluorophenyl)-5-methyl-2H-1,2,3-triazol-4-yl]oxy]-2-(trifluoromethyl)pyridine and 4-[[5-Methoxy-2-[4-(trifluoromethyl)phenyl]-2H-1,2,3-triazol-4-yl]methyl]-2-(trifluoromethyl)pyridine.

8. The compound of claim 1 selected from the group consisting of

4-[[2-(4-fluorophenyl)-5-methyl-2H-1,2,3-triazol-4-yl]methyl]-2-(trifluoromethyl)pyridine;

4-[[2-(4-fluorophenyl)-5-methyl-2H-1,2,3-triazol-4-yl]oxy]-2-(trifluoromethyl)pyridine;

4-[[5-ethoxy-2-(4-fluorophenyl)-2H-1,2,3-triazol-4-yl]methyl]-2-(trifluoromethyl)pyridine;

4-[[5-methoxy-2-[4-(trifluoromethyl)phenyl]-2H-1,2,3-triazol-4-yl]methyl]-2-(trifluoromethyl)pyridine;

4-[[5-methyl-2-[4-(trifluoromethyl)phenyl]-2H-1,2,3-triazol-4-yl]methyl]-2-(trifluoromethyl)pyridine;

4-[[5-ethoxy-2-[4-(trifluoromethyl)phenyl]-2H-1,2,3-triazol-4-yl]methyl]-2-(trifluoromethyl)pyridine; and 4-[[5-(2,2,2-trifluoroethoxy)-2-[4-(trifluoromethyl)phenyl]-2H-1,2,3-triazol-4-yl]methyl]-2-(trifluoromethyl) pyridine.

9. A herbicidal composition comprising a compound of claim 1 and at least one component selected from the group consisting of surfactants, solid diluents and liquid diluents.

10. A herbicidal composition comprising a compound of claim 1, at least one additional active ingredient selected from the group consisting of other herbicides and herbicide safeners, and at least one component selected from the group consisting of surfactants, solid diluents and liquid diluents.

11. A herbicidal mixture comprising (a) a compound of Formula 1, N-oxides, and salts thereof from claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, difenzoquat, bromobutide, flurenol, cinmethylin, cumyluron, dazomet, dymron, methyldymron, etobenzanid, fosamine, fosamine-ammonium, metam, oxaziclomefone, oleic acid, pelargonic acid and pyributicarb, and (b16) herbicide safeners;

and salts of compounds of (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, difenzoquat, bromobutide, flurenol, cinmethylin, cumyluron, dazomet, dymron, methyldymron, etobenzanid, fosamine, fosamine-ammonium, metam, oxaziclomefone, oleic acid, pelargonic acid and pyributicarb, and (b16) herbicide safeners.

12. A method for controlling the growth of undesired vegetation comprising contacting the vegetation or its environment with a herbicidally effective amount of a compound of claim 1.

* * * * *